United States Patent
Kelley et al.

(10) Patent No.: US 10,407,510 B2
(45) Date of Patent: Sep. 10, 2019

(54) ANTI-FACTOR D ANTIBODIES AND CONJUGATES

(71) Applicant: GENENTECH, INC., South San Francisco, CA (US)

(72) Inventors: Robert F. Kelley, South San Francisco, CA (US); Whitney Shatz, South San Francisco, CA (US); Devin Tesar, South San Francisco, CA (US); Justin M. Scheer, South San Francisco, CA (US); Michelle Dion, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 170 days.

(21) Appl. No.: 15/335,847

(22) Filed: Oct. 27, 2016

(65) Prior Publication Data

US 2017/0145112 A1  May 25, 2017

Related U.S. Application Data

(60) Provisional application No. 62/249,166, filed on Oct. 30, 2015, provisional application No. 62/250,995, filed on Nov. 4, 2015.

(51) Int. Cl.
| | | |
|---|---|---|
| *C07K 16/40* | (2006.01) | |
| *A61K 39/395* | (2006.01) | |
| *C07K 16/18* | (2006.01) | |
| *C07K 16/22* | (2006.01) | |
| *C07K 16/28* | (2006.01) | |
| *A61K 47/60* | (2017.01) | |
| *A61K 39/00* | (2006.01) | |

(52) U.S. Cl.
CPC .......... *C07K 16/40* (2013.01); *A61K 39/3955* (2013.01); *A61K 39/39591* (2013.01); *A61K 47/60* (2017.08); *C07K 16/18* (2013.01); *C07K 16/22* (2013.01); *C07K 16/2863* (2013.01); *A61K 2039/505* (2013.01); *A61K 2039/54* (2013.01); *C07K 2317/24* (2013.01); *C07K 2317/34* (2013.01); *C07K 2317/35* (2013.01); *C07K 2317/51* (2013.01); *C07K 2317/515* (2013.01); *C07K 2317/52* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/90* (2013.01); *C07K 2317/92* (2013.01); *C07K 2317/94* (2013.01)

(58) Field of Classification Search
CPC .......... A61K 39/3955; A61K 2039/505; A61K 9/0019; A61K 9/0048; A61K 38/00; A61K 35/30; A61K 39/00; A61K 39/395; A61K 47/60; A61K 39/39591; A61K 2039/54; C07K 16/18; C07K 2317/55; C07K 2317/565; C07K 16/22; C07K 16/00; C07K 16/40; C07K 16/2863; C07K 2317/34; C07K 2317/51; C07K 2317/56; C07K 2317/52; C07K 2317/515; C07K 2317/94; C07K 2317/92; C07K 2317/90; C07K 2317/76; C07K 2317/567; C07K 2317/35; C07K 2317/24; A61P 27/02

See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis et al. |
| 4,741,900 A | 5/1988 | Alvarez et al. |
| 4,816,567 A | 3/1989 | Cabilly |
| 4,935,465 A | 6/1990 | Garman |
| 4,946,778 A | 8/1990 | Ladner |
| 5,166,322 A | 11/1992 | Shaw et al. |
| 5,206,344 A | 4/1993 | Katre et al. |
| 5,225,539 A | 7/1993 | Winter |
| 5,244,800 A | 9/1993 | DeLucas et al. |
| 5,456,909 A | 10/1995 | March, Jr. |
| 5,530,101 A | 6/1996 | Queen |
| 5,534,615 A | 7/1996 | Baker |
| 5,571,894 A | 11/1996 | Wels et al. |
| 5,587,458 A | 12/1996 | King et al. |
| 5,627,264 A | 5/1997 | Fodor |
| 5,679,345 A | 10/1997 | Sanfilippo |
| 5,679,354 A | 10/1997 | Morein |
| 5,679,546 A | 10/1997 | Ko |
| 5,679,564 A | 10/1997 | Pace |
| 5,849,535 A | 12/1998 | Cunningham et al. |
| 5,851,528 A | 12/1998 | Ko |
| 5,853,722 A | 12/1998 | Rollins |
| 5,856,297 A | 1/1999 | Fearon |
| 5,856,300 A | 1/1999 | Rittershaus |

(Continued)

FOREIGN PATENT DOCUMENTS

| | | |
|---|---|---|
| EP | 0245993 B1 | 5/1993 |
| EP | 0239400 B1 | 8/1994 |

(Continued)

OTHER PUBLICATIONS

Martin et. al. "Antibodies". http://www.bioinf.org.uk/abs/. Accessed Oct. 5, 2018. (Year: 2018).*

(Continued)

*Primary Examiner* — Rachel B Gill

(74) *Attorney, Agent, or Firm* — McNeill Baur PLLC

(57) ABSTRACT

The invention provides anti-Factor D antibodies and conjugates and methods of using the same.

126 Claims, 42 Drawing Sheets

Specification includes a Sequence Listing.

(56) References Cited

U.S. PATENT DOCUMENTS

| | | |
|---|---|---|
| 5,858,969 A | 1/1999 | March, Jr. |
| 5,861,156 A | 1/1999 | George |
| 5,869,046 A | 2/1999 | Presta et al. |
| 5,919,623 A | 7/1999 | Taylor |
| 6,267,958 B1 | 7/2001 | Andya et al. |
| 6,333,034 B1 | 12/2001 | Gupta-Bansal |
| 6,376,653 B1 | 4/2002 | Holmes et al. |
| 6,407,213 B1 | 6/2002 | Carter |
| 6,410,708 B1 | 6/2002 | Ashkenazi et al. |
| 6,472,520 B2 | 10/2002 | Fisher |
| 6,534,058 B2 | 3/2003 | Fung |
| 6,569,992 B1 | 5/2003 | LaFleur et al. |
| 6,642,353 B1 | 11/2003 | McConnell et al. |
| 6,828,401 B2 | 12/2004 | Nho et al. |
| 6,838,554 B2 | 1/2005 | Ashkenazi et al. |
| 6,867,189 B2 | 3/2005 | Lucas et al. |
| 6,884,879 B2 | 4/2005 | Baca et al. |
| 6,956,107 B2 | 10/2005 | Fung |
| 7,005,504 B2 | 2/2006 | Hsei et al. |
| 7,112,327 B2 | 9/2006 | Fung |
| 7,122,636 B1 | 10/2006 | Hsei et al. |
| 7,192,589 B2 | 3/2007 | Ashkenazi et al. |
| 7,211,400 B2 | 5/2007 | Ashkenazi et al. |
| 7,282,565 B2 | 10/2007 | Goddard et al. |
| 7,351,524 B2 | 4/2008 | Hageman |
| 7,419,663 B2 | 9/2008 | Ashkenazi et al. |
| 7,432,356 B2 | 10/2008 | Hageman |
| 7,439,331 B2 | 10/2008 | Fung |
| 7,807,164 B2 | 10/2010 | Furfine et al. |
| 7,816,497 B2 | 10/2010 | Ambati |
| 7,943,135 B2 | 5/2011 | Fung |
| 8,007,791 B2 | 8/2011 | Hass et al. |
| 8,007,798 B2 | 8/2011 | Ashkenazi et al. |
| 8,067,002 B2 | 11/2011 | An et al. |
| 8,124,090 B2 | 2/2012 | Fung |
| 8,142,776 B2 | 3/2012 | Liu et al. |
| 8,187,604 B2 | 5/2012 | An et al. |
| 8,193,329 B2 | 6/2012 | An et al. |
| 8,236,317 B2 | 8/2012 | Fung |
| 8,268,310 B2 | 9/2012 | Hass |
| 8,273,352 B2 | 9/2012 | Huang |
| 8,277,830 B2 | 10/2012 | de Juan, Jr. et al. |
| 8,372,403 B2 | 2/2013 | An et al. |
| 8,383,802 B2 | 2/2013 | Fung |
| 8,399,006 B2 | 3/2013 | de Juan, Jr. et al. |
| 8,481,046 B2 | 7/2013 | Furfine et al. |
| 8,614,306 B2 | 12/2013 | Huang |
| 8,753,826 B2 | 6/2014 | An et al. |
| 8,765,131 B2 | 7/2014 | Fung et al. |
| 8,795,712 B2 | 8/2014 | de Juan, Jr. et al. |
| 2002/0081293 A1 | 6/2002 | Fung et al. |
| 2002/0136719 A1 | 9/2002 | Bhami et al. |
| 2003/0021790 A1 | 1/2003 | Vanessa et al. |
| 2003/0129187 A1 | 7/2003 | Fung |
| 2003/0207309 A1 | 11/2003 | Hageman |
| 2004/0152105 A1 | 8/2004 | Vogt et al. |
| 2004/0177387 A1 | 9/2004 | Ambati |
| 2005/0036991 A1 | 2/2005 | Fodor |
| 2005/0191298 A1 | 9/2005 | Bell |
| 2005/0196394 A1 | 9/2005 | Fung |
| 2005/0197285 A1 | 9/2005 | Rosan et al. |
| 2005/0222027 A1 | 10/2005 | Chiang |
| 2005/0232920 A1 | 10/2005 | Fung |
| 2006/0067935 A1 | 3/2006 | Ambati |
| 2006/0233803 A1 | 10/2006 | Ashkenazi et al. |
| 2006/0240020 A1 | 10/2006 | Fung |
| 2006/0281120 A1 | 12/2006 | Gorin et al. |
| 2007/0020647 A1 | 1/2007 | Hageman et al. |
| 2007/0077233 A1 | 4/2007 | Giordano |
| 2007/0092940 A1 | 4/2007 | Eigenbrot et al. |
| 2007/0098692 A1 | 5/2007 | Kovesdi |
| 2007/0190054 A1 | 8/2007 | Ashkenazi et al. |
| 2008/0118506 A1* | 5/2008 | An ................ C07K 16/40 424/133.1 |
| 2008/0146501 A1 | 6/2008 | Hageman et al. |
| 2008/0193442 A1 | 8/2008 | Fung |
| 2008/0280825 A1 | 11/2008 | Hageman et al. |
| 2009/0111708 A1 | 4/2009 | Seddon |
| 2009/0124542 A1 | 5/2009 | Hageman et al. |
| 2009/0181017 A1* | 7/2009 | Hass ................ C07K 16/40 424/133.1 |
| 2009/0214538 A1 | 8/2009 | Ashkenazi et al. |
| 2009/0233277 A1 | 9/2009 | Taku |
| 2009/0269338 A1 | 10/2009 | Huang et al. |
| 2009/0304694 A1 | 12/2009 | Oliner et al. |
| 2010/0104568 A1 | 4/2010 | Beirnaert et al. |
| 2010/0129379 A1 | 5/2010 | Carpenter et al. |
| 2010/0174272 A1 | 7/2010 | Alan |
| 2011/0014716 A1 | 1/2011 | Anand et al. |
| 2011/0123528 A1 | 5/2011 | An et al. |
| 2011/0165622 A1 | 7/2011 | An et al. |
| 2011/0195069 A1 | 8/2011 | Fung |
| 2011/0212433 A1 | 9/2011 | Barker et al. |
| 2011/0286956 A1 | 11/2011 | Xuan et al. |
| 2012/0141480 A1 | 6/2012 | Fung et al. |
| 2012/0190578 A1 | 7/2012 | Seddon et al. |
| 2012/0230985 A1 | 9/2012 | An et al. |
| 2012/0230990 A1 | 9/2012 | Beckman et al. |
| 2012/0322975 A1 | 12/2012 | Fung et al. |
| 2012/0328613 A1 | 12/2012 | Huang |
| 2013/0171070 A1 | 7/2013 | An |
| 2013/0171155 A1 | 7/2013 | Fung et al. |
| 2013/0302333 A1 | 11/2013 | Hass et al. |
| 2014/0065137 A1 | 3/2014 | Huang |
| 2014/0135486 A1 | 5/2014 | Zhao et al. |
| 2015/0071925 A1* | 3/2015 | Larson ................ A61K 47/24 424/134.1 |
| 2015/0073155 A1 | 3/2015 | Yoshioka et al. |
| 2015/0259419 A1 | 9/2015 | Liu et al. |
| 2016/0017052 A1 | 1/2016 | Kelley et al. |

FOREIGN PATENT DOCUMENTS

| | | |
|---|---|---|
| EP | 1287364 B1 | 10/2008 |
| EP | 2267028 A2 | 12/2010 |
| RU | 2232991 | 7/2004 |
| WO | WO 1993/000109 A1 | 1/1993 |
| WO | WO 1993/016185 A2 | 8/1993 |
| WO | WO 1994/004188 A1 | 3/1994 |
| WO | WO 1994/012219 A2 | 6/1994 |
| WO | WO 1994/022466 A1 | 10/1994 |
| WO | WO 1995/029697 A1 | 11/1995 |
| WO | WO 1998/045331 A2 | 10/1998 |
| WO | WO 1999/001556 A2 | 1/1999 |
| WO | WO 1999/003887 A1 | 1/1999 |
| WO | WO 1999/027098 A2 | 3/1999 |
| WO | WO 1999/040100 A1 | 8/1999 |
| WO | WO 1999/042133 | 8/1999 |
| WO | WO 1999/046281 A2 | 9/1999 |
| WO | WO 2000/012703 A2 | 3/2000 |
| WO | WO 2000/037638 A2 | 6/2000 |
| WO | WO 2000/042072 A2 | 7/2000 |
| WO | WO 2000/053749 A2 | 9/2000 |
| WO | WO 2000/053758 A2 | 9/2000 |
| WO | WO 2001/004311 A1 | 1/2001 |
| WO | WO 2001/036432 A2 | 5/2001 |
| WO | WO 2001/036102 A1 | 6/2001 |
| WO | WO 2001/040466 A2 | 6/2001 |
| WO | WO 2011/069104 A2 | 6/2001 |
| WO | WO 2001/084149 A2 | 11/2001 |
| WO | WO 2002/000690 A2 | 1/2002 |
| WO | WO 2002/008284 | 1/2002 |
| WO | WO 2002/030985 | 4/2002 |
| WO | WO 2002/030986 A2 | 4/2002 |
| WO | WO 2003/029420 | 4/2003 |
| WO | WO 2004/001009 A2 | 12/2003 |
| WO | WO 2004/014953 A2 | 2/2004 |
| WO | WO 2004/022594 A2 | 3/2004 |
| WO | WO 2004/032828 A2 | 4/2004 |
| WO | WO 2004/075837 A2 | 9/2004 |
| WO | WO 2005/012359 A2 | 2/2005 |
| WO | WO 2005/025509 A2 | 3/2005 |
| WO | WO 2005/044853 A2 | 5/2005 |
| WO | WO 2005/086770 A2 | 9/2005 |

(56) References Cited

FOREIGN PATENT DOCUMENTS

| | | |
|---|---|---|
| WO | WO 2005/102387 A2 | 11/2005 |
| WO | WO 2006/042329 A2 | 4/2006 |
| WO | WO 2006/062716 A2 | 6/2006 |
| WO | WO 2006/071856 A2 | 7/2006 |
| WO | WO 2006/083971 A2 | 8/2006 |
| WO | WO 2006/088950 A2 | 8/2006 |
| WO | WO 2006/133295 A2 | 12/2006 |
| WO | WO 2007/044668 A2 | 4/2007 |
| WO | WO 2007/053447 A2 | 5/2007 |
| WO | WO 2007/056227 A2 | 5/2007 |
| WO | WO 2007/087384 A2 | 8/2007 |
| WO | WO 2008/055206 A2 | 5/2008 |
| WO | 2008/147883 | 12/2008 |
| WO | WO 2008/147883 A1 | 12/2008 |
| WO | WO 2009/029587 A2 | 3/2009 |
| WO | WO 2009/042686 A1 | 4/2009 |
| WO | 2009/134711 A1 | 11/2009 |
| WO | WO 2009/134709 A2 | 11/2009 |
| WO | WO 2009/146204 A1 | 12/2009 |
| WO | WO 2010/054110 A2 | 5/2010 |
| WO | WO 2010/075519 A2 | 7/2010 |
| WO | WO 2010/085542 A2 | 7/2010 |
| WO | WO 2010/132459 A2 | 11/2010 |
| WO | 2011/006161 A2 | 1/2011 |
| WO | WO 2011/008092 A2 | 1/2011 |
| WO | WO 2011/017229 A2 | 2/2011 |
| WO | WO 2011/057014 A1 | 5/2011 |
| WO | WO 2012/061421 A1 | 5/2012 |
| WO | WO 2013/055998 A1 | 4/2013 |
| WO | WO 2014/008218 A1 | 1/2014 |
| WO | WO-2014074823 A1 * 5/2014 ........... A61K 9/0019 |
| WO | WO 2015/023596 A1 | 2/2015 |
| WO | WO 2015/032776 A1 | 3/2015 |
| WO | 2015/168468 | 11/2015 |

OTHER PUBLICATIONS

1000 Genomes Project Consortium "A Map of human genome variation form population—scale sequencing" Nature, 467: 1061-1073 (2010).
Accession NM_001928: "*Homo sapiens* complement factor D (adipsin) (cFD), mRNA", dated Mar. 12, 2011 (7 pages).
Aderem, et al. "Mechanisms of phagocytosis in macrophages", Annu. Rev. Immnuol., 17:593-623, 1999.
Ahamed, et al. "Phase Behavior of an Intact Monoclonal Antibody" Biophysical Journal 93: 610-619 (2007).
Almagro, et al. "Humanization of antibodies" Frontiers in Bioscience, 13: 1619-1633 (2008).
Altshuler, et. al., "Genetic mapping in human disease", Science, vol. 322, pp. 881-888 (2000).
Ambati, et. al., "An animal model of age-related macular degeneration in senescent Cel-2- or Cer-2-deficient mice", Nat. Med., vol. 9, No. 11, pp. 1390-1397 (2003).
Amin, et. al., "Genetic scoring analysis: A new way forward in genome wide association studies" Eur. J. Epidemiol., 2009, vol. 24, pp. 585-587.
Amit, et. al., "Three dimensional structure of an antigen-antibody complex at 2.8A resolution", Science, 1986, vol. 233, pp. 747-753.
Amsterdam, et. al., "Limitation of reperfusion injury by a monoclonal antibody to C5a during myocardial infraction in pugs", Am. J. Physiol., vol. 268, No. 1, Part 2, pp. H448-H457 (1995).
Anderson, et al. "The pivotal role of the complement system in aging and age-related macular degeneration: Hypothesis re-visited" Progress in Retinal and Eye Research, 29: 95-112 (2010).
Anderson, et. al., "A role for local inflammation in the formation of drusen in the aging eye", Am. J. Opthamol., vol. 134, pp. 411-431 (2002).
Areds Report No. 18 "A Simplified Severity Scale for Age-Related Macular Degeneration" Arch Ophthalmol. 123: 1570-1574 (2010).
Arrate, et al. "Cloning of human junctional adhesion molecule 3 (JAM3) and its identification as the JAM2 counter-receptor", Journal of Biological Chemistry 276(49) :45826-45832, 2001.
Attwood, "The Babel of Bioinformatics", Science 290: 471-473, 2000.
Avery, et al. "Systemic pharmacokinetics following intravitreal injections of ranibizumab, bevacizumab or aflibercept in patients with neovascular AMD" Br J Ophthalmol, 98: 1636-1641 (2014).
Badescu, et al. "A New Reagent for Stable Thiol-Specific Conjugation" Bioconjugate Chemistry, 25: 460-469 (2014).
Barnum, et. al. "Quantification of complement factor D in human serum by a solid phase radioimmunoassay", Immunol. Methods, vol. 67, No. 2, pp. 303-309 (1984).
Benvenuti, et al. "Crystallization of soluble proteins in vapor diffusion for x-ray crystallography" Nature Protocols 2(7): 1633-1651 (2007).
Bertozzi, et. al., "An ELISA for selections based on binding to a physiological ligand", J. Immunol. Methods, vol. 203, No. 2, pp. 157-165 (1997).
Bielefeld-Sevigny, "AlphaLISA Immunoassay Platform—The 'No Wash' High-Throughput Alternative to ELISA" Assay and Drug Development Technologies, 90-92 (2009).
Biomarkers Definitions Working Group, "Biomarkers and surrogate endpoints: preferred definitions and conceptual framework", Clin. Pharmacol. Ther., vol. 69, No. 3, pp. 89-95 (2001).
Blast Report, http://expasy.org/cgi-bininiceprot.p1/printable?ac=Q80WA3, dated Mar. 1, 2004.
Bok, D., "Evidence for an inflammatory process in age-related macular degeneration gains new support", Proc. Natl. Acad. Sci., vol. 102, pp. 7053-7054 (2005).
Bora, et. al., "Complement activation via alternative pathway is critical in the development oflaser-induced choroidal neovascularization: role of factor B and factor H", J. Immunol., vol. 177, pp. 1872-1878 (2006).
Bora, et. al., "The role of complement in ocular pathology", Semin. Immunopathol., vol. 30, pp. 85-95 (2008).
Bora, PS et al. "Role of complement and complement membrane attack complex in laser-induced choroidal neovascularization", J. Immunology 174(1)491-497, 2005.
Brown, "Complement receptors, adhesion and phagocytosis", Infectious Agents and Disease, 1: 63-70, 1992.
Brown, et. al., "Mechanisms of disease: the complement system in renal injury—new ways oflooking at an old foe", Nat. Clin. Pract. Nephrol., vol. 3, No. 5, pp. 277-286 (2007).
Buckmann, et al. "Functionalization of Poly(ethylene glycol) and Monomethoxy-Poly(ethylene glycol)" Makromol. Chem. 182: 1379-1384 (1981).
Cacia, et al. "Isomerization of an Aspartic Acid Residue in the Complementarity-Determining Regions of a Recombinant Antibody to Human IgE: Identification and Effect on Binding Affinity" Biochemistry, 35: 1897-1903 (1996).
Cancer Genome Atlas Research Network, "Comprehensive genomic characterization defines human glioblastoma genes and core pathways" Nature, 455: 1061-1068 (2008).
Carroll, "The complement system in regulation of adaptive immunity", Nature Immunology 5(10): 981-986, 2004.
Carroll, "Exposure of an executioner" 444: 159-160 (2006).
Carter, et. al., "Humanization of an anti-p185HER2 antibody for human cancer therapy", Proc. Natl. Acad. Sci., vol. 89, pp. 4285-4289 (1992).
Casset, et al. "A peptide mimetic of an anti-CD4 monoclonal antibody by rational design", BBRC, 307: 198-205, 2003.
Champe, et. al., "Monoclonal antibodies that block the activity of leukocyte function-associated antigen 1 recognize three discrete epi top es in the inserted domain of CD 11 a", J. Biol. Chem., vol. 270, pp. 1388-1394 (1995).
Chen et al., "Enhancement and destruction of antibody function by somatic mutation: unequal occurrence is controlled by V gene combinatorial associations" EMBO J, vol. 14, No. 12, pp. 2784-2794 (1995).
Chen, et al. "Association Between Variant Y402H in Age-Related Macular Degeneration (AMD) Susceptibility Gene CFH and Treatment Response of AMD: A Meta-Analysis" PLOS One 7(8): e42464-e42464 (2012).
Chen, et al. Modulating antibody pharmacokinetics using hydrophilic polymers Expert Opinion of Drug Delivery, 8(9): 1221-1236 (2011).

(56) References Cited

OTHER PUBLICATIONS

Chen, et. al., "Genetic variants near TIMP3 and high-density lipoprotein-associated loci influence susceptibility to age-related macular degeneration", PNAS, vol. 107, No. 16, pp. 7401-7406 (2010).
Chen, et. al., "Selection and analysis of an optimized anti-VEGF antibody: crystal structure on an affinity-matured Fav in complex with antigen", J. Mol. Biol., vol. 293, pp. 865-881 (1999).
Chothia, et. al., "Canonical structures for the hypervariable regions of immunoglobulins", J. Mol. Biol., vol. 196, pp. 901-917 (1987).
Clackson, et al. "Making antibody fragments using phage display libraries" Nature, 352: 624-628 (1991).
Collins, et al. "Pinpointing the genes involved in cancer will help chart a new course across the complex landscape of human malignancies" Scientific American 50-57 (2007).
Colman P.M., "Effects of amino acid sequence changes on antibody-antigen interactions" Res Immunol, vol. 145, pp. 33-36 (1994).
Cudney, "Protein Crystallization and Dumb Luck" The Rigaku Journal, 16(1): 1-7 (1999).
Cui, et al. "Noncoding Variant in the Complement Factor H Gene and Risk of Exudative Age-Related Macular Degeneration in a Chinese Population" 51(2): 1116-1120 (2010).
Cunningham, et al. "High-Resolution Epitope Mapping of hGH-Receptor Interactions by Alanine-Scanning Mutagenesis" Science, 244: 1081-1085 (1989).
Damico, et al. "New approaches and potential treatments for dry age-related macular degeneration" Arq Bras Oftalmol., 75(1): 71-75 (2012).
Database Accession No. NLM20510150, "Genetic factors associated with age-related macular degeneration", abstract (2010).
Database Genebank (Apr. 24, 2001), "Human Pro 1868 Protein" Database Accession No. AAB80272, XP002448361.
Database No. RS1329428, 6 pgs, 2004 (date retrieved: May 18, 2017).
Database No. RS17792825.
Database No. RS429608, 4 pgs, 2003 (date retrieved: May 18, 2017).
Database No. RS4698775, 1 pg, 2007 (date retrieved: Sep. 14, 2016).
Database No. ss66926822, pg, 2006 (date retrieved: 2016).
Database No. ss6697713, 2 pgs (date retrieved: Aug. 29, 2016).
Database No. ss67243395.
Database No. ss67486158, 2 pgs. 2006 (date retrieved: Aug. 29, 2016).
Database No. ss67520449, 2 pages.
Davies, et al. "Affinity improvement of single antibody VH domains: residues in all three hypervariable regions affect antigen binding" Immunotechnology, 2: 169-179 (1996).
Davis, et al. "Soluble, Nonantigenic Polyethylene Gylcol-Bound Enzymes" Biomedical Polymers: Polymeric Materials and Pharmaceuticals for Biomedical Use, Academic Press, Inc. 441-452 (1980).
De Jong, "Age-Related Macular Degeneration" The New England Journal of Medicine, 355(14): 1474-1485 (2006).
Demirkan, et. al., Genetic risk profiles for depression and anxiety in adult and elderly cohorts, Molecular Psychiatry, vol. 16, 99. 773-783 (2011).
Diamond, et. al., "Somatic mutation of the T15 heavy chain gives rise to an antibody with autoantibody specificity", PNAS, 1984, vol. 81, No. 18, pp. 5841-5844 (1984).
Do, et al. "A Phase IA Dose-Escalation Study of the Anti-Factor D Monoclonal Antibody Fragment FCFD4514S in Patients with Geographic Atrophy" Retina, The Journal of Retinal and Vitreous Diseases 34(2): 313-320 (2014).
Drenth, Principles of Protein X-Ray Crystallography "Chapter 1: Crystallizing a Protein" 2nd edition, New York: Springer 1-20 (1999).
Duddu, et al. "The Relationship Between Protein Aggregation and Molecular Mobility Below the Glass Transition Temperature of Lyophilized Formulations Containing a Monoclonal Antibody" Pharmaceutical Research, 14(5): 596-600 (1997).

Duvvuri et al. "Drug Delivery to the Retina: Challenges and Opportunities" Expert Opin Biol Ther. 3(1):45-56 (2003).
Edwards, et al. "Complement factor H polymorphism and age-related macular degeneration", Science 308: 421-424, 2005.
Ellman, et al. Biosynthetic method for introducing unnatural amino acids site-specifically into proteins Meth Enzym 202: 301-336 (1991).
Esparza-Gordillo, et. al., Genetic and environmental factors influencing the human factor H plasma levels, Immunogenetics, vol. 56, pp. 77-82 (2004).
Evans, et al. "Harnessing the information contained within genome-wide association studies to improve individual prediction of complex disease risk" Human Molecular Generics 18(18): 3525-3531 (2009).
Evans, et. al., "Rapid Expression of an Anti-Human C5 Chimeric Fab Utilizing a Vector that Replicates in COS and 293 Cells", J. Immunol., vol. 184, pp. 123-138 (1995).
Extended European Search Report dated Mar. 2, 2011 of EP 06836941.2 (16 pages).
Extended European Search Report dated Oct. 24, 2012 of EP 12172001.5 (6 pages).
Faelber, et al. "'The 1.85 A Resolution Crystal Structures of Tissue Factor in Complex with Humanized Fab D3h44 and of Free Humanized Fab D3h44: Revisiting the Solvation of Antigen Combining Sites" Journal of Molecular Biology, 313: 83-97 (2001).
Fageness, et. al., "Variation near complement factor 1 is associated with risk of advanced AMD", Eur. J. Hum. Genet., vol. 17, pp. 100-104 (2009).
Farries, et. al., "The mechanism of activation of the alternative pathway of complement by cell-bound C4b", Mol. Immunol., 1997, vol. 27, pp. 1155-1161 (1997).
Ferris, et. al., "A simplified seveity scale for age-related macular degeneration", Arch. Opthamol., vol. 123, pp. 1570-1574 (2005).
Fitch, et al. "Optimal Sequence Alignments" Proc. Natl. Acad. Sci. USA 80:1382-1386 (1983).
Foote, et. al., "Antibody framework residues affecting the conformation of the hypervariable loops", J. Mol. Biol., vol. 224, No. 2, pp. 487-499 (1992).
Francis, et. al., "Polymorphisms in C2, CFB and C3 are associated with progression to advanced age related macular degeneration associated with visual loss", J. Med. Genet., vol. 46, pp. 300-307 (2009).
Fritsche, et al., "Seven new loci associated with age-related macular degeneration" Nat Genet. 45(4): 433-439 (2013).
Fung et al. "Inhibition of complement, neutrophil, and platelet activation by an anti-factor D monoclonal antibody in simulated cardiopulmonary bypass circuits" J Thorac Cardiovasc Surg., vol. 122, No. 1, pp. 113-122 (2001).
Fung, et al., "Pre-Neutralization of C5a-Mediated Effects by the Monoclonal Antibody 137-26 Reacting with the C5a Moiety of Native C5 without Preventing C5 Cleavage" Clin Exp Immunol 133: 160-169 (2003).
Fung, et. al., "Inhibition of Complement, Neurophil, and Patelet Activation by an Anti-Factor D Antibody During Extracorporeal Circulation", Presented in the 18th Annual Houston Conference on Biomedical Engineering Research, Houston, Texas, Feb. 10, 2011, (abstract), p. 162 (2000).
Gagneux, et al., "Genetic Differences between Humans and Great Apes" Molecular Phylogenetics and Evolution 18(1): 2-13 (2001).
Gao, et. al., "An enzyme-linked immunosorbent assay to identify inhibitors of activation of platelet integrin alpha IIb beta 3", J. Immunol. Methods, vol. 181, No. 1, pp. 55-64 (1995).
Gaudreault, et al., "Preclinical pharmacokinetics of Ranibizumab (rhuFabV2) after a single intravitreal administration" Invest Ophthalmol Vis Sci. 46(2): 726-33 (Feb. 2005).
Gaudreault, et al., "Pharmacokinetics and Retinal Distribution of Ranibizumab, a Humanized Antibody Fragment Directed against VEGF-A, Following Intravitreal Administration in Rabbits" Retina 27(9):1260-1266 (2007).
Geiger and Clarke, "Deamidation, isomerization, and racemization at asparaginyl and aspartyl residues in peptides. Succinimide-linked reactions that contribute to protein degradation" Journal of Biological Chemistry 262(2): 785-794 (Jan. 15, 1987).

(56) References Cited

OTHER PUBLICATIONS

Ghate, et al., "Ocular Drug Delivery" Expert Opinion on Drug Delivery 3(2): 275-287 (2006).
Glickman, et al., "A Comparison of ALPHAScreen, TR-FRET, and TRF as Assay Methods for FXR Nuclear Receptors" Journal of Biomolecular Screening 7(1): 3-10 (2002).
Gold, et. al., "Variation in factor B (BF) and complement component 2 (C2) genes is associated with age-related macular degeneration", Nat. Genet., vol. 38, pp. 458-462 (2006).
Gorin, "Genetic Insights into Age-Related Macular Degeneration: Controversies Addressing Risk, Causality, and Therapeutics" Mol. Aspects Med. 33(4):467-486 (Aug. 2012).
Green, "Studies in the Physical Chemistry of the Proteins" Journal of Biological Chemistry 93:517-542 (1931).
Gullberg, et al., "Cytokine Detection by Antibody-Based Proximity Ligation" Proceedings of the National Academy of Sciences 101(22):8420-8424 (Jun. 1, 2004).
Hageman, et. al., "A common haplotype in the complement regulatory gene factor H (HFI/CFH) predisposes individuals to age related macular degeneration", PNAS, 2005, vol. 102, No. 20, pp. 7227-7232 (2005).
Hageman, et. al., "An integrated hypothesis that considers drusen as biomarkers of immune-mediatead processes at the RPE-Bruch' s membrane interface in aging and age-related macular regeneration", Pro. Retin. Eye Res., vol. 20, pp. 705-732 (2001).
Haines, et al. "Complement factor H variant increases the risk of age-related macular degeneration", Science, vol. 308, pp. 419-421 (2005).
Hakimi, et. al., "Reduced immogenicity and improved pharmacokinetics of humanized anti-Tac in cynomolgus monkeys", J. Immunol., vol. 147, No. 4, pp. 1352-1359 (1991).
Halushka, et al., "Patterns of Single-Nucleotide Polymorphisms in Candidate Genes for Blood-Pressure Homeostasis" Nature Genetics 22:239-247 (Jul. 1999).
Harboe, et al. "The quantitative role of alternative pathway amplification in classical pathway induced terminal complement activation", Clin Exp Immunol. 138(3):439-446, Dec. 2004.
Harboe, et al., "The Alternative Complement Pathway Revisited" J. Cell. Mol. Med. 12(4):1074-1084 (2008).
Harlow, et. al., "Chapter 14: Immunoassays", Antibodies: A Laboratory Manual, Harlow & Lane, Cold Spring Harbor, pp. 553-612 (1988).
Hattersley, et al., "What Makes a Good Genetic Association Study?" Lancet 366:1315-1323 (Oct. 8, 2005).
Haubenwaller, et. al., "A novel missense mutation in the gene for lipoprotein lipase resulting in a highly conservative amino acid substitution (ASP180→Glu) causes familial chylomicronemia (type I hyperlipoproteinemia)", Genomics, vol. 18, No. 2, pp. 392-396 (1993).
Heurich, et. al., "Common polymorphisms in C3, factor B, and factor H collaborate to determine systemic complement activity and disease risk", PNAS, vol. 108, No. 21, pp. 8761-8766 (2011).
Hirschhorn, et. al. "A comprehensive review of genetic association studies", Genetics in Medicine, vol. 4, No. 2, pp. 45-61 (2002).
Hoffman, et al., "Rare Complement Factor H Variant Associated with Age-Related Macular Degeneration in the Amish" Investigative Ophthalmology & Visual Science 55(7):4455-4460 (Jul. 2014).
Holers, et al. "The evolution of mouse and human complement C3-binding proteins: divergence of form but conservation of function", Immunology Today 13(6):231-236, 1992.
Holers, V.M. "Chapter 24: COMPLEMENT: Principles and Practice", Clinical Immunology, R. R. Rich edition, Mosby Press, pp. 363-391 (1996).
Holers, V.M., "The spectrum of complement alternative pathway-mediated diseases", Immunol. Rev., vol. 233, pp. 300-316 (2008).
Holland, et al., "Detection of specific polymerase chain reaction product by utilizing the 5'—3' exonuclease activity of Thermus aquaticus DNA polymerase" P Natl Acad Sci USA 88(16):7276-7280 (Aug. 15, 1991).

Holm, et. al., "Functional mapping and single chain construction of the anti-cytokeratin 8 monoclonal antibody TS1", Mol Immunol, vol. 44, No. 6, pp. 1075-1084 (2007).
Holt, et al., "Domain antibodies: proteins for therapy" Trends in Biotechnology 21(11):484-490 (Nov. 2003).
Holz, et al., "Geographic Atrophy: Clinical Features and Potential Therapeutic Approaches" Ophthalmology 121(5):1079-1091 (May 2014).
Holz, et al., "Recent Developments in the Treatment of Age-Related Macular Degeneration" Journal of Clinical Investigation 124(4):1430-1438 (Apr. 2014).
Homeister, et. al., "Soluble complement receptor type 1 prevents human complement-mediated damage of the rabbit isolated heart", J. Immunol., vol. 150, No. 3, pp. 1055-1064 (1993).
Houghten, et. al., "The use of synthetic peptide combinatorial libraries for the identification of bioreactive peptides", Biotechniques, vol. 13, No. 3, pp. 412-421 (1992).
Howie, et al., "A Flexible and Accurate Genotype Imputation Method for the Next Generation of Genome-Wide Association Studies" PLoS Genetics 5(6):1-15 (Jun. 2009).
Huber-Lang, et. al., "Role of C5a in Multiorgan Failure During Sepsis", J. Immunol., vol. 166, pp. 1193-1198 (2001).
Humphreys, et al., "Alternative Antibody Fab' Fragment PEGylation Strategies: Combination of Strong Reducing Agents, Disruption of the Interchain Disulphide Bond and Disulphide Engineering" Protein Engineering, Design & Selection 20(5):227-234 (2007).
Hutanu et al. "Recent Applications of Polyethylene Glycols (PEGs) and PEG Derivatives" Modern Chemistry & Applications 2(2): 1-6 (2014).
Igawa, et al., "Engineering the variable region of therapeutic IgG antibodies" mAbs 3(3):243-252 (2011).
Inagi, et. al., "Decreased Activity of Complement-Mediated Immune Complex Clearance in Hemodialysis Patients", Clinical Immunology and Immunotherapy, September vol. 68, No. 3, pp. 333-339 (1993).
International Preliminary Report on Patentability dated May 5, 2009 of PCT/US2007/083172, now WO 2008/055206 (8 pages).
International Preliminary Report on Patentability dated May 6, 2008 of PCT/US2006/043103, now WO 2007/056227 (6 pages).
International Preliminary Report on Patentability dated May 7, 2013 of PCT/US2011/058829, now WO 2012061421 (8 pages).
International Preliminary Report on Patentability dated Nov. 24, 2009 of PCT/US2008/064526, now WO 2008147883 (10 pages).
International Preliminary Report on Patentability dated Nov. 2, 2010 of PCT/US2009/041785, now WO 2009/134711 (6 pages).
International Preliminary Report on Patentability for PCT/US2015/028641x, 8 pages dated Nov. 1, 2016.
International Search Report and Written Opinion for PCT/US2016/059048, 32 pages dated Jun. 19, 2017.
International Search Report dated Aug. 10, 2007 of PCT/US2006/043103, now WO 2007/056227 (3 pages).
International Search Report dated Dec. 15, 2011 of PCT/US2011/058829, now WO 2012061421 (5 pages).
International Search Report dated Jul. 30, 2008 of PCT/US2008/064526, now WO 2008147883 (4 pages).
International Search Report dated Jun. 2, 1999 of PCT/US1999/003566, now WO 1999/042133 (2 pages).
International Search Report dated Jun. 20, 2008 of PCT/US2007/083172, now WO 2008/055206 (5 pages).
International Search Report dated Nov. 14, 2014 of PCT/US2014/050579, now WO 2015023596 (6 pages).
International Search Report dated Sep. 1, 2009 of PCT/US2009/041785, now WO 2009/134711 (2 pages).
International Search Report for PCT/US2015/028641, 8 pages dated Nov. 5, 2015.
International Search Report for PCT/US2016/059179, 8 pages dated May 4, 2017.
International SNP Working Group, "A map of human genome sequence variation containing 1.42 million single nucleotide polymorphisms", Nature, vol. 409, pp. 928-933 (2001).
Ioannidis, et. al., "Replication validity of genetic association studies", Nature Genetics, vol. 29, pp. 306-309 (2001).

(56) References Cited

OTHER PUBLICATIONS

Jaffe, et. al., Intraocular Drug Delivery, Taylor and Francis, pp. 85-95, 111-128, 193-202, 203-225, 249-263 (2006).
Jaffers, et. al., Monoclonal antibody therapy: anti-idiotypic and non-anti-idiotypic antibodies in OKT3 arising despite intense immunosuppression, Transplantation, vol. 41, No. 5, pp. 572-578 (1986).
Jager, et. al., "Age-related macular degeneration", New Eng. J. Med., vol. 359, No. 16, pp. 1735-1736 (2008).
Janeway, et. al., Immunobiology (13-5 to 13-7), 3ra Edition, London, England, Current Biology Ltd., (7 pages) (1997).
Janssen, et al. "Structural insights into the central complement component C3", Molecular Immunology, 44: 3-10 (2007).
Jevsevar, et al., "PEGylation of therapeutic proteins" Biotechnol. J. 5:113-128 (2010).
Jing, et al., "Structural Basis of Profactor D Activation: from a Highly Flexible Zymogen to a Novel Self-Inhibited Serine Protease, Complement Factor D" EMBO Journal 18(4):804-814 (1999).
Jing, et al., "Structures of Native and Complexed Complement Factor D: Implications of the Atypical His57 Conformation and Self-Inhibitory Loop in the Regulation of Specific Serine Protease Activity" Journal of Molecular Biology 282:1061-1081 (1998).
Johnson DH, et al., "Randomized phase II trial comparing bevacizumab plus carboplatin and paclitaxel with carboplatin and paclitaxel alone in previously untreated locally advanced or metastatic non-small cell lung cancer" J Clin Oncol 22: 2184-2191 (2004).
Johnson, et. al., "Complement activation and inflammatory processes in Drusen formation and age related macular degeneration", Exp. Eye Res., vol. 73, pp. 887-896 (2001).
Jones "Analysis of polypeptides and proteins." Advanced Drug Delivery Reviews, 10: 29-90 (1993).
Jones, et. al., "Replacing the complementarity-determining regions in a human antibody with those of a mouse", Nature, vol. 321, pp. 522-525 (1986).
Joubert, et al., "Classification and Characterization of Therapeutic Antibody Aggregates" Journal of Biological Chemistry 286(28):25118-25133 (Jul. 15, 2011).
Joubert, et al., "Highly Aggregated Antibody Therapeutics Can Enhance the In Vitro Innate and Late-Stage T-Cell Immune Responses" Journal of Biological Chemistry 287(30):25266-25279 (Jul. 20, 2012).
Junghans, et. al., "Anti-Tac-H, a humanized antibody to the interleukin 2 receptor with new features for immunotherapy in malignant and immune disorders", Cancer Res., vol. 50, pp. 1495-1502 (1990).
Junutula, et al., "Rapid identification of reactive cysteine residues for site-specific labeling of antibody-Fabs" J Immunol Methods 332:41-52 (2008).
Kabat, et al. Sequences of Proteins of Immunological Interest (NIH Publ. No. 91-3242) I:647-669 (1991).
Kathiresan, et. al., "Polymorphisms associated with cholesterol and risk of cardiovascular events", Journal of Vascular Surgery, Abstract 1372 (1 page) (2008).
Katre, N., "The Conjugation of Proteins with Polyethylene Glycol and other Polymers. Altering properties of proteins to enhance their therapeutic potential." Advanced Drug Delivery Reviews 10(1):91-114 (1993).
Katschke, et al. "A novel inhibitor of the alternative pathway of complement reverses inflammation and bone destruction in experimental arthritis", Brief Definitive Report 204(6):1319-1325, 2007.
Katschke, et al., "Inhibiting Alternative Pathway Complement Activation by Targeting the Factor D Exosite" Journal of Biological Chemistry 287(16):12886-12892 (Apr. 13, 2012).
Katschke, et al., "Structural and Functional Analysis of a C3b-Specific Antibody that Selectivity Inhibits the Alternative Pathway of Complement" Journal of Biological Chemistry 284(16):10473-10479 (Apr. 17, 2009).
Kelley and Meng, "Methods to Engineer and Identify IgG, Varients with Improved FcRn Binding or Effector Function", Chapter 28, Antibody Methods and Protocols, Humana Press (2012).
Khazaeli, et. al., "Phase I trial of multiple large doses of murine monoclonal antibodyCOI 7-IA II Pharmacokinetics and immune response", J. Natl. Cancer Inst., vol. 80, pp. 937-942 (1988).
Kim, et al. "Characterization of monoclonal antibody specific to the Z39Ig protein, a member of immunoglobulin superfamily", Immunology Letters, 99: 153-161, 2005.
Kim, et al., "Crystal Structure of a Complement Factor D Mutant Expressing Enhanced Catalytic Activity" Journal of Biological Chemistry 270(41):24399-24405 (Oct. 13, 1995).
Kindt, et al. "Immunology" Chapter 4: Antigens and Antibodies, W.H. Freeman and Company, p. 91 (2007).
Klein, et al. "Complement factor H polymorphism in age-related macular degeneration", Science, 308: 385-389 (2005).
Kloeckener-Gruissem, et al., "Genetic Association with Response to Intravitreal Ranibizumab in Patients with Neovascular AMD" Investigative Ophthalmology & Visual Science 52(7):4694-4702 (Jun. 2011).
Klohs, et. al., "Inhibitors of tyrosine kinase", Curr. Opin. Oncol. 19, vol. 9, No. 6, pp. 562-568 (1997).
Kontermann, "Strategies to Extend Plasma Half-Lives of Recombinant Antibodies" Biodrugs 23(2):93-109 (2009).
Kostavasili, et. al., Mechanism of complement inactivation by glycoprotein c of herpes simplex virus, Immunol., vol. 158, No. 4, pp. 1763-1771 (1997).
Kozlov et al., "Isotyping of human C4 complement using differences in the functional activity of C4A and C4B isotypes (English translation)" Bioorg Khim., vol. 26, No. 7, pp. 539-547 (2000).
Kroshus, et. al., "Complement inhibition with an anti-CS monoclonal antibody prevents acute cardiac tissue injury in an ex vivo model of pig-to-human xenotransplantation", Transplantation, vol. 60, No. 11, pp. 1194-1202 (1995).
Kryztolik, et. al., "Prevention of experimental choroidal neovascularization with intravitreal anti-vascular endothelial growth factor antibody fragment", Ach. Optham., vol. 120, pp. 338-346 (2002).
Kumagai, et. al., "Generation of novel functional antibody molecules by in vitro selection system", Tanpakushitsu Kakusan Koso (Protein Nucleic Acid and Enzyme), vol. 43, No. 2, pp. 159-167 (in Japanese with English translation of abstract) (1998).
Kundrot, "Which Strategy for a Protein Crystallization Project?" Cellular and Molecular Life Sciences 61:525-536 (2004).
Kunkel, "Rapid and Efficient Site-Specific Mutagenesis Without Phenotypic Selection" Proc. Natl. Acad. Sci.:488-492 (Jan. 1985).
Kussie et al., "A single engineered amino acid substitution changes antibody fine specificity" J Immunol, vol. 152, No. 1, pp. 146-52 (1994).
Lam, et. al., "Application of combinatorial library methods in cancer research and drug discovery", Anticancer Drug Des., vol. 12, No. 3, pp. 145-167 (1997).
Langnaese, et al. "Cloning of Z39Ig, a novel gene with immunoglobulin-like domains located on human chromosome XI", BBA: 522-525 (2000).
Le, et al., "A Mechanistic Pharmacokinetic/Pharmacodynamic Model of Factor D Inhibition in Cynomolgus Monkeys by Lampalizumab for the Treatment of Geographic Atrophy" Journal of Pharmacology and Experimental Therapeutics 355:288-296 (Nov. 2015).
Lee, et al. "Z39Ig is expressed on macrophages and may mediate inflammatory reactions in arthritis and atherosclerosis", Journal of Leukocyte Biology 80: 922-928, 2006.
Lesavre, et. al., "Mechanism of action of factor D of the alternative complement pathway", J. Exp. Med, vol. 148, No. 6, pp. 1498-1509 (1978).
Lettre, et. al., "Autoimmune diseases: insights from genome-wide association studies", Human Molecular Genetics, vol. 17, pp. RI 16-R121 (2008).
Lewis, et al., "Maleimidocysteineamido-DOTA derivatives: new reagents for radiometal chelate conjugation to antibody sulfhydryl groups undergo pH-dependent cleavage reactions" Bioconjug Chem 9(1):72-86 (Jan. 1998).
Lim, et al., "Age-Related Macular Degeneration" Lancet 379(9827):1728-1738 (May 5, 2012).
Loubser, et. al., "Inhibition of Complement, Neutrophil and Platelet Activation by an Anti-Factor D Antibody During Extracorporeal

(56) References Cited

OTHER PUBLICATIONS

Circulation", Presented at the Annual Meeting of American Society of Anesthesiologists, San Francisco, CA, Oct. 14-18, 2000, Abstract A-657 (1 page) (2000).
Lowe, et al., "Aggregation, Stability, and Formulation of Human Antibody Therapeutics" Advances in Protein Chemistry and Structural Biology 84:41-61 (2011).
Loyet, et al., "Activation of the Alternative Complement Pathway in Vitreous is Controlled by Genetics in Age-Related Macular Degeneration" Investigative Ophthalmology & Visual Science 53(10):6628-6637 (Sep. 2012).
Loyet, et al., "Complement Inhibition in Cynomolgus Monkeys by Anti-Factor D Antigen-Binding Fragment for the Treatment of an Advanced Form of Dry Age-Related Macular Degeneration" Journal of Pharmacology and Experimental Therapeutics 351:527-537 (Dec. 2014).
Loyet, et. al., "Anti-factor D Fab Specifically Inhibits the Alternative Complement Pathway: in vitro characterization and in vivo effects following administration to cynomolgus monkeys", AAPS J, vol. 12, p. sl (abstract) (2010).
Lucentini, J., "Gene Association Studies Typically Wrong" The Scientist 18(24): 20 (2004,) 4 pages.
Maccallum, et al. "Antibody-antigen interactions: Contact analysis and binding site topography", J. Mol. Biol., 262:732-745, 1996.
Makrides, et. al., "Therapeutic Inhibition of the Complement System", Pharmacological Reviews, 1998, vol. 50, No. 1, pp. 59-87 (1998).
Matson, et. al., "Evolving concepts of therapy for sepsis and septic shock and the use of hyperpermeable membranes", Current Opinion in Critical Care, 2000, vol. 6, pp. 431-436 (2000).
Maynard, et al., "Antibody Engineering" Annu. Rev. Biomed. Eng. 02:339-76 (2000).
Mcpherson "Current approaches to macromolecular crystallization" Eur. J. Biochem. 189: 1-23 (1990).
Michels et al., "Quantitative Impurity Analysis of Monoclonal Antibody Size Heterogeneity by CE-LIF: Example of Development and Validation Through a Quality-By-Design Framework" Electrophoresis 33:815-826 (2012).
Michels, et al., "Fluorescent Derivatization Method of Proteins for Characterization by Capillary Electrophoresis-Sodium Dodecyl Sulfate with Laser-Induced Fluorescence Detection" Analytical Chemistry 79(15):5963-5971 (Aug. 1, 2007).
Miller, et. al., "Monoclonal antibody therapeutic trials in seven patients with T-cell lymphoma", Blood, vol. 62, pp. 988-995 (1983).
Mohkle, et. al., "Metabolic and cardiovascular traits: an abundance of recently identified common genetic variants", Human Molecular Genetics, vol. 17, pp. RI 02-RI 08 (2008).
Moon, et al., "A Synergistic Approach to Protein Crystallization: Combination of a Fixed-Arm Carrier with Surface Entropy Reduction" Protein Science 19:901-913 (2010).
Moore, et al., "Role of Aggregated Human Growth Hormone (hGH) in Development of Antibodies to hGH" Journal of Clinical Endocrinology and Metabolism 51(4):691-697 (1980).
Morgan, "Clinical complementology: recent progress and future trends", Eur. J. Clin. Invest, 1994, vol. 24, No. 4, pp. 219-228 (1994).
Morley, et. al., "Factor D", Complements Fact Book, vol. 17, pp. 69-72 (2000).
Morrison Time-Resolved Detection of Energy Transfer: Theory and Application to Immunoassays, 174: 101-120 (1988).
Mulligan, et. al., "Protective Effects of Soluble CRI in Complement and Neutrophil-Medicated Tissue Injury", J. Immunol., vol. 148, No. 5, pp. 1479-1485 (1992).
Mullins, et. al., "Drusen associated with aging and age-related macular degeneration contain proteins common to extracellular deposits associated with atherosclerosis, elastosis, amyloidosis, and dense deposit disease", F ASEB J., vol. 14, pp. 83 5-846 (2000).
Narayana, et. al., "Structure of Human Factor D: A Complement System Protein at 20 Degree Resolution", J. Mol. Biol., 1994, vol. 23 5, pp. 695-708 (1994).

Neale, et al., "Genome-Wide Association Study of Advanced Age-Related Macular Degeneration Identifies a Role of the Hepatic Lipase Gene (LIPC)" PNAS 107(16):7395-7400 (Apr. 20, 2010).
Needleman and Wunsch, "A General Method Applicable to the Search for Similarities in the Amino Acid Sequence of Two Proteins" J. Mol. Biol. 48:443-453 (1970).
New American Handy College Dictionary, New American Library, Albert & Loy Morehead, Fourth Edition, pp. 556-567, 694 (2006).
Niemann, et. al., "The Use of Monoclonal Antibodies as Probes of the Three Dimensional Structure of Human Complement Factor D", J. Immunol., vol. 132, No. 2, pp. 809-815 (1984).
Noren, et al., "A general method for site-specific incorporation of unnatural amino acids into proteins" Science 244(4901):182-188 (Apr. 14, 1989).
Nozaki, et al., "Drusen Complement Components C3a and C5a Promote Choroidal Neovascularization" PNAS 103(7):2328-2333 (Feb. 14, 2006).
Ohno, et. al., "Antigen-binding specificities of antibodies are primarily determined by seven residues of VH", PNAS, vol. 82, pp. 2945-2949 (1985).
Oliphant, et al., "BeadArray(TM) Technology: Enabling an Accurate, Cost-Effective Approach to High-Throughput Genotyping" BioTechniques 32 (SUPPL S56-S61): 56-61 (Jun. 2002).
Omer, et. al., "CA1A2X-competitive inhibitors of famesyltransferase as anti-cancer agents", Trends Pharmacol. Sci., vol. 18, No. 11, pp. 434-445 (1997).
Padlan, et. al., "Structure of an anti-antigen complex, crystal structure of the HyHEL-10 Fab-lysozyme complex", PNAS, vol. 86, No. 15, pp. 5938-5942 (1989).
Pangburn "Alternative Pathway of Complement" Methods in Enzymology 162:639-653 (1988).
Pascual et. al., "A monoclonal which antibody which blocks the function of factor D of human complement", J. Immunol. Methods, vol. 127, No. 2, pp. 263-269 (1990).
Pascual, "Inhibition of complement alternative pathway in mice with Fab antibody to recombinant adipsin/factor D", Eur. J. Immonol., vol. 23, No. 6, pp. 1389-1392 (1993).
Pascual, et. al., "Metabolism of complement factor Din renal failure", Kidney International, vol. 34, No. 4, pp. 529-536 (1988).
Patel, et al., "Ocular Drug Delivery Systems: An Overview" World J Pharmacol. 2(2): 47-64 (2013).
Paul, Fundamental Immunology: Structure and Diversity in Three Dimensions, 3rd edition, Raven Press, William Paul, pp. 292-295 (1993).
Pearlman and Nguyen, "Analysis of Protein Drugs", Marcel Dekker, Inc., Peptide and Protein Drug Delivery, pp. 247-297 (1991).
Pedley, et al., "The potential for enhanced tumour localisation by poly(ethylene glycol) modification of anti-CEA antibody" British Journal of Cancer 70(6):1126-1130 (Dec. 1994).
Petrukhin (2007) "New therapeutic targets in atrophic agerelated macular degeneration," Expert Opinion on Therapeutic Targets, 11(5): 625-639 (2007).
Pikal, et al., "Solid State Chemistry of Proteins: II. The Correlation of Storage Stability of Freeze-Dried Human Growth Hormone (hGH) with Structure and Dynamics in the Glassy Solid" Journal of Pharmaceutical Sciences 97(12):5106-5121 (Dec. 2008).
Pini et al., "Design and Use of a Phage Display Library—Human Antibodies With Subnanomolar Affinity Against a Marker of Angiogenesis Eluted From a Two-Dimensional Gel" The Journal of Biological Chemistry 273(34): 21769-21776 (1998).
Plackett, "Studies in the History of Probability and Statistics. XXIX: The Discovery of the Method of Least Squares" Biometricka 59(2):239-251 (1972).
Portolano, et al., "Lack of promiscuity in autoantigen-specific H and L chain combinations as revealed by human H and L chanin 'Roulette'" J Immunol 150(3):880-887 (Feb. 1, 1993).
Powell, et. al., "A compendium and hydropathy/flexibility analysis of common reactive sites in proteins: reactivity at Asn, Asp, Gln, and Met motifs in neutral pH solution", Pharm Biotech, vol. 9, pp. 1-140 (1996).
Presta, et al., "Humanization of an Antibody Directed Against IgE" J Immunol 151(5):2623-2632 (Sep. 1, 1993).

(56) References Cited

OTHER PUBLICATIONS

Prosser, et al., "Structural Basis for Complement Factor H-Linked Age-Related Macular Degeneration" Journal of Experimental Medicine 204(10):2277-2283 (Oct. 1, 2007).
Purcell, et. al., "Common polygenic variation contributes to risk of schizophrenia and bipolar disorder", Nature Letters, vol. 460, pp. 748-752 (2009).
Pyz, et al. "C-type lectin-like receptors on myeloid cells", Annals of Medicine, 38: 242-251 (2006).
Rabinovici, et. al., "Role of complement in endotoxim/platelet-activating factor-induced lung injury", J. Immunol., vol. 149, No. 5, pp. 1744-1750 (1992).
Rattner et al., "Macular degeneration: recent advances and therapeutic opportunities," Nature Reviews Neuroscience, 7: 860-872 (Nov. 2006).
Ray, et. al., "Thrombin Receptor: A Novel Target for Antiplatelet Drug Development", Thrombosis Research, vol. 81, No. 1, pp. 37-50 (1997).
Remington's Pharmaceutical Sciences, Oslo et al., eds., 16th edition, Mack Publishing Co. (1980).
Reynolds, et. al., "Plasma complement components and activation fragments: associations with age-related macular degeneration genotypes and phenotypes", Invest. Opthalmol. Vis. Sci., pp. 50, pp. 5818-5827 (2009).
Ricklin, et al., "Complement: A Key System for Immune Surveillance and Homeostasis" Nat. Immunol. 11(9):785-797 (Sep. 2010).
Ricklin, et. al., "Complement-targeted therapeutics", Nat. Biotechnol., vol. 25, No. 11, pp. 1265-1275 (2007).
Riechmann, et. al., "Reshaping human antibodies for therapy", Nature, vol. 332, pp. 323-327 (1988).
Rinder, et. al., "Blockage of C5a and C5b-9 gneration inhibits leukocyte and platelet activation during extracorporeal circulation", J. Clin. Invest., vol. 96, No. 3, pp. 1564-1572 (1995).
Rodriguez de Cordoba, et. al., "The human complement factor H: functional roles, genetic variations and disease associations", Mol. Immunol., vol. 41, pp. 355-367 (2004).
Roher, et. al., "A targeted inhibitor of the alternative complement pathway reduces angiogenesis in a mouse model of age-related macular degeneration", Invest. Opthalmol. Vis. Sci., vol. 7, pp. 3056-3064 (2009).
Rohrer et al., Eliminating Complement Factor D Reduces Photoreceptor Susceptibility to Light-Induced Damage. Investigative Ophthalmology & Visual Science, vol. 48, No. 11, 5282-5289 (2007).
Roitt, et. al., "Antibodies and cell receptors for antibodies", Immunology, pp. 110-113 (translation) (1998).
Rosenberg, "Effects of Protein Aggregates: An Immunologic Perspective" The AAPS Journal 8(3):E501-507 (Aug. 4, 2006).
Ross, et al. "Membrane complement receptors specific for bound fragments of C3", Advances in Immunology, 37:217-267 (1985).
Roversi, et. al., "Structural basis for complement factor I control and its disease-associated sequence polymorphisms", PNAS, vol. 108, No. 31, pp. 12839-12844 (2011).
Rudikoff et al. "Single amino acid substitution altering antigen-binding specificity." Proc Natl Acad Sci USA, 79(6):1979-1983 (1982).
Ryan, et al., "Advances in PEGylation of Important Biotech Molecules: Delivery Aspects" Expert Opinion on Drug Delivery 5(4):371-383 (2008).
Sahu, et al., "Identification of multiple sites of interaction between heparin and the complement system", Mol. Immunol., vol. 30, No. 7, pp. 679-684 (1993).
Salas-Solano, et al., "Robustness of iCIEF Methodology for the Analysis of Monoclonal Antibodies: An Interlaboratory Study" J Sep. Sci. 35(22):3124-3129 (2012).
Sallo, et. al., "The International Classification system and to progression of age-related macular degeneration", Curr. Eye. Res., vol. 34, No. 3, pp. 238-240 (2009).
Sambrook "Molecular Cloning", vol. 1, Chapter 5: Gel Electrophoresis of DNA and Pulsed-field Agarose Gel Electrophoresis, Cold Spring Harbor Laboratory Press, pp. 4.35-5.90 (2001).
Sambrook "Molecular Cloning", vol. 2, Chapter 9: Preparation of Radiolabeled DNA and RNA Probes, Cold Spring Harbor Laboratory Press, pp. 4.35-5.90 (2001).
Sato, et. al., "A new method for studying the binding of human IgE to CD23 and the inhibition of this binding", J. Immunol. Methods, vol. 201, No. 1, pp. 59-66 (1997).
Scheffe "The Analysis of Variance", Point Estimation, John Wiley & Sons, Inc., pp. 6-8 (1999).
Scholl, et. al., "Systemic complement activation in age-related macular degeneration", PLoS One, vol. 3, p. e2593 (2008).
Schweitzer, et. al., "Combining nucleic acid amplification and detection", Current Opinion in Biotechnology, vol. 12, pp. 21-27 (2001).
Sears, et. al., "Effects of monoclonal antibody immunotherapy on patients with gastrointestinal adenocarcinoma", J. Biol. Response Modifiers, vol. 3, pp. 138-150 (1984).
Seddon, et al., "Rare Variants in CFI, C3 and C9 are Associated with High Risk of Advanced Age-Related Macular Degeneration" Nature Genetics 45(11):1366-1370 (Nov. 2013).
Seddon, et al., "Risk Models for Progression to Advanced Age-Related Macular Degeneration Using Demographic, Environmental, Genetic, and Ocular Factors" Ophthalmology 118(11):2203-2211 (Nov. 2011).
Seddon, et. al., Association of CFH Y402H and LOC387715 A69S with progression of age-related macular regeneration, JAMA, vol. 297, pp. 1793-1800 (2007).
Seddon, et. al., "Prediction model for prevalence and incidence of advanced age-related macular degeneration based on genetic, demographic, and environmental variables", Invest. Opthalm. and Vis. Sci., vol. 50, pp. 2044-2052 (2009).
Selvin, "Fluorescence Resonance Energy Transfer" Methods in Enzymology 246: 300-335 (1995).
Shawler, et. al., "Human immune response to multiple injections of murine monoclonal IgG", J. Immunol., vol. 135, No. 2, pp. 1530-1535 (1985).
Sim, et. al., "Serine Proteases of the Complement System", Biochemical Society Transactions, vol. 28, Pt. 5, pp. 545-550 (2000).
Sims, et. al., "A humanized CD18 antibody can block function without cell destruction", J. Immunol., vol. 151, No. 4, pp. 2296-2308 (1993).
Sivakumaran, et al., "A 32 kb Critical Region Excluding Y402H in CFH Mediates Risk for Age-Related Macular Degeneration" PLoS One 6(10 SUPPL e25598):1-13 (Oct. 2011).
Skolnick, et al. "From genes to protein structure and function: novel applications of computational approaches in the genomic era", Trends in Biotech.18:34-39 (2000).
Stadel, et. al., "Orphan G protein-coupled receptors: a neglected opportunity for pioneer drug discovery", Trends Pharmacol. Sci., vol. 18, No. 11, pp. 430-437 (1997).
Stanton, et al., "Complement Factor D in Age-Related Macular Degeneration" Investigative Ophthalmology & Visual Science 52(12):8828-8834 (Nov. 2011).
Strausberg, et al. "Generation and initial analysis of more than 15,000 full-length human and mouse cDNA sequences", PNAS 99(26):16899-16903 (2002).
Strawn, et. al., "Flk-1 as a target for tumor growth inhibition", Cancer Research, vol. 56, No. 15, pp. 3540-3545 (1996).
Streiner, Encyclopedia of Research Design "Last Observation Carried Forward" Salkind, Thousand Oaks: Sage Publications, Inc., vol. 2:687-689 (2010).
Stryer, "Fluorescence Energy Transfer as a Spectroscopic Ruler" Ann. Rev. Biochem. 47:819-846 (1978).
Stuart, et al. "Phagocytosis: Elegant complexity", Immunity 22: 539-550 (2005).
Sunness, et al., "Designing Clinical Trials for Age-Related Geographic Atrophy of the Macula" Retina 27(2):204-210 (2007).
Sunness, et al., "Visual Function Abnormalities and Prognosis in Eyes with Age-Related Geographic Atrophy of the Macula and Good Visual Acuity" Ophthalmology 104(10):1677-1691 (Oct. 1997).

(56) References Cited

OTHER PUBLICATIONS

Tamura, et. al., "Structural correlates of an anticarcinoma antibody: identification of specificity-determining residues (SDRs) and development of a minimally immunogenic antibody variant by retention of SDRs only", J. Immunol., vol. 164, No. 3, pp. 1432-1441 (2000).
Tanhehco, et al. "The anti-factor D antibody, Mab 166-32, inhibits the alternative pathway of the human complement system", Tranplant Proc. 31(5):2168-2171 (Aug. 31, 1999).
Taylor, et al. "Pattern recognition receptors and differentiation antigens define murine myeloid cell heterogeneity ex vivo", Eur. J. Immunology 33: 2090-2097 (2003).
Taylor, et al."Macrophage receptors and immune recognition", Annu. Rev. Immunol., 23: 901-944 (2005).
Tedeschi-Blok, et al., "Population-Based Study of Early Age-Related Macular Degeneration; Role of the Complement Factor H Y402H Polymorphism in Bilateral but not Unilateral Disease" Ophthalmology 114(1):99-103 (Jan. 2007).
Teo, et al., "A Genotype Calling Algorithm for the Illumina BeadArray Platform" Bioinformatics 23(20):2741-2746 (2007).
The Eye Diseases Prevalence Research Group (EDPRG) Prevalence of Age-Related Macular Degeneration in the United States, Arch Ophthalmol. 122: 564-572 (2004).
Thurman, et al. "The central role of the alternative complement pathway in human disease", Journal of Immunology 176: 1305-1310 (2006).
Tsuchihashi, et al., "Complement Factor H and High-Temperature Requirement A-1 Genotypes and Treatment Response of Age-Related Macular Degeneration" Ophthalmology 118(1):93-100 (Jan. 2011).
Tsukita, et al. "Multifunctional strands in tight junctions", Nature Reviews 2: 285-293 (2001).
Ullman, et al., "Luminescent Oxygen Channeling Assay (LOCI ^ TM): Sensitive, Broadly Applicable Homogeneous Immunoassay Method" Clinical Chemistry 42(9):1518-1526 (Sep. 1996).
Ullman, et al., "Luminescent Oxygen Channeling Immunoassay: Measurement of Particle Binding Kinetics by Chemiluminescence" PNAS 91:5426-5430 (Jun. 1994).
Undar, A et al. "Novel anti-factor D monoclonal antibody inhibits complement and leukocyte activation in a baboon model of cardiopulmonary bypass", Annals of Thoracic Surgery 74(2):355-362 (2002).
Undar, et. al., "Novel Anti-Factor D Monoclonal Antibody Inhibits Complement, Neutrophil, and Platelet Activation in a Simulated Pediatric Cardiopulmonary Bypass Circuit", Presented in the 46th Annual Conference of the American Society for Artificial Internal Organs, New York, NY, Jun. 28-Jul. 1, 2000 (abstract), p. 160 (2000).
Underhill, et al. "Phagocytosis of microbes: Complexity in action", Annu. Rev. Immunol., 20: 825-852 (2002).
Uniprot P00746 (1986).
Urtti, "Challenges and Obstacles of Ocular Pharmacokinetics and Drug Delivery" Advanced Drug Delivery Reviews 58:1131-1135 (2006).
Vaj dos, et. al., "Comprehensive functional maps of the antigen-binding site of an anti-ErbB2 antibody obtained with shotgun scanning mutagenesis", J. Mol. Biol., vol. 320,No. 2,pp. 415-428 (2002).
Van De Ven, et al. "A functional variant in the CFI gene confers a high risk of age-related macular degeneration" Nature Genetice 45(7): 813-819 (2013).
Van Lookeren Campagne, et al., "Mechanisms of Age-Related Macular Degeneration and Therapeutic Opportunities" Journal of Pathology 232(2): 151-164 (2014).
Verhoeyen, et. al., "Reshaping human antibodies: grafting an antilysozyme activity", Science, 1988, vol. 239 pp. 1534-1536 (1988).
Vlasak and Ionescu "Fragmentation of monoclonal antibodies", Landes Biosciences, 3(3): 253-263 (2011).
Volanakis, et. al., "Complement Complement Factor D: ANovel Serine Protease", Protein Science, vol. 5, pp. 553-564 (1996).

Volanakis, et. al., "Complement Enzymes", The Homan Complement System in Health & Disease, Chapter 4, Eds. J. Volonakis & M.M. Frank, Published by Marcel Dekker, Inc., New York, pp. 49-81 (1998).
Volanakis, et. al., "Renal filtration and catabolism of complement protein D", N. Engl. J. Med, vol. 312, No. 7, pp. 395-399 (1985).
Wal Port, "Complement: first of two parts", Advances in Immunology, N. Eng. J. Medicine344(14) 1058-1066 (2001).
Walker, et al. Z39Ig is co-expressed with activation macrophage genes Biochimica et Biophysica Acta, 1574: 387-390 (2002).
Walsh, "Biopharmaceutical Benchmarks" Nature Biotechnology 18:831-833 (Aug. 2000).
Wang, et al., "Age-Related Macular Degeneration Susceptibility Genes in an Older Australian Population: Comparison of Distributions and Clinical Significance of Two Major Genes with Other Known Genes (Abstract)" Investigative Ophthalmology & Visual Science 53:1-3 (Mar. 2012).
Wang, et al., "Antibody Structure, Instability, and Formulation" J Pharm Sci 96(1):1-26 (Jan. 2007).
Wang, et al., "Effect of Ionic Strength and pH on the Physical and Chemical Stability of a Monoclonal Antibody Antigen-Binding Fragment" Journal of Pharmaceutical Sciences 102(8):2520-2537 (Aug. 2013).
Wang, et. al., "Amelioration of lupus-like autoimmune disease in NZB/WPI mice after treatment with a blocking monoclonal antibody specific for complement component C5", PNAS, vol. 93, No. 16, pp. 8563-8568 (1996).
Wang, et. al., "Anti-CS monoclonal antibody therapy prevents collagen-induced arthritis and ameliorates established disease", PNAS, vol. 92, No. 19, pp. 8955-8959 (1995).
Weber, et al., "The Role of the Complement System in Age-Related Macular Degeneration" Deutsches Arzteblatt International 111(8):133-138 (2014).
Weber, "Overview of Protein Crystallization Methods" Methods in Enzymology 276:13-22 (1997).
Wei, et. al., "From disease association to risk assessment: an optimistic view from genome-wide association studies on type 1 diabetes", PLoS Genetics, vol. 5, No. 10, e1 000678, pp. 1-11 (2009).
Weisman, et. al., "Soluble human complement receptor type 1: in vivo inhibitor of complement suppressing post-ischemic myocardial inflammation and necrosis", Science, vol. 249, No. 4695, pp. 146-151 (1990).
Weismann, et. al., "Structure of C3b in complex with CRig gives insight into regulation of complement activation", Nature, vol. 444, No. 7116, pp. 217-220 (2006).
White, et. al., "Human Adispin is Identical to Complement Factor D and is Expressed at High Levels in Adipose Tissue", J. Bio. Chem., vol. 267, No. 13, pp. 9210-9213 (1992).
Wilson, et. al., "A competitive inhibition ELISA for the quantification of human interferon-gamma", J. Immunol. Methods, vol. 162, No. 2, pp. 247-255 (1993).
Wong, et al., "Global Prevalence of Age-Related Macular Degeneration and Disease Burden Projection for 2020 and 2040: A Systematic Review and Meta-Analysis" Lancet Global Health 2(2): e106-116 (Feb. 2014).
Written Opinion dated Aug. 10, 2007 of PCT/US2006/043103, now WO 2007/056227 (5 pages).
Written Opinion dated Feb. 19, 2015 of PCT/US2014/050579, now WO 2015023596 (9 pages).
Written Opinion dated Jun. 2, 2009 of PCT/US2007/083172, now WO 2008/055206 (5 pages).
Written Opinion dated May 1, 2013 of PCT/US2011/058829, now WO 2012061421 (7 pages).
Written Opinion dated Oct. 28, 2010 of PCT/US2009/041785, now WO 2009/134711 (6 pages).
Written Opinion for PCT/US2008/064526, 9 pages dated Nov. 23, 2009.
Written Opinion for PCT/US2015/028641, 7 pages dated Nov. 5, 2015.
Wu, et al. "Humanization of a murine monoclonal antibody by simultaneous optimization of framework and CRD residues", JMB, 294: 151-162 (1999).

(56) References Cited

OTHER PUBLICATIONS

Wu, et al., "BioGPS: An Extensible and Customizable Portal for Querying and Organizing Gene Annotation Resources" Genome Biology 10(11): R130.1-R130.8 (2009).
Wu, et al., "Fast and SNP-tolerant detection of complex variants and splicing in short reads" Bioinformatics 26(7):873-81 (2010).
Xie, et al., "Secondary Structure and Protein Deamidation" Journal of Pharmaceutical Sciences 88(1):8-13 (Jan. 1999).
Xu, et al., "Diversity in the CDR3 region of V(H) is sufficient for most antibody specificities" Immunity 13(1):37-45 (Jul. 2000).
Yates, et. al., "Complement C3 variant and the risk of age-related macular degeneration", N. Eng. J. Med., vol. 357, pp. 553-561 (2007).
Yi, et al., "Isomerization of Asp-Asp Motif in Model Peptides and a Monoclonal Antibody Fab Fragment" Journal of Pharmaceutical Sciences 102(3):947-959 (Mar. 2013).
Yu, et al., "Prospective Assessment of Genetic Effects on Progression to Different Stages of Age-Related Macular Degeneration Using Multistate Markov Models" Investigative Ophthalmology & Visual Science 53(3):1548-1556 (Mar. 2012).
Zareparsi, et. al., "Strong association of the Y402H variant in complement factor Hat Iq32 with susceptibility to age-related macular degeneration", Am. J. Hum. Genet., vol. 77, pp. 149-153 (2005).
Zeng, et. al., "Lack of Association of CFD polymorphisms with advanced age-related macular degeneration", Molec. Vis., vol. 16, pp. 2273-2278 (2010).
Zhang et al. "Identification of isomerization and racemization of aspartate in the Asp-Asp motifs of a therapeutic protein." Analytical Biochemistry, 410: 234-243 (2011).
U.S. Appl. No. 60/856,505, filed Nov. 2, 2006.
U.S. Appl. No. 61/048,431, filed Apr. 28, 2008.
U.S. Appl. No. 61/048,689, filed Apr. 28, 2008.
U.S. Appl. No. 60/733,763, filed Nov. 4, 2005.
U.S. Appl. No. 60/939,791, filed May 23, 2007.
U.S. Appl. No. 60/075,328, filed Feb. 20, 1998.
U.S. Appl. No. 61/987,298, filed May 1, 2014.
U.S. Appl. No. 62/076,372, filed Nov. 6, 2014.
U.S. Appl. No. 61/409,039, filed Nov. 1, 2010.
U.S. Appl. No. 61/573,602, filed Sep. 9, 2011.
U.S. Appl. No. 61/864,941, filed Aug. 12, 2013.
U.S. Appl. No. 61/866,651, filed Aug. 16, 2013.
U.S. Appl. No. 61/988,012, filed May 2, 2014.
U.S. Appl. No. 61/872,098, filed Aug. 30, 2013.
U.S. Appl. No. 61/988,016, filed May 2, 2014.
U.S. Appl. No. 62/021,487, filed Jul. 7, 2014.
U.S. Appl. No. 61/280,460, filed Nov. 4, 2009.
U.S. Appl. No. 61/281,716, filed Nov. 20, 2009.
U.S. Appl. No. 62/249,073, filed Oct. 30, 2015.
U.S. Appl. No. 62/250,885, filed Nov. 4, 2015.
U.S. Appl. No. 62/249,045, filed Oct. 30, 2015.
U.S. Appl. No. 62/249,082, filed Oct. 30, 2015.
U.S. Appl. No. 62/250,993, filed Nov. 4, 2015.
U.S. Appl. No. 62/251,015, filed Nov. 4, 2015.
U.S. Appl. No. 62/249,166, filed Oct. 30, 2015.
U.S. Appl. No. 62/250,995, filed Nov. 4, 2015.
U.S. Appl. No. 62/249,020, filed Oct. 30, 2015.
U.S. Appl. No. 62/250,965 filed Nov. 4, 2015.
Jevsevar et al., "PEGylation of antibody fragments for half-life extension" Methods in Molecular Biology 901:233-246 (Jan. 1, 2012).
Durairaj et al., "Prediction of Vitreal Half-Life Based on Drug Physicochemical Properties: Quantitative Structure-Pharmacokinetic Relationships (QSPKR)" Pharmaceutical Research, Kluwer Academic Publishers—Plenum Publishers 26(5):1236-1260 (Oct. 8, 2008)
Khalili et al., "Fab-PEG-Fab as a Potential Antibody Mimetic" Bioconju Gate Chemistry 24(11):1870-1882 (Sep. 27, 2013).
Patterson et al., "Improving the Serum Stability of Site-Specific Antibody Conjugates with Sufone Linkers," Bioconjugate Chemistry, 25(8):1402-1407 (Aug. 20, 2014).
Vugmeyster et al., "Pharmacokinetic, biodistribution, and biophysical profiles of TNF nanobodies conjugated to linear or branched poly(ethylene glycol)" Bioconjugate Chemistry 23(7):1454-1462 (Jul. 18, 2012).
Invitation to Pay Additional Fees and, Where Applicable, Protest Fee for International Application No. PCT/US2016/059048, pp. 11 (dated Feb. 15, 2017).

\* cited by examiner

| Kabat Number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | SEQ ID NO |
|---|---|---|---|---|---|---|---|---|---|---|---|---|---|---|---|---|---|---|---|---|---|---|---|---|
| murine 20D12 | E | Y | P | C | Q | Q | Y | Y | S | Y | P | L | T | F | G | S | G | T | K | V | E | I | K | 7 |
| K1VH1 | T | Y | Y | C | Q | Q | Y | Y | S | Y | P | E | T | F | G | Q | G | T | K | V | E | I | K | 26 |
| hu20D12.v2.0 | T | Y | Y | C | Q | Q | Y | N | N | Y | P | L | T | F | G | Q | G | T | K | V | E | I | K | 32 |
| hu20D12.v2.1 | T | Y | Y | C | Q | Q | Y | N | N | Y | P | L | T | F | G | Q | G | T | K | V | E | I | K | 34 |
| hu20D12.v2.3 | T | Y | Y | C | Q | Q | Y | N | N | Y | P | L | T | F | G | Q | G | T | K | V | E | I | K | 38 |
| hu20D12.v1 | T | Y | Y | C | Q | Q | Y | N | N | Y | P | L | T | F | G | Q | G | T | K | V | E | I | K | 28 |
| hu20D12.v1.1 | T | Y | Y | C | Q | Q | Y | N | N | Y | P | L | T | F | G | Q | G | T | K | V | E | I | K | 30 |
| hu20D12.v2.2 | T | Y | Y | C | Q | Q | Y | N | N | Y | P | L | T | F | G | Q | G | T | K | V | E | I | K | 36 |
| hu20D12.v2.4 | T | Y | Y | C | Q | Q | Y | N | N | Y | P | L | T | F | G | Q | G | T | K | V | E | I | K | 40 |
| hu20D12.v2.5 | T | Y | Y | C | Q | Q | Y | N | N | Y | P | L | T | F | G | Q | G | T | K | V | E | I | K | 42 |
| hu20D12.v2.6 | T | Y | Y | C | Q | Q | Y | N | N | Y | P | L | T | F | G | Q | G | T | K | V | E | I | K | 44 |
| hu20D12.v2.7 | T | Y | Y | C | Q | Q | Y | N | N | Y | P | L | T | F | G | Q | G | T | K | V | E | I | K | 46 |
| hu20D12.v2.8 | T | Y | Y | C | Q | Q | Y | N | N | Y | P | L | T | F | G | Q | G | T | K | V | E | I | K | 48 |
| hu20D12.v2.9 | T | Y | Y | C | Q | Q | Y | N | N | Y | P | L | T | F | G | Q | G | T | K | V | E | I | K | 50 |
| hu20D12.v2.10 | T | Y | Y | C | Q | Q | Y | N | N | Y | P | L | T | F | G | Q | G | T | K | V | E | I | K | 52 |
| hu20D12.v2.11 | T | Y | Y | C | Q | Q | Y | N | N | Y | P | L | T | F | G | Q | G | T | K | V | E | I | K | 54 |
| hu20D12.v2.12 | T | Y | Y | C | Q | Q | Y | N | N | Y | P | L | T | F | G | Q | G | T | K | V | E | I | K | 56 |
| hu20D12.v2.13 | T | Y | Y | C | Q | Q | Y | E | N | Y | P | L | T | F | G | Q | G | T | K | V | E | I | K | 58 |
| hu20D12.v2.14 | T | Y | Y | C | Q | Q | Y | N | N | Y | P | L | T | F | G | Q | G | T | K | V | E | I | K | 60 |
| hu20D12.v2.15 | T | Y | Y | C | Q | Q | Y | N | N | Y | P | L | T | F | G | Q | G | T | K | V | E | I | K | 62 |

| Kabat Number | 82b | 82c | 83 | 84 | 85 | 86 | 87 | 88 | 89 | 90 | 91 | 92 | 93 | 94 | 95 | 96 | 97 | 98 | 101 | 102 | 103 | 104 | 105 | 106 | 107 | 108 | 109 | 110 | 111 | 112 | 113 | SEQ ID NO |
|---|---|---|---|---|---|---|---|---|---|---|---|---|---|---|---|---|---|---|---|---|---|---|---|---|---|---|---|---|---|---|---|---|
| murine 20D12 | S | L | T | S | E | D | S | A | V | Y | Y | C | A | R | E | G | G | F | D | Y | W | G | Q | G | T | L | V | T | V | S | A | 8 |
| K1VH1 | S | L | R | S | E | D | T | A | V | Y | Y | C | A | R | E | · | · | · | D | Y | W | G | Q | G | T | L | V | T | V | S | S | 27 |
| hu20D12.v2.0 | S | L | R | S | E | D | T | A | V | Y | Y | C | A | R | E | G | G | F | A | Y | W | G | Q | G | T | L | V | T | V | S | S | 33 |
| hu20D12.v2.1 | S | L | R | S | E | D | T | A | V | Y | Y | C | A | R | E | G | G | F | A | Y | W | G | Q | G | T | L | V | T | V | S | S | 35 |
| hu20D12.v2.3 | S | L | R | S | E | D | T | A | V | Y | Y | C | A | R | E | G | G | F | A | Y | W | G | Q | G | T | L | V | T | V | S | S | 39 |
| hu20D12.v1 | S | L | R | S | E | D | T | A | V | Y | Y | C | A | R | E | G | G | F | A | Y | W | G | Q | G | T | L | V | T | V | S | S | 29 |
| hu20D12.v1.1 | S | L | R | S | E | D | T | A | V | Y | Y | C | A | R | E | G | G | F | A | Y | W | G | Q | G | T | L | V | T | V | S | S | 31 |
| hu20D12.v2.2 | S | L | R | S | E | D | T | A | V | Y | Y | C | A | R | E | G | G | F | A | Y | W | G | Q | G | T | L | V | T | V | S | S | 37 |
| hu20D12.v2.4 | S | L | R | S | E | D | T | A | V | Y | Y | C | A | R | E | G | G | F | A | Y | W | G | Q | G | T | L | V | T | V | S | S | 41 |
| hu20D12.v2.5 | S | L | R | S | E | D | T | A | V | Y | Y | C | A | R | E | G | G | F | A | Y | W | G | Q | G | T | L | V | T | V | S | S | 43 |
| hu20D12.v2.6 | S | L | R | S | E | D | T | A | V | Y | Y | C | A | R | E | G | G | F | A | Y | W | G | Q | G | T | L | V | T | V | S | S | 45 |
| hu20D12.v2.7 | S | L | R | S | E | D | T | A | V | Y | Y | C | A | R | E | G | G | F | A | Y | W | G | Q | G | T | L | V | T | V | S | S | 47 |
| hu20D12.v2.8 | S | L | R | S | E | D | T | A | V | Y | Y | C | A | R | E | G | G | F | A | Y | W | G | Q | G | T | L | V | T | V | S | S | 49 |
| hu20D12.v2.9 | S | L | R | S | E | D | T | A | V | Y | Y | C | A | R | E | G | G | F | A | Y | W | G | Q | G | T | L | V | T | V | S | S | 51 |
| hu20D12.v2.10 | S | L | R | S | E | D | T | A | V | Y | Y | C | A | R | E | G | G | F | A | Y | W | G | Q | G | T | L | V | T | V | S | S | 53 |
| hu20D12.v2.11 | S | L | R | S | E | D | T | A | V | Y | Y | C | A | R | E | G | G | F | A | Y | W | G | Q | G | T | L | V | T | V | S | S | 55 |
| hu20D12.v2.12 | S | L | R | S | E | D | T | A | V | Y | Y | C | A | R | E | G | G | F | A | Y | W | G | Q | G | T | L | V | T | V | S | S | 57 |
| hu20D12.v2.13 | S | L | R | S | E | D | T | A | V | Y | Y | C | A | R | E | G | G | F | A | Y | W | G | Q | G | T | L | V | T | V | S | S | 59 |
| hu20D12.v2.14 | S | L | R | S | E | D | T | A | V | Y | Y | C | A | R | E | G | G | F | A | Y | W | G | Q | G | T | L | V | T | V | S | S | 61 |
| hu20D12.v2.15 | S | L | R | S | E | D | T | A | V | Y | Y | C | A | R | E | G | G | F | A | Y | W | G | Q | G | T | L | V | T | V | S | S | 63 |

Light Chain, Kappa: Humanized Antibody Aligned to lampalizumab

Heavy Chain: Humanized Antibody Aligned to lampalizumab

FIG. 4

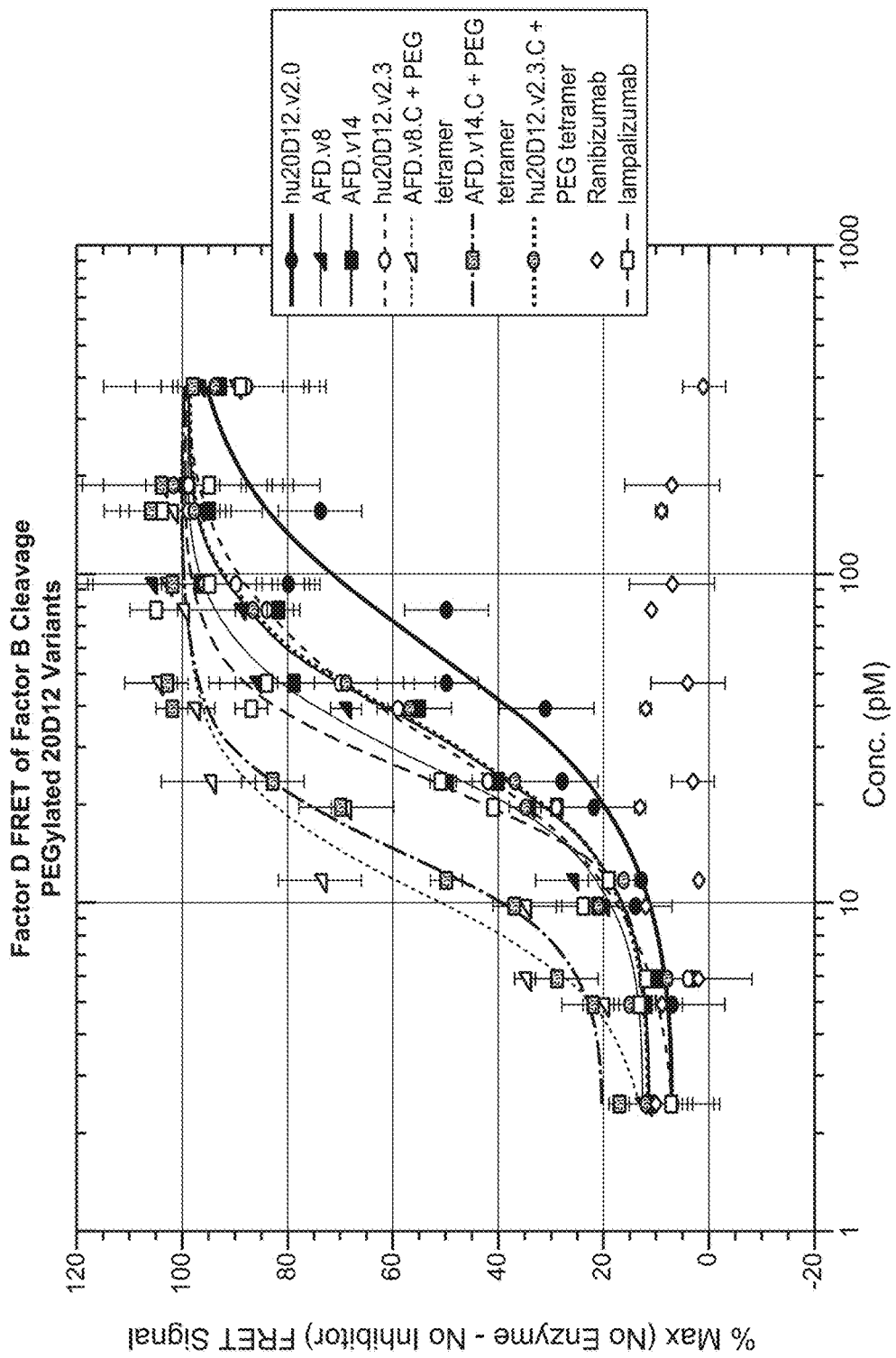

| | Theoretical Mw (kDa) | Measured Mw (kDa) | Polydispersity (Mw/Mn) | $R_h$ (nm) |
|---|---|---|---|---|
| V3.2.1 | 422.1 (±0.2%) | 411.7 | 1.001 (±0.24%) | 10.3 (±3.2%) |

| Fraction # | Mw (kDa) | Polydispersity (Mw/Mn) | $R_h$ (nm) |
|---|---|---|---|
| C1 | 283.3 (±0.5%) | 1.002 | 8.3 |
| C12 | 339.8 (±0.2%) | 1.002 | 9.4 |
| D1 | 356.8 (±0.2%) | 1.003 | 9.6 |
| D3 | 361.5 (±0.2%) | 1.003 | 9.7 |
| E1 | 407.8 (±0.2%) | 1.002 | 10.1 |
| E4 | 421.8 (±0.2%) | 1.002 | 10.2 |
| E8 | 437.0 (±0.2%) | 1.003 | 10.4 |
| E11 | 460.0 (±0.2%) | 1.004 | 10.5 |
| F6 | 523.2 (±0.2%) | 1.005 | 10.9 |
| F10 | 587.5 (±0.2%) | 1.004 | 11.2 |

*FIG. 8C*

| Antibody | Name | On-Rate (M⁻¹s⁻¹) | Off-Rate (s⁻¹) | KD (pM) hFD (Human) | KD (pM) cFD (cyno) | FRET IC50 (pM) | Viscosity on PEG-octamer | Viscosity on (Fab; No PEG) | Solubility (PBS pH 7.4) | MA Solubility (PBS pH 7.4) |
|---|---|---|---|---|---|---|---|---|---|---|
| hu20D12.v1.N54S | hu20D12.v2.0 | 1.4e7 | 5.5e-4 | 39 | 152 | 51, 59 | | 12 cP @ 280 mg/ml | Clear @ 292 mg/ml | |
| hu20D12.v1.N54S.G56D | hu20D12.v2.2 | 1.5e7 | 9.5e-4 | 65 | | | | | | |
| hu20D12.v1.N54S.G56E | hu20D12.v2.4 | 1.7e7 | 4.9e-4 | 28 | | | | | | |
| hu20D12.v1.N54S.T53Y | hu20D12.v2.5 | 1.7e7 | 7.9e-4 | 45 | | | | | | |
| hu20D12.v1.N54S.Y49S | hu20D12.v2.6 | 2.1e6 | 3.0e-4 | 143 | | | | | | |
| hu20D12.v1.N54S.Y49K | hu20D12.v2.7 | 1.1e7 | 5.5e-4 | 49 | | | | | | |
| hu20D12.v1.N54S.Y49Q | hu20D12.v2.8 | 6.6e7 | 4e-3 | 61 | | | | | | |
| hu20D12.v1.N54S.Y49R | hu20D12.v2.1 | 1.2e7 | 8.1e-5 | <10(6.8) | 17 | 33, 32 | 288 cP @ 201 mg/ml | 7.1 cP @ 177 mg/ml | Clear @ 260 mg/ml | 0.443 OD @ 150 mg/ml |
| hu20D12.v1.N54S.E50W | hu20D12.v2.9 | 3.4e7 | 6.3e-3 | 185 | | | | | | |
| hu20D12.v1.N54S.Y55K | hu20D12.v2.10 | 5e6 | 3e-2 | 6000 | | | | | | |
| hu20D12.v1.N54S.Y55R | hu20D12.v2.11 | 3e6 | 3e-2 | 10000 | | | | | | |
| hu20D12.v1.N54S.Y49R.T53Y | hu20D12.v2.12 | 1.9e7 | 1.5e-4 | <10(8.3) | | | | | | |
| hu20D12.v1.N54S.N92E.Y49R | hu20D12.v2.13 | 4.1e7 | 1.3e-4 | <10(3.1) | | | | | | |
| hu20D12.v1.N54S.Y49R.G56E | hu20D12.v2.14 | 1.5e7 | 8e-5 | <10(5.3) | 50 | 25 | | | | |
| hu20D12.v1.N54S.Y49R.T53Y.G56E | hu20D12.v2.15 | 1.9e7 | 6e-5 | <10(3.2) | 27 | 24 | | | | |
| hu20D12.v1.N54S.Y49R.T53Y.G56D | hu20D12.v2.3 | 1.2e7 | 2.9e-5 | <10(2.4) | 24 | 25, 31, 31 | 577 cP @194 mg/ml | | | |
| AFD.v8 | | 2.0e7 | 2.1e-4 | 10.5 | 24 | 21, 28 | | 14.4 cP @ 261 mg/ml | | |
| AFD.v14 | | 0.9e7 | 2.1e-4 | 23.3 | 56 | 25, 34, 26 | 979 cP @ 117 mg/ml | 21 cP @ 240 mg/ml | | |
| lampalizumab | | 8.2e7 | 3.3e-4 | <10(4.0) | 30 | 24 | | 14.8 cP @ 264 mg/ml | Precipitates @ 227 mg/ml | Precipitates @ 150 mg/ml; no OD value |

*FIG. 11*

SEQUENCE LISTING

<160> NUMBER OF SEQ ID NOS: 183

<210> SEQ ID NO 1
<211> LENGTH: 11
<212> TYPE: PRT
<213> ORGANISM: Mus musculus

<400> SEQUENCE: 1

Lys Ala Ser Gln Asn Val Asp Thr Asp Val Ala
1               5                   10

<210> SEQ ID NO 2
<211> LENGTH: 7
<212> TYPE: PRT
<213> ORGANISM: Mus musculus

<400> SEQUENCE: 2

Ser Ala Ser Ser Arg Tyr Ser
1               5

<210> SEQ ID NO 3
<211> LENGTH: 9
<212> TYPE: PRT
<213> ORGANISM: Mus musculus

<400> SEQUENCE: 3

Gln Gln Tyr Asn Asn Tyr Pro Leu Thr
1               5

<210> SEQ ID NO 4
<211> LENGTH: 5
<212> TYPE: PRT
<213> ORGANISM: Mus musculus

<400> SEQUENCE: 4

Ser Tyr Tyr Met Tyr
1               5

<210> SEQ ID NO 5
<211> LENGTH: 17
<212> TYPE: PRT
<213> ORGANISM: Mus musculus

<400> SEQUENCE: 5

Glu Ile Asn Pro Thr Asn Gly Gly Thr Asn Phe Asn Glu Lys Phe Lys
1               5                   10                  15

Ser

<210> SEQ ID NO 6

```
<211> LENGTH: 6
<212> TYPE: PRT
<213> ORGANISM: Mus musculus

<400> SEQUENCE: 6

Glu Gly Gly Phe Ala Tyr
1               5

<210> SEQ ID NO 7
<211> LENGTH: 107
<212> TYPE: PRT
<213> ORGANISM: Mus musculus

<400> SEQUENCE: 7

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asp
            20                  25                  30

Val Ala Trp Phe Gln Gln Lys Pro Gly Gln Ser Pro Arg Gly Leu Ile
        35                  40                  45

Tyr Ser Ala Ser Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ser Gly Thr Lys Val Glu Ile Lys
            100                 105

<210> SEQ ID NO 8
<211> LENGTH: 115
<212> TYPE: PRT
<213> ORGANISM: Mus musculus

<400> SEQUENCE: 8

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Glu Arg Pro Gly Gln Gly Leu Glu Trp Ile
        35                  40                  45

Gly Glu Ile Asn Pro Thr Asn Gly Gly Thr Asn Phe Asn Glu Lys Phe
    50                  55                  60

Lys Ser Lys Ala Thr Leu Thr Val Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ala
        115

<210> SEQ ID NO 9
<211> LENGTH: 11
<212> TYPE: PRT
<213> ORGANISM: Artificial Sequence
<220> FEATURE:
<223> OTHER INFORMATION: HVR-L1 of antibodies: hu20D12.v1; hu20D12.v1.1;
      hu20D12.v2.0; hu20D12.v2.1; hu20D12.v2.2; hu20D12.v2.3;
      hu20D12.v2.4; hu20D12.v2.5; hu20D12.v2.6; hu20D12.v2.7;
```

```
            hu20D12.v2.8; hu20D12.v2.9; hu20D12.v2.10; hu20D12.v2.11;
            hu20D12.v2.12

<400> SEQUENCE: 9

Lys Ala Ser Gln Asn Val Asp Thr Asp Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: HVR-L2 of antibodies: hu20D12.v1; hu20D12.v1.1;
            hu20D12.v2.0; hu20D12.v2.1; hu20D12.v2.2; hu20D12.v2.3;
            hu20D12.v2.4; hu20D12.v2.5; hu20D12.v2.6; hu20D12.v2.7;
            hu20D12.v2.8; hu20D12.v2.9; hu20D12.v2.12 hu20D12.v2.13;
            hu20D12.v2.14

<400> SEQUENCE: 10

Ser Ala Ser Ser Arg Tyr Ser
1               5

<210> SEQ ID NO 11
<211> LENGTH: 7
<212> TYPE: PRT
<213> ORGANISM: Artificial Sequence
<220> FEATURE:
<223> OTHER INFORMATION: hu20D12.v2.10 HVR-L2

<400> SEQUENCE: 11

Ser Ala Ser Ser Arg Lys Ser
1               5

<210> SEQ ID NO 12
<211> LENGTH: 7
<212> TYPE: PRT
<213> ORGANISM: Artificial Sequence
<220> FEATURE:
<223> OTHER INFORMATION: hu20D12.v2.11 HVR-L2

<400> SEQUENCE: 12

Ser Ala Ser Ser Arg Arg Ser
1               5

<210> SEQ ID NO 13
<211> LENGTH: 9
<212> TYPE: PRT
<213> ORGANISM: Artificial Sequence
<220> FEATURE:
<223> OTHER INFORMATION: HVR-L3 of antibodies: hu20D12.v1; hu20D12.v1.1;
            hu20D12.v2.0; hu20D12.v2.1; hu20D12.v2.2; hu20D12.v2.3;
            hu20D12.v2.4; hu20D12.v2.5; hu20D12.v2.6; hu20D12.v2.7;
            hu20D12.v2.8; hu20D12.v2.9; hu20D12.v2.10; hu20D12.v2.11;
            hu20D12.v2.12

<400> SEQUENCE: 13

Gln Gln Tyr Asn Asn Tyr Pro Leu Thr
1               5

<210> SEQ ID NO 14
<211> LENGTH: 9
<212> TYPE: PRT
<213> ORGANISM: Artificial Sequence
<220> FEATURE:
<223> OTHER INFORMATION: hu20D12.v2.13 HVR-L3

<400> SEQUENCE: 14

Gln Gln Tyr Glu Asn Tyr Pro Leu Thr
```

```
<210> SEQ ID NO 15
<211> LENGTH: 5
<212> TYPE: PRT
<213> ORGANISM: Artificial Sequence
<220> FEATURE:
<223> OTHER INFORMATION: HVR-H1 of antibodies: hu20D12.v1; hu20D12.v1.1;
      hu20D12.v2.0; hu20D12.v2.1; hu20D12.v2.2; hu20D12.v2.3;
      hu20D12.v2.4; hu20D12.v2.5; hu20D12.v2.6; hu20D12.v2.7;
      hu20D12.v2.8; hu20D12.v2.9; hu20D12.v2.10; hu20D12.v2.11;
      hu20D12.v2.12

<400> SEQUENCE: 15

Ser Tyr Tyr Met Tyr
1               5

<210> SEQ ID NO 16
<211> LENGTH: 17
<212> TYPE: PRT
<213> ORGANISM: Artificial Sequence
<220> FEATURE:
<223> OTHER INFORMATION: HVR-H2 of antibodies: hu20D12.v2.0;
      hu20D12.v2.1; hu20D12.v2.6; hu20D12.v2.7; hu20D12.v2.8;
      hu20D12.v2.10; hu20D12.v2.11; hu20D12.v2.13

<400> SEQUENCE: 16

Glu Ile Asn Pro Thr Ser Gly Gly Thr Asn Phe Asn Glu Lys Phe Lys
1               5                   10                  15

Ser

<210> SEQ ID NO 17
<211> LENGTH: 17
<212> TYPE: PRT
<213> ORGANISM: Artificial Sequence
<220> FEATURE:
<223> OTHER INFORMATION: hu20D12.v1 HVR-H2

<400> SEQUENCE: 17

Glu Ile Asn Pro Thr Asn Gly Gly Thr Asn Phe Asn Glu Lys Phe Lys
1               5                   10                  15

Ser

<210> SEQ ID NO 18
<211> LENGTH: 17
<212> TYPE: PRT
<213> ORGANISM: Artificial Sequence
<220> FEATURE:
<223> OTHER INFORMATION: hu20D12.v1.1 HVR-H2

<400> SEQUENCE: 18

Glu Ile Asn Pro Thr Gln Gly Gly Thr Asn Phe Asn Glu Lys Phe Lys
1               5                   10                  15

Ser

<210> SEQ ID NO 19
<211> LENGTH: 17
<212> TYPE: PRT
<213> ORGANISM: Artificial Sequence
<220> FEATURE:
<223> OTHER INFORMATION: hu20D12.v2.2 HVR-H2

<400> SEQUENCE: 19

Glu Ile Asn Pro Thr Ser Gly Asp Thr Asn Phe Asn Glu Lys Phe Lys
1               5                   10                  15
```

Ser

<210> SEQ ID NO 20
<211> LENGTH: 17
<212> TYPE: PRT
<213> ORGANISM: Artificial Sequence
<220> FEATURE:
<223> OTHER INFORMATION: hu20D12.v2.3 HVR-H2

<400> SEQUENCE: 20

Glu Ile Asn Pro Tyr Ser Gly Asp Thr Asn Phe Asn Glu Lys Phe Lys
1               5                   10                  15

Ser

<210> SEQ ID NO 21
<211> LENGTH: 17
<212> TYPE: PRT
<213> ORGANISM: Artificial Sequence
<220> FEATURE:
<223> OTHER INFORMATION: hu20D12.v2.4 HVR-H2; hu20D12.v2.14 HVR-H2

<400> SEQUENCE: 21

Glu Ile Asn Pro Thr Ser Gly Glu Thr Asn Phe Asn Glu Lys Phe Lys
1               5                   10                  15

Ser

<210> SEQ ID NO 22
<211> LENGTH: 17
<212> TYPE: PRT
<213> ORGANISM: Artificial Sequence
<220> FEATURE:
<223> OTHER INFORMATION: hu20D12.v2.5 HVR-H2; hu20D12.v2.12 HVR-H2

<400> SEQUENCE: 22

Glu Ile Asn Pro Tyr Ser Gly Gly Thr Asn Phe Asn Glu Lys Phe Lys
1               5                   10                  15

Ser

<210> SEQ ID NO 23
<211> LENGTH: 17
<212> TYPE: PRT
<213> ORGANISM: Artificial Sequence
<220> FEATURE:
<223> OTHER INFORMATION: hu20D12.v2.9 HVR-H2

<400> SEQUENCE: 23

Trp Ile Asn Pro Thr Ser Gly Gly Thr Asn Phe Asn Glu Lys Phe Lys
1               5                   10                  15

Ser

<210> SEQ ID NO 24
<211> LENGTH: 17
<212> TYPE: PRT
<213> ORGANISM: Artificial Sequence
<220> FEATURE:
<223> OTHER INFORMATION: hu20D12.v2.15 HVR-H2

<400> SEQUENCE: 24

Glu Ile Asn Pro Tyr Ser Gly Glu Thr Asn Phe Asn Glu Lys Phe Lys
1               5                   10                  15

Ser

<210> SEQ ID NO 25

-continued

```
<211> LENGTH: 6
<212> TYPE: PRT
<213> ORGANISM: Artificial Sequence
<220> FEATURE:
<223> OTHER INFORMATION: HVR-H3 of antibodies: hu20D12.v1; hu20D12.v1.1;
      hu20D12.v2.0; hu20D12.v2.1; hu20D12.v2.2; hu20D12.v2.3;
      hu20D12.v2.4; hu20D12.v2.5; hu20D12.v2.6; hu20D12.v2.7;
      hu20D12.v2.8; hu20D12.v2.9; hu20D12.v2.10; hu20D12.v2.11;
      hu20D12.v2.12

<400> SEQUENCE: 25

Glu Gly Gly Phe Ala Tyr
1               5

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys
            100                 105

<210> SEQ ID NO 27
<211> LENGTH: 112
<212> TYPE: PRT
<213> ORGANISM: Homo sapiens

<400> SEQUENCE: 27

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 28
<211> LENGTH: 107
<212> TYPE: PRT
<213> ORGANISM: Artificial Sequence
<220> FEATURE:
```

<223> OTHER INFORMATION: hu20D12.v1 VL

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105
```

<210> SEQ ID NO 29
<211> LENGTH: 115
<212> TYPE: PRT
<213> ORGANISM: Artificial Sequence
<220> FEATURE:
<223> OTHER INFORMATION: hu20D12.v1 VH

<400> SEQUENCE: 29

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Asn Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115
```

<210> SEQ ID NO 30
<211> LENGTH: 107
<212> TYPE: PRT
<213> ORGANISM: Artificial Sequence
<220> FEATURE:
<223> OTHER INFORMATION: hu20D12.v1.1 VL

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys
            100                 105

<210> SEQ ID NO 31
<211> LENGTH: 115
<212> TYPE: PRT
<213> ORGANISM: Artificial Sequence
<220> FEATURE:
<223> OTHER INFORMATION: hu20D12.v1.1 VH

<400> SEQUENCE: 31

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
             35                  40                  45

Gly Glu Ile Asn Pro Thr Gln Gly Gly Thr Asn Phe Asn Glu Lys Phe
         50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: hu20D12.v2.0 VL

<400> SEQUENCE: 32

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Asp Thr Asp
                20                  25                  30

Val Ala Trp Phe Gln Gln Lys Pro Gly Lys Ala Pro Lys Gly Leu Ile
             35                  40                  45

Tyr Ser Ala Ser Ser Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys
            100                 105

<210> SEQ ID NO 33
<211> LENGTH: 115
```

```
<212> TYPE: PRT
<213> ORGANISM: Artificial Sequence
<220> FEATURE:
<223> OTHER INFORMATION: hu20D12.v2.0 VH

<400> SEQUENCE: 33
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

```
<210> SEQ ID NO 34
<211> LENGTH: 107
<212> TYPE: PRT
<213> ORGANISM: Artificial Sequence
<220> FEATURE:
<223> OTHER INFORMATION: hu20D12.v2.1 VL

<400> SEQUENCE: 34
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

```
<210> SEQ ID NO 35
<211> LENGTH: 115
<212> TYPE: PRT
<213> ORGANISM: Artificial Sequence
<220> FEATURE:
<223> OTHER INFORMATION: hu20D12.v2.1 VH

<400> SEQUENCE: 35
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile

```
                35                  40                  45
Gly Glu Ile Asn Pro Thr Ser Gly Gly Thr Asn Phe Asn Glu Lys Phe
         50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: hu20D12.v2.2 VL

<400> SEQUENCE: 36

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Asp Thr Asp
             20                  25                  30

Val Ala Trp Phe Gln Gln Lys Pro Gly Lys Ala Pro Lys Gly Leu Ile
         35                  40                  45

Tyr Ser Ala Ser Ser Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys
            100                 105

<210> SEQ ID NO 37
<211> LENGTH: 115
<212> TYPE: PRT
<213> ORGANISM: Artificial Sequence
<220> FEATURE:
<223> OTHER INFORMATION: hu20D12.v2.2 VH

<400> SEQUENCE: 37

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met Tyr Trp Val Arg Gln Ala Pro Gly Gln Gly Leu Glu Trp Ile
         35                  40                  45

Gly Glu Ile Asn Pro Thr Ser Gly Asp Thr Asn Phe Asn Glu Lys Phe
         50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110
```

Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: hu20D12.v2.3 VL

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 39
<211> LENGTH: 115
<212> TYPE: PRT
<213> ORGANISM: Artificial Sequence
<220> FEATURE:
<223> OTHER INFORMATION: hu20D12.v2.3 VH

<400> SEQUENCE: 39

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 40
<211> LENGTH: 107
<212> TYPE: PRT
<213> ORGANISM: Artificial Sequence
<220> FEATURE:
<223> OTHER INFORMATION: hu20D12.v2.4 VL

<400> SEQUENCE: 40

Asp Ile Gln Met Thr Gln Ser Pro Ser Ser Leu Ser Ala Ser Val Gly

```
                1               5                  10                  15
Asp Arg Val Thr Ile Thr Cys Lys Ala Ser Gln Asn Val Asp Thr Asp
                    20                  25                  30

Val Ala Trp Phe Gln Gln Lys Pro Gly Lys Ala Pro Lys Gly Leu Ile
            35                  40                  45

Tyr Ser Ala Ser Ser Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
                100                 105

<210> SEQ ID NO 41
<211> LENGTH: 115
<212> TYPE: PRT
<213> ORGANISM: Artificial Sequence
<220> FEATURE:
<223> OTHER INFORMATION: hu20D12.v2.4 VH

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Glu Thr Asn Phe Asn Glu Lys Phe
        50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
                100                 105                 110

Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: hu20D12.v2.5 VL

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
                20                  25                  30

Val Ala Trp Phe Gln Gln Lys Pro Gly Lys Ala Pro Lys Gly Leu Ile
            35                  40                  45

Tyr Ser Ala Ser Ser Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 43
<211> LENGTH: 115
<212> TYPE: PRT
<213> ORGANISM: Artificial Sequence
<220> FEATURE:
<223> OTHER INFORMATION: hu20D12.v2.5 VH

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: hu20D12.v2.6 VL

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Ser Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 45
<211> LENGTH: 115
<212> TYPE: PRT
<213> ORGANISM: Artificial Sequence
<220> FEATURE:
<223> OTHER INFORMATION: hu20D12.v2.6 VH

```
<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: hu20D12.v2.7 VL

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Lys Ser Ala Ser Ser Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 47
<211> LENGTH: 115
<212> TYPE: PRT
<213> ORGANISM: Artificial Sequence
<220> FEATURE:
<223> OTHER INFORMATION: hu20D12.v2.7 VH

<400> SEQUENCE: 47

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
50                  55                  60
```

-continued

```
Lys Ser Arg Ala Thr Leu Thr Val Asp Thr Ser Thr Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 48
<211> LENGTH: 107
<212> TYPE: PRT
<213> ORGANISM: Artificial Sequence
<220> FEATURE:
<223> OTHER INFORMATION: hu20D12.v2.8 VL

<400> SEQUENCE: 48

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Val Asp Thr Asp
                 20                  25                  30

Val Ala Trp Phe Gln Gln Lys Pro Gly Lys Ala Pro Lys Gly Leu Ile
             35                  40                  45

Gln Ser Ala Ser Ser Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys
            100                 105

<210> SEQ ID NO 49
<211> LENGTH: 115
<212> TYPE: PRT
<213> ORGANISM: Artificial Sequence
<220> FEATURE:
<223> OTHER INFORMATION: hu20D12.v2.8 VH

<400> SEQUENCE: 49

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met Tyr Trp Val Arg Gln Ala Pro Gly Gln Gly Leu Glu Trp Ile
             35                  40                  45

Gly Glu Ile Asn Pro Thr Ser Gly Gly Thr Asn Phe Asn Glu Lys Phe
 50                  55                  60

Lys Ser Arg Ala Thr Leu Thr Val Asp Thr Ser Thr Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 50
```

```
<211> LENGTH: 107
<212> TYPE: PRT
<213> ORGANISM: Artificial Sequence
<220> FEATURE:
<223> OTHER INFORMATION: hu20D12.v2.9 VL

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 51
<211> LENGTH: 115
<212> TYPE: PRT
<213> ORGANISM: Artificial Sequence
<220> FEATURE:
<223> OTHER INFORMATION: hu20D12.v2.9 VH

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Trp Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 52
<211> LENGTH: 107
<212> TYPE: PRT
<213> ORGANISM: Artificial Sequence
<220> FEATURE:
<223> OTHER INFORMATION: hu20D12.v2.10 VL

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30
```

```
Val Ala Trp Phe Gln Gln Lys Pro Gly Lys Ala Pro Lys Gly Leu Ile
            35                  40                  45

Tyr Ser Ala Ser Ser Arg Lys Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys
            100                 105

<210> SEQ ID NO 53
<211> LENGTH: 115
<212> TYPE: PRT
<213> ORGANISM: Artificial Sequence
<220> FEATURE:
<223> OTHER INFORMATION: hu20D12.v2.10 VH

<400> SEQUENCE: 53

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
 50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110

Val Ser Ser
       115

<210> SEQ ID NO 54
<211> LENGTH: 107
<212> TYPE: PRT
<213> ORGANISM: Artificial Sequence
<220> FEATURE:
<223> OTHER INFORMATION: hu20D12.v2.11 VL

<400> SEQUENCE: 54

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Asp Thr Asp
                 20                  25                  30

Val Ala Trp Phe Gln Gln Lys Pro Gly Lys Ala Pro Lys Gly Leu Ile
            35                  40                  45

Tyr Ser Ala Ser Ser Arg Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys
            100                 105
```

-continued

<210> SEQ ID NO 55
<211> LENGTH: 115
<212> TYPE: PRT
<213> ORGANISM: Artificial Sequence
<220> FEATURE:
<223> OTHER INFORMATION: hu20D12.v2.11 VH

<400> SEQUENCE: 55

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115
```

<210> SEQ ID NO 56
<211> LENGTH: 107
<212> TYPE: PRT
<213> ORGANISM: Artificial Sequence
<220> FEATURE:
<223> OTHER INFORMATION: hu20D12.v2.12 VL

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105
```

<210> SEQ ID NO 57
<211> LENGTH: 115
<212> TYPE: PRT
<213> ORGANISM: Artificial Sequence
<220> FEATURE:
<223> OTHER INFORMATION: hu20D12.v2.12 VH

<400> SEQUENCE: 57

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 58
<211> LENGTH: 107
<212> TYPE: PRT
<213> ORGANISM: Artificial Sequence
<220> FEATURE:
<223> OTHER INFORMATION: hu20D12.v2.13 VL

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Asn Tyr Pro Leu
                85                  90                  95

Thr Phe Gly Gln Gly Thr Lys Val Glu Ile Lys
            100                 105

<210> SEQ ID NO 59
<211> LENGTH: 115
<212> TYPE: PRT
<213> ORGANISM: Artificial Sequence
<220> FEATURE:
<223> OTHER INFORMATION: hu20D12.v2.13 VH

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Ala Arg Glu Gly Gly Phe Ala Tyr Trp Gly Gln Gly Thr Leu Val Thr
            100                 105                 110

Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: hu20D12.v2.14 VL

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 61
<211> LENGTH: 115
<212> TYPE: PRT
<213> ORGANISM: Artificial Sequence
<220> FEATURE:
<223> OTHER INFORMATION: hu20D12.v2.14 VH

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Glu Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 62
<211> LENGTH: 107
<212> TYPE: PRT
<213> ORGANISM: Artificial Sequence
<220> FEATURE:
<223> OTHER INFORMATION: hu20D12.v2.15 VL
```

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys
            100                 105

<210> SEQ ID NO 63
<211> LENGTH: 115
<212> TYPE: PRT
<213> ORGANISM: Artificial Sequence
<220> FEATURE:
<223> OTHER INFORMATION: hu20D12.v2.15 VH

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Glu Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser
        115

<210> SEQ ID NO 64
<211> LENGTH: 214
<212> TYPE: PRT
<213> ORGANISM: Artificial Sequence
<220> FEATURE:
<223> OTHER INFORMATION: hu20D12.v1 light chain (LC)

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 223
<212> TYPE: PRT
<213> ORGANISM: Artificial Sequence
<220> FEATURE:
<223> OTHER INFORMATION: hu20D12.v1 heavy chain Fab (HC Fab)

<400> SEQUENCE: 65

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Met Tyr Trp Val Arg Gln Ala Pro Gly Gln Gly Leu Glu Trp Ile
         35                  40                  45

Gly Glu Ile Asn Pro Thr Asn Gly Gly Thr Asn Phe Asn Glu Lys Phe
     50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

Val Asp Lys Lys Val Glu Pro Lys Ser Cys Asp Lys Thr His Thr
    210                 215                 220

<210> SEQ ID NO 66
<211> LENGTH: 214
<212> TYPE: PRT
<213> ORGANISM: Artificial Sequence
<220> FEATURE:
<223> OTHER INFORMATION: hu20D12.v1.1 LC

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 223
<212> TYPE: PRT
<213> ORGANISM: Artificial Sequence
<220> FEATURE:
<223> OTHER INFORMATION: hu20D12.v1.1 HC Fab

<400> SEQUENCE: 67

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Gln Gly Gly Thr Asn Phe Asn Glu Lys Phe
    50                  55                  60

Lys Ser Arg Ala Thr Leu Thr Val Asp Thr Ser Thr Ser Thr Ala Tyr

```
                65                  70                  75                  80
Leu Glu Leu Ser Ser Leu Arg Ser Glu Asp Thr Ala Val Tyr Tyr Cys
                    85                  90                  95

Ala Arg Glu Gly Gly Phe Ala Tyr Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr
210                 215                 220

<210> SEQ ID NO 68
<211> LENGTH: 214
<212> TYPE: PRT
<213> ORGANISM: Artificial Sequence
<220> FEATURE:
<223> OTHER INFORMATION: hu20D12.v2.0 LC

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
                20                  25                  30

Val Ala Trp Phe Gln Gln Lys Pro Gly Lys Ala Pro Lys Gly Leu Ile
            35                  40                  45

Tyr Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

<210> SEQ ID NO 69
<211> LENGTH: 223
<212> TYPE: PRT
<213> ORGANISM: Artificial Sequence
<220> FEATURE:
<223> OTHER INFORMATION: hu20D12.v2.0 HC Fab

<400> SEQUENCE: 69

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220
```

<210> SEQ ID NO 70
<211> LENGTH: 214
<212> TYPE: PRT
<213> ORGANISM: Artificial Sequence
<220> FEATURE:
<223> OTHER INFORMATION: hu20D12.v2.1 LC

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 71
<211> LENGTH: 223
<212> TYPE: PRT
<213> ORGANISM: Artificial Sequence
<220> FEATURE:
<223> OTHER INFORMATION: hu20D12.v2.1 HC Fab ("CDKTHT")

<400> SEQUENCE: 71

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
            85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
    210                 215                 220
```

<210> SEQ ID NO 72
<211> LENGTH: 214
<212> TYPE: PRT
<213> ORGANISM: Artificial Sequence
<220> FEATURE:
<223> OTHER INFORMATION: hu20D12.v2.2 LC

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 73
<211> LENGTH: 223
<212> TYPE: PRT
<213> ORGANISM: Artificial Sequence
<220> FEATURE:
<223> OTHER INFORMATION: hu20D12.v2.2 HC Fab

<400> SEQUENCE: 73

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
210                 215                 220
```

<210> SEQ ID NO 74
<211> LENGTH: 214
<212> TYPE: PRT
<213> ORGANISM: Artificial Sequence
<220> FEATURE:
<223> OTHER INFORMATION: hu20D12.v2.3 LC

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
            35                  40                  45

Arg Ser Ala Ser Ser Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 75

```
<211> LENGTH: 223
<212> TYPE: PRT
<213> ORGANISM: Artificial Sequence
<220> FEATURE:
<223> OTHER INFORMATION: hu20D12.v2.3 HC Fab ("CDKTHT")

<400> SEQUENCE: 75
```

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |

| Tyr | Met | Tyr | Trp | Val | Arg | Gln | Ala | Pro | Gly | Gln | Gly | Leu | Glu | Trp | Ile |
| | | 35 | | | | | 40 | | | | | 45 | | | |

| Gly | Glu | Ile | Asn | Pro | Tyr | Ser | Gly | Asp | Thr | Asn | Phe | Asn | Glu | Lys | Phe |
| 50 | | | | | 55 | | | | | 60 | | | | | |

| Lys | Ser | Arg | Ala | Thr | Leu | Thr | Val | Asp | Thr | Ser | Thr | Ser | Thr | Ala | Tyr |
| 65 | | | | | 70 | | | | | 75 | | | | | 80 |

| Leu | Glu | Leu | Ser | Ser | Leu | Arg | Ser | Glu | Asp | Thr | Ala | Val | Tyr | Tyr | Cys |
| | | | | 85 | | | | | 90 | | | | | 95 | |

| Ala | Arg | Glu | Gly | Gly | Phe | Ala | Tyr | Trp | Gly | Gln | Gly | Thr | Leu | Val | Thr |
| | | | 100 | | | | | 105 | | | | | 110 | | |

| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |

| Ser | Ser | Lys | Ser | Thr | Ser | Gly | Gly | Thr | Ala | Ala | Leu | Gly | Cys | Leu | Val |
| 130 | | | | | 135 | | | | | 140 | | | | | |

| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |

| Leu | Thr | Ser | Gly | Val | His | Thr | Phe | Pro | Ala | Val | Leu | Gln | Ser | Ser | Gly |
| | | | | 165 | | | | | 170 | | | | | 175 | |

| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |

| Thr | Gln | Thr | Tyr | Ile | Cys | Asn | Val | Asn | His | Lys | Pro | Ser | Asn | Thr | Lys |
| | | 195 | | | | | 200 | | | | | 205 | | | |

| Val | Asp | Lys | Lys | Val | Glu | Pro | Lys | Ser | Cys | Asp | Lys | Thr | His | Thr | |
| 210 | | | | | 215 | | | | | 220 | | | | | |

```
<210> SEQ ID NO 76
<211> LENGTH: 214
<212> TYPE: PRT
<213> ORGANISM: Artificial Sequence
<220> FEATURE:
<223> OTHER INFORMATION: hu20D12.v2.4 LC

<400> SEQUENCE: 76
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Lys | Ala | Ser | Gln | Asn | Val | Asp | Thr | Asp |
| | | | 20 | | | | | 25 | | | | | 30 | | |

| Val | Ala | Trp | Phe | Gln | Gln | Lys | Pro | Gly | Lys | Ala | Pro | Lys | Gly | Leu | Ile |
| | | 35 | | | | | 40 | | | | | 45 | | | |

| Tyr | Ser | Ala | Ser | Ser | Arg | Tyr | Ser | Gly | Val | Pro | Ser | Arg | Phe | Ser | Gly |
| 50 | | | | | 55 | | | | | 60 | | | | | |

| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Gln | Gln | Tyr | Asn | Asn | Tyr | Pro | Leu |
| | | | | 85 | | | | | 90 | | | | | 95 | |

| Thr | Phe | Gly | Gln | Gly | Thr | Lys | Val | Glu | Ile | Lys | Arg | Thr | Val | Ala | Ala |

```
                100              105              110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145             150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 77
<211> LENGTH: 223
<212> TYPE: PRT
<213> ORGANISM: Artificial Sequence
<220> FEATURE:
<223> OTHER INFORMATION: hu20D12.v2.4 HC Fab

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Glu Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 78
<211> LENGTH: 214
<212> TYPE: PRT
```

<213> ORGANISM: Artificial Sequence
<220> FEATURE:
<223> OTHER INFORMATION: hu20D12.v2.5 LC

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
<211> LENGTH: 223
<212> TYPE: PRT
<213> ORGANISM: Artificial Sequence
<220> FEATURE:
<223> OTHER INFORMATION: hu20D12.v2.5 HC Fab

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Gly Thr Asn Phe Asn Glu Lys Phe
50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
210                 215                 220
```

<210> SEQ ID NO 80
<211> LENGTH: 214
<212> TYPE: PRT
<213> ORGANISM: Artificial Sequence
<220> FEATURE:
<223> OTHER INFORMATION: hu20D12.v2.6 LC

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Ser Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 81
<211> LENGTH: 223
<212> TYPE: PRT
<213> ORGANISM: Artificial Sequence
<220> FEATURE:

<223> OTHER INFORMATION: hu20D12.v2.6 HC Fab

<400> SEQUENCE: 81

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 82
<211> LENGTH: 214
<212> TYPE: PRT
<213> ORGANISM: Artificial Sequence
<220> FEATURE:
<223> OTHER INFORMATION: hu20D12.v2.7 LC

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Lys Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 83
<211> LENGTH: 223
<212> TYPE: PRT
<213> ORGANISM: Artificial Sequence
<220> FEATURE:
<223> OTHER INFORMATION: hu20D12.v2.7 HC Fab

<400> SEQUENCE: 83

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met Tyr Trp Val Arg Gln Ala Pro Gly Gln Gly Leu Glu Trp Ile
        35                  40                  45
Gly Glu Ile Asn Pro Thr Ser Gly Gly Thr Asn Phe Asn Glu Lys Phe
    50                  55                  60
Lys Ser Arg Ala Thr Leu Thr Val Asp Thr Ser Thr Ser Thr Ala Tyr
65                  70                  75                  80
Leu Glu Leu Ser Ser Leu Arg Ser Glu Asp Thr Ala Val Tyr Tyr Cys
                85                  90                  95
Ala Arg Glu Gly Gly Phe Ala Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr
    210                 215                 220
```

<210> SEQ ID NO 84
<211> LENGTH: 214
<212> TYPE: PRT
<213> ORGANISM: Artificial Sequence
<220> FEATURE:
<223> OTHER INFORMATION: hu20D12.v2.8 LC

<400> SEQUENCE: 84

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Gln Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 85
<211> LENGTH: 223
<212> TYPE: PRT
<213> ORGANISM: Artificial Sequence
<220> FEATURE:
<223> OTHER INFORMATION: hu20D12.v2.8 HC Fab

<400> SEQUENCE: 85

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
```

```
                130                 135                 140
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr
210                 215                 220

<210> SEQ ID NO 86
<211> LENGTH: 214
<212> TYPE: PRT
<213> ORGANISM: Artificial Sequence
<220> FEATURE:
<223> OTHER INFORMATION: hu20D12.v2.9 LC

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
                20                  25                  30

Val Ala Trp Phe Gln Gln Lys Pro Gly Lys Ala Pro Lys Gly Leu Ile
            35                  40                  45

Tyr Ser Ala Ser Ser Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 87
<211> LENGTH: 223
<212> TYPE: PRT
<213> ORGANISM: Artificial Sequence
<220> FEATURE:
<223> OTHER INFORMATION: hu20D12.v2.9 HC Fab

<400> SEQUENCE: 87
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Trp Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 88
<211> LENGTH: 214
<212> TYPE: PRT
<213> ORGANISM: Artificial Sequence
<220> FEATURE:
<223> OTHER INFORMATION: hu20D12.v2.10 LC

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 223
<212> TYPE: PRT
<213> ORGANISM: Artificial Sequence
<220> FEATURE:
<223> OTHER INFORMATION: hu20D12.v2.10 HC Fab

<400> SEQUENCE: 89

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr
210                 215                 220

<210> SEQ ID NO 90
<211> LENGTH: 214
<212> TYPE: PRT
<213> ORGANISM: Artificial Sequence
<220> FEATURE:
<223> OTHER INFORMATION: hu20D12.v2.11 LC

<400> SEQUENCE: 90

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Tyr Ser Ala Ser Ser Arg Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 223
<212> TYPE: PRT
<213> ORGANISM: Artificial Sequence
<220> FEATURE:
<223> OTHER INFORMATION: hu20D12.v2.11 HC Fab

<400> SEQUENCE: 91

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 92
<211> LENGTH: 214
<212> TYPE: PRT
<213> ORGANISM: Artificial Sequence
<220> FEATURE:
<223> OTHER INFORMATION: hu20D12.v2.12 LC

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 93
<211> LENGTH: 223
<212> TYPE: PRT
<213> ORGANISM: Artificial Sequence
<220> FEATURE:
<223> OTHER INFORMATION: hu20D12.v2.12 HC Fab

<400> SEQUENCE: 93

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                20                  25                  30
Tyr Met Tyr Trp Val Arg Gln Ala Pro Gly Gln Gly Leu Glu Trp Ile
            35                  40                  45
Gly Glu Ile Asn Pro Tyr Ser Gly Gly Thr Asn Phe Asn Glu Lys Phe
        50                  55                  60
Lys Ser Arg Ala Thr Leu Thr Val Asp Thr Ser Thr Ser Thr Ala Tyr
 65                  70                  75                  80
Leu Glu Leu Ser Ser Leu Arg Ser Glu Asp Thr Ala Val Tyr Tyr Cys
                85                  90                  95
Ala Arg Glu Gly Gly Phe Ala Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr
    210                 215                 220

<210> SEQ ID NO 94
<211> LENGTH: 214
<212> TYPE: PRT
<213> ORGANISM: Artificial Sequence
<220> FEATURE:
<223> OTHER INFORMATION: hu20D12.v2.13 LC

<400> SEQUENCE: 94

Asp Ile Gln Met Thr Gln Ser Pro Ser Ser Leu Ser Ala Ser Val Gly
 1               5                  10                  15
Asp Arg Val Thr Ile Thr Cys Lys Ala Ser Gln Asn Val Asp Thr Asp
            20                  25                  30
Val Ala Trp Phe Gln Gln Lys Pro Gly Lys Ala Pro Lys Gly Leu Ile
        35                  40                  45
Arg Ser Ala Ser Ser Arg Tyr Ser Gly Val Pro Ser Arg Phe Ser Gly
    50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Glu Asn Tyr Pro Leu
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 223
<212> TYPE: PRT
<213> ORGANISM: Artificial Sequence
<220> FEATURE:
<223> OTHER INFORMATION: hu20D12.v2.13 HC Fab

<400> SEQUENCE: 95

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 96
<211> LENGTH: 214
<212> TYPE: PRT
<213> ORGANISM: Artificial Sequence
<220> FEATURE:
<223> OTHER INFORMATION: hu20D12.v2.14 LC

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
         35                  40                  45

Arg Ser Ala Ser Ser Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
         210

<210> SEQ ID NO 97
<211> LENGTH: 223
<212> TYPE: PRT
<213> ORGANISM: Artificial Sequence
<220> FEATURE:
<223> OTHER INFORMATION: hu20D12.v2.14 HC Fab

<400> SEQUENCE: 97

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
             20                  25                  30

Tyr Met Tyr Trp Val Arg Gln Ala Pro Gly Gln Gly Leu Glu Trp Ile
         35                  40                  45

Gly Glu Ile Asn Pro Thr Ser Gly Glu Thr Asn Phe Asn Glu Lys Phe
 50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

```
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 98
<211> LENGTH: 214
<212> TYPE: PRT
<213> ORGANISM: Artificial Sequence
<220> FEATURE:
<223> OTHER INFORMATION: hu20D12.v2.15 LC

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asp
            20                  25                  30

Val Ala Trp Phe Gln Gln Lys Pro Gly Lys Ala Pro Lys Gly Leu Ile
        35                  40                  45

Arg Ser Ala Ser Ser Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 99
<211> LENGTH: 223
<212> TYPE: PRT
<213> ORGANISM: Artificial Sequence
<220> FEATURE:
<223> OTHER INFORMATION: hu20D12.v2.15 HC Fab

<400> SEQUENCE: 99

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45
```

```
Gly Glu Ile Asn Pro Tyr Ser Gly Glu Thr Asn Phe Asn Glu Lys Phe
        50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
210                 215                 220

<210> SEQ ID NO 100
<211> LENGTH: 107
<212> TYPE: PRT
<213> ORGANISM: Artificial Sequence
<220> FEATURE:
<223> OTHER INFORMATION: Lampalizumab VL

<400> SEQUENCE: 100

Asp Ile Gln Val Thr Gln Ser Pro Ser Ser Leu Ser Ala Ser Val Gly
  1               5                  10                  15

Asp Arg Val Thr Ile Thr Cys Ile Thr Ser Thr Asp Ile Asp Asp Asp
                 20                  25                  30

Met Asn Trp Tyr Gln Gln Lys Pro Gly Lys Val Pro Lys Leu Leu Ile
             35                  40                  45

Ser Gly Gly Asn Thr Leu Arg Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Val Glu Ile Lys
            100                 105

<210> SEQ ID NO 101
<211> LENGTH: 115
<212> TYPE: PRT
<213> ORGANISM: Artificial Sequence
<220> FEATURE:
<223> OTHER INFORMATION: Lampalizumab VH

<400> SEQUENCE: 101

Glu Val Gln Leu Val Gln Ser Gly Pro Glu Leu Lys Lys Pro Gly Ala
  1               5                  10                  15

Ser Val Lys Val Ser Cys Lys Ala Ser Gly Tyr Thr Phe Thr Asn Tyr
```

```
                20                  25                  30
Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
               100                 105                 110

Val Ser Ser
        115

<210> SEQ ID NO 102
<211> LENGTH: 214
<212> TYPE: PRT
<213> ORGANISM: Artificial Sequence
<220> FEATURE:
<223> OTHER INFORMATION: Lampalizumab LC

<400> SEQUENCE: 102

Asp Ile Gln Val Thr Gln Ser Pro Ser Ser Leu Ser Ala Ser Val Gly
 1               5                  10                  15

Asp Arg Val Thr Ile Thr Cys Ile Thr Ser Asp Ile Asp Asp Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
           115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
               165                 170                 175

Ser Thr Leu Thr Leu Ser Lys Ala Asp Tyr Glu Lys His Lys Val Tyr
           180                 185                 190

Ala Cys Glu Val Thr His Gln Gly Leu Ser Ser Pro Val Thr Lys Ser
       195                 200                 205

Phe Asn Arg Gly Glu Cys
    210

<210> SEQ ID NO 103
<211> LENGTH: 223
<212> TYPE: PRT
<213> ORGANISM: Artificial Sequence
<220> FEATURE:
<223> OTHER INFORMATION: Lampalizumab HC Fab
```

<400> SEQUENCE: 103

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 104
<211> LENGTH: 253
<212> TYPE: PRT
<213> ORGANISM: Homo sapiens

<400> SEQUENCE: 104

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Ala Pro
    130                 135                 140

```
Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
        195                 200                 205

Gly Gly Pro Leu Val Cys Gly Gly Val Leu Glu Gly Val Val Thr Ser
    210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250
```

<210> SEQ ID NO 105
<211> LENGTH: 234
<212> TYPE: PRT
<213> ORGANISM: Homo sapiens

<400> SEQUENCE: 105

```
Ala Pro Pro Arg Gly Arg Ile Leu Gly Gly Arg Glu Ala Glu Ala His
1               5                   10                  15

Ala Arg Pro Tyr Met Ala Ser Val Gln Leu Asn Gly Ala His Leu Cys
            20                  25                  30

Gly Gly Val Leu Val Ala Glu Gln Trp Val Leu Ser Ala Ala His Cys
        35                  40                  45

Leu Glu Asp Ala Ala Asp Gly Lys Val Gln Val Leu Leu Gly Ala His
    50                  55                  60

Ser Leu Ser Gln Pro Glu Pro Ser Lys Arg Leu Tyr Asp Val Leu Arg
65                  70                  75                  80

Ala Val Pro His Pro Asp Ser Gln Pro Asp Thr Ile Asp His Asp Leu
                85                  90                  95

Leu Leu Leu Gln Leu Ser Glu Lys Ala Thr Leu Gly Pro Ala Val Arg
            100                 105                 110

Pro Leu Pro Trp Gln Arg Val Asp Arg Asp Val Ala Pro Gly Thr Leu
        115                 120                 125

Cys Asp Val Ala Gly Trp Gly Ile Val Asn His Ala Gly Arg Arg Pro
130                 135                 140

Asp Ser Leu Gln His Val Leu Leu Pro Val Leu Asp Arg Ala Thr Cys
145                 150                 155                 160

Asn Arg Arg Thr His His Asp Gly Ala Ile Thr Glu Arg Leu Met Cys
                165                 170                 175

Ala Glu Ser Asn Arg Arg Asp Ser Cys Lys Gly Asp Ser Gly Gly Pro
            180                 185                 190

Leu Val Cys Gly Gly Val Leu Glu Gly Val Val Thr Ser Gly Ser Arg
        195                 200                 205

Val Cys Gly Asn Arg Lys Lys Pro Gly Ile Tyr Thr Arg Val Ala Ser
210                 215                 220

Tyr Ala Ala Trp Ile Asp Ser Val Leu Ala
225                 230
```

<210> SEQ ID NO 106
<211> LENGTH: 227
<212> TYPE: PRT

<213> ORGANISM: Homo sapiens

<400> SEQUENCE: 106

```
Leu Gly Gly Arg Glu Ala Glu Ala His Ala Arg Pro Tyr Met Ala Ser
1               5                   10                  15
Val Gln Leu Asn Gly Ala His Leu Cys Gly Gly Val Leu Val Ala Glu
                20                  25                  30
Gln Trp Val Leu Ser Ala Ala His Cys Leu Glu Asp Ala Ala Asp Gly
            35                  40                  45
Lys Val Gln Val Leu Leu Gly Ala His Ser Leu Ser Gln Pro Glu Pro
        50                  55                  60
Ser Lys Arg Leu Tyr Asp Val Leu Arg Ala Val Pro His Pro Asp Ser
65                  70                  75                  80
Gln Pro Asp Thr Ile Asp His Asp Leu Leu Leu Leu Gln Leu Ser Glu
                85                  90                  95
Lys Ala Thr Leu Gly Pro Ala Val Arg Pro Leu Pro Trp Gln Arg Val
                100                 105                 110
Asp Arg Asp Val Ala Pro Gly Thr Leu Cys Asp Val Ala Gly Trp Gly
            115                 120                 125
Ile Val Asn His Ala Gly Arg Arg Pro Asp Ser Leu Gln His Val Leu
        130                 135                 140
Leu Pro Val Leu Asp Arg Ala Thr Cys Asn Arg Arg Thr His His Asp
145                 150                 155                 160
Gly Ala Ile Thr Glu Arg Leu Met Cys Ala Glu Ser Asn Arg Arg Asp
                165                 170                 175
Ser Cys Lys Gly Asp Ser Gly Gly Pro Leu Val Cys Gly Gly Val Leu
                180                 185                 190
Glu Gly Val Val Thr Ser Gly Ser Arg Val Cys Gly Asn Arg Lys Lys
            195                 200                 205
Pro Gly Ile Tyr Thr Arg Val Ala Ser Tyr Ala Ala Trp Ile Asp Ser
        210                 215                 220
Val Leu Ala
225
```

<210> SEQ ID NO 107
<211> LENGTH: 253
<212> TYPE: PRT
<213> ORGANISM: Macaca fascicularis

<400> SEQUENCE: 107

```
Met His Ser Trp Glu His Leu Ala Val Leu Val Leu Leu Gly Val Ala
1               5                   10                  15
Ala Cys Ala Ala Gln Pro Arg Gly Arg Ile Leu Gly Gly Arg Glu Ala
                20                  25                  30
Glu Ala His Ala Arg Pro Tyr Met Ala Ser Val Gln Val Asn Gly Glu
            35                  40                  45
His Leu Cys Gly Gly Val Leu Val Ala Glu Gln Trp Val Leu Ser Ala
        50                  55                  60
Ala His Cys Leu Glu Asp Ala Ala Asp Gly Lys Val Gln Val Leu Leu
65                  70                  75                  80
Gly Ala His Ser Leu Ser Gln Pro Glu Pro Ser Lys Arg Leu Tyr Asp
                85                  90                  95
Val Leu Arg Ala Val Pro His Pro Asp Ser Arg Pro Asp Thr Ile Asp
                100                 105                 110
His Asp Leu Leu Leu Leu Gln Leu Ser Glu Lys Ala Thr Leu Gly Pro
```

```
                115                 120                 125
Ala Val Arg Pro Leu Pro Trp Gln Arg Val Asp Arg Asp Val Glu Pro
            130                 135                 140

Gly Thr Leu Cys Asp Val Ala Gly Trp Gly Ile Val Ser His Ala Gly
145                 150                 155                 160

Arg Arg Pro Asp Arg Leu Gln His Val Leu Pro Val Leu Asp Arg
                165                 170                 175

Ala Thr Cys Asn Arg Arg Thr His His Asp Gly Ala Ile Thr Gln Arg
            180                 185                 190

Met Met Cys Ala Glu Ser Asn Arg Arg Asp Ser Cys Lys Gly Asp Ser
            195                 200                 205

Gly Gly Pro Leu Val Cys Gly Val Leu Glu Gly Val Val Thr Ser
            210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 108
<211> LENGTH: 7
<212> TYPE: PRT
<213> ORGANISM: Artificial Sequence
<220> FEATURE:
<223> OTHER INFORMATION: hu20D12 consensus HVR-L2
<220> FEATURE:
<221> NAME/KEY: MISC_FEATURE
<222> LOCATION: (6)..(6)
<223> OTHER INFORMATION: X is selected from Y, K, and R

<400> SEQUENCE: 108

Ser Ala Ser Ser Arg Xaa Ser
1               5

<210> SEQ ID NO 109
<211> LENGTH: 8
<212> TYPE: PRT
<213> ORGANISM: Artificial Sequence
<220> FEATURE:
<223> OTHER INFORMATION: hu20D12 consensus extended HVR-L2
<220> FEATURE:
<221> NAME/KEY: MISC_FEATURE
<222> LOCATION: (1)..(1)
<223> OTHER INFORMATION: X is selected from Y, K, and R
<220> FEATURE:
<221> NAME/KEY: MISC_FEATURE
<222> LOCATION: (7)..(7)
<223> OTHER INFORMATION: X is selected from Y, R, S, K, and Q

<400> SEQUENCE: 109

Xaa Ser Ala Ser Ser Arg Xaa Ser
1               5

<210> SEQ ID NO 110
<211> LENGTH: 9
<212> TYPE: PRT
<213> ORGANISM: Artificial Sequence
<220> FEATURE:
<223> OTHER INFORMATION: hu20D12 consensus HVR-L3
<220> FEATURE:
<221> NAME/KEY: MISC_FEATURE
<222> LOCATION: (4)..(4)
<223> OTHER INFORMATION: X is selected from N and E

<400> SEQUENCE: 110

Gln Gln Tyr Xaa Asn Tyr Pro Leu Thr
```

```
<210> SEQ ID NO 111
<211> LENGTH: 17
<212> TYPE: PRT
<213> ORGANISM: Artificial Sequence
<220> FEATURE:
<223> OTHER INFORMATION: hu20D12 consensus HVR-H2
<220> FEATURE:
<221> NAME/KEY: MISC_FEATURE
<222> LOCATION: (1)..(1)
<223> OTHER INFORMATION: X is selected from E and W
<220> FEATURE:
<221> NAME/KEY: MISC_FEATURE
<222> LOCATION: (5)..(5)
<223> OTHER INFORMATION: X is selected from T and Y
<220> FEATURE:
<221> NAME/KEY: MISC_FEATURE
<222> LOCATION: (6)..(6)
<223> OTHER INFORMATION: X is selected from N, S, and Q
<220> FEATURE:
<221> NAME/KEY: MISC_FEATURE
<222> LOCATION: (8)..(8)
<223> OTHER INFORMATION: X is selected from G, D, and E

<400> SEQUENCE: 111

Xaa Ile Asn Pro Xaa Xaa Gly Xaa Thr Asn Phe Asn Glu Lys Phe Lys
1               5                   10                  15

Ser

<210> SEQ ID NO 112
<211> LENGTH: 107
<212> TYPE: PRT
<213> ORGANISM: Artificial Sequence
<220> FEATURE:
<223> OTHER INFORMATION: Fab light chain constant region

<400> SEQUENCE: 112

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 113
<211> LENGTH: 108
<212> TYPE: PRT
<213> ORGANISM: Artificial Sequence
<220> FEATURE:
<223> OTHER INFORMATION: Fab heavy chain constant region ("CDKTHT (SEQ
      ID NO: 165)")

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                    20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105
```

<210> SEQ ID NO 114
<211> LENGTH: 214
<212> TYPE: PRT
<213> ORGANISM: Artificial Sequence
<220> FEATURE:
<223> OTHER INFORMATION: AFD.v8 LC

<400> SEQUENCE: 114

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 115
<211> LENGTH: 223
<212> TYPE: PRT
<213> ORGANISM: Artificial Sequence
<220> FEATURE:
<223> OTHER INFORMATION: AFD.v8 HC Fab

<400> SEQUENCE: 115

Glu Val Gln Leu Val Gln Ser Gly Pro Glu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 116
<211> LENGTH: 214
<212> TYPE: PRT
<213> ORGANISM: Artificial Sequence
<220> FEATURE:
<223> OTHER INFORMATION: AFD.v14 LC

<400> SEQUENCE: 116

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 117
<211> LENGTH: 223
<212> TYPE: PRT
<213> ORGANISM: Artificial Sequence
<220> FEATURE:
<223> OTHER INFORMATION: AFD.v14 HC Fab

<400> SEQUENCE: 117

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr
210                 215                 220

<210> SEQ ID NO 118
<211> LENGTH: 223
<212> TYPE: PRT
<213> ORGANISM: Artificial Sequence
<220> FEATURE:
<223> OTHER INFORMATION: hu20D12.v2.1 HC Fab ("CDKTHL")

<400> SEQUENCE: 118

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
 50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
             100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
 130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
             195                 200                 205

Val Asp Lys Lys Val Glu Pro Lys Ser Cys Asp Lys Thr His Leu
 210                 215                 220

<210> SEQ ID NO 119
<211> LENGTH: 224
<212> TYPE: PRT
<213> ORGANISM: Artificial Sequence
<220> FEATURE:
<223> OTHER INFORMATION: hu20D12.v2.1 HC Fab ("CDKTHTC")

<400> SEQUENCE: 119

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
 50                  55                  60

Lys Ser Arg Ala Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Gly Phe Ala Tyr Trp Gly Gln Gly Thr Leu Val Thr
             100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
 130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220
```

<210> SEQ ID NO 120
<211> LENGTH: 227
<212> TYPE: PRT
<213> ORGANISM: Artificial Sequence
<220> FEATURE:
<223> OTHER INFORMATION: hu20D12.v2.1 HC Fab ("CDKTHTCPPC")

<400> SEQUENCE: 120

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
        50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
            85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys
225
```

<210> SEQ ID NO 121
<211> LENGTH: 227
<212> TYPE: PRT
<213> ORGANISM: Artificial Sequence
<220> FEATURE:
<223> OTHER INFORMATION: hu20D12.v2.1 HC Fab ("CDKTHTSPPC")

<400> SEQUENCE: 121

```
Glu Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
        50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
210                 215                 220

Pro Pro Cys
225
```

<210> SEQ ID NO 122
<211> LENGTH: 227
<212> TYPE: PRT
<213> ORGANISM: Artificial Sequence
<220> FEATURE:
<223> OTHER INFORMATION: hu20D12.v2.1 HC Fab ("CDKTHTCPPS")

<400> SEQUENCE: 122

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
        50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
```

-continued

```
                130                 135                 140
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
    210                 215                 220

Pro Pro Ser
225
```

<210> SEQ ID NO 123
<211> LENGTH: 223
<212> TYPE: PRT
<213> ORGANISM: Artificial Sequence
<220> FEATURE:
<223> OTHER INFORMATION: hu20D12.v2.3 HC Fab ("CDKTHL")

<400> SEQUENCE: 123

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Leu
    210                 215                 220
```

<210> SEQ ID NO 124
<211> LENGTH: 224
<212> TYPE: PRT
<213> ORGANISM: Artificial Sequence
<220> FEATURE:
<223> OTHER INFORMATION: hu20D12.v2.3 HC Fab ("CDKTHTC")

<400> SEQUENCE: 124

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

<210> SEQ ID NO 125
<211> LENGTH: 227
<212> TYPE: PRT
<213> ORGANISM: Artificial Sequence
<220> FEATURE:
<223> OTHER INFORMATION: hu20D12.v2.3 HC Fab ("CDKTHTCPPC")

<400> SEQUENCE: 125

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys
225

<210> SEQ ID NO 126
<211> LENGTH: 227
<212> TYPE: PRT
<213> ORGANISM: Artificial Sequence
<220> FEATURE:
<223> OTHER INFORMATION: hu20D12.v2.3 HC Fab ("CDKTHTSPPC")

<400> SEQUENCE: 126

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Tyr Ser Gly Asp Thr Asn Phe Asn Glu Lys Phe
        50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Ser
210                 215                 220

Pro Pro Cys
225

<210> SEQ ID NO 127
<211> LENGTH: 227

<212> TYPE: PRT
<213> ORGANISM: Artificial Sequence
<220> FEATURE:
<223> OTHER INFORMATION: hu20D12.v2.3 HC Fab ("CDKTHTCPPS")

<400> SEQUENCE: 127

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Ser
225

<210> SEQ ID NO 128
<211> LENGTH: 108
<212> TYPE: PRT
<213> ORGANISM: Artificial Sequence
<220> FEATURE:
<223> OTHER INFORMATION: Fab heavy chain constant region ("CDKTHL")

<400> SEQUENCE: 128

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Leu
            100                 105
```

<210> SEQ ID NO 129
<211> LENGTH: 109
<212> TYPE: PRT
<213> ORGANISM: Artificial Sequence
<220> FEATURE:
<223> OTHER INFORMATION: Fab heavy chain constant region ("CDKTHTC");
      "Fab-C" in Examples refers to this sequence

<400> SEQUENCE: 129

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys
            100                 105
```

<210> SEQ ID NO 130
<211> LENGTH: 112
<212> TYPE: PRT
<213> ORGANISM: Artificial Sequence
<220> FEATURE:
<223> OTHER INFORMATION: Fab heavy chain constant region ("CDKTHTCPPC")

<400> SEQUENCE: 130

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

<210> SEQ ID NO 131
<211> LENGTH: 112
<212> TYPE: PRT
<213> ORGANISM: Artificial Sequence
<220> FEATURE:
<223> OTHER INFORMATION: Fab heavy chain constant region ("CDKTHTCPPS")

<400> SEQUENCE: 131

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Ser
            100                 105                 110
```

<210> SEQ ID NO 132
<211> LENGTH: 112
<212> TYPE: PRT
<213> ORGANISM: Artificial Sequence
<220> FEATURE:
<223> OTHER INFORMATION: Fab heavy chain constant region ("CDKTHTSPPC")

<400> SEQUENCE: 132

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ser Pro Pro Cys
            100                 105                 110
```

<210> SEQ ID NO 133
<211> LENGTH: 224
<212> TYPE: PRT
<213> ORGANISM: Artificial Sequence
<220> FEATURE:
<223> OTHER INFORMATION: AFD.v14 HC Fab ("CDKTHTC")

<400> SEQUENCE: 133

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
```

```
                100             105             110
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
            210                 215                 220

<210> SEQ ID NO 134
<211> LENGTH: 107
<212> TYPE: PRT
<213> ORGANISM: Artificial Sequence
<220> FEATURE:
<223> OTHER INFORMATION: Fab heavy chain constant region ("CDKTH")

<400> SEQUENCE: 134

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 135
<211> LENGTH: 106
<212> TYPE: PRT
<213> ORGANISM: Artificial Sequence
<220> FEATURE:
<223> OTHER INFORMATION: Fab heavy chain constant region ("CDKT")

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr
            100                 105
```

<210> SEQ ID NO 136
<211> LENGTH: 105
<212> TYPE: PRT
<213> ORGANISM: Artificial Sequence
<220> FEATURE:
<223> OTHER INFORMATION: Fab heavy chain constant region ("CDK")

<400> SEQUENCE: 136

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys
            100                 105
```

<210> SEQ ID NO 137
<211> LENGTH: 104
<212> TYPE: PRT
<213> ORGANISM: Artificial Sequence
<220> FEATURE:
<223> OTHER INFORMATION: Fab heavy chain constant region ("CD")

<400> SEQUENCE: 137

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100
```

<210> SEQ ID NO 138
<211> LENGTH: 101
<212> TYPE: PRT
<213> ORGANISM: Artificial Sequence
<220> FEATURE:
<223> OTHER INFORMATION: Fab heavy chain constant region (IgG2)

<400> SEQUENCE: 138

```
Ala Ser Thr Lys Gly Pro Ser Val Phe Pro Leu Ala Pro Cys Ser Arg
```

```
                1               5                   10                  15
Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100
```

<210> SEQ ID NO 139
<211> LENGTH: 105
<212> TYPE: PRT
<213> ORGANISM: Artificial Sequence
<220> FEATURE:
<223> OTHER INFORMATION: Fab heavy chain constant region (IgG4)
      ("KYGPP")

<400> SEQUENCE: 139

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro
            100                 105
```

<210> SEQ ID NO 140
<211> LENGTH: 222
<212> TYPE: PRT
<213> ORGANISM: Artificial Sequence
<220> FEATURE:
<223> OTHER INFORMATION: hu20D12.v2.1 HC Fab ("CDKTH")

<400> SEQUENCE: 140

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Thr Ser Gly Gly Thr Asn Phe Asn Glu Lys Phe
        50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His
    210                 215                 220
```

<210> SEQ ID NO 141
<211> LENGTH: 221
<212> TYPE: PRT
<213> ORGANISM: Artificial Sequence
<220> FEATURE:
<223> OTHER INFORMATION: hu20D12.v2.1 HC Fab ("CDKT")

<400> SEQUENCE: 141

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr
    210                 215                 220
```

<210> SEQ ID NO 142

<211> LENGTH: 220
<212> TYPE: PRT
<213> ORGANISM: Artificial Sequence
<220> FEATURE:
<223> OTHER INFORMATION: hu20D12.v2.1 HC Fab ("CDK")

<400> SEQUENCE: 142

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys
    210                 215                 220

<210> SEQ ID NO 143
<211> LENGTH: 219
<212> TYPE: PRT
<213> ORGANISM: Artificial Sequence
<220> FEATURE:
<223> OTHER INFORMATION: hu20D12.v2.1 HC Fab ("CD")

<400> SEQUENCE: 143

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Thr Ser Gly Gly Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr

```
                100              105              110
Val Ser Ser Ala Ser Thr Lys Gly Pro Ser Val Phe Pro Leu Ala Pro
            115              120              125

Ser Ser Lys Ser Thr Ser Gly Gly Thr Ala Ala Leu Gly Cys Leu Val
    130              135              140

Lys Asp Tyr Phe Pro Glu Pro Val Thr Val Ser Trp Asn Ser Gly Ala
145              150              155              160

Leu Thr Ser Gly Val His Thr Phe Pro Ala Val Leu Gln Ser Ser Gly
                165              170              175

Leu Tyr Ser Leu Ser Ser Val Val Thr Val Pro Ser Ser Ser Leu Gly
            180              185              190

Thr Gln Thr Tyr Ile Cys Asn Val Asn His Lys Pro Ser Asn Thr Lys
        195              200              205

Val Asp Lys Lys Val Glu Pro Lys Ser Cys Asp
210              215
```

<210> SEQ ID NO 144
<211> LENGTH: 221
<212> TYPE: PRT
<213> ORGANISM: Artificial Sequence
<220> FEATURE:
<223> OTHER INFORMATION: hu20D12.v2.1 HC Fab ("APPC")

<400> SEQUENCE: 144

```
Glu Val Gln Leu Val Gln Ser Gly Ala Glu Val Lys Lys Pro Gly Ala
1               5                10               15

Ser Val Lys Val Ser Cys Lys Ala Ser Gly Tyr Thr Phe Thr Ser Tyr
            20               25               30

Tyr Met Tyr Trp Val Arg Gln Ala Pro Gly Gln Gly Leu Glu Trp Ile
        35               40               45

Gly Glu Ile Asn Pro Thr Ser Gly Gly Thr Asn Phe Asn Glu Lys Phe
    50               55               60

Lys Ser Arg Ala Thr Leu Thr Val Asp Thr Ser Thr Ser Thr Ala Tyr
65               70               75               80

Leu Glu Leu Ser Ser Leu Arg Ser Glu Asp Thr Ala Val Tyr Tyr Cys
            85               90               95

Ala Arg Glu Gly Gly Phe Ala Tyr Trp Gly Gln Gly Thr Leu Val Thr
        100              105              110

Val Ser Ser Ala Ser Thr Lys Gly Pro Ser Val Phe Pro Leu Ala Pro
    115              120              125

Ser Ser Lys Ser Thr Ser Gly Gly Thr Ala Ala Leu Gly Cys Leu Val
130              135              140

Lys Asp Tyr Phe Pro Glu Pro Val Thr Val Ser Trp Asn Ser Gly Ala
145              150              155              160

Leu Thr Ser Gly Val His Thr Phe Pro Ala Val Leu Gln Ser Ser Gly
            165              170              175

Leu Tyr Ser Leu Ser Ser Val Val Thr Val Pro Ser Ser Ser Leu Gly
        180              185              190

Thr Gln Thr Tyr Ile Cys Asn Val Asn His Lys Pro Ser Asn Thr Lys
    195              200              205

Val Asp Lys Lys Val Glu Pro Lys Ser Ala Pro Pro Cys
210              215              220
```

<210> SEQ ID NO 145
<211> LENGTH: 221
<212> TYPE: PRT

<213> ORGANISM: Artificial Sequence
<220> FEATURE:
<223> OTHER INFORMATION: hu20D12.v2.1 HC Fab ("SGGC")

<400> SEQUENCE: 145

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Tyr | Met | Tyr | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | | 35 | | | | | 40 | | | | | 45 | | |

| Gly | Glu | Ile | Asn | Pro | Thr | Ser | Gly | Gly | Thr | Asn | Phe | Asn | Glu | Lys | Phe |
|---|---|---|---|---|---|---|---|---|---|---|---|---|---|---|---|
| | 50 | | | | | 55 | | | | | 60 | | | | |

| Lys | Ser | Arg | Ala | Thr | Leu | Thr | Val | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Leu | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Gly | Gly | Phe | Ala | Tyr | Trp | Gly | Gln | Gly | Thr | Leu | Val | Thr |
|---|---|---|---|---|---|---|---|---|---|---|---|---|---|---|---|
| | | | 100 | | | | | 105 | | | | | 110 | | |

| Val | Ser | Ser | Ala | Ser | Thr | Lys | Gly | Pro | Ser | Val | Phe | Pro | Leu | Ala | Pro |
|---|---|---|---|---|---|---|---|---|---|---|---|---|---|---|---|
| | | 115 | | | | | 120 | | | | | 125 | | | |

| Ser | Ser | Lys | Ser | Thr | Ser | Gly | Gly | Thr | Ala | Ala | Leu | Gly | Cys | Leu | Val |
|---|---|---|---|---|---|---|---|---|---|---|---|---|---|---|---|
| 130 | | | | | 135 | | | | | 140 | | | | | |

| Lys | Asp | Tyr | Phe | Pro | Glu | Pro | Val | Thr | Val | Ser | Trp | Asn | Ser | Gly | Ala |
|---|---|---|---|---|---|---|---|---|---|---|---|---|---|---|---|
| 145 | | | | | 150 | | | | | 155 | | | | | 160 |

| Leu | Thr | Ser | Gly | Val | His | Thr | Phe | Pro | Ala | Val | Leu | Gln | Ser | Ser | Gly |
|---|---|---|---|---|---|---|---|---|---|---|---|---|---|---|---|
| | | | | 165 | | | | | 170 | | | | | 175 | |

| Leu | Tyr | Ser | Leu | Ser | Ser | Val | Val | Thr | Val | Pro | Ser | Ser | Ser | Leu | Gly |
|---|---|---|---|---|---|---|---|---|---|---|---|---|---|---|---|
| | | | 180 | | | | | 185 | | | | | 190 | | |

| Thr | Gln | Thr | Tyr | Ile | Cys | Asn | Val | Asn | His | Lys | Pro | Ser | Asn | Thr | Lys |
|---|---|---|---|---|---|---|---|---|---|---|---|---|---|---|---|
| | | | 195 | | | | | 200 | | | | | 205 | | |

| Val | Asp | Lys | Lys | Val | Glu | Pro | Lys | Ser | Ser | Gly | Gly | Cys |
|---|---|---|---|---|---|---|---|---|---|---|---|---|
| | 210 | | | | | 215 | | | | | 220 | |

<210> SEQ ID NO 146
<211> LENGTH: 223
<212> TYPE: PRT
<213> ORGANISM: Artificial Sequence
<220> FEATURE:
<223> OTHER INFORMATION: hu20D12.v2.1 HC Fab ("CYGPPC")

<400> SEQUENCE: 146

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Tyr | Met | Tyr | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | | 35 | | | | | 40 | | | | | 45 | | |

| Gly | Glu | Ile | Asn | Pro | Thr | Ser | Gly | Gly | Thr | Asn | Phe | Asn | Glu | Lys | Phe |
|---|---|---|---|---|---|---|---|---|---|---|---|---|---|---|---|
| | 50 | | | | | 55 | | | | | 60 | | | | |

| Lys | Ser | Arg | Ala | Thr | Leu | Thr | Val | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Leu | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Gly | Gly | Phe | Ala | Tyr | Trp | Gly | Gln | Gly | Thr | Leu | Val | Thr |
|---|---|---|---|---|---|---|---|---|---|---|---|---|---|---|---|
| | | | 100 | | | | | 105 | | | | | 110 | | |

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Tyr Gly Pro Pro Cys
210                 215                 220
```

<210> SEQ ID NO 147
<211> LENGTH: 222
<212> TYPE: PRT
<213> ORGANISM: Artificial Sequence
<220> FEATURE:
<223> OTHER INFORMATION: hu20D12.v2.3 HC Fab ("CDKTH")

<400> SEQUENCE: 147

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His
210                 215                 220
```

<210> SEQ ID NO 148
<211> LENGTH: 221
<212> TYPE: PRT
<213> ORGANISM: Artificial Sequence
<220> FEATURE:

<223> OTHER INFORMATION: hu20D12.v2.3 HC Fab ("CDKT")

<400> SEQUENCE: 148

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr
    210                 215                 220
```

<210> SEQ ID NO 149
<211> LENGTH: 220
<212> TYPE: PRT
<213> ORGANISM: Artificial Sequence
<220> FEATURE:
<223> OTHER INFORMATION: hu20D12.v2.3 HC Fab ("CDK")

<400> SEQUENCE: 149

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125
```

```
Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys
210                 215                 220
```

<210> SEQ ID NO 150
<211> LENGTH: 219
<212> TYPE: PRT
<213> ORGANISM: Artificial Sequence
<220> FEATURE:
<223> OTHER INFORMATION: hu20D12.v2.3 HC Fab ("CD")

<400> SEQUENCE: 150

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Tyr Ser Gly Asp Thr Asn Phe Asn Glu Lys Phe
50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp
210                 215
```

<210> SEQ ID NO 151
<211> LENGTH: 221
<212> TYPE: PRT
<213> ORGANISM: Artificial Sequence
<220> FEATURE:
<223> OTHER INFORMATION: hu20D12.v2.3 HC Fab ("APPC")

<400> SEQUENCE: 151

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Ala Pro Pro Cys
    210                 215                 220

<210> SEQ ID NO 152
<211> LENGTH: 221
<212> TYPE: PRT
<213> ORGANISM: Artificial Sequence
<220> FEATURE:
<223> OTHER INFORMATION: hu20D12.v2.3 HC Fab ("SGGC")

<400> SEQUENCE: 152

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Tyr Ser Gly Asp Thr Asn Phe Asn Glu Lys Phe
    50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Ser Gly Gly Cys
210                 215                 220
```

<210> SEQ ID NO 153
<211> LENGTH: 223
<212> TYPE: PRT
<213> ORGANISM: Artificial Sequence
<220> FEATURE:
<223> OTHER INFORMATION: hu20D12.v2.3 HC Fab ("CYGPPC")

<400> SEQUENCE: 153

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
            35                  40                  45

Gly Glu Ile Asn Pro Tyr Ser Gly Asp Thr Asn Phe Asn Glu Lys Phe
50                  55                  60

Lys Ser Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
            85                  90                  95

Ala Arg Glu Gly Gly Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Tyr Gly Pro Pro Cys
210                 215                 220
```

<210> SEQ ID NO 154
<211> LENGTH: 112
<212> TYPE: PRT
<213> ORGANISM: Artificial Sequence
<220> FEATURE:
<223> OTHER INFORMATION: Fab heavy chain constant region ("CDKTHTAPPC")

<400> SEQUENCE: 154

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ala Pro Pro Cys
            100                 105                 110

<210> SEQ ID NO 155
<211> LENGTH: 112
<212> TYPE: PRT
<213> ORGANISM: Artificial Sequence
<220> FEATURE:
<223> OTHER INFORMATION: Fab heavy chain constant region ("CDKTHTSGGC")

<400> SEQUENCE: 155

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ser Gly Gly Cys
            100                 105                 110

<210> SEQ ID NO 156
<211> LENGTH: 108
<212> TYPE: PRT
<213> ORGANISM: Artificial Sequence
<220> FEATURE:
<223> OTHER INFORMATION: Fab heavy chain constant region ("CYGPPC")

<400> SEQUENCE: 156

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Tyr Gly Pro Pro Cys
            100                 105

<210> SEQ ID NO 157
<211> LENGTH: 102
<212> TYPE: PRT
<213> ORGANISM: Artificial Sequence
<220> FEATURE:
<223> OTHER INFORMATION: Fab heavy chain constant region (IgG2 Fab-C)
      ("VERKC")

<400> SEQUENCE: 157

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys
            100

<210> SEQ ID NO 158
<211> LENGTH: 106
<212> TYPE: PRT
<213> ORGANISM: Artificial Sequence
<220> FEATURE:
<223> OTHER INFORMATION: Fab heavy chain constant region (IgG4 Fab-C)
      ("KYGPPC")

<400> SEQUENCE: 158

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys
            100                 105

<210> SEQ ID NO 159
<211> LENGTH: 103
<212> TYPE: PRT
<213> ORGANISM: Artificial Sequence
<220> FEATURE:
<223> OTHER INFORMATION: Fab heavy chain constant region (IgG4) ("KYG")

<400> SEQUENCE: 159

Ala Ser Thr Lys Gly Pro Ser Val Phe Pro Leu Ala Pro Cys Ser Arg

```
                1               5                  10                  15
Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
                100
```

<210> SEQ ID NO 160
<211> LENGTH: 102
<212> TYPE: PRT
<213> ORGANISM: Artificial Sequence
<220> FEATURE:
<223> OTHER INFORMATION: Fab heavy chain constant region (IgG4) ("KY")

<400> SEQUENCE: 160

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr
                100
```

<210> SEQ ID NO 161
<211> LENGTH: 101
<212> TYPE: PRT
<213> ORGANISM: Artificial Sequence
<220> FEATURE:
<223> OTHER INFORMATION: Fab heavy chain constant region (IgG4) ("K")

<400> SEQUENCE: 161

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

Arg Val Glu Ser Lys
            100

<210> SEQ ID NO 162
<211> LENGTH: 4
<212> TYPE: PRT
<213> ORGANISM: Artificial Sequence
<220> FEATURE:
<223> OTHER INFORMATION: CPPC

<400> SEQUENCE: 162

Cys Pro Pro Cys
1

<210> SEQ ID NO 163
<211> LENGTH: 104
<212> TYPE: PRT
<213> ORGANISM: Artificial Sequence
<220> FEATURE:
<223> OTHER INFORMATION: Fab heavy chain constant region (IgG4) ("KYGP")

<400> SEQUENCE: 163

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro
            100

<210> SEQ ID NO 164
<211> LENGTH: 108
<212> TYPE: PRT
<213> ORGANISM: Artificial Sequence
<220> FEATURE:
<223> OTHER INFORMATION: Fab heavy chain constant region ("CDKTHX")
<220> FEATURE:
<221> NAME/KEY: MISC_FEATURE
<222> LOCATION: (108)..(108)
<223> OTHER INFORMATION: X is selected from any amino acid except T

<400> SEQUENCE: 164

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Xaa
            100                 105

<210> SEQ ID NO 165
<211> LENGTH: 6
<212> TYPE: PRT
<213> ORGANISM: Artificial Sequence
<220> FEATURE:
<223> OTHER INFORMATION: C-terminus of heavy chain of a Fab fragment for
      SEQ ID NO: 113

<400> SEQUENCE: 165

Cys Asp Lys Thr His Thr
1               5

<210> SEQ ID NO 166
<211> LENGTH: 6
<212> TYPE: PRT
<213> ORGANISM: Artificial Sequence
<220> FEATURE:
<223> OTHER INFORMATION: C-terminus of heavy chain of a Fab fragment for
      SEQ ID NO: 128

<400> SEQUENCE: 166

Cys Asp Lys Thr His Leu
1               5

<210> SEQ ID NO 167
<211> LENGTH: 5
<212> TYPE: PRT
<213> ORGANISM: Artificial Sequence
<220> FEATURE:
<223> OTHER INFORMATION: C-terminus of heavy chain of a Fab fragment for
      SEQ ID NO: 134

<400> SEQUENCE: 167

Cys Asp Lys Thr His
1               5

<210> SEQ ID NO 168
<211> LENGTH: 4
<212> TYPE: PRT
<213> ORGANISM: Artificial Sequence
<220> FEATURE:
<223> OTHER INFORMATION: C-terminus of heavy chain of a Fab fragment for
      SEQ ID NO: 135

<400> SEQUENCE: 168

Cys Asp Lys Thr
1

<210> SEQ ID NO 169
<211> LENGTH: 6
<212> TYPE: PRT
<213> ORGANISM: Artificial Sequence
<220> FEATURE:
<223> OTHER INFORMATION: C-terminus of heavy chain of a Fab fragment
<220> FEATURE:
<221> NAME/KEY: MISC_FEATURE
<222> LOCATION: (6)..(6)
<223> OTHER INFORMATION: X is any amino acid except T

<400> SEQUENCE: 169

Cys Asp Lys Thr His Xaa
1               5

<210> SEQ ID NO 170
<211> LENGTH: 7

```
<212> TYPE: PRT
<213> ORGANISM: Artificial Sequence
<220> FEATURE:
<223> OTHER INFORMATION: C-terminus of heavy chain of a Fab fragment for
      SEQ ID NO: 129

<400> SEQUENCE: 170

Cys Asp Lys Thr His Thr Cys
1               5

<210> SEQ ID NO 171
<211> LENGTH: 10
<212> TYPE: PRT
<213> ORGANISM: Artificial Sequence
<220> FEATURE:
<223> OTHER INFORMATION: C-terminus of heavy chain of a Fab fragment for
      SEQ ID NO: 130

<400> SEQUENCE: 171

Cys Asp Lys Thr His Thr Cys Pro Pro Cys
1               5                   10

<210> SEQ ID NO 172
<211> LENGTH: 10
<212> TYPE: PRT
<213> ORGANISM: Artificial Sequence
<220> FEATURE:
<223> OTHER INFORMATION: C-terminus of heavy chain of a Fab fragment for
      SEQ ID NO: 131

<400> SEQUENCE: 172

Cys Asp Lys Thr His Thr Cys Pro Pro Ser
1               5                   10

<210> SEQ ID NO 173
<211> LENGTH: 10
<212> TYPE: PRT
<213> ORGANISM: Artificial Sequence
<220> FEATURE:
<223> OTHER INFORMATION: C-terminus of heavy chain of a Fab fragment for
      SEQ ID NO: 132

<400> SEQUENCE: 173

Cys Asp Lys Thr His Thr Ser Pro Pro Cys
1               5                   10

<210> SEQ ID NO 174
<211> LENGTH: 10
<212> TYPE: PRT
<213> ORGANISM: Artificial Sequence
<220> FEATURE:
<223> OTHER INFORMATION: C-terminus of heavy chain of a Fab fragment

<400> SEQUENCE: 174

Cys Asp Lys Thr His Thr Ala Pro Pro Cys
1               5                   10

<210> SEQ ID NO 175
<211> LENGTH: 10
<212> TYPE: PRT
<213> ORGANISM: Artificial Sequence
<220> FEATURE:
<223> OTHER INFORMATION: C-terminus of heavy chain of a Fab fragment

<400> SEQUENCE: 175

Cys Asp Lys Thr His Thr Ser Gly Gly Cys
1               5                   10
```

```
<210> SEQ ID NO 176
<211> LENGTH: 6
<212> TYPE: PRT
<213> ORGANISM: Artificial Sequence
<220> FEATURE:
<223> OTHER INFORMATION: C-terminus of heavy chain of a Fab fragment for
      SEQ ID NO: 156

<400> SEQUENCE: 176

Cys Tyr Gly Pro Pro Cys
1               5

<210> SEQ ID NO 177
<211> LENGTH: 4
<212> TYPE: PRT
<213> ORGANISM: Artificial Sequence
<220> FEATURE:
<223> OTHER INFORMATION: C-terminus of heavy chain of a Fab fragment for
      SEQ ID NO: 154

<400> SEQUENCE: 177

Ala Pro Pro Cys
1

<210> SEQ ID NO 178
<211> LENGTH: 4
<212> TYPE: PRT
<213> ORGANISM: Artificial Sequence
<220> FEATURE:
<223> OTHER INFORMATION: C-terminus of heavy chain of a Fab fragment for
      SEQ ID NO: 155

<400> SEQUENCE: 178

Ser Gly Gly Cys
1

<210> SEQ ID NO 179
<211> LENGTH: 4
<212> TYPE: PRT
<213> ORGANISM: Artificial Sequence
<220> FEATURE:
<223> OTHER INFORMATION: C-terminus of heavy chain of a Fab fragment for
      SEQ ID NO: 138

<400> SEQUENCE: 179

Val Glu Arg Lys
1

<210> SEQ ID NO 180
<211> LENGTH: 5
<212> TYPE: PRT
<213> ORGANISM: Artificial Sequence
<220> FEATURE:
<223> OTHER INFORMATION: C-terminus of heavy chain of a Fab fragment for
      SEQ ID NO: 157

<400> SEQUENCE: 180

Val Glu Arg Lys Cys
1               5

<210> SEQ ID NO 181
<211> LENGTH: 5
<212> TYPE: PRT
<213> ORGANISM: Artificial Sequence
<220> FEATURE:
<223> OTHER INFORMATION: C-terminus of heavy chain of a Fab fragment for
      SEQ ID NO: 139
```

```
<400> SEQUENCE: 181

Lys Tyr Gly Pro Pro
1               5

<210> SEQ ID NO 182
<211> LENGTH: 4
<212> TYPE: PRT
<213> ORGANISM: Artificial Sequence
<220> FEATURE:
<223> OTHER INFORMATION: C-terminus of heavy chain of a Fab fragment for
      SEQ ID NO: 163

<400> SEQUENCE: 182

Lys Tyr Gly Pro
1

<210> SEQ ID NO 183
<211> LENGTH: 6
<212> TYPE: PRT
<213> ORGANISM: Artificial Sequence
<220> FEATURE:
<223> OTHER INFORMATION: C-terminus of heavy chain of a Fab fragment for
      SEQ ID NO: 158

<400> SEQUENCE: 183

Lys Tyr Gly Pro Pro Cys
1               5
```

ANTI-FACTOR D ANTIBODIES AND CONJUGATES

CROSS-REFERENCE TO RELATED APPLICATIONS

This application claims the benefit of priority of U.S. Provisional Application No. 62/249,166, filed Oct. 30, 2015, and U.S. Provisional Application No. 62/250,995, filed Nov. 4, 2015, each of which is incorporated by reference herein in its entirety for any purpose.

FIELD

The present invention relates to anti-Factor D antibodies and conjugates and methods of using the same.

BACKGROUND

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses three distinct activation pathways, designated the classical, mannose-binding lectin, and the alternative pathways. V. M. Holers In Clinical Immunology: Principles and Practice, ed. R. R. Rich, Mosby Press; 1996, 363-391. The classical pathway is a calcium/magnesium-dependent cascade which is normally activated by the formation of antigen-antibody complexes. The mannose-binding lectin (MBL) pathway is initiated by the binding of MBL to carbohydrate structures on pathogens, resulting in the activation of MBL protease (MASP) that cleaves C2 and C4 to form active C2a, C2b, C4a and C4b. The alternative pathway is a magnesium-dependent cascade which is activated by deposition and activation of C3 on certain susceptible surfaces (e.g. cell wall polysaccharides of yeast and bacteria, and certain biopolymer materials). Activation of the complement pathway generates biologically active fragments of complement proteins, e.g. C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 μg/ml), and it has been shown to be the limiting enzyme for activation of the alternative complement pathway. P. H. Lesavre and H. J. Müller-Eberhard. (1978) J. Exp. Med. 148: 1498-1510; J. E. Volanakis et al. (1985) New Eng. J. Med. 312: 395-401.

The down-regulation of complement activation has been demonstrated to be effective in treating several disease indications in animal models and in ex vivo studies, e.g. systemic lupus erythematosus and glomerulonephritis, rheumatoid arthritis, cardiopulmonary bypass and hemodialysis, hyperacute rejection in organ transplantation, myocardial infarction, reperfusion injury, and adult respiratory distress syndrome. In addition, other inflammatory conditions and autoimmune/immune complex diseases are also closely associated with complement activation, including thermal injury, severe asthma, anaphylactic shock, bowel inflammation, urticaria, angioedema, vasculitis, multiple sclerosis, myasthenia gravis, membranoproliferative glomerulonephritis, and Sjogren's syndrome.

Age-related macular degeneration (AMD) is a progressive chronic disease of the central retina with significant consequences for visual acuity. Lim et al. (2012) Lancet 379:1728. Late forms of the disease are the leading cause of vision loss in industrialized countries. For the Caucasian population ≥40 years of age the prevalence of early AMD is estimated at 6.8% and advanced AMD at 1.5%. de Jong (2006) N. Engl. J. Med. 355: 1474. The prevalence of late AMD increases dramatically with age rising to 11.8% after 80 years of age. Two types of AMD exist, non-exudative (dry) and exudative (wet) AMD. The more common dry form AMD involves atrophic and hypertrophic changes in the retinal pigment epithelium (RPE) underlying the central retina (macula) as well as deposits (drusen) on the RPE. Advanced dry AMD can result in significant retinal damage, including geographic atrophy (GA), with irreversible vision loss. Moreover, patients with dry AMD can progress to the wet form, in which abnormal blood vessels called choroidal neovascular membranes (CNVMs) develop under the retina, leak fluid and blood, and ultimately cause a blinding disciform scar in and under the retina.

Drugs targeting new blood vessel formation (neovasculazation) have been the mainstay for treating wet AMD. Ranibizumab, which is an anti-VEGFA antibody fragment, has proven to be highly effective in improving vision for patients afflicted with wet AMD. Recent studies have implicated an association between AMD and key proteins in the complement cascade and a number of therapies targeting specific complement components are being developed to treat dry AMD. A humanized anti-Factor D Fab fragment (aFD.WT; lampalizumab; FCFD4514S) that potently inhibits Factor D and the alternative complement pathway, through binding to an exosite on factor D is currently in clinical development for the treatment of GA associated with dry AMD. Katschke et al. (2012) J. Biol. Chem. 287:12886. A recent phase II clinical trial has shown that monthly intravitreal injection of lampalizumab effectively slowed the progression of GA lesions in patients with advanced dry AMD.

Eyes have many unique biophysical and anatomic features that make the ocular drug delivery more challenging. For example, blood-ocular barriers are defense mechanisms to protect the eye from infection, but at the same time make it hard for drug to penetrate, especially for diseases in the posterior segments of the eye. Consequently, high-dose administration is often desired to achieve and maintain drug's onsite bioavailability (e.g., ocular residence time) in order to improve efficacy. Meanwhile, the limited space in the back of the eye restrains the drug volume to be delivered, which in turn demands drugs to be delivered in a high concentration formulation.

Patients with ocular diseases can also benefit from long acting/slow released delivery of therapeutics. Less frequent dosing would provide improved convenience to the patient, have potential benefits of decreased infection rate and increased clinical efficacy. Controlled release of high dose drugs could also minimize drug side effects. Two promising systems for long-acting delivery are PLGA-based solid implants and an implantable port delivery system (PDS). Both systems have the potential to provide near zero-order release kinetics for an extended period of time. For PLGA implants the protein drug is encapsulated in a hydrophobic polymer matrix and drug release is accomplished via slow hydrolysis of the polymer. The rate of release can be controlled by changing the drug loading, polymer hydrophobicity, or polymer molecular weight. The PDS is a refillable device where release into the vitreous is controlled by a porous metal membrane comprising a titanium frit. Since the reservoir has a low volume, a high protein concentration is required for effective delivery with the PDS.

In addition to or in lieu of high concentration and long acting delivery, increased bioavailability (e.g., ocular residence time) of the drug can be achieved, or facilitated, by post-translational modifications, wherein the protein drug is covalently conjugated with natural or synthetic polymers such as polysialylation, HESylation (conjugation with hydroxyethyl starch) and PEGylation. Chen et al (2011) Expert. Opin. Drug Deliv. 8:1221-36; Kontermann (2009) BioDrugs 23:93-109. PEGylation, the covalent attachment of polymer polyethylene glycol (PEG) to a protein, is a well-established technology especially useful for extending the half-life of antibody fragment therapeutics. Jevsevar et al. (2010) Biotech. J. 5:113-128.

The conditions that a drug is exposed to vary depending on the delivery system used. For incorporation into solid PLGA implants, lyophilized or spray-dried drug is used. Implants are produced using a hot-melt extrusion process such that the drug is briefly exposed to temperatures approaching 90° C. Although the drug remains in solid state for the duration of release, degradation of PLGA may expose the drug to a low pH environment. In contrast, drug delivered with the PDS is maintained at high concentration in liquid state and exposed to vitreous which is characterized as a reducing environment at physiological ionic strength and pH.

Thus, there exists great needs for anti-factor D antibodies with improved stabilities, preferably suitable for high concentration formulation and/or long acting delivery.

SUMMARY

Lampalizumab is currently in phase III clinical trials for treatment of geographic atrophy (GA), an advanced form of dry AMD. While human clinical trials in GA indicate that a treatment effect is obtained with monthly intravitreal injection of lampalizumab, there exist incentives to use higher drug doses to achieve even better efficacy. Further, less frequent dosing would provide improved convenience to the patient, have potential benefits of decreased infection rate and increased clinical efficacy, and could facilitate treatment of patients with less advanced forms of dry AMD. In order to develop an anti-Factor D antibody with improved solubility and chemical stability suitable for higher drug doses or long-acting delivery, anti-Factor D variants have been investigated. Anti-Factor D variants have been identified with improved solubility and chemical stability. In order to further extend the effect of anti-Factor D antibodies, conjugation to a polyol, such as PEG, would be beneficial. The anti-Factor D variants with improved solubility and chemical stability were found to be very viscous when conjugated to PEG in high concentration solutions, however, making them less suitable for intravitreal injection. The present inventors have developed additional anti-Factor D antibodies that have comparable affinity for human Factor D as lampalizumab, improved affinity for cynomolgus Factor D, as well as improved solubility and chemical stability, and are less viscous when conjugated to PEG, making them more suitable as long-acting therapeutic agents.

The invention provides improved anti-Factor D antibodies and conjugates and methods of using the same.

In some embodiments, an isolated antibody that binds to Factor D, wherein the antibody comprises (a) HVR-H1 comprising the amino acid sequence SYYMY (SEQ ID NO: 15); (b) HVR-H2 comprising the amino acid sequence $X_4$INP$X_5X_6$G$X_7$TNFNEKFKS (SEQ ID NO: 111), wherein $X_4$ is selected from E and W; $X_5$ is selected from T and Y; $X_6$ is selected from N, S, and Q; and $X_7$ is selected from G, D, and E; (c) HVR-H3 comprising the amino acid sequence EGGFAY (SEQ ID NO: 25); (d) HVR-L1 comprising the amino acid sequence KASQNVDTDVA (SEQ ID NO:9); (e) HVR-L2 comprising the amino acid sequence SASSR$X_1$S (SEQ ID NO: 108), wherein $X_1$ is selected from Y, K, and R; and (f) HVR-L3 comprising the amino acid sequence QQY$X_3$NYPLT (SEQ ID NO: 110), wherein $X_3$ is selected from N and E is provided.

In some aspects, the antibody comprises the sequence $X_2$SASSR$X_1$S (SEQ ID NO: 109), wherein $X_1$ is selected from Y, K, and R, and $X_2$ is selected from Y, R, S, K, and Q. In some embodiments, $X_2$ is R. In other aspects, $X_1$ is Y.

In some embodiments, the antibody comprises HVR-H1 comprising the amino acid sequence of SEQ ID NO: 15, HVR-H2 comprising an amino acid sequence selected from SEQ ID NOs: 16 to 24, HVR-H3 comprising the amino acid sequence of SEQ ID NO: 25, HVR-L1 comprising the amino acid sequence of SEQ ID NO: 9, HVR-L2 comprising an amino acid sequence selected from SEQ ID NOs: 10 to 12, and HVR-L3 comprising the amino acid sequence of SEQ ID NO: 13 or 14.

In certain embodiments, the antibody comprises:
a. HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
b. HVR-H1 comprising the amino acid sequence of SEQ ID NO: 15, HVR-H2 comprising the amino acid sequence of SEQ ID NO: 20, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
c. HVR-H1 comprising the amino acid sequence of SEQ ID NO: 15, HVR-H2 comprising the amino acid sequence of SEQ ID NO: 17, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
d. HVR-H1 comprising the amino acid sequence of SEQ ID NO: 15, HVR-H2 comprising the amino acid sequence of SEQ ID NO: 18, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
e. HVR-H1 comprising the amino acid sequence of SEQ ID NO: 15, HVR-H2 comprising the amino acid sequence of SEQ ID NO: 19, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
f. HVR-H1 comprising the amino acid sequence of SEQ ID NO: 15, HVR-H2 comprising the amino acid sequence of SEQ ID NO: 21, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
g. HVR-H1 comprising the amino acid sequence of SEQ ID NO: 15, HVR-H2 comprising the amino acid sequence of SEQ ID NO: 22, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
h. HVR-H1 comprising the amino acid sequence of SEQ ID NO: 15, HVR-H2 comprising the amino acid sequence of SEQ ID NO: 23, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;
i. HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 11, HVR-L3 comprising the amino acid sequence of SEQ ID NO: 13;
j. HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 12, HVR-L3 comprising the amino acid sequence of SEQ ID NO: 13;
k. HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 14; or
l. HVR-H1 comprising the amino acid sequence of SEQ ID NO: 15, HVR-H2 comprising the amino acid sequence of SEQ ID NO: 24, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13.

In some embodiments, the amino acid at position 49 of the light chain is arginine (R).

In certain aspects, the antibody comprises a heavy chain variable region comprising an amino acid sequence selected from SEQ ID NOs: 27, 29, 31, 33, 35, 37, 39, 41, 43, 45, 47, 49, 51, 53, 55, 57, 59, 61, and 63.

In other aspects, the antibody comprises a light chain variable region comprising an amino acid sequence selected from SEQ ID NOs: 26, 28, 30, 32, 34, 36, 38, 40, 42, 44, 46, 48, 50, 52, 54, 56, 58, 60, and 62.

The antibody may comprise:

a heavy chain variable region comprising the amino acid sequence of SEQ ID NO: 35 and a light chain variable region comprising the amino acid sequence of SEQ ID NO: 34;

a heavy chain variable region comprising the amino acid sequence of SEQ ID NO: 39 and a light chain variable region comprising the amino acid sequence of SEQ ID NO: 38;

a heavy chain variable region comprising the amino acid sequence of SEQ ID NO: 33 and a light chain variable region comprising the amino acid sequence of SEQ ID NO: 32;

a heavy chain variable region comprising the amino acid sequence of SEQ ID NO: 45 and a light chain variable region comprising the amino acid sequence of SEQ ID NO: 44;

a heavy chain variable region comprising the amino acid sequence of SEQ ID NO: 47 and a light chain variable region comprising the amino acid sequence of SEQ ID NO: 46;

a heavy chain variable region comprising the amino acid sequence of SEQ ID NO: 49 and a light chain variable region comprising the amino acid sequence of SEQ ID NO: 48;

a heavy chain variable region comprising the amino acid sequence of SEQ ID NO: 29 and a light chain variable region comprising the amino acid sequence of SEQ ID NO: 28;

a heavy chain variable region comprising the amino acid sequence of SEQ ID NO: 31 and a light chain variable region comprising the amino acid sequence of SEQ ID NO: 30;

a heavy chain variable region comprising the amino acid sequence of SEQ ID NO: 37 and a light chain variable region comprising the amino acid sequence of SEQ ID NO: 36;

a heavy chain variable region comprising the amino acid sequence of SEQ ID NO: 41 and a light chain variable region comprising the amino acid sequence of SEQ ID NO: 40;

a heavy chain variable region comprising the amino acid sequence of SEQ ID NO: 61 and a light chain variable region comprising the amino acid sequence of SEQ ID NO: 60;

a heavy chain variable region comprising the amino acid sequence of SEQ ID NO: 43 and a light chain variable region comprising the amino acid sequence of SEQ ID NO: 42;

a heavy chain variable region comprising the amino acid sequence of SEQ ID NO: 57 and a light chain variable region comprising the amino acid sequence of SEQ ID NO: 56;

a heavy chain variable region comprising the amino acid sequence of SEQ ID NO: 51 and a light chain variable region comprising the amino acid sequence of SEQ ID NO: 50;

a heavy chain variable region comprising the amino acid sequence of SEQ ID NO: 53 and a light chain variable region comprising the amino acid sequence of SEQ ID NO: 52;

a heavy chain variable region comprising the amino acid sequence of SEQ ID NO: 55 and a light chain variable region comprising the amino acid sequence of SEQ ID NO: 54;

a heavy chain variable region comprising the amino acid sequence of SEQ ID NO: 59 and a light chain variable region comprising the amino acid sequence of SEQ ID NO: 58; or a heavy chain variable region comprising the amino acid sequence of SEQ ID NO: 63 and a light chain variable region comprising the amino acid sequence of SEQ ID NO: 62.

In some embodiments, the antibody comprises a heavy chain variable region comprising the amino acid sequence of SEQ ID NO: 35 and a light chain variable region comprising the amino acid sequence of SEQ ID NO: 34, or wherein the antibody comprises a heavy chain variable region comprising the amino acid sequence of SEQ ID NO: 39 and a light chain variable region comprising the amino acid sequence of SEQ ID NO: 38.

The antibody may be a monoclonal antibody, a humanized antibody, or a chimeric antibody, or any combination of monoclonal, humanized, and chimeric.

In some embodiments, the antibody binds Factor D.

In certain aspects the antibody is a fragment. In some embodiments, the fragment is a Fab fragment.

In some embodiments, the antibody light chain comprises a light chain constant region comprising the sequence of SEQ ID NO: 112.

In some embodiments, the antibody heavy chain comprises a heavy chain constant region comprising a sequence selected from SEQ ID NOs: 113, 128 to 132, 134 to 137, and 154-156.

In certain aspects, the antibody comprises:

a heavy chain comprising an amino acid sequence selected from SEQ ID NOs: 71, 118 to 122, and 140 to 146, and a light chain comprising the amino acid sequence of SEQ ID NO: 70;

a heavy chain comprising an amino acid sequence selected from SEQ ID NO: 75, 123 to 127, and 147 to 153 and a light chain comprising the amino acid sequence of SEQ ID NO: 74;

a heavy chain comprising the amino acid sequence of SEQ ID NO: 65 and a light chain comprising the amino acid sequence of SEQ ID NO: 64;

a heavy chain comprising the amino acid sequence of SEQ ID NO: 65 and a light chain comprising the amino acid sequence of SEQ ID NO: 64;

a heavy chain comprising the amino acid sequence of SEQ ID NO: 67 and a light chain comprising the amino acid sequence of SEQ ID NO: 66;

a heavy chain comprising the amino acid sequence of SEQ ID NO: 69 and a light chain comprising the amino acid sequence of SEQ ID NO: 68;

a heavy chain comprising the amino acid sequence of SEQ ID NO: 73 and a light chain comprising the amino acid sequence of SEQ ID NO: 72;

a heavy chain comprising the amino acid sequence of SEQ ID NO: 77 and a light chain comprising the amino acid sequence of SEQ ID NO: 76;

a heavy chain comprising the amino acid sequence of SEQ ID NO: 79 and a light chain comprising the amino acid sequence of SEQ ID NO: 78;

a heavy chain comprising the amino acid sequence of SEQ ID NO: 81 and a light chain comprising the amino acid sequence of SEQ ID NO: 80;

a heavy chain comprising the amino acid sequence of SEQ ID NO: 83 and a light chain comprising the amino acid sequence of SEQ ID NO: 82;

a heavy chain comprising the amino acid sequence of SEQ ID NO: 85 and a light chain comprising the amino acid sequence of SEQ ID NO: 84;

a heavy chain comprising the amino acid sequence of SEQ ID NO: 87 and a light chain comprising the amino acid sequence of SEQ ID NO: 86;

a heavy chain comprising the amino acid sequence of SEQ ID NO: 89 and a light chain comprising the amino acid sequence of SEQ ID NO: 88;

a heavy chain comprising the amino acid sequence of SEQ ID NO: 91 and a light chain comprising the amino acid sequence of SEQ ID NO: 90;

a heavy chain comprising the amino acid sequence of SEQ ID NO: 93 and a light chain comprising the amino acid sequence of SEQ ID NO: 92;

a heavy chain comprising the amino acid sequence of SEQ ID NO: 95 and a light chain comprising the amino acid sequence of SEQ ID NO: 94;

a heavy chain comprising the amino acid sequence of SEQ ID NO: 97 and a light chain comprising the amino acid sequence of SEQ ID NO: 96; or a heavy chain comprising the amino acid sequence of SEQ ID NO: 99 and a light chain comprising the amino acid sequence of SEQ ID NO: 98.

In some aspects, the antibody comprises:

a heavy chain comprising an amino acid sequence selected from SEQ ID NOs: 71, 118 to 122, and 140 to 146, and a light chain comprising the amino acid sequence of SEQ ID NO: 70; or a heavy chain comprising an amino acid sequence selected from SEQ ID NO: 75, 123 to 127, and 147 to 153 and a light chain comprising the amino acid sequence of SEQ ID NO: 74.

In some embodiments, the antibody comprises an engineered cysteine. The engineered cysteine may be selected from a T110C, A136C, L170C, L175C, T183C, or T205C mutation in the heavy chain, and I106C, R108C, R142C, K149C, and V205C mutation in the light chain, wherein the residue number is according to Kabat numbering.

In certain aspects, Factor D is human Factor D comprising the amino acid sequence of SEQ ID NO: 106.

In some embodiments, the antibody binds to cynomolgus monkey Factor D. The cynomolgus monkey Factor D may comprise the amino acid sequence of SEQ ID NO: 107.

In some aspects, the antibody binds to cynomolgus monkey Factor D with a $K_D$ that is less than 10-fold, or less than 7-fold, or less than 5-fold, or less than 3-fold higher than the $K_D$ for human Factor D.

An isolated nucleic acid encoding any of the antibodies described herein is encompassed. A host cell comprising the nucleic acid is provided.

In some embodiments, the invention encompasses a method of producing any of the antibodies disclosed herein, comprising culturing the host cell so that the antibody is produced.

A pharmaceutical formulation comprising any of the antibodies disclosed herein and a pharmaceutically acceptable carrier is encompassed. The pharmaceutically acceptable carrier may comprise a buffer having a pH between about 5.5 and about 8.0. The antibody may be present in the pharmaceutical formulation at a concentration of at least 150 mg/ml, at least 160 mg/ml, at least 170 mg/ml, at least 180 mg/ml, at least 190 mg/ml, at least 200 mg/ml, or at least 210 mg/ml, or at least 220 mg/ml, or at least 230 mg/ml, or at least 240 mg/ml, or at least 250 mg/ml, or at least 260 mg/ml, or at least 270 mg/ml, or at least 280 mg/ml, or at least 290 mg/ml, or at least 300 mg/ml.

The antibody may be present in the pharmaceutical formulation at a concentration of between 150 mg/ml and 350 mg/ml, or between 150 mg/ml and 300 mg/ml, or between 170 mg/ml and 300 mg/ml, or between 200 mg/ml and 300 mg/ml.

In some embodiments, the pharmaceutical formulation comprises no visible precipitate after storage at 4° C. for at least one week, at least two weeks, at least four weeks, at least six weeks, at least eight weeks, at least 12 weeks, at least 16 weeks, at least 20 weeks, at least 24 weeks, or at least 28 weeks.

In some embodiments, the viscosity of the composition at 25° C. is less than 30 cP, less than 25 cP, less than 20 cP, less than 15 cP, or less than 10 cP.

In some aspects, the concentration of the anti-Factor D antibody in the composition is between 100 mg/ml and 300 mg/ml, or between 150 mg/ml and 300 mg/ml.

In some embodiments, the pharmaceutical formulation is suitable for intravitreal administration through a narrow bore needle. The narrow bore needle may be about 30, 29, 28, 27, 26, 25, 24, 23, or 22 gauge.

The invention further comprises a conjugate comprising at least one antibody described herein covalently linked to one or more polyols. In some embodiments, the polyol is a multi-armed polyol. In some aspects, the conjugate comprises at least two, at least three, at least four, at least five, or at least six antibodies covalently linked to a multi-armed polyol.

The polyol of the conjugate may be covalently linked to at least one antibody through a free sulfhydryl group of a cysteine amino acid. The cysteine amino acid may be an engineered cysteine. The cysteine amino acid may be in a constant region of the antibody. The cysteine amino acid may be at the C-terminus of the heavy chain or light chain of the antibody.

In some embodiments, the conjugate comprises a polyol that is covalently linked to at least one antibody through a free amino group of a lysine amino acid. The lysine amino acid may be in a constant region of the antibody. The lysine amino acid may be at the C-terminus of the heavy chain or light chain of the antibody.

In some embodiments, the polyol is a multi-armed polyol selected from a dimer, a tetramer, a hexamer, and an octamer.

In some aspects, the multi-armed polyol is an octamer.

In some embodiments, the polyol is polyethylene glycol. In some aspects, the polyethylene glycol has a weight average molecular weight of from about 500 D to about 300,000 D. In other aspects the polyethylene glycol has a weight average molecular weight of from about 20,000 D to about 60,000 D. In other aspects the polyethylene glycol has a weight average molecular weight of about 40,000 D.

In some embodiments, the conjugate described herein has a polyethylene glycol having the structure of general formula (Ia):

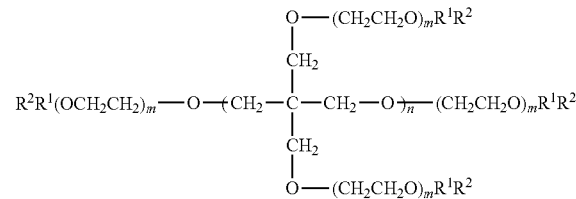

(Ia)

wherein each m is independently an integer from 45-1000 or 3-250 or 50-200 or 100-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the anti-Factor D antibody or the antibody variant.

In some embodiments, the polyethylene glycol has the structure of general formula (Ib):

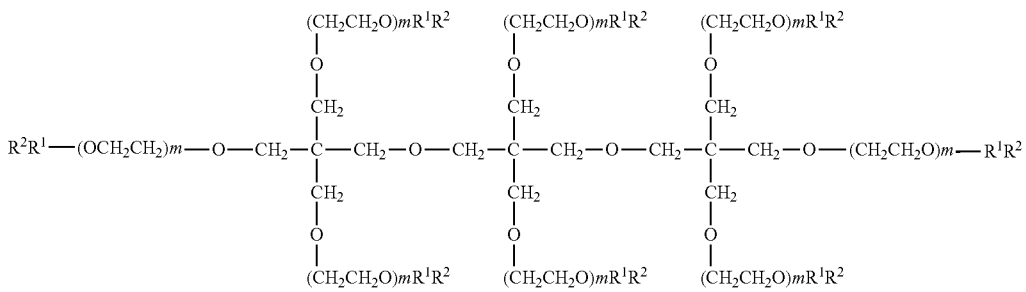

(Ib)

wherein each m is independently an integer from 45-1000 or 3-250 or 50-200 or 100-250; each $R^1$ is independently either absent, or is a linking group; and each $R^2$ is independently either hydrogen or a terminal reactive group; wherein at least one $R^2$ is a terminal reactive group and is covalently linked to the anti-Factor D antibody or the antibody variant.

In some embodiments, the polyethylene glycol has the structure of general formula (IIa):

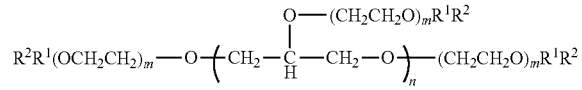

(IIa)

wherein each m is independently an integer of from 45-1000 or 3-250 or 50-200 or 100-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the anti-Factor D antibody or the antibody variant. In some embodiments n is 4.

In some aspects, the polyethylene glycol has the structure of general formula (IIIa):

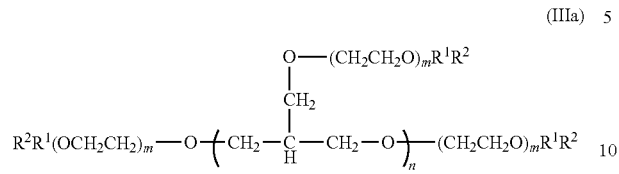

(IIIa)

wherein each m is independently an integer of from 45-1000 or 3-250 or 50-200 or 100-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the anti-Factor D antibody or the antibody variant. In some embodiments, n is 4.

In some aspects, the polyethylene glycol has the structure of general formula (IVa):

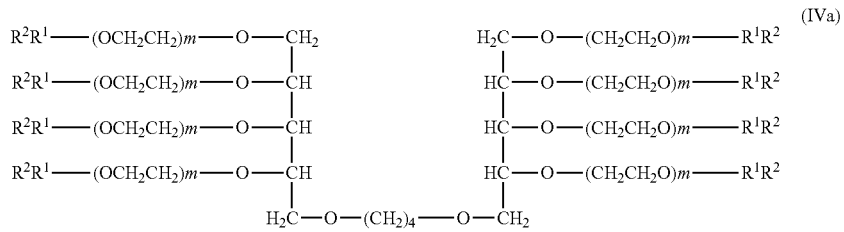

(IVa)

wherein each m is independently an integer of from 45-1000 or 3-250 or 50-200 or 100-250; each $R^1$ is independently either absent, or is a linking group; and each $R^2$ is independently either hydrogen or a terminal reactive group; wherein at least one $R^2$ is a terminal reactive group and is covalently linked to the anti-Factor D antibody or the antibody variant. In some embodiments, m is an integer of 50-200. In other embodiments, m is an integer of 100-150.

In some embodiments, the at least one $R^1$ is a linking group, wherein $R^1$ and $R^2$ when taken together are selected from:

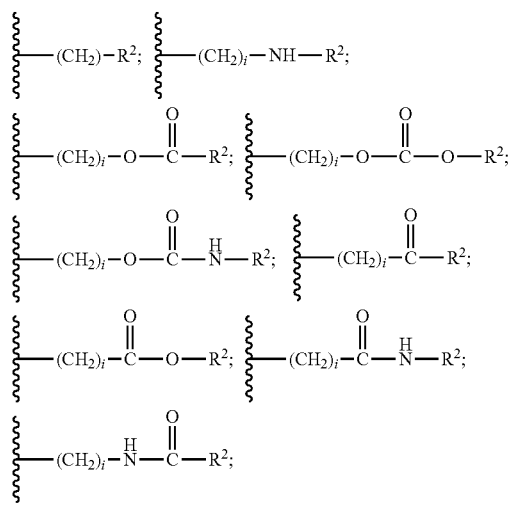

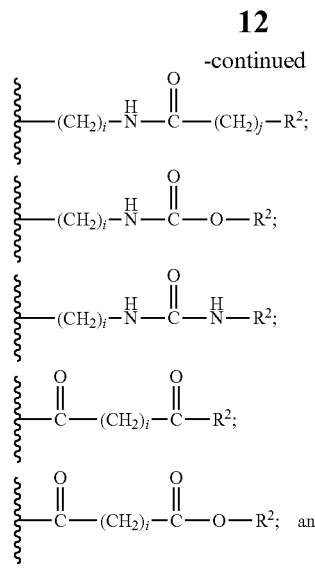

-continued

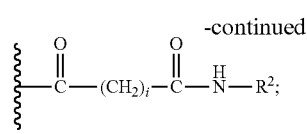

and combinations thereof; wherein each i is independently an integer of 0-10; and j is an integer of 0-10.

In some embodiments, $R^2$ is independently selected from a thiol reactive group, an amino reactive group, and combinations thereof.

In some embodiments, each $R^2$ is independently selected from a maleimide, a sulfhydryl, a thiol, trifluoromethanesulfonate, tosylate, aziridine, epoxide, a pyridyl disulfide, succinimidyl ester, —NH$_2$, an aldehyde, a haloacetate, a haloacetamide, and a para-nitrophenyl carbonate.

In some aspects, $R^2$ is a maleimide.

The conjugate may have a $R^1$ and $R^2$, when taken together, are

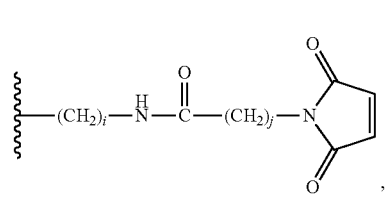

i is an integer of 0-10; and j is an integer of 0-10.

In some embodiments, at least seven of the $R^2$ groups are covalently linked to one of the anti-Factor D antibodies or the antibody variants.

In some embodiments, at least eight of the $R^2$ groups are covalently linked to one of the anti-Factor D antibodies or the antibody variants.

In some embodiments, the conjugate is prepared by covalently linking at least one antibody described herein to a multi-armed polyol.

A pharmaceutical formulation comprising the conjugate as described herein and a pharmaceutically acceptable carrier is encompassed. The concentration of the antibody is at least 100 mg/ml, or at least 150 mg/ml, or at least 200 mg/ml, or at least 300 mg/ml. In other embodiments, the concentration of the anti-Factor D antibody or the antibody variant is from about 50 mg/ml to about 300 mg/ml.

In some embodiments, the viscosity of the pharmaceutical formulation or composition is at 25° C. is less than 1000 cP, less than 900 cP, less than 800 cP, less than 700 cP, less than 600 cP, less than 500 cP, less than 400 cP, or less than 300 cP.

In some embodiments, the concentration of the anti-Factor D antibody in the formulation or composition is at least 100 mg/ml or at least 150 mg/ml.

Also encompassed is a delivery device for ocular delivery comprising the pharmaceutical formulation described herein and a means for delivering the formulation intravitreally to a patient.

In some embodiments, the delivery device formulation remains effective on site for a prolonged period of time.

In some embodiments, a method of treating a complement-mediated disorder in a subject comprising administering to the subject an effective amount of an antibody, the conjugate, or the pharmaceutical formulation described herein is encompassed.

In some embodiments, the complement-mediated disorder is systemic.

In another embodiment, the complement-mediated disorder is a complement-associated eye condition.

In some aspects, the complement-associated eye condition is selected from age-related macular degeneration (AMD), including dry and wet (non-exudative and exudative) forms, choroidal neovascularization (CNV), uveitis, diabetic retinopathy, ischemia-related retinopathy, diabetic macular edema, pathological myopia, von Hippel-Lindau disease, histoplasmosis of the eye, Central Retinal Vein Occlusion (CRVO), corneal neovascularization, and retinal neovascularization.

In some embodiments, the complement-associated eye condition is selected from intermediate dry form AMD or geographic atrophy (GA).

In some aspects, the method comprises administering the antibody, conjugate, or pharmaceutical formulation using an implantable port delivery system.

In some embodiments, the method comprises administering the antibody, conjugate, or pharmaceutical formulation by intravitreal administration. The intravitreal administration may be through a narrow bore needle. In some embodiments, the narrow bore needle is about 30, 29, 28, 27, 26, 25, 24, 23, or 22 gauge.

In some aspects, the method of treating further comprising administering an additional therapeutic agent to the individual. In some embodiments, the additional therapeutic agent is selected from an an ANG2 antagonist, a TIE2 antagonist, a VEGF antagonist, and a second complement component antagonist.

In some embodiments, the additional therapeutic agent is an anti-ANG2 antibody.

In other embodiments, the additional therapeutic agent is an anti-TIE2 antibody.

In some aspects, the additional therapeutic agent is selected from a VEGF trap and an anti-VEGF antibody.

In other aspects, the additional therapeutic agent is a second complement component antagonist, wherein the second complement component antagonist inhibits a complement component selected from C1, C2, C3, C4, C5, C6, C7, C8 and C9.

Use of the antibody or the conjugate described herein for the preparation of a medicament for treating a complement-mediated disorder in a subject is encompassed. In some embodiments, the complement-mediated disorder is a complement-associated eye condition. In other embodiments, the complement-mediated disorder is systemic. In some aspects, the complement-associated eye condition is selected from age-related macular degeneration (AMD), including dry and wet (non-exudative and exudative) forms, choroidal neovascularization (CNV), uveitis, diabetic retinopathy, ischemia-related retinopathy, diabetic macular edema, pathological myopia, von Hippel-Lindau disease, histoplasmosis of the eye, Central Retinal Vein Occlusion (CRVO), corneal neovascularization, and retinal neovascularization. The complement-associated eye condition may be selected from intermediate dry form AMD or geographic atrophy (GA).

In some aspects, the antibody or the conjugate described herein is for use in therapy.

In some embodiments, the antibody or the conjugate described herein is for use in a method of treating a complement-mediated disorder in a subject.

In some embodiments, the antibody, conjugate, or formulation is for use in a method of treating a systemic complement-mediated disorder in a subject. In some embodiments, the complement-mediated disorder is a complement-associated eye condition. In some aspects, the complement-associated eye condition is selected from age-related macular degeneration (AMD), including dry and wet (non-exudative and exudative) forms, choroidal neovascularization (CNV), uveitis, diabetic retinopathy, ischemia-related retinopathy, diabetic macular edema, pathological myopia, von Hippel-Lindau disease, histoplasmosis of the eye, Central Retinal Vein Occlusion (CRVO), corneal neovascularization, and retinal neovascularization. In some embodiments, the complement-associated eye condition is selected from intermediate dry form AMD or geographic atrophy (GA).

BRIEF DESCRIPTION OF THE FIGURES

FIGS. 1A-C show an alignment of the murine 20D12 light chain variable region, human VL kappa I (VL$_K$) consensus sequence, and light chain variable regions of humanized variants of 20D12.

FIGS. 2A-C show an alignment of the murine 20D12 heavy chain variable region, human VH subgroup I (VH$_I$) consensus sequence, and heavy chain variable regions of humanized variants of 20D12.

FIG. 4 shows alignments of the lampalizumab light chain (SEQ ID NO: 100) and heavy chain variable regions (SEQ ID NO: 101) and hu20D12.v2.0 ("hu20D12.v1.N54S") light chain (SEQ ID NO: 32) and heavy chain (SEQ ID NO: 33) variable regions.

FIGS. 5A-B show inhibition of Factor D by humanized 20D12 antibody Fabs and conjugates, as measured using a TR-FRET assay of factor B activation.

FIGS. 8A-C shows the CEX chromatogram (8A), SEC-MALS profile (8B) of PEG-octamer conjugated hu20D12.v2.1.C fractions, and a table of the Mw (kDa), polydispersity (Mw/Mn), and $R_H$ (nm) of the fractions (8C).

FIG. 11 shows various characteristics of humanized 20D12 antibodies, lampalizumab, and anti-Factor D variants AFD.v8 and AFD.v14.

DETAILED DESCRIPTION

Figure 3A:
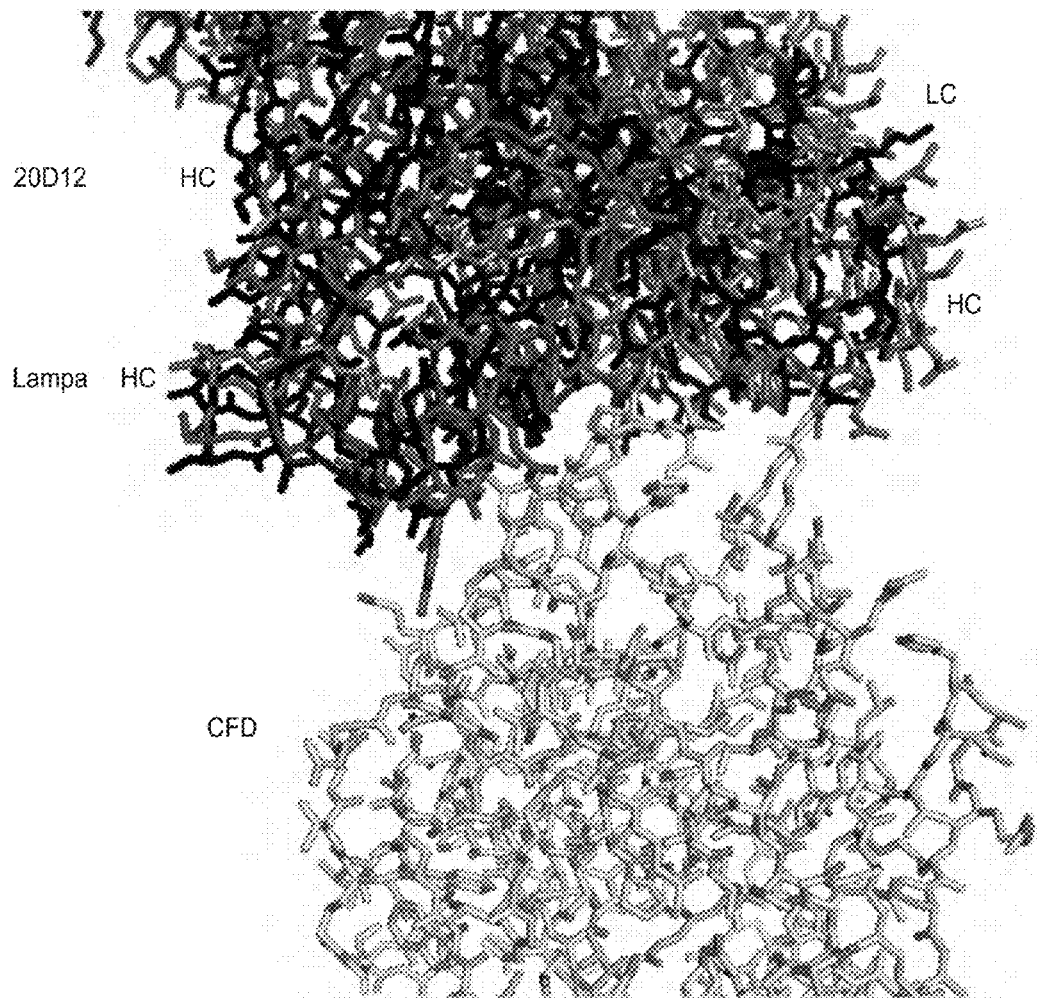
FIGS. 3A-C show overlays of portions of the hu20D12.v2.0-Factor D co-crystal structure and the lampalizumab-Factor D co-crystal structure. A) Overlay of the binding interface between the antibodies and Factor D. B) Detail of certain heavy chain contacts between the antibodies and Factor D. C) Detail of certain light chain contacts between the antibodies and Factor D.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

I. Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Factor D antibody", "aFD antibody", "AFD.Ab", and "an antibody that binds to Factor D" refer to an antibody that is capable of binding Factor D with sufficient affinity such that the antibody is useful as a diagnostic and/or therapeutic agent in targeting Factor D. In some embodiments, the extent of binding of an anti-Factor D antibody to an unrelated, non-Factor D protein is less than about 10% of the binding of the antibody to Factor D as measured, e.g., by a radioimmunoassay (MA). In certain embodiments, an antibody that binds to Factor D has a dissociation constant (Kd) of $\leq 1$ µM, $\leq 100$ nM, $\leq 10$ nM, $\leq 5$ nm, $\leq 4$ nM, $\leq 3$ nM, $\leq 2$ nM, $\leq 1$ nM, $\leq 0.1$ nM, $\leq 0.01$ nM, or $\leq 0.001$ nM (e.g., $10^{-8}$ M or less, e.g. from $10^{-8}$ M to $10^{-13}$ M, e.g., from $10^{-9}$ M to $10^{-13}$ M). In certain embodiments, an anti-Factor D antibody binds to an epitope of Factor D that is conserved among Factor D from different species. The anti-Factor D antibodies include without limitation AFD.v# variants and hu20D12.v# variants with # being a number used to identify the particular variant.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab-SH, Fab'-SH, Fab', Fab-C, Fab'-C, Fab'-C-SH, Fab-C-SH, scFv, diabody, or F(ab')$_2$; diabodies; linear antibodies; single-chain antibody molecules (e.g. scFv); and multispecific antibodies formed from antibody fragments.

As used herein, a "Fab" refers to an antibody that comprises a heavy chain constant region that comprises the CH1 domain, or a sufficient portion of the CH1 domain to form a disulfide bond with the light chain constant region, but does not contain a CH2 domain or a CH3 domain. As used herein, a Fab may comprise one or more amino acids of the hinge region. Thus, as used herein, the term "Fab" encompasses Fab' antibodies. A Fab may comprise additional non-native amino acids, such as a C-terminal cysteine, in which case it may be referred to as a Fab-C. As discussed below, the term Fab-C also encompasses Fabs comprising native amino acids of the hinge region, including a native cysteine at the C-terminus. In some embodiments, a Fab comprises an engineered cysteine (i.e., a Fab may be a THIOMAB).

A "Fab-C" refers to a Fab with a C-terminal cysteine, which may be a native cysteine that occurs at that residue position (such as a cysteine from the hinge region), or may be a cysteine added to the C-terminus that does not correspond to a native cysteine. The anti-Factor D antibodies include without limitation AFD.C antibodies and hu20D12.C antibodies, with "C" indicating that the antibody is a Fab with a C-terminal cysteine. Nonlimiting exemplary Fab-C heavy chain constant regions include the sequences of SEQ ID NOs: 129, 130, 132, 154, 155, 156, 157, and 158.

A "Fab-SH" refers to a Fab with a free thiol group. In some embodiments, the free thiol group is located in the last 10 amino acids of the C-terminus of the Fab. Fab-C antibodies are typically also Fab-SH antibodies. A further nonlimiting exemplary Fab-SH heavy chain constant region having the amino acid sequence of SEQ ID NO: 131. Typically, a Fab comprising an engineered cysteine (i.e., a Fab that is a THIOMAB) is a Fab-SH.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "complement-associated disorder" is used in the broadest sense and includes disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Complement activation is also associated with ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions includes age-related macular degeneration (AMD), including non-exudative (e.g. intermediate dry AMD or geographic atrophy (GA)) and exudative (e.g. wet AMD (choroidal neovascularization (CNV)) AMD, diabetic retinopathy (DR), endophthalmitis and uveitis. In a further example, nonexudative AMD may include the presence of hard drusen, soft drusen, geographic atrophy and/or pigment clumping. In one example, complement-associated eye conditions include age-related macular degeneration (AMD), including early AMD (e.g. includes multiple small to one or more non-extensive medium sized drusen), intermediate AMD (e.g. includes extensive medium drusen to one or more large drusen) and advanced AMD (e.g. includes geographic atrophy or advanced wet AMD (CNV). (Ferris et al., AREDS Report No. 18, Sallo et al., Eye Res., 34(3): 238-40 (2009); Jager et al., *New Engl. J. Med.,* 359(1): 1735 (2008)). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, complement-associated eye condition is intermediate dry AMD. In one example, complement-associated eye condition is geographic atrophy. In one example, complement-associated eye condition is wet AMD (choroidal neovascularization (CNV)).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "polyol" when used herein refers broadly to polyhydric alcohol compounds. Polyols can be any water-soluble poly(alkylene oxide) polymer for example, and can have a linear or branched chain. Preferred polyols include those substituted at one or more hydroxyl positions with a chemical group, such as an alkyl group having between one and four carbons. Typically, the polyol is a poly(alkylene glycol), preferably polyethylene glycol (PEG). However, those skilled in the art recognize that other polyols, such as, for example, poly (propylene glycol) and polyethylene-polypropylene glycol copolymers, can be employed using the techniques for conjugation described herein for PEG. The polyols of the disclosure include those well known in the art and those publicly available, such as from commercially available sources.

The term "conjugate" is used herein according to its broadest definition to mean joined or linked together. Molecules are "conjugated" when they act or operate as if joined. In particular embodiments, "conjugate" refers to an antibody (e.g., an antibody fragment, as detailed herein) covalently bound to a multi-armed polyol.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result, such as a measurable improvement in the state, e.g. pathology, of the target disease or condition, such as, for example, a complement-associated eye condition.

The term "epitope" refers to the particular site on an antigen molecule to which an antibody binds.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of Factor D" refers to naturally occurring forms of Factor D that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In some embodiments, for the VL, the subgroup is subgroup kappa I as in Kabat et al., supra. In some embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-

917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

A protein including an antibody is said to be "stable" if it essentially retains the intact conformational structure and biological activity. Various analytical techniques for measuring protein stability are available in the art and are reviewed in, e.g., Peptide and Protein Drug Delivery, 247-301, Vincent Lee Ed., Marcel Dekker, Inc., New York, N.Y., Pubs. (1991) and Jones (1993) *Adv. Drug Delivery Rev.* 10: 29-90. An antibody variant with "improved stability" refers to an antibody variant that is more stable comparing to the starting reference antibody. Preferably, antibody variants with improved stability are variants of the native (wild-type) antibodies in which specific amino acid residues are altered for the purpose of improving physical stability, and/or chemical stability, and/or biological activity, and/or reducing immunogenicity of the native antibodies. Walsh (2000) *Nat. Biotech.* 18:831-3.

The term "isomerization" refers generally to a chemical process by which a chemical compound is transformed into any of its isomeric forms, i.e., forms with the same chemical composition but with different structure or configuration and, hence, generally with different physical and chemical properties. Specifically used herein is aspartate isomerization, a process wherein one or more aspartic acid (D or Asp) residue(s) of a polypeptide have been transformed to isoaspartic acid residue(s). Geiger and Clarke (1987) *J. Biol. Chem.* 262:785-94.

The term "deamidation" refers generally to a chemical reaction wherein an amide functional group is removed from an organic compound. Specifically used herein is asparagine deamidation, a process wherein one or more asparagine (N or Asn) residue(s) of a polypeptide have been converted to aspartic acid (D or Asp), i.e., the neutral amide side chain has been converted to a residue with an overall acidic property. Xie and Schowen (1999) *J. Pharm. Sci.* 88:8-13.

A "conjugate" is an antibody conjugated to one or more heterologous molecule(s), including but not limited to a polyol.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human.

By "monotherapy" is meant a therapeutic regimen that includes only a single therapeutic agent for the treatment of the target disease or condition, such as, for example, a complement-associated eye condition, during the course of the treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Factor D antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "Factor D" and "fD" and "FD," as used herein, refers to any native, mature Factor D which results from processing of a Factor D precursor protein in a cell. The term includes Factor D from any vertebrate source, including mammals such as primates (e.g. humans and cynomolgus monkeys) and rodents (e.g., mice and rats), unless otherwise indicated. The term also includes naturally occurring variants of Factor D, e.g., splice variants or allelic variants. The amino acid sequence of an exemplary human Factor D prepropeptide is shown in SEQ ID NO: 104. The amino acid sequence of an exemplary mature human Factor D is amino acids 26-253 of SEQ ID NO: 104 (SEQ ID NO: 106).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "vial" is a container suitable for holding a liquid or lyophilized preparation. In some embodiments, the vial is a single-use vial, e.g. a 20-cc single-use vial with a stopper.

A "port delivery system" or "PDS" is an implantable device for the eye with a refillable reservoir that allows delivery of a therapeutic agent over an extended period of time. The implant is constructed having a refill port in communication with a reservoir and a release control element that determines the rate of drug release into the eye. See, for example, US20100174272, U.S. Pat. Nos. 8,277,830; 8,399,006; 8,795,712; and 8,808,727.

A "small-bore needle" refers to a needle for injection of fluid composition of about 30, 29, 28, 27, 26, 25, 24, 23, or 22 gauge or higher, such as a 30 gauge needle. In some embodiments, the small-bore needle has standard sized walls. In another embodiment, the small-bore needle has thin walls, which may be preferred for viscous solutions.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated eye condition, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

Administration "in combination with" one or more further therapeutic agents includes simultaneous (concurrent) and consecutive administration in any order.

A drug that is administered "concurrently" with one or more other drugs is administered during the same treatment cycle, on the same day of treatment as the one or more other drugs, and, optionally, at the same time as the one or more other drugs.

"Therapeutically effective amount" is the amount of a Factor D antagonist that is required to achieve a measurable improvement in the state, e.g., pathology, of the target disease or condition, such as, for example, a complement-associated eye condition.

The terms "long-acting delivery", "sustained-release" and "controlled release" are used generally to describe a delivery mechanism using formulation, dosage form, device or other types of technologies to achieve the prolonged or extended release or bioavailability of a therapeutic drug. It may refer to technologies that provide prolonged or extended release or bioavailability of the drug to the general systemic circulation or a subject or to local sites of action in a subject including, but not limited to, cells, tissues, organs, joints, regions, and the like. Furthermore, these terms may refer to a technology that is used to prolong or extend the release of the drug from a formulation or dosage form or they may refer to a technology used to extend or prolong the bioavailability or the pharmacokinetics or the duration of action of the drug to a subject or they may refer to a technology that is used to extend or prolong the pharmacodynamic effect elicited by a formulation. A "long-acting formulation," a "sustained release formulation," or a "controlled release formulation" is a pharmaceutical formulation, dosage form, or other technology that is used to provide long-acting delivery. In some embodiments, the controlled release is used to improve drug's local bioavailability, specifically ocular residence time in the context of ocular delivery. "Increased ocular residence time" refers to the post-delivery period during which the delivered ocular drug remains effective both in terms of quality (activity) and in terms of quantity (effective amount). In addition to or in lieu of high dose and controlled release, the drug can be modified post-translationally, such as via PEGylation, to achieve increased in vivo half-life.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In some embodiments, the invention is based, in part, on antibodies that bind to Factor D and conjugates comprising such antibodies. Antibodies and conjugates of the invention are useful, e.g., for the treatment of complement-associated disorders, such as complement-associated eye conditions.

A. Exemplary Anti-Factor D Antibodies

Provided herein are isolated antibodies that bind to Factor D. In particular, provided herein are antibodies that bind Factor D with very high affinity, such as with a $K_D$ of less than 100 pM, or less than 75 pM, or less than 50 pM, or less than 10 pM. Further, provided herein are antibodies, such as Fabs, that are highly soluble. For example, in some embodiments, a pharmaceutical formulation comprising a high concentration of an antibody provided herein contains no visible precipitate following storage at 4° C. for at least 20 weeks. In some embodiments, a pharmaceutical formulation comprising a high concentration of an antibody provided herein comprises at least 200 mg/ml, or at least 230 mg/ml, or at least 250 mg/ml, or at least 270 mg/ml of the antibody (such as a Fab). In some embodiments, an antibody provided herein may be formulated at high concentration, such as at least 150 mg/ml, with a viscosity of less than 30 cP, or less than 20 cP, or less than 15 cP, or less than 10 cP at 25° C. In any of the embodiments described herein, the antibodies may be monoclonal antibodies. In some embodiments, the antibodies may be human antibodies, humanized antibodies, or chimeric antibodies. In any of the embodiments described herein, the antibodies may be Fab fragments.

In some embodiments, the invention provides an anti-Factor D antibody comprising at least one, two, three, four, five, or six HVRs selected from (a) HVR-H1 comprising the amino acid sequence SYYMY (SEQ ID NO: 15); (b) HVR-H2 comprising the amino acid sequence $X_4$INPX$_5$X$_6$GX$_7$TNFNEKFKS (SEQ ID NO: 111), wherein $X_4$ is selected from E and W; $X_5$ is selected from T and Y; $X_6$ is selected from N, S, and Q; and $X_7$ is selected from G, D, and E; (c) HVR-H3 comprising the amino acid sequence EGGFAY (SEQ ID NO: 25); (d) HVR-L1 comprising the amino acid sequence KASQNVDTDVA (SEQ ID NO:9); (e) HVR-L2 comprising the amino acid sequence SASSRX$_1$S (SEQ ID NO: 108), wherein $X_1$ is selected from Y, K, and R; and (f) HVR-L3 comprising the amino acid sequence QQYX$_3$NYPLT (SEQ ID NO: 110), wherein $X_3$ is selected from N and E. In some embodiments, the invention provides an anti-Factor D antibody comprising the sequence $X_2$SASSRX$_1$S (SEQ ID NO: 109; i.e., comprises the amino acid $X_2$ immediately preceding HVR-L2), wherein $X_1$ is selected from Y, K, and R; $X_2$ is selected from Y, R, S, K, and Q. In some embodiments, $X_2$ is R. In some embodiments, $X_1$ is Y.

In some embodiments, the invention provides an anti-Factor D antibody comprising at least one, two, three, four, five, or six HVRs selected from (a) HVR-H1 comprising the amino acid sequence of SEQ ID NO: 15; (b) HVR-H2 comprising an amino acid sequence selected from SEQ ID NOs: 16 to 24; (c) HVR-H3 comprising the amino acid sequence of SEQ ID NO: 25, (d) HVR-L1 comprising the amino acid sequence of SEQ ID NO: 9, (e) HVR-L2 comprising an amino acid sequence selected from SEQ ID NOs: 10 to 12, and (f) HVR-L3 comprising the amino acid sequence of SEQ ID NO: 13 or 14.

In some embodiments, the invention provides an antibody comprising at least one, at least two, or all three VH HVR sequences selected from (a) HVR-H1 comprising the amino acid sequence SYYMY (SEQ ID NO: 15); (b) HVR-H2 comprising the amino acid sequence $X_4INPX_5X_6GX_7TNFNEKFKS$ (SEQ ID NO: 111), wherein $X_4$ is selected from E and W; $X_5$ is selected from T and Y; $X_6$ is selected from N, S, and Q; and $X_7$ is selected from G, D, and E; (c) HVR-H3 comprising the amino acid sequence EGGFAY (SEQ ID NO: 25). In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising an amino acid sequence selected from SEQ ID NOs: 16 to 24; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 17; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 18; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 19; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 20; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 21; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 22; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 23; and (c) HVR-H3 comprising the amino acid sequence of SEQ ID NO: 25. In some embodiments, the invention provides an anti-Factor D antibody comprising at least one, at least two, or all three HVRs selected from (a) HVR-H1 comprising the amino acid sequence of SEQ ID NO: 15; (b) HVR-H2 comprising the amino acid sequence of SEQ ID NO: 24; and (c) HVR-H3 comprising the amino acid sequence of SEQ ID NO: 25.

In some embodiments, the invention provides an antibody comprising at least one, at least two, or all three VL HVR sequences selected from (a) HVR-L1 comprising the amino acid sequence KASQNVDTDVA (SEQ ID NO:9); (b) HVR-L2 comprising the amino acid sequence $SASSRX_1S$ (SEQ ID NO: 108), wherein $X_1$ is selected from Y, K, and R; and (c) HVR-L3 comprising the amino acid sequence $QQYX_3NYPLT$ (SEQ ID NO: 110), wherein $X_3$ is selected from N and E. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising an amino acid sequence selected from SEQ ID NOs: 10 to 12; and (c) HVR-L3 comprising the amino acid sequence of SEQ ID NO: 13 or 14. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 13. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising the amino acid sequence of SEQ ID NO: 11; and (c) HVR-L3 comprising the amino acid sequence of SEQ ID NO: 13. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising the amino acid sequence of SEQ ID NO: 12; and (c) HVR-L3 comprising the amino acid sequence of SEQ ID NO: 13. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 14. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 13. In some embodiments, the invention provides an anti-Factor D antibody comprising at least one, at least two, or all three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 14. In any of the foregoing embodiments, the amino acid immediately preceding HVR-L2 may be selected from Y, R, S, K, and Q. In some embodiments, the amino acid immediately preceding HVR-L2 is R.

In some embodiments, an anti-Factor D antibody is provided, wherein the antibody comprises (a) a VH domain comprising at least one, at least two, or all three VH HVR sequences selected from (i) HVR-H1 comprising the amino acid sequence SYYMY (SEQ ID NO: 15), (ii) HVR-H2 comprising the amino acid sequence $X_4INPX_5X_6GX_7TNFNEKFKS$ (SEQ ID NO: 111), wherein $X_4$ is selected from E and W; $X_5$ is selected from T and Y; $X_6$ is selected from N, S, and Q; and $X_7$ is selected from G, D, and E, and (iii) HVR-H3 comprising the amino acid sequence EGGFAY (SEQ ID NO: 25); and (b) a VL domain comprising at least one, at least two, or all three VL HVR sequences selected from (i) HVR-L1 comprising the amino acid sequence KASQNVDTDVA (SEQ ID NO:9), (ii) HVR-L2 comprising the amino acid sequence SASSRX$_1$S (SEQ ID NO: 108), wherein X$_1$ is selected from Y, K, and R, and (c) HVR-L3 comprising the amino acid sequence QQYX$_3$NYPLT (SEQ ID NO: 110), wherein X$_3$ is selected from N and E.

In some embodiments, an anti-Factor D antibody is provided, wherein the antibody comprises (a) a VH domain comprising at least one, at least two, or all three VH HVR sequences selected from (i) HVR-H1 comprising the amino acid sequence SYYMY (SEQ ID NO: 15), (ii) HVR-H2 comprising the amino acid sequence X$_4$INPX$_5$X$_6$GX$_7$TNFNEKFKS (SEQ ID NO: 111), wherein X$_4$ is selected from E and W; X$_5$ is selected from T and Y; X$_6$ is selected from N, S, and Q; and X$_7$ is selected from G, D, and E, and (iii) HVR-H3 comprising the amino acid sequence EGGFAY (SEQ ID NO: 25); and (b) a VL domain comprising at least one, at least two, or all three VL HVR sequences selected from (i) HVR-L1 comprising the amino acid sequence KASQNVDTDVA (SEQ ID NO:9), (ii) HVR-L2 comprising the amino acid sequence SASSRX$_1$S (SEQ ID NO: 108), wherein X$_1$ is selected from Y, K, and R, and (c) HVR-L3 comprising the amino acid sequence QQYX$_3$NYPLT (SEQ ID NO: 110), wherein X$_3$ is selected from N and E. In some embodiments, the invention provides an anti-Factor D antibody comprising the sequence X$_2$SASSRX$_1$S (i.e., comprises the amino acid X$_2$ immediately preceding HVR-L2), wherein X$_1$ is selected from Y, K, and R; X$_2$ is selected from Y, R, S, K, and Q. In some embodiments, X$_2$ is R. In some embodiments, X$_1$ is Y.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 16, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 20, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 17, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 18, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 19, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 21, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 22, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 23, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 24, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 16, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 11, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 16, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 12, and (c) HVR-L3 comprising the amino acid sequence of SEQ ID NO: 13.

In some embodiments, an anti-Factor D antibody is provided, wherein the antibody comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 16, and (iii) HVR-H3 comprising an amino acid sequence selected from SEQ ID NO: 25; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 14.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 20; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 17; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 18; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 19; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 21; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 22; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 23; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 11; and (f) HVR-L3 comprising the amino acid sequence of SEQ ID NO: 13.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 12; and (f) HVR-L3 comprising the amino acid sequence of SEQ ID NO: 14.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 14.

In some embodiments, an anti-Factor D antibody is provided, comprising (a) HVR-H1 comprising the amino acid sequence of SEQ ID NO: 15; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 13.

In any of the embodiments herein, an anti-Factor D antibody may be humanized. In some embodiments, an anti-Factor D antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the mutations described herein.

In another aspect, an anti-Factor D antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs: 27, 29, 31, 33, 35, 37, 39, 41, 43, 45, 47, 49, 51, 53, 55, 57, 59, 61, and 63. In certain embodiments, a VH sequence having at least 90%, 91%, 92%, 93%, 94%, 95%, 96%, 97%, 98%, or 99% identity to an amino acid sequence selected from SEQ ID NOs: 27, 29, 31, 33, 35, 37, 39, 41, 43, 45, 47, 49, 51, 53, 55, 57, 59, 61, and 63 contains substitutions (e.g., conservative substitutions), insertions, or deletions relative to the reference sequence, but an anti-Factor D antibody comprising that sequence retains the ability to bind to Factor D. In certain embodiments, a total of 1 to 10 amino acids have been substituted, inserted and/or deleted in SEQ ID NO: 27, 29, 31, 33, 35, 37, 39, 41, 43, 45, 47, 49, 51, 53, 55, 57, 59, 61, or 63. In certain embodiments, a total of 1 to 5 amino acids have been substituted, inserted and/or deleted in SEQ ID NO: 27, 29, 31, 33, 35, 37, 39, 41, 43, 45, 47, 49, 51, 53, 55, 57, 59, 61, or 63. In certain embodiments, substitutions, insertions, or deletions occur in regions outside the HVRs (i.e., in the FRs). Optionally, the anti-Factor D antibody comprises the VH sequence of SEQ ID NO: 27, 29, 31, 33, 35, 37, 39, 41, 43, 45, 47, 49, 51, 53, 55, 57, 59, 61, or 63, including post-translational modifications of that sequence. In a particular embodiment, the VH comprises one, two or three HVRs selected from: (a) HVR-H1 comprising the amino acid sequence SYYMY (SEQ ID NO: 15), (b) HVR-H2 comprising the amino acid sequence $X_4INPX_5X_6GX_7TNFNEKFKS$ (SEQ ID NO: 111), wherein $X_4$ is selected from E and W; $X_5$ is selected from T and Y; $X_6$ is selected from N, S, and Q; and $X_7$ is selected from G, D, and E, and (c) HVR-H3 comprising the amino acid sequence EGGFAY (SEQ ID NO: 25). In some embodiments, the VH comprises one, two or three HVRs selected from: (a) HVR-H1 comprising the amino acid sequence of SEQ ID NO: 15, (b) HVR-H2 comprising the amino acid sequence of SEQ ID NO: 16 or 20; and (c) HVR-H3 comprising the amino acid sequence of SEQ ID NO: 25.

In another aspect, an anti-Factor D antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs: 26, 28, 30, 32, 34, 36, 38, 40, 42, 44, 46, 48, 50, 52, 54, 56, 58, 60, and 62. In certain embodiments, a VL sequence having at least 90%, 91%, 92%, 93%, 94%, 95%, 96%, 97%, 98%, or 99% identity to an amino acid sequence selected from SEQ ID NOs: 26, 28, 30, 32, 34, 36, 38, 40, 42, 44, 46, 48, 50, 52, 54, 56, 58, 60, and 62 contains substitutions (e.g., conservative substitutions), insertions, or deletions relative to the reference sequence, but an anti-Factor D antibody comprising that sequence retains the ability to bind to Factor D. In certain embodiments, a total of 1 to 10 amino acids have been substituted, inserted and/or deleted in SEQ ID NO: 26, 28, 30, 32, 34, 36, 38, 40, 42, 44, 46, 48, 50, 52, 54, 56, 58, 60, or 62. In certain embodiments, a total of 1 to 5 amino acids have been substituted, inserted and/or deleted in SEQ ID NO: 26, 28, 30, 32, 34, 36, 38, 40, 42, 44, 46, 48, 50, 52, 54, 56, 58, 60, or 62. In certain embodiments, the substitutions, insertions, or deletions occur in regions outside the HVRs (i.e., in the FRs). Optionally, the anti-Factor D antibody comprises the VL sequence of SEQ ID NO: 26, 28, 30, 32, 34, 36, 38, 40, 42, 44, 46, 48, 50, 52, 54, 56, 58, 60, or 62, including post-translational modifications of that sequence. In a particular embodiment, the VL comprises one, two or three HVRs selected from (a) HVR-L1 comprising the amino acid sequence KASQNVDTDVA (SEQ ID NO:9); (b) HVR-L2 comprising the amino acid sequence SASSRX1S (SEQ ID NO: 108), wherein X1 is selected from Y, K, and R; and (c) HVR-L3 comprising the amino acid sequence QQYX3NYPLT (SEQ ID NO: 110), wherein X3 is selected from N and E. In some embodiments, the VL comprises one, two or three HVRs selected from (a) HVR-L1 comprising the amino acid sequence of SEQ ID NO:9; (b) HVR-L2 comprising the amino acid sequence of SEQ ID NO: 10; and (c) HVR-L3 comprising the amino acid sequence of SEQ ID NO: 13. In any of the foregoing embodiments, the amino acid immediately preceding HVR-L2 may be selected from Y, R, S, K, and Q. In some embodiments, the amino acid immediately preceding HVR-L2 is R.

In another aspect, an anti-Factor D antibody is provided, wherein the antibody comprises a VH as in any of the embodiments provided above, and a VL as in any of the embodiments provided above.

In some embodiments, the antibody comprises the VH and VL sequences in SEQ ID NO: 35 and SEQ ID NO: 34, respectively, including post-translational modifications of those sequences. In some embodiments, the antibody comprises the VH and VL sequences in SEQ ID NO: 39 and SEQ ID NO: 38, respectively, including post-translational modifications of those sequences.

In a further aspect, provided herein are antibodies that bind to the same epitope as an anti-Factor D antibody. For example, in certain embodiments, an antibody is provided that binds to the same epitope as an anti-Factor D antibody comprising a VH sequence of SEQ ID NO: 35 and a VL sequence of SEQ ID NO: 34, respectively. In certain embodiments, an antibody is provided that binds to the same epitope as an anti-Factor D antibody comprising a VH sequence of SEQ ID NO: 39 and a VL sequence of SEQ ID NO: 38, respectively.

Figure 1A:
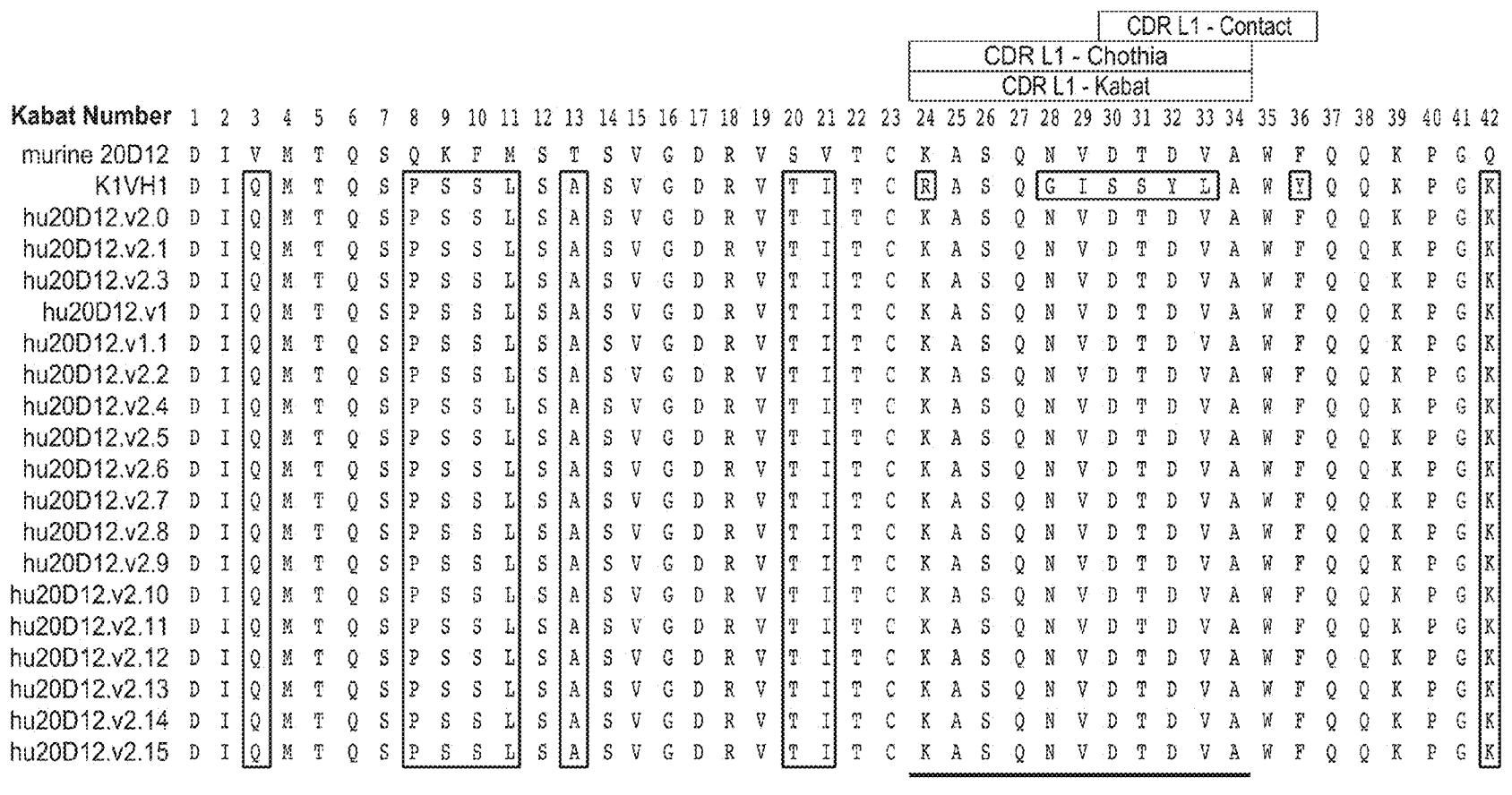
Figure 1B:
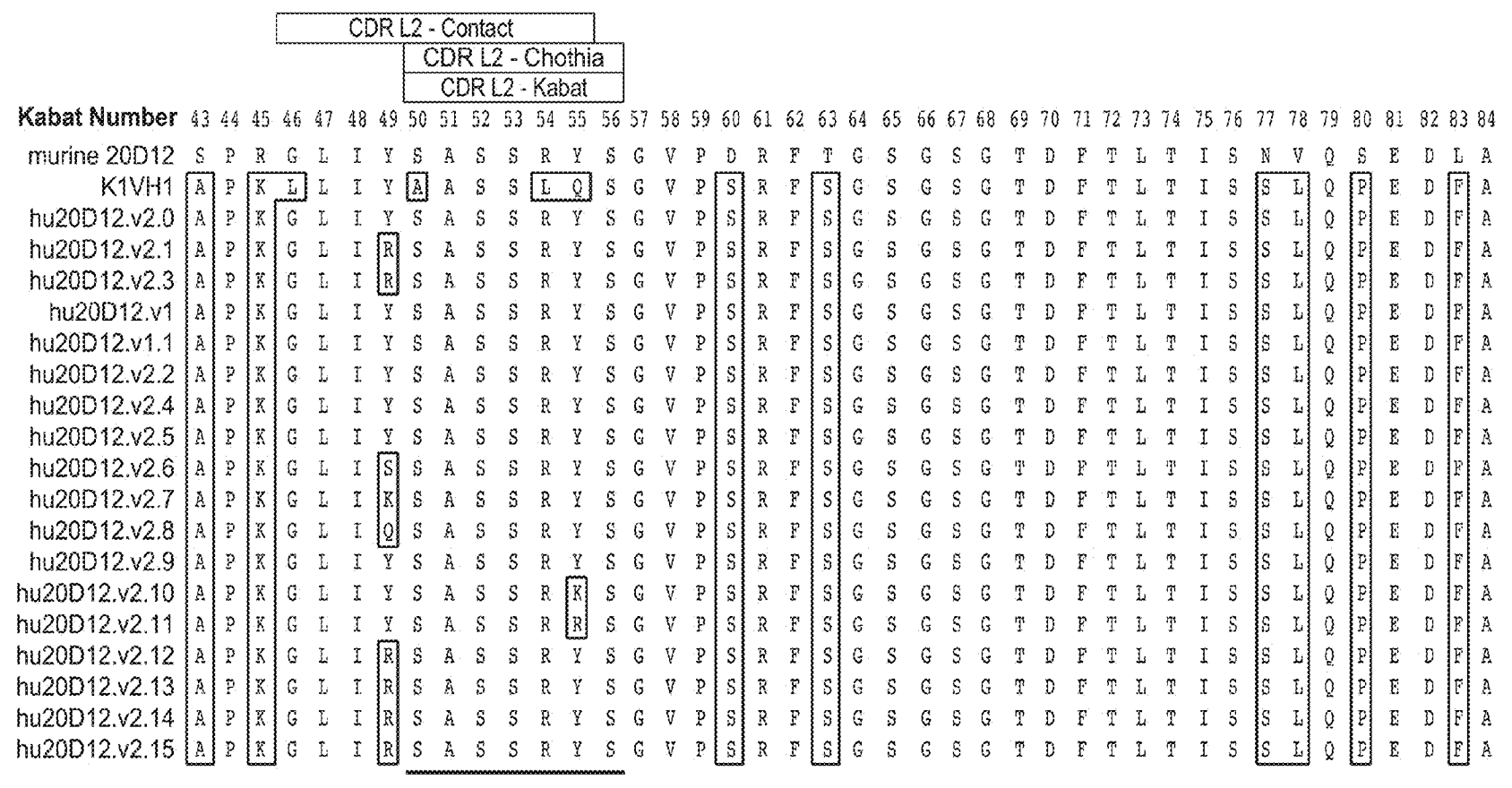
Figure 2A:
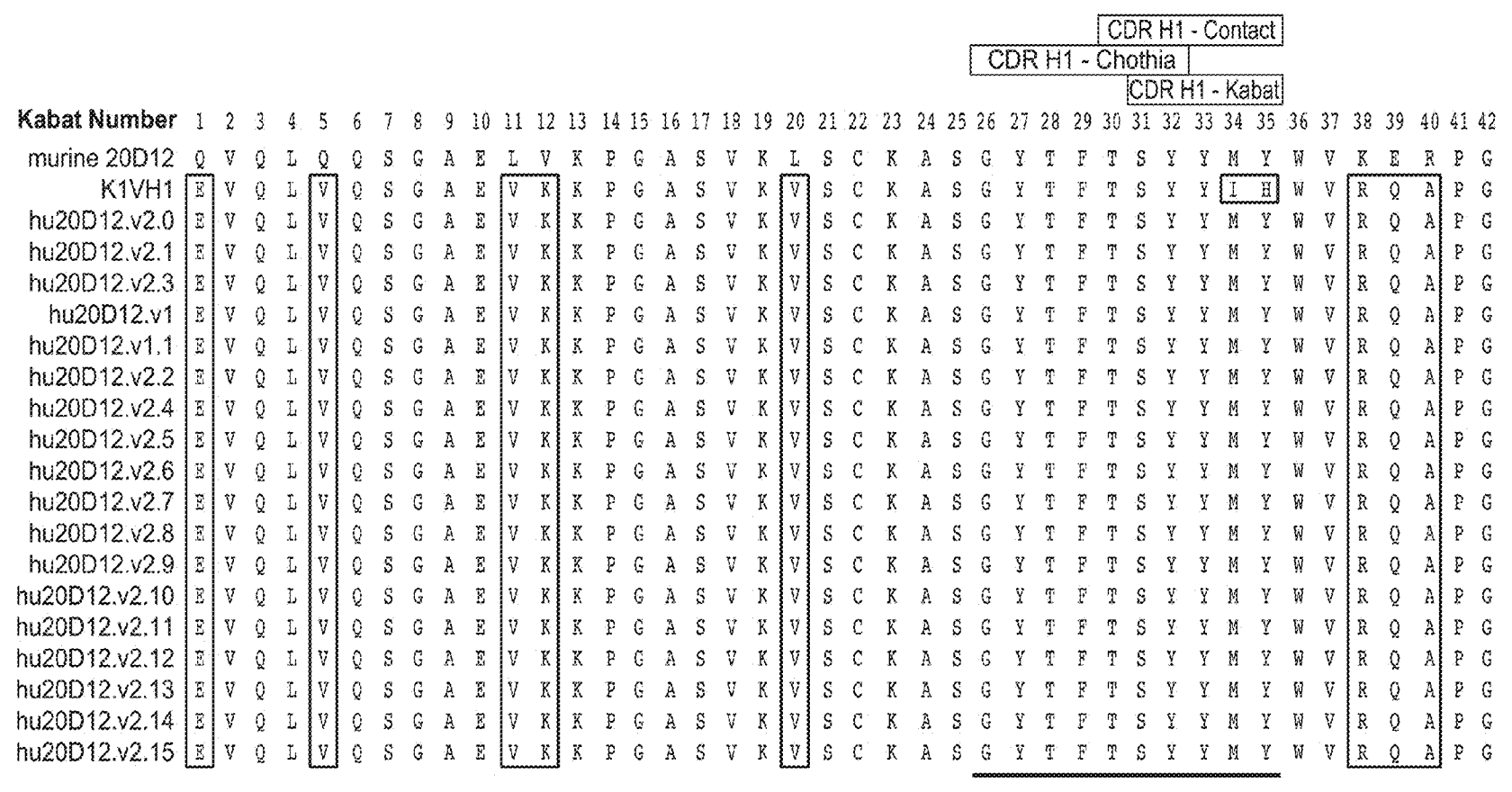
Figure 2B:
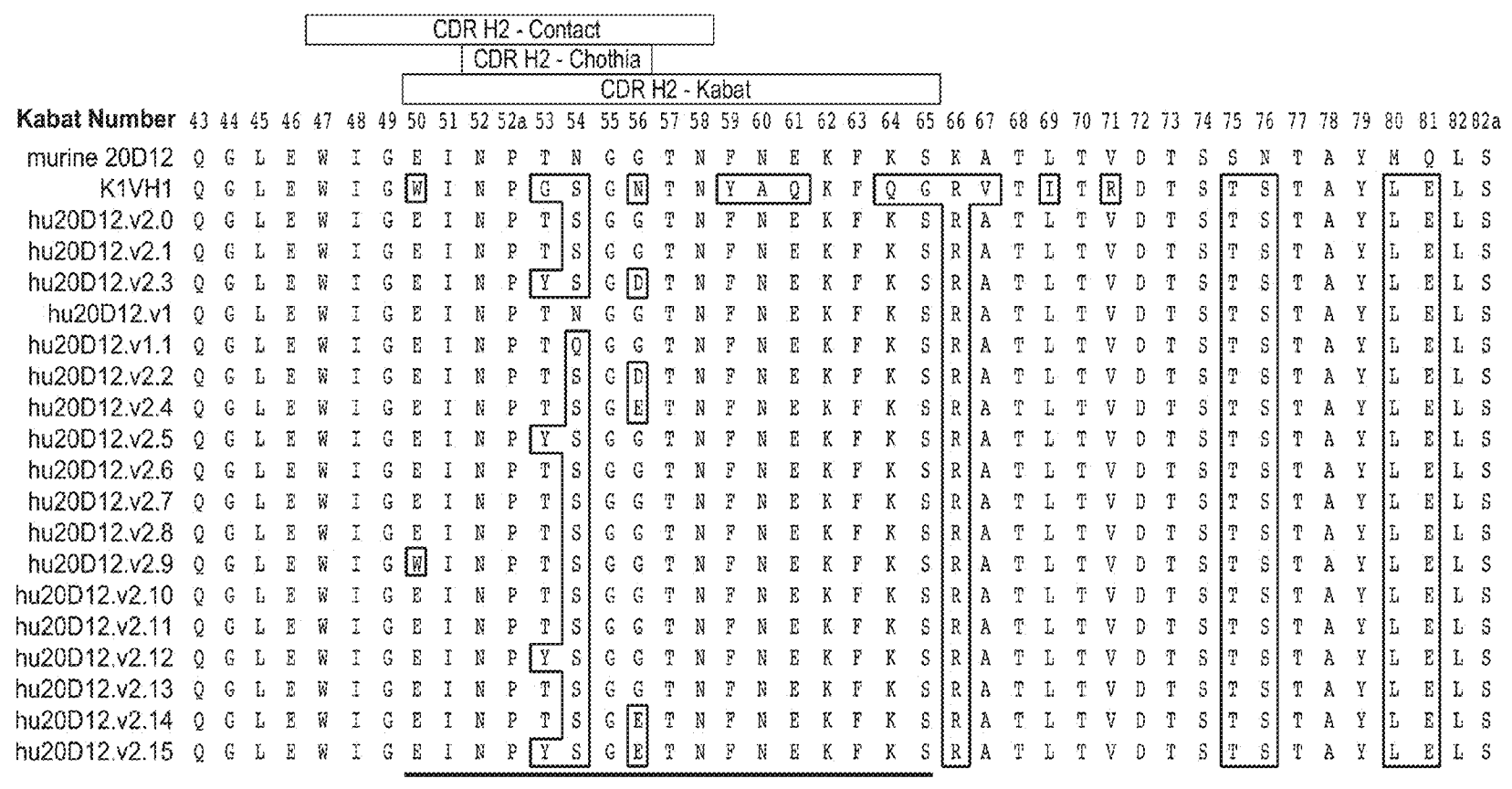

Provided herein are antibodies comprising a light chain variable domain comprising the HVR1-LC, HVR2-LC and HVR3-LC sequence according to Kabat numbering as depicted in FIGS. 1A-C and a heavy chain variable domain comprising the HVR1-HC, HVR2-HC and HVR3-HC sequence according to Kabat numbering as depicted in FIGS. 2A-C. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIGS. 1A-C. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIGS. 2A-C.

In a further aspect of the invention, an anti-Factor D antibody according to any of the above embodiments is a monoclonal antibody, including a human antibody. In some embodiments, an anti-Factor D antibody is an antibody fragment, e.g., a Fv, Fab, Fab-SH, Fab'-SH, Fab', Fab-C, Fab'-C, Fab'-C-SH, Fab-C-SH, scFv, diabody, or F(ab')$_2$ fragment. In another embodiment, the antibody is a substantially full length antibody, e.g., an IgG1 antibody, IgG2a antibody or other antibody class or isotype as defined herein. In some embodiments, the anti-Factor D antibody is a Fab.

In a further aspect, an anti-Factor D antibody according to any of the above embodiments may incorporate any of the features, singly or in combination, as described below.

1. Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In some embodiments, Kd is measured by a radiolabeled antigen binding assay (MA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, twofold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fv, Fab, Fab-SH, Fab'-SH, Fab', Fab-C, Fab' -C, Fab'-C-SH, Fab-C-SH, scFv, diabody, or F(ab')$_2$ fragments, and other fragments described herein. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Antibody fragments with free thiol groups may be indicated with an "-SH." For example, Fab-SH (including Fab-C-SH) is the designation for Fab in which at least one cysteine residue of the constant domains bears a free thiol group.

In some embodiments, the C-terminus of the heavy chain of a Fab fragment ends in the amino acids "CDKTHT" (SEQ ID NO: 165), "CDKTHL" (SEQ ID NO: 166), "CDKTH" (SEQ ID NO: 167), "CDKT" (SEQ ID NO: 168), "CDK," or "CD." In some embodiments, the C-terminus of the heavy chain of the Fab fragment ends in the sequence CDKTH$\underline{X}$ (SEQ ID NO: 169), wherein $\underline{X}$ is any amino acid except T. Truncations and/or mutations at the C terminus may be able to reduce or eliminate AHA-reactivity against the Fab, without compromising thermostability or expression. In some embodiments, the C-terminus of the heavy chain of a Fab fragment ends in the amino acids "CDKTHTC" (SEQ ID NO: 170), "CDKTHTCPPC" (SEQ ID NO: 171), "CDKTHTCPPS" (SEQ ID NO: 172), "CDKTHTSPPC" (SEQ ID NO: 173), "CDKTHTAPPC" (SEQ ID NO: 174), "CDKTHTSGGC" (SEQ ID NO: 175), or "CYGPPC" (SEQ ID NO: 176). In some such embodiments, a free cysteine in the C-terminal amino acids may be amenable to conjugation, for example, to a polymer such as PEG. In some embodiments, a Fab fragment comprises a heavy chain constant region selected from SEQ ID NOs: 113 (CDKTHT (SEQ ID NO: 165)), 128 to 132 (CDKTHL (SEQ ID NO: 166), CDKTHTC (SEQ ID NO: 170), CDKTHTCPPC (SEQ ID NO: 171), CDKTHTCPPS (SEQ ID NO: 172), CDKTHTSPPC (SEQ ID NO: 173)), 154 to 156 (APPC (SEQ ID NO: 177), SGGC (SEQ ID NO: 178), CYGPPC (SEQ ID NO: 176)), and 134 to 137 (CDKTH (SEQ ID NO: 167), CDKT (SEQ ID NO: 168), CDK, CD). In some embodiments, a Fab is an IgG2 Fab fragment comprising a heavy chain constant region of SEQ ID NO: 138 (VERK (SEQ ID NO: 179)) or IgG2 Fab-C fragment comprising a heavy chain constant region of SEQ ID NO: 157 (VERKC (SEQ ID NO: 180)). In some embodiments, a Fab is an IgG4 Fab fragment comprising a heavy chain constant region selected from SEQ ID NOs: 139 (KYGPP (SEQ ID NO: 181)), SEQ ID NO: 163 (KYGP (SEQ ID NO: 182)), and 159-161 (KYG, KY, K), or an IgG4 Fab-C fragment comprising a heavy chain constant region of SEQ ID NO: 158 (KYGPPC (SEQ ID NO: 183)). As an alternative to truncating and/or mutation at the C terminus, to avoid pre-existing anti-hinge antibody (PE-AHA) responses, IgG2 or IgG4 Fab fragments may be used, since these do not show PE-AHA response.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Factor D and the other is for any other antigen. In certain embodiments, bispecific antibodies may bind to two different epitopes of Factor D. Bispecific antibodies may also be used to localize cytotoxic agents to cells which express Factor D. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VHNL interfaces of antibodies (see, e.g., US 2011/0287009, US2007/0178552, WO 96/027011, WO 98/050431, Zhu et al., 1997, Protein Science 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see,e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Factor D as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |

TABLE 1-continued

| Original Residue | Exemplary Substitutions | Preferred Substitutions |
|---|---|---|
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g.

complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, the proline at position 329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophane residues W87 and W110 of FcγRIII (Sondermann et al.: Nature 406, 267-273 (20 July 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wildtype human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., a "THIOMAB™," in which one or more residues of an antibody are substituted with cysteine residues. In particular embodiments, the substituted residues occur at sites of the antibody that are available for conjugation. By substituting those residues with cysteine, reactive thiol groups are thereby positioned at accessible sites of the antibody and may be used to conjugate the antibody to other moieties to create an conjugate, as described further herein. In certain embodiments, any one or more of the following residues may be substituted with cysteine: K149 (Kabat numbering) of the light chain; V205 (Kabat numbering) of the light chain; A118 (EU numbering) of the heavy chain; A140 (EU numbering) of the heavy chain; L174 (EU numbering) of the heavy chain; Y373 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. No. 7,521,541.

In certain embodiments, the antibody comprises one of the following heavy chain cysteine substitutions:

TABLE 2A

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

Suitable residues in the heavy chain for cysteine substitution in antibody Fab fragments include positions 110, 136, 170, 175, 183, and 205 (Kabat numbering).

In certain embodiments, the antibody comprises one of the following light chain cysteine substitutions:

TABLE 2B

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 |
| LC | V | 205 | 205 | e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In some embodiments, isolated nucleic acid encoding an anti-Factor D antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-Factor D antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Factor D antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frupperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-Factor D antibodies provided herein may be identified, screened for, or characterized for their physical/chemical properties and/or biological activities by various assays known in the art.

In some embodiments, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to Factor D. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Factor D is incubated in a solution comprising a first labeled antibody that binds to Factor D (e.g., any of the antibodies described herein) and a second unlabeled antibody that is being tested for its ability to compete with the first antibody for binding to Factor D. The second antibody may be present in a hybridoma supernatant. As a control, immobilized Factor D is incubated in a solution comprising the first labeled antibody but not the second unlabeled antibody. After incubation under conditions permissive for binding of the first antibody to Factor D, excess unbound antibody is removed, and the amount of label associated with immobilized Factor D is measured. If the amount of label associated with immobilized Factor D is substantially reduced in the test sample relative to the control sample, then that indicates that the second antibody is competing with the first antibody for binding to Factor D. See Harlow and Lane (1988) *Antibodies: A Laboratory Manual* ch.14 (Cold Spring Harbor Laboratory, Cold Spring Harbor, N.Y.).

To determine whether an anti-Factor D antibody, or variant or fragment thereof (e.g. antigen-binding fragment) is capable of binding to Factor D and exerting a biological effect, for example, inhibition of alternative pathway hemolysis, a hemolytic inhibition assay, e.g., using rabbit RBCs may be used. Such hemolytic inhibition may be determined using standard assays (Kostavasili et al. (1997) *J of Immunology* 158:1763-72; Wiesmann et al. (2006) *Nature* 444:159-60). Activation of complement in such assays may be initiated with serum or plasma. Appropriate concentrations of Factor D in serum or plasma (Pascual et al. (1998) *Kidney International* 34:529-536; Complement Facts Book, Bernard J. Morley and Mark J. Walport, editors, Academic Press (2000); Barnum et al. (1984) *J. Immunol. Methods*, 67: 303-309) can be routinely determined according to methods known in the art, including those that have been described in references such as Pascual et al. (1998) *Kidney International* 34:529-536 and Barnum et al. (1984) *J. Immunol. Methods* 67:303-309. The present disclosure relates generally to antibodies capable of inhibiting biological activities associated with Factor D. For example, at a concentration of 18 μm/ml (equivalent to about 1.5 times the molar concentration of human factor D in the blood; molar ratio of anti-Factor D antibody to Factor D of about 1.5:1), significant inhibition of the alternative complement activity by the antibody can be observed (see, e.g., U.S. Pat. No. 6,956,107)

In some embodiments, the present disclosure is directed to anti-Factor D antibodies and conjugates thereof, wherein a Fab fragment of such antibodies inhibits alternative pathway hemolysis with $IC_{50}$ values less than 30 nM, or less than 15 nM, or less than 10 nM, or less than 5 nM. In some embodiments, the disclosure is directed to anti-Factor D antibodies and conjugates, wherein a Fab fragment of such antibodies inhibits alternative pathway hemolysis with $IC_{50}$ values between 30 nM and 2 nM, or between 25 nM and 2 nM, or between 20 nM and 2 nM, or between 10 nM and 2 nM, or between 7 nM and 2 nM.

In some embodiments, the present disclosure is directed to anti-Factor D antibodies and conjugates thereof, wherein a Fab fragment of such antibodies inhibits alternative pathway hemolysis with $IC_{90}$ values less than 80 nM, or less than 50 nM, or less than 40 nM, or less than 20 nM, or less than 15 nM. In some embodiments, the present disclosure is directed to anti-Factor D antibodies and conjugates thereof, wherein a Fab fragment of such antibodies inhibits alternative pathway hemolysis with $IC_{90}$ values between 80 nM and 5 nM, or between 75 nM and 5 nM, or between 70 nM and 5 nM, or between 65 nM and 5 nM, or between 60 nM and 5 nM, or between 55 nM and 5 nM, or between 50 nM and 5 nM, or between 50 nM and 10 nM.

In some embodiments, the disclosure is directed to anti-Factor D antibodie and conjugates wherein a Fab fragment of such antibodies inhibits alternative pathway hemolysis in an antibody to Factor D molar ratio of about 0.05:1 (0.05) to about 10:1 (10), or about 0.09:1 (0.09) to about 8:1 (8), or about 0.1:1 (0.1) to about 6:1 (6), or about 0.15:1 (0.15) to about 5:1 (5), or about 0.19:1 (0.19) to about 4:1 (4), or about 0.2:1 (0.2) to about 3:1 (3), or about 0.3:1 (0.3) to about 2:1 (2), or about 0.4:1 (0.4) to about 1:1 (1), or about 0.5:1 (0.5) to about 1:2 (0.5), or about 0.6:1 (0.6) to about 1:3 (0.33), or about 0.7:1 (0.7) to about 1:4 (0.25), or about 0.8:1 (0.8) to about 1:5 (0.2) or about 0.9:1 (0.9) to about 1:6 (0.17).

In some embodiments, the disclosure is directed to anti-Factor D antibodies and conjugates comprising fragments of humanized anti-Factor D antibodies (e.g. antigen-binding fragments). The antibody fragments of the present disclosure may, for example, be Fv, Fab, Fab-SH, Fab'-SH, Fab', Fab-C, Fab'-C, Fab'-C-SH, Fab-C-SH, scFv, diabody, or F(ab')₂, dAb, complementarity determining region (CDR) fragments, linear antibodies, single-chain antibody molecules, minibodies, diabodies, or multispecific antibodies formed from antibody fragments. In a further embodiment, the disclosure is directed to a humanized anti-Factor D antibody fragment or conjugate thereof (e.g. antigen-binding fragment) that is capable of penetrating substantially all of the retina. In an even further embodiment, the disclosure is directed to a humanized anti-Factor D antibody fragment or conjugate thereof (e.g. antigen-binding fragment) that is capable of penetrating throughout the entire thickness of the retina.

In some embodiments, the disclosure is directed to conjugates comprising anti-Factor D antibodies, wherein an unconjugated Fab fragment of such antibodies has a half life of at least 3, 5, 7, 10 or 12 days after administration into a mammalian eye (e.g. human) via a single intravitreal injection. In some embodiments, the disclosure is directed to conjugates comprising humanized anti-Factor D antibodies, wherein an unconjugated Fab fragment of such antibodies inhibits alternative pathway (AP) complement activation for at least 40, 45, 50, 55, 60, 65, 70, 75, 80, 85, 90, 95, 100, 105, 110 or 115 days after administration into a mammalian eye (e.g. human) via a single intravitreal injection. In another embodiment, the disclosure is directed to conjugates comprising humanized anti-Factor D antibodies, wherein the concentration of an unconjugated Fab fragment of such antibodies that inhibits alternative pathway (AP) complement activation is maintained in retinal tissue for at least 40, 45, 50, 55, 60, 65, 70, 75, 80 or 85 days after administration into a mammalian eye (e.g. human) via a single intravitreal injection. In another embodiment, the disclosure is directed to conjugates comprising humanized anti-Factor D antibodies, wherein the concentration of an unconjugated Fab fragment of such antibodies that inhibits alternative pathway (AP) complement activation is maintained in the vitreous humor for at least 80, 85, 90, 95, 100, 105, 110 or 115 days after administration into a mammalian eye (e.g. human) via a single intravitreal injection.

D. Conjugates

The invention also provides conjugates comprising any anti-Factor D antibody provided herein conjugated to one or more heterologous molecules, such as polyols.

1. Multi-Armed Polymers

In some embodiments, the conjugates of the present disclosure can be made by derivatizing the anti-Factor D antibodies described herein by conjugating the antibodies or variants thereof with a multi-armed polymer. It will be appreciated that any multi-armed polymer that provides the conjugate with the desired size or that has the selected average molecular weight as described herein is suitable for use in constructing the antibody-polymer conjugates of the disclosure.

Many polymers are suitable for use in pharmaceuticals. See, e.g., Davis et al., Biomedical Polymers: Polymeric Materials and Pharmaceuticals for Biomedical Use, pp. 441-451 (1980). In all embodiments of the present disclosure, a non-proteinaceous polymer is used to form the conjugates of the disclosure. The non-proteinaceous polymer ordinarily is a hydrophilic synthetic polymer, i.e., a polymer not otherwise found in nature. However, polymers which exist in nature and are produced by recombinant or in vitro methods may also be useful, as are polymers which are isolated from native sources.

In some embodiments, the anti-Factor D antibodies are derivitized by conjugating (e.g., covalently linking) the antibodies or variants thereof to a multi-armed polyol. Thus, in some embodiments, the disclosure is directed to a conjugate comprising one or more anti-Factor D antibody or antibody variant disclosed herein covalently linked to one or more multi-armed polyol. The polyol employed can be any water-soluble poly (alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as polyethylene glycol (PEG), and thus, for ease of description, the remainder of the discussion relates to an exemplary embodiment wherein the polyol employed is PEG, and the process of conjugating the polyol to a polypeptide is termed "PEGylation." However, those skilled in the art will recognize that other polyols, such as, for example, poly(propylene glycol) and polyethylene-polypropylene glycol copolymers, can be employed using the techniques for conjugation described herein for PEG.

The polyols used to form the conjugates of the present disclosure are multi-armed polyols. As used herein, "multi-armed polyol" refers to a polyol comprising a core structure to which at least two arms are attached. The multi-armed polyol may be, for example, a dimer (two arms), a tetramer (four arms), a hexamer (six arms), an octamer (eight arms), etc. In some aspects, the multi-armed polyol is a multi-armed PEG.

The weight average molecular weight of the multi-armed PEG used in the PEGylation of the anti-Factor D antibodies and antibody variants can vary, and typically may range from about 500 to about 300,000 daltons (D). In some embodiments, the weight average molecular weight of the multi-armed PEG is from about 1,000 to about 100,000 D, and, in some embodiments, from about 20,000 to about 60,000 D. In some embodiments, PEGylation is carried out with a multi-armed PEG having a weight average molecular weight of about 40,000 D.

A variety of methods for PEGylating proteins are known in the art. Specific methods of producing proteins conjugated to PEG include the methods described in U.S. Pat. Nos. 4,179,337, 4,935,465, and 5,849,535, all of which are herein incorporated by reference in their entirety. Typically the protein is covalently bonded via one or more of the amino acid residues of the protein to a terminal reactive group on the polymer. The polymer with the reactive group(s) is designated herein as an activated or functionalized polymer (e.g., a functionalized PEG). The reactive group selectively reacts with free sulfhydryl or amino or other reactive groups on the antibody or antibody variant. The multi-armed PEG polymer can be coupled to the sulfhydryl or amino or other reactive group on the antibody or antibody variant in either a random or a site specific manner. It will be understood, however, that the type and amount of the reactive group chosen, as well as the type of polymer employed, to obtain optimum results, will depend on the particular antibody or antibody variant employed to limit, and preferably substantially prevent, having the reactive group react with too many active groups on the antibody. As it may not be possible to sufficiently limit or prevent this in some instances, typically from about 0.05 to about 1000 moles, or, in some embodiments, from about 0.05 to about 200 moles of functionalized polymer per mole of antibody, depending on antibody concentration, may be employed. The final amount of functionalized polymer per mole of antibody is a balance to maintain optimum activity, while at the same time optimizing, if possible, the vitreous humor, retina, and/or aqueous humor half-life of the antibody.

While the residues may be any reactive amino acids on the antibody or antibody variant, such as the N-terminal amino acid group, in some embodiments, the reactive amino acid is cysteine, which is linked to the reactive group of the functionalized polymer through its free thiol group as shown, for example, in WO 99/03887, WO 94/12219, WO 94/22466, U.S. Pat. Nos. 5,206, 344, 5,166,322, and 5,206, 344, all of which are herein incorporated by reference in their entirety. In such embodiments, the polymer may comprise at least one terminal reactive group that is capable of reacting specifically with the free sulfhydryl or thiol group (s) on the parental antibody. Such groups include, but are not limited to, maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate, among others. The polymer can be coupled to the parental antibody using any protocol suitable for the chemistry of the coupling system selected, such as the protocols and systems described in U.S. Pat. Nos. 4,179,337, 7,122,636, and Jevsevar, et al., *Biotech J.*, Vol. 5, pp. 113-128 (2010). Alternatively, the reactive amino acid may be lysine, which is linked to the reactive group of the functionalized polymer through its free epsilon-amino group (see, e.g., WO 93/00109, incorporated by reference herein), or glutamic or aspartic acid, which is linked to the polymer through an amide bond. The reactive group of the polymer can then react with, for example, the α (alpha) and ε (epsilon) amines or sulfhydryl groups of proteins to form a covalent bond. It will be appreciated that the present disclosure is not limited to conjugates utilizing any particular type of linkage between an antibody or antibody fragment and a polymer.

Suitable functionalized multi-armed PEGs for use in preparing the conjugates of the disclosure can be produced by a number of conventional reactions. For example, a N-hydroxysuccinimide ester of a PEG (M-NHS-PEG) can be prepared from a PEG-monomethyl ether by reaction with N,N'-dicyclohexylcarbodiimide (DCC) and N-hydroxysuccinimide (NHS), according to the method of Buckmann and Merr, *Makromol. Chem.*, Vol. 182, pp. 1379-1384 (1981). In addition, a PEG terminal hydroxy group can be converted to an amino group, for example, by reaction with thionyl bromide to form PEG-Br, followed by aminolysis with excess ammonia to form PEG-NH$_2$. The PEG-NH$_2$ can then be conjugated to the antibody or antibody variant of interest using standard coupling reagents, such as Woodward's Reagent K. Furthermore, a PEG terminal-CH$_2$OH group can be converted to an aldehyde group, for example, by oxidation with MnO$_2$. The aldehyde group can be conjugated to the antibody or antibody variant by reductive alkylation with a reagent such as cyanoborohydride.

In some embodiments, the multi-armed PEG used to prepare the conjugates of the present disclosure has the structure of general formula (I):

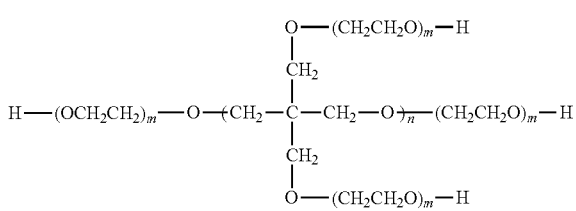

(I)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10.

In some embodiments, the multi-armed PEG has the structure of general formula (I), wherein n is 1, and the multi-armed PEG is a tetramer. In another embodiment, the multi-armed PEG has the structure of general formula (I), wherein n is 2, and the multi-armed PEG is a hexamer. In another embodiment, the multi-armed PEG has the structure of general formula (I), wherein n is 3, and the multi-armed PEG is an octamer.

In another aspect, the multi-armed PEG used to prepare the conjugates of the present disclosure has the structure of general formula (II):

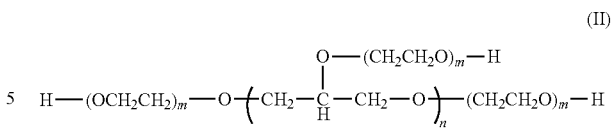

(II)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10.

In some embodiments, the multi-armed PEG has the structure of general formula (II), wherein n is 2, and the multi-armed PEG is a tetramer. In another embodiment, the multi-armed PEG has the structure of general formula (II), wherein n is 4, and the multi-armed PEG is a hexamer. In another embodiment, the multi-armed PEG has the structure of general formula (II), wherein n is 6, and the multi-armed PEG is an octamer.

In another aspect, the multi-armed PEG used to prepare the conjugates of the present disclosure has the structure of general formula (III):

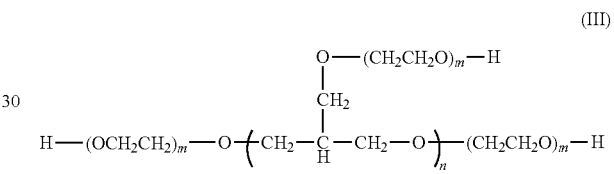

(III)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10.

In some embodiments, the multi-armed PEG has the structure of general formula (III), wherein n is 2, and the multi-armed PEG is a tetramer. In another embodiment, the multi-armed PEG has the structure of general formula (III), wherein n is 4, and the multi-armed PEG is a hexamer. In another embodiment, the multi-armed PEG has the structure of general formula (III), wherein n is 6, and the multi-armed PEG is an octamer.

In another aspect, the multi-armed PEG used to prepare the conjugates of the present disclosure has the structure of general formula (IV):

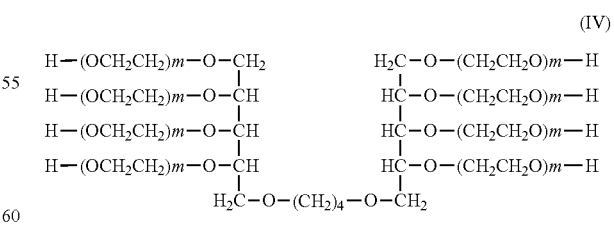

(IV)

wherein each m denotes the length or size of the particular arm of the polyol (PEG) and is independently an integer of from about 45 to about 1000, about 3 to about 250, or from about 50 to about 200, or from about 100 to about 150.

The multi-armed PEG having the structure of any of general formulas (I) to (IV) may be functionalized to, for example, attach a terminal reactive group suitable for reacting with or conjugating to the antibody (e.g., antibody fragment) using any of the techniques described above to produce a functionalized multi-armed PEG. In other embodiments, however, the multi-armed PEG can be covalently linked to the anti-Factor D antibodies through a multifunctional crosslinking agent which reacts with the PEG and one or more amino acid residues of the antibody or antibody variant to be linked, as described in, for example, U.S. Pat. No. 7,122,636, which is herein incorporated by reference in its entirety.

In other aspects, the multi-armed PEG used to prepare the conjugates of the present disclosure is a functionalized multi-armed PEG comprising at least one terminal reactive group. The terminal reactive group can conjugate directly to the anti-Factor D antibodies to form the conjugates of the present disclosure. In some embodiments, the functionalized multi-armed PEG has the structure of general formula (Ia):

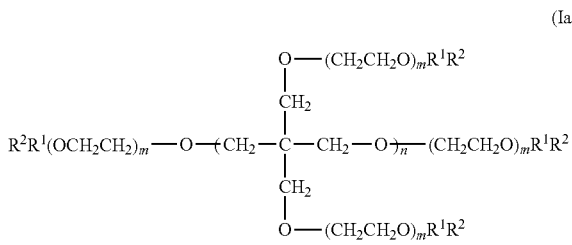

(Ia)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

In some embodiments, the functionalized multi-armed PEG has the structure of general formula (Ia), wherein n is an integer from 1 to 3. In some embodiments, the functionalized multi-armed PEG has the structure of general formula (Ia), wherein n is 1, and the multi-armed PEG is a tetramer. In another embodiment, the functionalized multi-armed PEG has the structure of general formula (Ia), wherein n is 2, and the multi-armed PEG is a hexamer. In another embodiment, the functionalized multi-armed PEG has the structure of general formula (Ia), wherein n is 3, and the multi-armed PEG is an octamer. In such embodiments, the octamer has the structure of general formula (Ib):

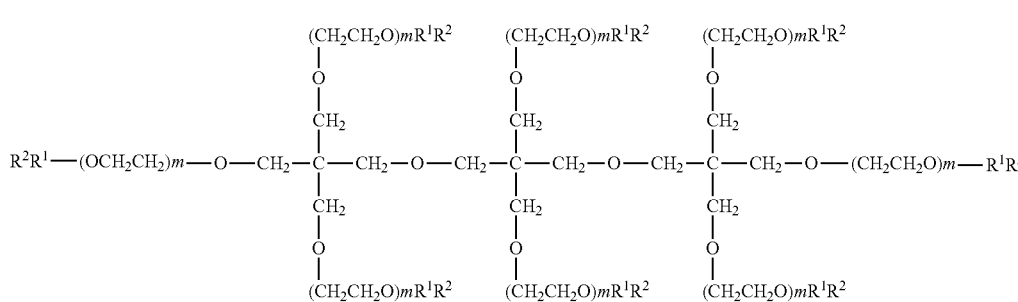

(Ib)

wherein m, $R^1$, and $R^2$ are as defined above.

Multi-armed PEGs having the structure of general formula (Ib) have a tripentaerythritol (TP) core structure, and are also referred to herein as TP octamers.

In some embodiments, the functionalized multi-armed PEG has the structure of general formula (Ia) or (Ib), wherein each $R^1$, when present, is the same or different, and $R^1$ and $R^2$ when taken together are selected from

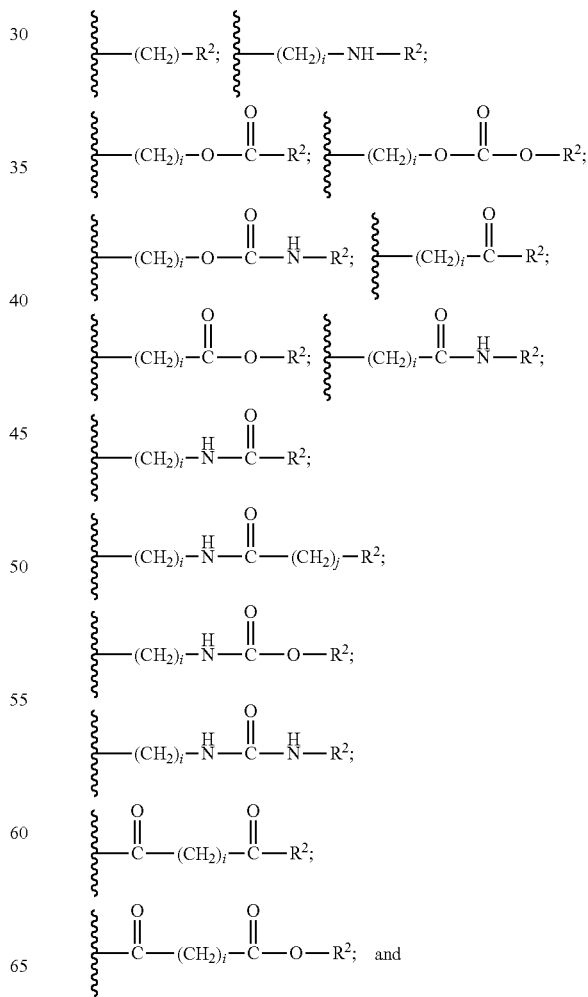

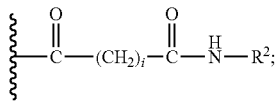

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (Ia) or (Ib), wherein $R^1$ and $R^2$, when taken together, are

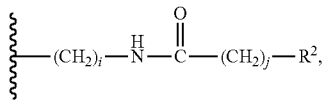

wherein i, j, and $R^2$ are as defined herein. In some embodiments, $R^1$ and $R^2$, when taken together, are

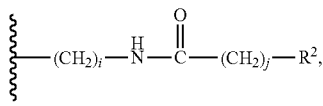

wherein i is 2; j is 2 or 3, and $R^2$ is as defined herein.

In some embodiments, the functionalized multi-armed PEG has the structure of general formula (Ia) or (Ib), wherein each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (Ia) or (Ib), wherein each $R^2$ is a maleimide. In some embodiments, the functionalized multi-armed PEG has the structure of general formula (Ia) or (Ib), wherein $R^1$ and $R^2$, when taken together, are

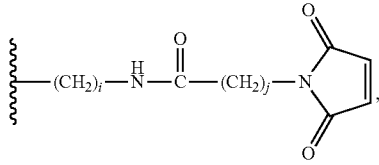

wherein i and j are as defined above. In some embodiments, the functionalized multi-armed PEG has the structure of general formula (Ia) or (Ib), wherein $R^1$ and $R^2$, when taken together, are

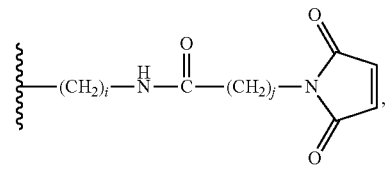

wherein i is 2 and j is 2.

In another aspect, the functionalized multi-armed PEG used to prepare the conjugates of the present disclosure has the structure of general formula (IIa):

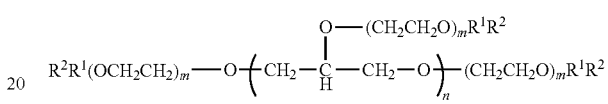

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

In some embodiments, the functionalized multi-armed PEG has the structure of general formula (IIa), wherein n is an integer from 2 to 6. In some embodiments, the functionalized multi-armed PEG has the structure of general formula (IIa), wherein n is 2, and the multi-armed PEG is a tetramer. In some embodiments, the functionalized multi-armed PEG has the structure of general formula (IIa), wherein n is 3. In another embodiment, the functionalized multi-armed PEG has the structure of general formula (IIa), wherein n is 4, and the multi-armed PEG is a hexamer. In another embodiment, the functionalized multi-armed PEG has the structure of general formula (IIa), wherein n is 6, and the multi-armed PEG is an octamer. Octamers having the structure of general formula (IIa) have a hexaglycerin (HG) core structure, and are also referred to herein as HG octamers.

In some embodiments, the functionalized multi-armed PEG has the structure of general formula (IIa), wherein each $R^1$, when present, is the same or different, and $R^1$ and $R^2$ when taken together are selected from

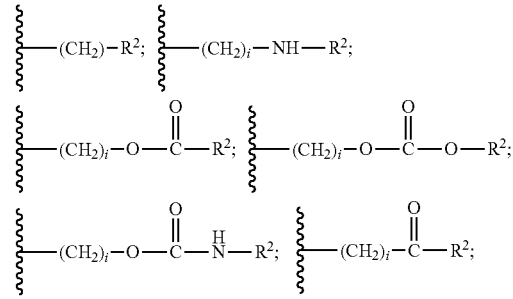

-continued

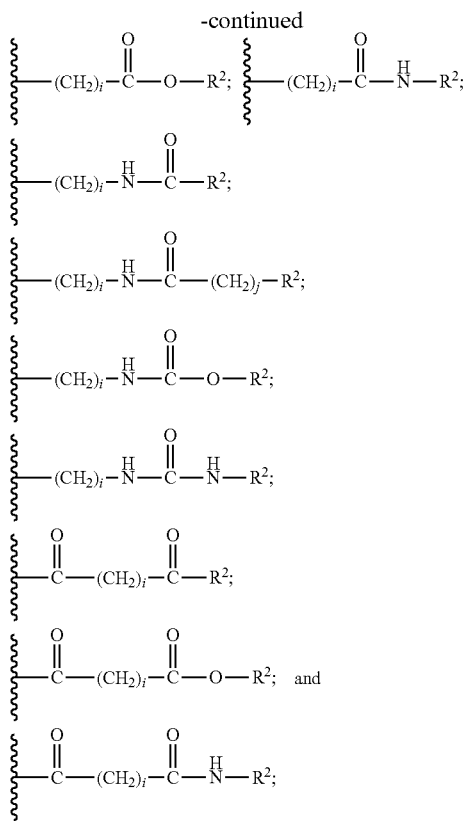

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IIa), wherein $R^1$ and $R^2$, when taken together, are

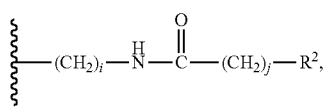

wherein i, j, and $R^2$ are as defined herein. In some embodiments, $R^1$ and $R^2$, when taken together, are

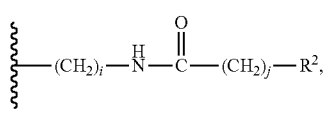

wherein i is 2; j is 2 or 3, and $R^2$ is as defined herein.

In some embodiments, the functionalized multi-armed PEG has the structure of general formula (IIa), wherein each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (IIa), wherein each $R^2$ is a maleimide. In some embodiments, the functionalized multi-armed PEG has the structure of general formula (IIa), wherein $R^1$ and $R^2$, when taken together, are

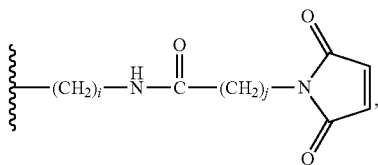

wherein i and j are as defined above. In some embodiments, the functionalized multi-armed PEG has the structure of general formula (IIa), wherein $R^1$ and $R^2$, when taken together, are

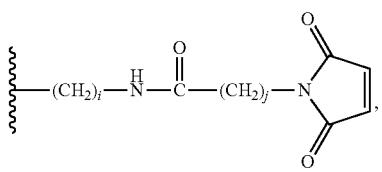

wherein i is 2 and j is 2.

In another aspect, the functionalized multi-armed PEG has the structure of general formula (IIIa):

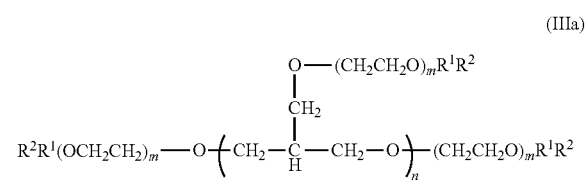

(IIIa)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

In some embodiments, the functionalized multi-armed PEG has the structure of general formula (IIIa), wherein n is an integer from 2 to 6. In some embodiments, the functionalized multi-armed PEG has the structure of general formula (IIIa), wherein n is 2, and the multi-armed PEG is a tetramer. In another embodiment, the functionalized multi-armed PEG has the structure of general formula (IIIa), wherein n is 4, and the multi-armed PEG is a hexamer. In another embodiment, the functionalized multi-armed PEG has the structure of general formula (IIIa), wherein n is 6, and the multi-armed PEG is an octamer. Octamers having the structure of general formula (IIIa) have a hexaglycerol (HGEO) core structure, and are also referred to herein as HGEO octamers.

In some embodiments, the functionalized multi-armed PEG has the structure of general formula (IIIa), wherein each $R^1$, when present, is the same or different, and $R^1$ and $R^2$ when taken together are selected from

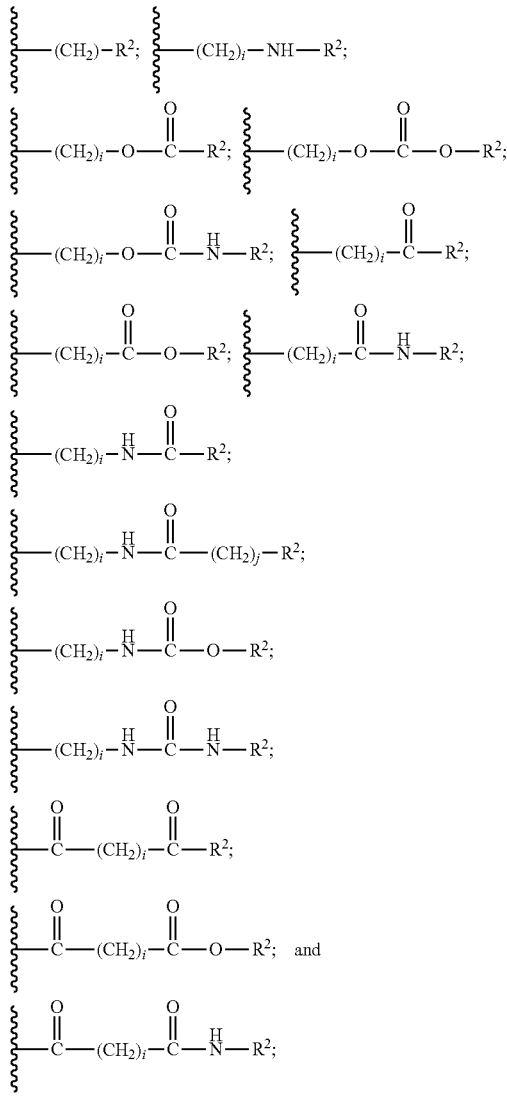

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IIIa), wherein $R^1$ and $R^2$, when taken together, are

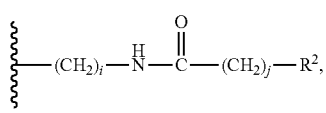

wherein i, j, and $R^2$ are as defined herein. In some embodiments, $R^1$ and $R^2$, when taken together, are

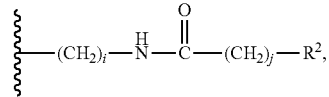

wherein i is 2; j is 2 or 3, and $R^2$ is as defined herein.

In some embodiments, the functionalized multi-armed PEG has the structure of general formula (IIIa), wherein each $R^2$ is independently selected from a maleimide, a sulfhydryl, a thiol, trifluoromethanesulfonate, tosylate, aziridine, epoxide, a pyridyl disulfide, succinimidyl ester, $-NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (IIIa), wherein each $R^2$ is a maleimide. In some embodiments, the functionalized multi-armed PEG has the structure of general formula (IIIa), wherein $R^1$ and $R^2$, when taken together, are

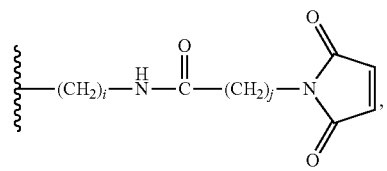

wherein i and j are as defined above. In some embodiments, the functionalized multi-armed PEG has the structure of general formula (IIIa), wherein $R^1$ and $R^2$, when taken together, are

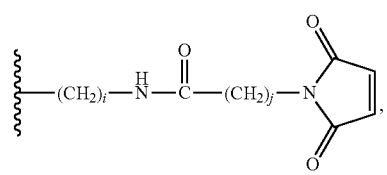

wherein i is 3 and j is 2.

In another aspect, the functionalized multi-armed PEG has the structure of general formula (IVa):

(IVa)

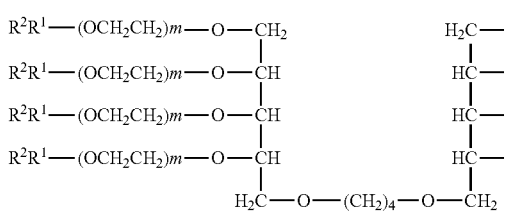
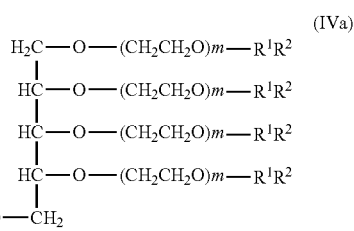

wherein each m denotes the length or size of the particular arm of the polyol (PEG) and is independently an integer of from about 45 to about 1000, or from about 3 to about 250, or from about 50 to about 200, or from about 100 to about 150; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

Multi-armed PEGs having the structure of general formula (IVa) have a butanediol core structure, and are also referred to herein as DX octamers.

In some embodiments, the functionalized multi-armed PEG has the structure of general formula (IVa), wherein each $R^1$, when present, is the same or different, and $R^1$ and $R^2$ when taken together are selected from

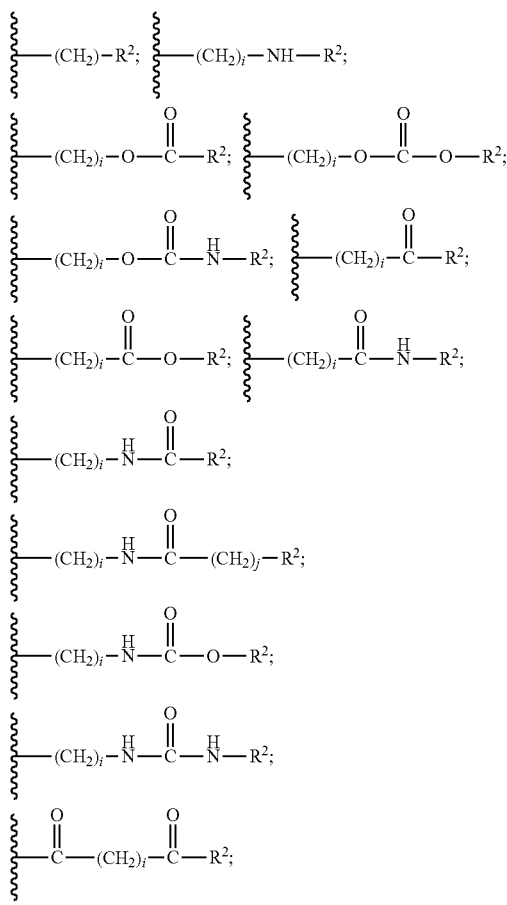

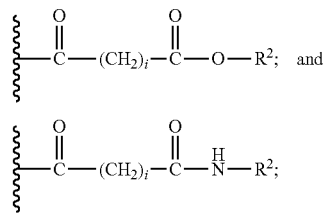

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IVa), wherein $R^1$ and $R^2$, when taken together, are

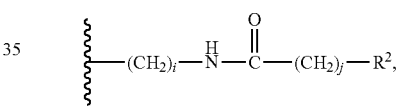

wherein i, j, and $R^2$ are as defined herein. In some embodiments, $R^1$ and $R^2$, when taken together, are

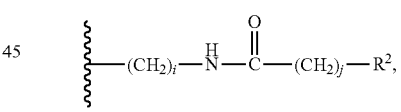

wherein i is 2; j is 2 or 3, and $R^2$ is as defined herein.

In some embodiments, each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (IVa), wherein each $R^2$ is a maleimide. In some embodiments, the functionalized multi-armed PEG has the structure of general formula (IVa), wherein $R^1$ and $R^2$, when taken together, are

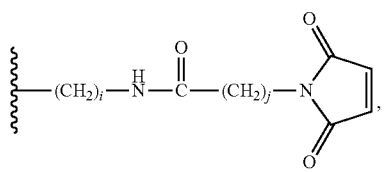

wherein i and j are as defined above. In some embodiments, the functionalized multi-armed PEG has the structure of general formula (IVa), wherein $R^1$ and $R^2$, when taken together, are

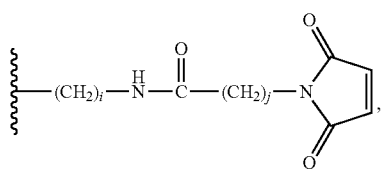

wherein i is 3 and j is 2.

Other functionalized multi-armed PEGs suitable for use in the present disclosure are described in U.S. Pat. App. Publ. No. 2011/0286956, and U.S. Pat. App. Publ. No. 2015/0073155, both of which are herein incorporated by reference in their entirety.

Functionalized multi-armed PEGs suitable for use in the present disclosure can also be purchased from a number of vendors. For example, JenKem Technology, USA sells maleimide-functionalized PEG octamers (e.g., 8ARM (TP)-PEG-MAL and 8ARM (HG)-PEG-MAL) and tetramers. NOF America Corp. also sells maleimide functionalized PEG octamers (e.g., Sunbright® HGEO-400MA; Sunbright® DX-400MA) and tetramers (e.g., Sunbright® PTE-400MA). Such octamers and tetramers are available in a variety of molecular weights, including a weight average molecular weight of 40,000 D.

2. Conjugates

In some embodiments, the disclosure is directed to a conjugate comprising one or more anti-Factor D antibody or antibody variant disclosed herein and one or more multi-armed polyol, wherein the conjugate is prepared by covalently linking at least one anti-Factor D antibody or antibody variant to the polyol. In some embodiments, the multi-armed polyol is a PEG. In some embodiments, the PEG is an octamer. In some embodiments, the PEG has the structure of general formula (Ia), (Ib), (IIa), (IIIa), or (IVa).

The conjugates of the present disclosure may be characterized by the number of anti-Factor D antibodies conjugated to each multi-armed PEG. This is referred to herein as "fabylation" or "degree of fabylation". The number of anti-Factor D antibodies conjugated to each PEG may vary depending on a variety of factors, including: 1) the number of arms in the PEG; 2) the number and/or reactivity of the terminal reactive groups on the PEG; 3) the core structure of the PEG; and/or, 4) PEGylation reaction conditions. A high polydispersity of the multi-armed PEG used to prepare the conjugate may in some instances complicate the analysis of the final conjugate, in particular making an accurate determination of the number of antibodies (e.g., Fabs) per PEG more difficult and uncertain. Accordingly, the PEG used to form the conjugate will typically have a polydispersity (determined using methods known in the art) within a range of about 1 to about 1.35, and in various embodiments will have a polydispersity of about 1 to about 1.25, about 1 to about 1.2, about 1 to about 1.15, about 1 to about 1.1, about 1.05, or even about 1.

In some embodiments, the conjugate of the disclosure comprises an eight-armed PEG, wherein at least one anti-Factor D antibody or antibody variant is covalently linked to the PEG. In another embodiment, the conjugate of the disclosure comprises an eight-armed PEG, wherein at least two anti-Factor D antibodies are covalently linked to the PEG. In another embodiment, the conjugate of the disclosure comprises an eight-armed PEG, wherein at least three anti-Factor D antibodies are covalently linked to the PEG. In another embodiment, the conjugate of the disclosure comprises an eight-armed PEG, wherein at least four anti-Factor D antibodies are covalently linked to the PEG. In another embodiment, the conjugate of the disclosure comprises an eight-armed PEG, wherein at least five anti-Factor D antibodies are covalently linked to the PEG. In another embodiment, the conjugate of the disclosure comprises an eight-armed PEG, wherein at least six anti-Factor D antibodies are covalently linked to the PEG. In another embodiment, the conjugate comprises an eight-armed PEG, wherein at least seven anti-Factor D antibodies are covalently linked to the PEG. In another embodiment, the conjugate of the disclosure comprises an eight-armed PEG, wherein eight anti-Factor D antibodies are covalently linked to the PEG. In some embodiments, the conjugate of the disclosure comprises an eight-armed PEG, wherein from 5-8 anti-Factor D antibodies are covalently linked to the PEG. In another embodiment, the conjugate of the disclosure comprises an eight-armed PEG, wherein from 6-8 anti-Factor D antibodies are covalently linked to the PEG. In another embodiment, the conjugate of the disclosure comprises an eight-armed PEG, 7-8 anti-Factor D antibodies are covalently linked to the PEG.

In some embodiments, the conjugate of the disclosure comprises a multi-armed PEG having the structure of any one of general formulas (Ia), (Ib), (IIa), (IIIa), or (IVa). In such embodiments, at least one $R^2$ is covalently linked to an anti-Factor D antibody or antibody variant described herein. In some embodiments, the multi-armed PEG having the structure of any one of general formulas (Ia), (Ib), (IIa), (IIIa), or (IVa) is an octamer, and at least two, at least three, at least four, at least five, at least six, at least seven, or all eight $R^2$ groups are covalently linked to an anti-Factor D antibody or antibody variant described herein.

In some embodiments, the conjugates of the present disclosure include species wherein the multi-armed polyol is covalently attached to a specific site or specific sites on the parental antibody; i.e., polymer attachment is targeted to a particular region or a particular amino acid residue or residues in the parental antibody or antibody fragments. Standard mutagenesis techniques can be used to alter the number and/or location of potential PEGylation sites in the parental antibody or antibody fragments. Thus, to the extent that amino acid substitutions introduce or replace amino acids such as cysteine and lysine, the anti-Factor D antibodies and variants thereof of the present disclosure can contain a greater or lesser number of potential PEGylation sites than a native sequence anti-Factor D (shown in FIGS. 1A-C).

As discussed above, site specific conjugation of polymers is most commonly achieved by attachment to cysteine residues in the parental antibody or antibody fragment. In such embodiments, the coupling chemistry can, for example, utilize the free sulfhydryl group of a cysteine residue not in a disulfide bridge in the parental antibody.

In some embodiments, one or more cysteine residue(s) naturally present in the parental antibody is (are) used as attachment site(s) for polymer conjugation. In other embodiments, free amino groups on the antibody or antibody variant can be thiolated with 2-imino-thiolane (Traut's reagent) and then coupled to, e.g., a maleimide-functionalized PEG, as described in Pedley, et al., *Br. J. Cancer, Vol.* 70, pp. 1126-1130 (1994). In another embodiment, one or more cysteine residue(s) is (are) engineered into a selected site or sites in the parental antibody for the purpose of providing a specific attachment site or sites for polymer.

Cysteine engineered antibodies have been described previously (U.S. Pat. Pub. No. 2007/0092940 and Junutula, J. R., et al, *J. Immunol Methods, Vol.* 332(1-2), pp. 41-52 (2008), all herein incorporated by reference in their entirety). In some embodiments, cysteine engineered antibodies can be parental antibodies. These are useful for generating antibody fragments having a free cysteine in a particular location, typically in a constant region, e.g., $C_L$ or $C_H1$. A parent antibody engineered to contain a cysteine is referred to herein as a "ThioMab" and Fab fragments produced from such cysteine engineered antibodies, regardless of the method of production, are referred to herein as "ThioFabs." As described previously (see, e.g., U.S. Pat. Pub. No. 2007/0092940 and Junutula, J. R., et al, *J. Immunol Methods*, Vol. 332(1-2), pp. 41-52 (2008)), mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. In addition to having a reactive thiol group, ThioMabs should be selected such that they retain antigen binding capability. The design, selection, and preparation of cysteine engineered antibodies were described in detail previously (see, e.g., WO 2011/069104, which is herein incorporated by reference). In some embodiments, engineered cysteines are introduced into the constant domains of heavy or light chains. As such, the cysteine engineered antibodies retain the antigen binding capability of their wild type, parent antibody counterparts and, as such, are capable of binding specifically, to antigens.

In some embodiments, the present disclosure relates to antibody fragment-polymer conjugates, wherein the antibody fragment is a Fab, and the polymer is attached to one or more cysteine residue in the light or heavy chain of the Fab fragment that would ordinarily form the inter-chain disulfide bond linking the light and heavy chains.

In another aspect, the present disclosure relates to antibody fragment-polymer conjugates, wherein the antibody fragment is a Fab-C, and the polymer attachment is targeted to the hinge region of the Fab-C fragment. In some embodiments, one or more cysteine residue(s) naturally present in the hinge region of the antibody fragment is (are) used to attach the polymer. In another embodiment, one or more cysteine residues is (are) engineered into the hinge region of the Fab-C fragment for the purpose of providing a specific attachment site or sites for polymer. In some embodiments, an anti-Factor D antibody variant Fab fragment disclosed herein is modified by adding one cysteine at the C'-terminal end for the purpose of providing one attachment site for polymer conjugation. In another embodiment, an anti-Factor D antibody variant Fab fragment described herein is modified by adding four additional residues, Cys-Pro-Pro-Cys (SEQ ID NO: 162), at the C'-terminal end for the purpose of providing two attachment sites for polymer conjugation. In still another embodiment, an anti-Factor D antibody variant Fab fragment described herein is modified by adding four additional residues, Ser-Pro-Pro-Cys (see, e.g., SEQ ID NO: 121), at the C'-terminal end for the purpose of providing one attachment sites for polymer conjugation.

The degree and sites of PEGylation can also be manipulated by adjusting reaction conditions, such as the relative concentrations of the functionalized PEG and the protein as well as the pH. Suitable conditions for a desired degree of PEGylation can be determined empirically by varying the parameters of standard PEGylation reactions.

PEGylation of anti-Factor D antibodies and antibody variants is carried out by any convenient method. Suitable PEGylation conditions are set forth in WO 2011/069104 and WO 03/029420, both of which are herein incorporated by reference in their entirety.

3. Characterization

The PEGylated proteins can be characterized by SDS-PAGE, gel filtration, NMR, peptide mapping, liquid chromatography-mass spectrophotometry, and in vitro biological assays. The extent of fabylation is typically first shown by SDS-PAGE. Polyacrylamide gel electrophoresis in 10% SDS is typically run in 10 mM Tris-HCl pH 8.0, 100 mM NaCl as elution buffer. To demonstrate which residue is PEGylated, peptide mapping using proteases such as trypsin and Lys-C protease can be performed. Thus, samples of PEGylated and non-PEGylated antibodies can be digested with a protease such as Lys-C protease and the resulting peptides separated by a technique such as reverse phase HPLC. The chromatographic pattern of peptides produced can be compared to a peptide map previously determined for the anti-Factor D polypeptide.

Each peak can then be analyzed by mass spectrometry to verify the size of the conjugate in the peak. Depending on the PEG used in the conjugation, and the size of the conjugate in the peak, the number of antibodies or variants thereof conjugated to the PEG can be estimated. The fragment(s) that conjugated to PEG groups are usually not retained on the HPLC column after injection and disappear from the chromatograph. Such disappearance from the chromatograph is an indication of PEGylation on that particular fragment that should contain at least one PEGylatable amino acid residue. PEGylated anti-Factor D antibodies and antibody variants may further be assayed for ability to interact with Factor D and other biological activities using known methods in the art.

PEGylation changes the physical and chemical properties of the antibody drug, and may results in improved pharmacokinetic behaviors such as improved stability, decreased immunogenicity, extended circulating life as well as increased ocular residence time.

In some embodiments, the conjugates of the present disclosure have an increased half-life after administration into a mammalian eye (e.g. human) via a single intravitreal injection, as compared to the corresponding unconjugated anti-Factor D antibody or antibody variant. In some embodiments, the increase in half-life is at least 1.4 times, or at least 1.8 times, or at least 2 times the half-life of the corresponding unconjugated anti-Factor D antibody or antibody variant.

In some embodiments, the conjugate is stable over an extended period of time, with loss of Factor D binding capacity of less than 20%, less than 15%, or less than 10% per month at physiological conditions.

In some embodiments, the conjugate has a viscosity that makes it suitable for administration through a narrow bore needle. In some embodiments, the viscosity of the conjugate is less than 800 cP, less than 700 cP, less than 600 cP, less than 500 cP, less than 400 cP, or less than 300 cP at a concentration of 150-250 mg/ml. In some embodiments, the viscosity of the conjugate is less than 300 cP at a concentration of 200 mg/ml.

In some embodiments, the $R_H$ ranges from 3-30 nM.

E. Methods and Compositions for Diagnostics and Detection

In certain embodiments, any of the anti-Factor D antibodies provided herein is useful for detecting the presence of Factor D in a biological sample. The term "detecting" as used herein encompasses quantitative or qualitative detection. A "biological sample" comprises, e.g., a cell or tissue.

In some embodiments, an anti-Factor D antibody for use in a method of diagnosis or detection is provided. In a further aspect, a method of detecting the presence of Factor D in a biological sample is provided. In certain embodiments, the method comprises contacting the biological sample with an anti-Factor D antibody as described herein under conditions permissive for binding of the anti-Factor D antibody to Factor D, and detecting whether a complex is formed between the anti-Factor D antibody and Factor D in the biological sample. Such method may be an in vitro or in vivo method. In some embodiments, an anti-Factor D antibody is used to select subjects eligible for therapy with an anti-Factor D antibody, e.g. where Factor D is a biomarker for selection of patients. In a further embodiment, the biological sample is a cell or tissue.

In further embodiments, a method of diagnosis or detection comprises contacting a first anti-Factor D antibody immobilized to a substrate with a biological sample to be tested for the presence of Factor D, exposing the substrate to a second anti-Factor D antibody, and detecting whether the second anti-Factor D is bound to a complex between the first anti-Factor D antibody and Factor D in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-Factor D antibody is any of the antibodies described herein.

In certain embodiments, labeled anti-Factor D antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}Ga$, $^{18}F$, $^{64}Cu$, $^{86}Y$, $^{76}Br$, $^{89}Zr$, and $^{124}I$. In a particular embodiment, a positron emitter is $^{89}Zr$.

F. Pharmaceutical Formulations

Pharmaceutical formulations of an anti-Factor D antibody or conjugate as described herein are prepared by mixing such antibody or conjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In some embodiments, a sHASEGP is combined with one or more additional glycosaminoglycanases such as chondroitinases.

Exemplary lyophilized antibody or conjugate formulations are described in U.S. Pat. No. 6,267,958. Aqueous antibody or conjugate formulations include those described in U.S. Pat. No. 6,171,586 and WO2006/044908, the latter formulations including a histidine-acetate buffer.

The formulation herein may also contain more than one active ingredient as necessary for the particular indication being treated. In some embodiments, the active ingredients have complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or conjugate, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations to be used for in vivo administration are generally sterile. Sterility may be readily accomplished, e.g., by filtration through sterile filtration membranes.

The antibodies and conjugates described herein for prevention or treatment of an ocular disease or condition are typically administered by ocular, intraocular, and/or intravitreal injection, and/or juxtascleral injection, and/or sub-tenon injection, and/or suprachoroidal injection and/or topical administration in the form of eye drops and/or ointment. Such compounds of the invention may be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a min pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Other methods of administration may also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred.

For ocular administration, in some embodiments, the antibodies and conjugates described herein may be formulated in a pharmaceutically acceptable carrier at pH5.5.

In some embodiments, the antibodies and conjugates described herein may be formulated for delivery using an implantable port delivery system (PDS). As noted previously, the PDS is a refillable device where release into the vitreous is controlled by a porous metal membrane comprising a titanium frit. Since the reservoir has a low volume, in some embodiments, a high protein concentration is required for effective delivery with the PDS. Accordingly, in some embodiments, the antibodies and conjugates described herein are formulated at high concentration. In some embodiments, the antibodies and conjugates described herein may be formulated at a concentration of at least 150 mg/ml, at least 160 mg/ml, at least 170 mg/ml, at least 180 mg/ml, at least 190 mg/ml, at least 200 mg/ml, or at least 210 mg/ml, or at least 220 mg/ml, or at least 230 mg/ml, or at least 240 mg/ml, or at least 250 mg/ml, or at least 260 mg/ml, or at least 270 mg/ml, or at least 280 mg/ml, or at least 290 mg/ml, or at least 300 mg/ml. In some embodiments, the antibodies and conjugates described herein may be formulated at a concentration of between 150 mg/ml and 350 mg/ml, or between 150 mg/ml and 300 mg/ml, or between 170 mg/ml and 300 mg/ml, or between 200 mg/ml and 300 mg/ml.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slit-lamp pressure, assessing intraocular inflammation, etc.

In some embodiments, an anti-Factor D antibody of conjugate thereof is administered intravitreally at a dose of about 0.3 mg to about 30 mg per eye.

The dosing schedule for administration may vary form once a month to daily depending on a number of clinical factors, including the type of disease, severity of disease, and the subject's sensitivity to the therapeutic agent.

G. Therapeutic Methods and Compositions

Any of the anti-Factor D antibodies or conjugates provided herein may be used in methods, e.g., therapeutic methods.

An "individual," "patient," or "subject" according to any of the embodiments herein may be a human.

The anti-Factor D antibodies and conjugates of the present disclosure may be used to treat a mammal. In some embodiments, the anti-Factor D antibody or conjugate is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody, or may be used to study toxicity of the antibody of interest. In each of these embodiments, dose escalation studies may be performed on the mammal.

The anti-Factor D antibody or conjugate may be administered by any suitable means, including parenteral, subcutaneous, intraperitoneal, intravitreal, intrapulmonary, and intranasal, and, if desired for local immunosuppressive treatment, intralesional administration. Parenteral infusions include intramuscular, intravenous, intraarterial, intraperitoneal, intravitreal, and subcutaneous administration. In addition, the conjugate is suitably administered by pulse infusion, particularly with declining doses of the antibody, or antibody variant thereof or fragment thereof (e.g. antigen-binding fragment). In some embodiments, the dosing is given by injections, such as intravenous or subcutaneous injections, depending in part on whether the administration is brief or chronic.

For the prevention or treatment of disease, the appropriate dosage of the anti-Factor D antibody or conjugate will depend on the type of disease to be treated, the severity and course of the disease, whether the antibody is administered for preventive or therapeutic purposes, previous therapy, the patient's clinical history and response to the antibody and the discretion of the attending physician.

Depending on the type and severity of the disease, about 1-25 mg/eye (0.015 mg/kg-0.36 mg/kg per eye) of the antibody is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

The conjugate compositions may be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the conjugate to be administered will be governed by such considerations, and is the minimum amount necessary to prevent, ameliorate, or treat a disease or disorder. The conjugate need not be, but is optionally formulated with one or more agents currently used to prevent or treat the disorder in question. The effective amount of such other agents depends on the amount of antibody, or antibody variant thereof or fragment thereof (e.g. antigen-binding fragment), present in the formulation, the type of disorder or treatment, and other factors discussed above. These are generally used in the same dosages and with administration routes as used hereinbefore or about from 1 to 99% of the heretofore employed dosages.

The antibodies disclosed herein which recognize Factor D as their target and the conjugates comprising these antibodies may be used to treat complement-mediated disorders. These disorders are associated with excessive or uncontrolled complement activation. They include: complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease or condition is an inflammatory condition such as severe burns, endotoxemia, septic shock, adult respiratory distress syndrome, hemodialysis, anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Recently there has been a strong correlation shown between complement activation and ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

An anti-Factor D antibody of conjugate can be administered alone or in combination with at least a second therapeutic compound. Administration of the conjugate and any second therapeutic compound can be done simultaneously, e.g., as a single composition or as two or more distinct compositions using the same or different administration routes. Alternatively, or additionally the administration can be done sequentially, in any order. In certain embodiments, intervals ranging from minutes to days, to weeks to months, can be present between the administrations of the two or more compositions. For example, the conjugate comprising the Factor D antagonist may be administered first, followed by the second therapeutic compound. However, simultaneous administration or administration of the second therapeutic compound prior to the conjugate is also contemplated. In some embodiments, the second therapeutic compound is selected from an HTRA1 antagonist, an ANG2 antagonist (such as anti-ANG2 antibodies as disclosed, for example, in US20090304694 A1), a TIE2 antagonist (such as anti-TIE2 antibodies as disclosed, for example, in U.S. Pat. No. 6,376,653), a VEGF antagonist (such as VEGF antagonists as disclosed, for example, in U.S. Pat. No. 6,884,879 issued Feb. 26, 2015 and WO98/45331 (bevacizumab and other humanized anti-VEGF antibodies); WO2005/012359 and WO2005/044853 (G6 or B20 series antibodies (e.g. G6-31, B20-4.1); WO98/45331 (ranabizumab), and a second complement component antagonist. In some embodiments, the HTRA1 antagonist is an anti-HTRA1 antibody. In some embodiments, the ANG2 antagonist is an anti-ANG2 antibody. In some embodiments, the TIE2 antagonist is an anti-TIE2 antibody. In some embodiments, a VEGF antagonist is selected from a VEGF trap (such as aflibercept (Eylea®) and an anti-VEGF antibody (such as bevacizumab (Avastin®) or ranabizumab (Lucentis®)). In some embodiments, the second complement component antagonist inhibits various members of the classical or alternative complement pathway (complement inhibitors), selected from from C1, C2, C3, C4, C5, C6, C7, C8, C9 complement components.

In some embodiments, the treatment of the present disclosure for complement-mediated disorders in a human subject with a complement-mediated disorder comprises administering to the subject an effective amount of a therapeutic compound, such as an anti-Factor D antibody of conjugate, and further comprising administering to the subject an effective amount of a second therapeutic compound. In some embodiments, the second therapeutic compound is an HTRA1 antagonist. In some embodiments, the second therapeutic compound is an ANG2 antagonist. In some embodiments, the second therapeutic compound is a TIE2 antagonist. In some embodiments, the second therapeutic compound is a VEGF antagonist. In some embodiments, the second therapeutic compound is a second complement component antagonist. In some embodiments, the complement-mediated disorder is an complement-associated eye condition. In some embodiments, the ocular disorder is age-related macular degeneration (AMD), including non-exudative (e.g. intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In some embodiments, the complement-associated eye condition is geographic atrophy. In some embodiments, the complement-associated eye condition is wet AMD (choroidal neovascularization (CNV)).

Combined administration herein includes co-administration, using separate formulations or a single pharmaceutical formulation, and consecutive administration in either order, wherein generally there is a time period while both (or all) active agents simultaneously exert their biological activities.

In a further aspect, the invention provides pharmaceutical formulations comprising any of the anti-Factor D antibodies or conjugates provided herein, e.g., for use in any of the above therapeutic methods. In some embodiments, a pharmaceutical formulation comprises any of the anti-Factor D antibodies or conjugates provided herein and a pharmaceutically acceptable carrier. In another embodiment, a pharmaceutical formulation comprises any of the anti-Factor D antibodies or conjugates provided herein and at least one additional therapeutic agent.

It is understood that any of the above formulations or therapeutic methods may be carried out using either or both a conjugate of the invention and/or an anti-Factor D antibody.

H. Articles of Manufacture

Articles of manufacture, or "kits", containing an anti-Factor D antibody described herein useful for the treatment methods herein are provided. In some embodiments, the kit comprises a container comprising an anti-Factor D antibody. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold an anti-Factor D antibody described herein or a formulation thereof which is effective for use in a treatment method herein, and may have a sterile access port (for example, the container may be a vial having a stopper pierceable by a hypodermic injection needle). The label or package insert indicates that the composition is used in a treatment method as described and claimed herein. The article of manufacture may also contain a further container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the anti-Factor D antibody described herein. In some embodiments, the label or package insert indicates that the composition is used for treating complement-associated disorders, such as, for example, any of the conditions listed before, including eye disorders e.g. age-related macular degeneration (AMD). The label or package insert may further comprise instructions for administering the antibody composition to the patient. In some embodiments, if the kit comprises a first composition comprising the anti-Factor D antibody and a second pharmaceutical formulation, the kit may further comprise directions for the simultaneous, sequential or separate administration of the first and second pharmaceutical compositions to a patient in need thereof.

According to some embodiments, a kit may comprise the anti-Factor D antibody described herein and a container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, a kit comprises an implantable port delivery system (PDS) and a composition comprising the anti-Factor D antibody or conjugate described herein. In some embodiments, the kit comprises instructions for implanting the PDS and filling the reservoir with the antibody or conjugate. In some embodiments, a kit comprises a composition comprising the anti-Factor D antibody or conjugate formulated for refilling a PDS.

In another embodiment, kits are also provided that are useful for various purposes, e.g., for treatment, prevention and/or diagnosis of complement-associated disorders, for complement-associated hemolysis assays, for purification or immunoprecipitation of Factor D polypeptide from cells. For isolation and purification of Factor D polypeptide, the kit can contain an anti-Factor D antibody coupled to beads (e.g., sepharose beads). Kits can be provided which contain the antibodies for detection and quantitation of Factor D polypeptide in vitro, e.g., in an ELISA or a Western blot. As with the article of manufacture, the kit comprises a container and a label or package insert on or associated with the container. The container holds a composition comprising a conjugate of the disclosure comprising at least one anti-Factor antibody. Additional containers may be included that contain, e.g., diluents and buffers, control antibodies. The label or package insert may provide a description of the composition as well as instructions for the intended in vitro or detection use. The label or package insert may provide instructions for the administration (e.g. the antibody, or antibody fragment thereof (e.g. antigen-binding fragment) to a subject.

III. EXAMPLES

The following are examples of methods and compositions of the invention. It is understood that various other embodiments may be practiced, given the general description provided above.

Example 1

Generation of Anti-Factor D Humanized Antibodies

Lampalizumab (sometimes also referred to as "aFD.WT" or "FCFD4515S"), a humanized anti-Factor D Fab fragment that potently inhibits Factor D and the alternative complement pathway, through binding to an exosite on factor D is currently in clinical development for the treatment of geographic atrophy (GA), an advanced form of dry AMD. Lampalizumab comprises a 214 residue light chain (SEQ ID NO: 102) and a 223 residue heavy chain (SEQ ID NO: 103).

While results of a phase II human clinical trial in GA indicate that a treatment effect is obtained with monthly intravitreal injection of aFD.WT, there exist incentives to use higher drug doses to achieve even better efficacy.

Meanwhile, less frequent dosing would provide improved convenience to the patient, have potential benefits of decreased infection rate and increased clinical efficacy, and could facilitate treatment of patients with less advanced forms of dry AMD.

In order to develop a Factor D inhibitor that may be formulated at high concentration, with lower viscosity, and which could be stored without precipitation, a new humanized anti-Factor D antibody was developed based on anti-Factor D murine antibody 20D12. See PCT Publication No. 2008/147883 A1. Briefly, the VL and VH domains from murine 20D12 (VH of SEQ ID NO: 8 and VL of SEQ ID NO: 7) were aligned with the human VL kappa I ($VL_{KI}$) and human VH subgroup I ($VH_I$) consensus sequences. Hypervariable regions (HVR) from the murine 20D12 antibody were engineered into $VL_{KI}$ and $VH_I$ acceptor frameworks to generate CDR-grafted variants, as discussed below.

From the 20D12 VL domain, positions 24-34 (L1), 50-56 (L2) and 89-97 (L3) were grafted into $VL_{KI}$. From the 20D12 VH domain, positions 31-35 (H1), 50-65 (H2) and 95-102 (H3) were grafted into $VH_I$. The HVR definitions are defined by their sequence hypervariability (Wu, T. T. & Kabat, E. A. (1970)), their structural location (Chothia, C. & Lesk, A. M. (1987)) and their involvement in antigen-antibody contacts (MacCallum et al. J. Mol. Biol. 262: 732-745 (1996)). Certain vernier positions were mutated back to the murine sequence, including positions 36 and 46 in VL and positions 67, 69, and 71 in VH. See FIGS. 1A-C and 2A-C.

Synthetic genes encoding the variable domains of the initial humanized version of antibody 20D12, hu20D12.v1 (FIGS. 1A-C and 2A-C; VH of SEQ ID NO: 29, VL of SEQ ID NO: 28), were produced and cloned into vectors for expression as full length IgG. Antibody was expressed transiently in CHO cells and purified as previously described (Kelley & Meng (2012) Methods Mol Biol 901:277-93). Binding affinity to human factor D was determined by surface plasmon resonance (SPR) measurements on a Biacore® T200 instrument using anti-Fc capture for murine 20D12 (capture kit #BR-1008-38) and hu20D12.v1 IgG (capture kit #BR-1008-39). As shown below in Table 3, murine 20D12 and hu20D12.v1 have comparable affinities for human factor D.

The antibodies were also assayed for Factor D inhibition in the hemolysis assay, as follows. The AP hemolysis assay using rabbit erythrocytes (Er) has been previously described (Pangburn (1998) Methods. Enzymol. 162:639; Katschke et al. (2009) J. Biol. Chem. 284:10473). Er (Colorado Serum) were washed three times with 0.5% bovine skin gelatin in veronal buffer (GVB) and re-suspended. Dilutions of anti-factor D antibodies were prepared at a 2× concentration and added to 96-well polypropylene plates. Er suspension were mixed with GVB/0.1M EGTA/0.1M MgCl2 and added to the plates. Complement activation was initiated by the addition of C1q-depleted human serum to avoid any complement activation through the classical pathway (CompTech; diluted 1:3 in GVB). After a 30 minute incubation at room temperature, the reaction stopped by adding 10 mM EDTA in GVB. The plates were centrifuged and the supernatants transferred. The absorbance of the supernatant was read at 412 nm. The AFD.Ab concentrations causing half-maximal inhibition (IC50) were determined by a nonlinear regression analysis. The results of that analysis are shown in Table 3.

TABLE 3

Human Factor D binding kinetics data for IgG-formateed mouse and humanized 20D12

| Antibody | On-rate ($M^{-1}s^{-1}$) | Off-Rate ($s^{-1}$) | KD (pM) | Hemolysis IC50 (nM) |
|---|---|---|---|---|
| Mu20D12 | 5.9e6 | 3.9e−4 | 66 | 4.0 |
| Hu20D12.v1 | 1.5e7 | 6.7e−4 | 46 | 4.3 |

As shown in Table 3, the affinity of humanized antibody hu20D12.v1 is comparable to the affinity of the parental murine antibody. Hu20D12.v1 also retained inhibitory activity against Factor D in the hemolysis assay.

Example 2

Production and Characterization of hu20D12 Fab Fragments

The portion of the gene encoding the Fab fragment of hu20D12.v1 was subcloned into an *E. coli* expression vector similar to that previously described (Carter et al. (1992) BioTechnology 10:163). For small scale expression and purification, DNA was transformed into *E. coli* strain 64B4. Single colonies were picked into 5 mL LB media (media prep code A2008) containing 50 μg/mL carbenecillin (media prep code A3232) and grown overnight in 14 mL culture tubes with shaking at 200 RPM in an Innova incubator at 37° C. These cultures were used to inoculate 250 mLs of complete soy crap media (media prep code A4564), 50 μg/mL carbenecillin, in a 1 L baffled shake flask. Cultures were grown overnight at 30° C. with shaking at 200 RPM and then harvested by centrifugation. The cell pellet was lysed using PopCulture media (invitrogen), and Fabs purified on Gravitrap Protein G columns (GE Healthcare), following protocols supplied by the manufacturers. For larger scale production of Fab, cell paste from 10 L fermentation of transformed cells was suspended in extraction buffer and homogenized using a microfluidizer. Fab was captured by immunoaffinity chromatography on kappa-select and eluted with a low pH buffer. The eluate was immediately neutralized with 1M TRIS (pH 8.0) and buffer exchanged into PBS using an Amicon centricon filtration device (EMD Millipore). This pool was further purified using hydrophobic interaction chromatography (HIC). The solution was prepared for HIC by adjusting the pH to 6.5 through acetic acid addition and adding ammonium sulfate to a final concentration of 2.5 M. HIC was on a 3 mL ProPac HIC-10 column (Thermo Scientific) that had been equilibrated with 25 mM $NaPO_4$, 2.5M Ammonium Sulfate (pH 6.5). A two-step gradient with 25 mM $NaPO_4$, 25% Isopropyl Alcohol (pH 6.5) elution buffer was used to elute the bound protein. Fractions were analyzed using intact Fab liquid chromatography mass spectrometry (LCMS) to determine peak identity. Fractions containing Fab protein were buffer exchanged into PBS.

Example 3

Stability and Molecular Assessment of hu20D12

To simulate the exposure of hu20D12.v1 to conditions that may be found in long-acting delivery systems, the antibody Fab at 100 mg/mL in PBS was stressed for four weeks at 37° C. PBS was used as a mimic of the pH and ionic strength of human vitreous. Hu20D12.v1 showed good resistance to aggregation for this stress condition, with only a 0.6% loss of monomer, but a deamidation of Asn-54 (CDR-H2) was revealed by using tryptic peptide mapping.

As noted above, hu20D12.v1 includes an NG deamidation site in HVR-H2. N54 in HVR-H2 was therefore mutated to S (N54S) or Q (N54Q) to remove the NG deamidation site. Point mutations were introduced by site-directed mutagenesis using the QuikChangeII® (Agilent) mutagenesis kit following the protocol supplied with the kit. Oligonucleotide primers specifying the required codon changes were synthesized. Plasmids with designed changes were identified and confirmed by DNA sequencing. Variant Fabs were expressed in E. coli and purified as described above for hu20D12.v1. In FIGS. 1A-C and 2A-C, hu20D12.v1 (VH of SEQ ID NO: 29, VL of SEQ ID NO: 28) shows the CDR grafted antibody without the N54 mutation and hu20D12.v2.0 shows the CDR grafted antibody with the N54S mutation (VH of SEQ ID NO: 33, VL of SEQ ID NO: 32) and hu20D12.v1.1 shows the CDR grafted antibody with the N54Q mutation (VH of SEQ ID NO: 31, VL of SEQ ID NO: 30). The binding affinities ($K_D$) of the two variant Fabs and parental hu20D12.v1 Fab for Factor D were assessed by surface plasmon resonance (SPR) measurements using the anti-huFab capture protocol described herein (see, e.g., Example 5). The Fabs were also assayed for Factor D inhibition in the hemolysis assay. Table 4 shows the affinities of the N54S and N54Q variants of hu20D12.v1 and IC50 of each antibody in the hemolysis assay.

TABLE 4

Relative binding affinity of Fab-formatted antibodies for human Factor D

| Variant | Name | KD (pM) | IC50 Hemolysis (nM) |
| --- | --- | --- | --- |
| hu20D12.v1 | hu20D12.v1 | 33 | 2.8 |
| Hu20D12.v1.N54Q | hu20D12.v1.1 | 45 | 6.7 |
| Hu20D12.v1.N54S | hu20D12.v2.0 | 40 | 4.7 |

As shown in Table 4, the N54S variant of hu20D12.v1 (hu20D12.v2.0) had comparable affinities for Factor D. The N54S and N54Q variants also retained inhibitory activity against Factor D in the hemolysis assay. Hu20D12.v2.0 was selected for further analysis and affinity improvement.

Molecular assessment (MA) was performed on hu20D12.v2.0 to determine suitability of the antibody for further development. In these experiments, the molecule is tested in accelerated stability tests involving incubation at 37° C. or 40° C. Chemical stability is evaluated using peptide mapping, SEC is used to determine susceptibility to aggregation, and for some conditions SPR-measurements of antigen-binding are used to assess retention of activity. These tests indicate if the molecule poses any challenges to standard methods of manufacture, formulation, or delivery. Table 5 shows the results of the stress test.

TABLE 5

Stress test of hu20D12.v2.0

| Category | Parameter | hu20D12.v2.0 |
| --- | --- | --- |
| Stability | Thermal Stress: 40° C., 2 weeks | DT (CDR-L1) Stable<br>NN (CDR-L3) Stable<br>SEC monomer loss: 0% |

TABLE 5-continued

Stress test of hu20D12.v2.0

| Category | Parameter | hu20D12.v2.0 |
| --- | --- | --- |
| | Trp/Met Oxidation Assay | IEC main peak loss: 10%<br>M (CDR-H1) Stable |
| Ocular Specific TCP Tests | Sustained delivery stress: 37° C., 4 weeks | DT (CDR-L1): 3% isomerization<br>NN (CDR-L3): 3% deamidation<br>M (CDR-H1): 4% increase in oxidation<br>1% monomer loss<br>No loss in antigen binding relative to control via Biacore |

Similar to hu20D12.v1, hu20D12.v2.0 did not aggregate when stressed at 100 mg/mL in PBS at 37° C. for 4 weeks. Unlike hu20D12.v1, hu20D12.v2.0 did not show a deamidation site under this stress condition, suggesting that the N54S substitution abrogated the deamidation and that the variant would have higher stability at physiological pH and ionic strength. Hu20D12.v2.0 also showed good stability in a pH 5.5 formulation suitable for ocular drugs.

Example 4

Structure Determination of hu20D12.v2.0:Factor D Complex

Figure 3B:
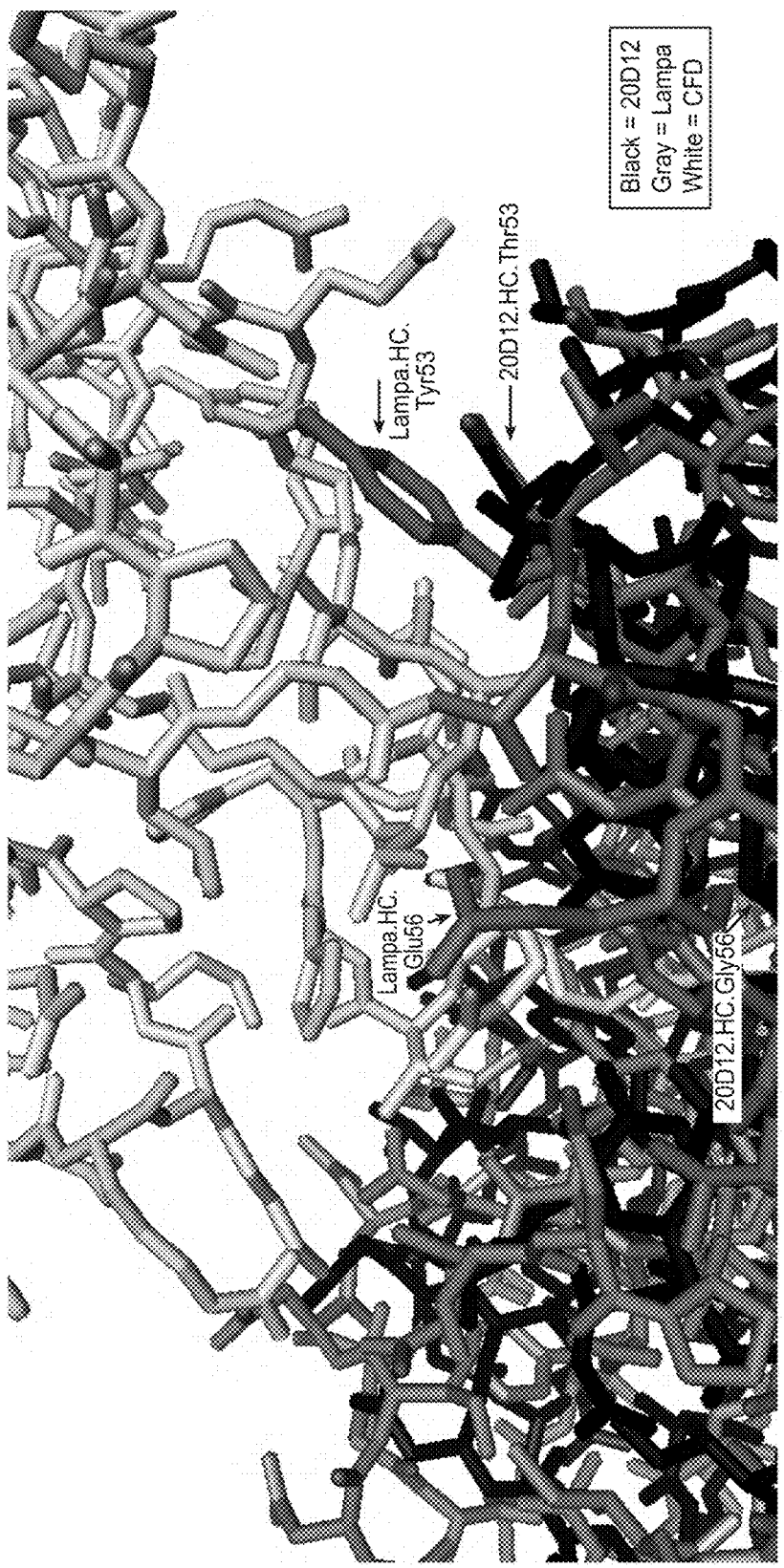
Figure 3C:
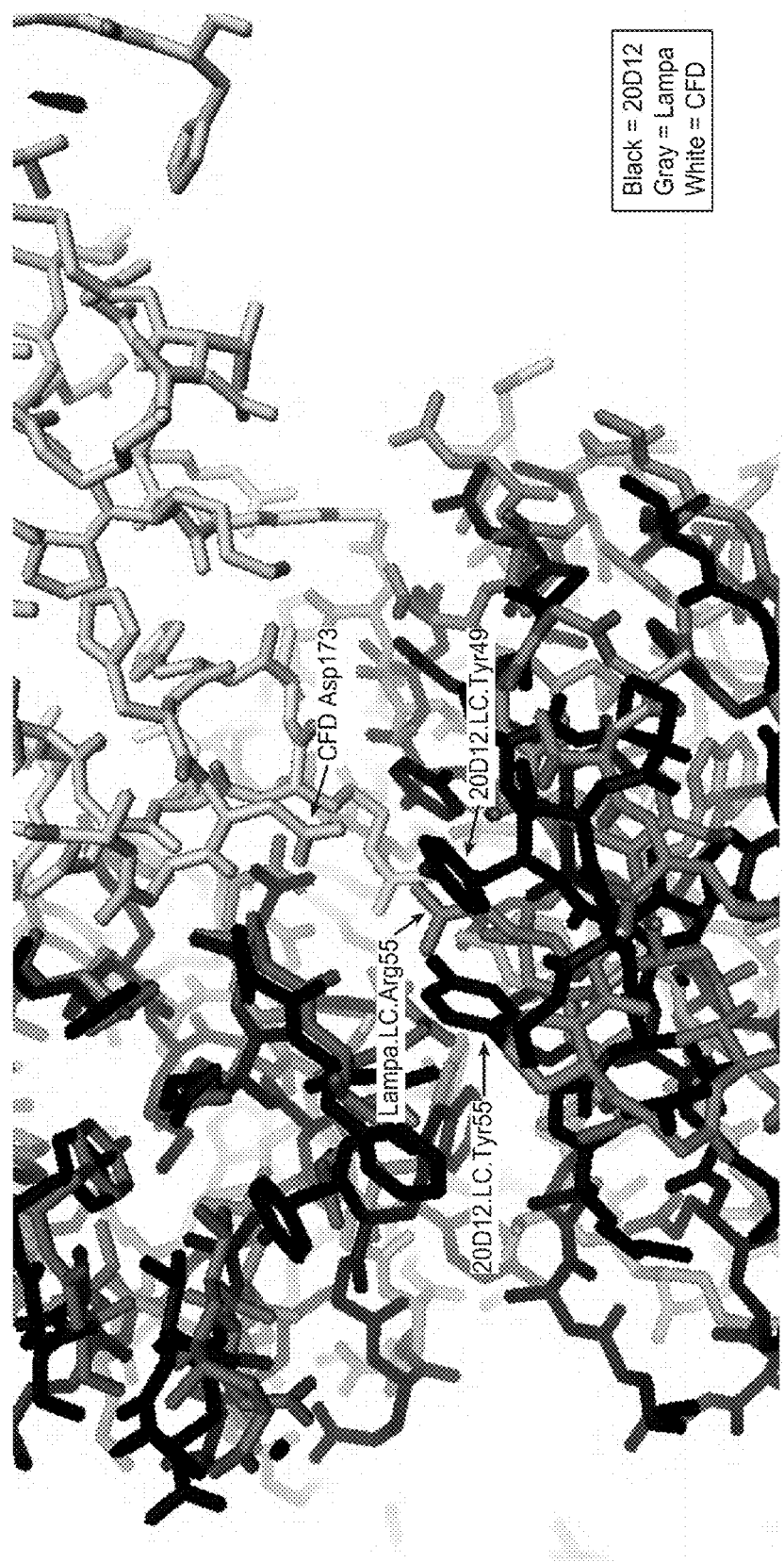

To better understand how hu20D12.v2.0 binds human factor D, the structure of hu20D12.v2.0 Fab in complex with Factor D was determined. Human factor D protein and hu20D12.v2.0 Fab were mixed in 1:1 molar ratio and purified over a Superdex 200 column pre-equilibrated with 20 mM Hepes pH 7.2 and 150 mM NaCl. The peak fractions containing the complex were pooled, concentrated to 32 mg/ml and used in crystallization trial. Crystals were grown at 4° C. using vapor diffusion method by mixing protein in 2:1 (v/v) with a reservoir solution containing 0.1 M sodium cacodylate pH 6.5 and 1M sodium citrate. The crystals were cryo-protected in artificial mother liquor containing 20% ethylene glycol and flash frozen in liquid nitrogen. A 2.9 A data set was collected at ALS 5.0.2 and the structure solved by molecular replacement method. A comparison to another anti-Factor D Fab:Factor D complex previously solved (Katschke et al. (2012) J. Biol. Chem. 287, 12886) is shown in the overlay of FIGS. 3A-C. Although these two antibodies have different CDR sequences, they bind to nearly identical epitopes on Factor D. An alignment of the prior Factor D antibody (lampalizumab) with hu20D12.v2.0 ("hu20D12.v1.N54S") is shown in FIG. 4.

Example 5

Design of Higher Affinity Anti-Factor D Humanized Antibody Variants

Improving the affinity of an antibody with a pM affinity by conventional screening methods, such as phage display, is typically very difficult. Thus, a structure-based analysis of the binding of 20D12 to Factor D using the crystal structure described above was used to identify specific amino acid residues that could be mutated to improve affinity.

Certain contacts between hu20D12.v2.0 and Factor D were identified as potentially sub-optimal and those residues were selected for mutation to the corresponding lampalizumab amino acid, which may provide greater affinity for the antigen. Examination of fD:hu20D12.v2.0 complex structure indicates that although the side chain of Asp-173 is in contact with hu20D12.v2.0, the fD Asp does not make a salt bridge or complete hydrogen bonds with the antibody Fab. See FIG. 3C. Introduction of a positively charged residue on the antibody, such as Arg or Lys, could satisfy ion pairing requirements for the Asp. A position on hu20D12.v2.0 that appears to be close enough to build such an interaction is position 49 in FR2 of the light chain. This position is a Tyr in hu20D12.v2.0 so we tested whether Lys or Arg substitution at this position would increase the fD-binding affinity. In addition, lampalizumab binds with higher affinity to fD than hu20D12.v2.0 (<10 pM versus 39 pM, see FIG. 11) and has different residues at key contacts within the interface. For example, hu20D12.v2.0 CDR-H2 residues Glu-50, Thr-53, Gly56 are Trp-50, Tyr-53 and Glu-56 in lampalizumab. See FIG. 3B. The tryptophan (W) at position 50 of the lampalizumab heavy chain may form a hydrophobic interaction with Factor D, while hu20D12.v2.0 has a glutamic acid (E) at that position. The tyrosine at position 53 of the lampalizumab heavy chain may also pack better with the residues nearby in Factor D than the threonine (T) at that position in hu20D12.v2.0. In the light chain, CDR-L2 Tyr-55 and CDR-L3-Asn92 in hu20D12.v2.0 are CDR-L2 Arg-55 and CDR-L3-Asp92 in lampalizumab. Each of these residues appears to contact Factor D in the Factor D:lampalizumab complex structure, with CDR-L-Asp92 making a charged interaction with Lys223a of Factor D. See Katschke et al. (2012) for Lys223a numbering.

Based on these observations, and others, additional 20D12 variants were designed. The light chain and heavy chain sequences for 20D12 variants are shown in FIGS. 1A-C and 2A-C, respectively. The variants were tested for the effect on binding to fD. Mutations were introduced into the E. coli Fab expression plasmid, and variant Fabs were expressed and purified as described above.

Factor D Binding Affinity by Surface Plasmon Resonance (SPR) Measurements

Kinetics and binding constant $K_D$ for Factor D binding to immobilized hu20D12 versions was determined by surface plasmon resonance (SPR) measurements on a Biacore®T200 instrument. Antibody Fab fragments were immobilized on a Series S CM5 sensor chip using the anti-huFab capture kit (GE healthcare Cat. #28-9583-25) following a protocol described by the manufacturer. Kinetics of binding were calculated from sensorgrams recorded for injection of 60 µL aliquots of solutions of human Factor D varied in concentration from 0.39 nM to 25 nM in 2-fold increments. The flow rate was 30 µL/min, the running buffer was BIBS-P+ (GE Healthcare cat #BR-1006-71), the temperature of analysis was 25° C., real-time reference cell subtraction was employed, and dissociation following factor D injection was followed for 10 minutes. For some variants with high affinity and slow off-rate, dissociation was monitored for 2 hours to obtain a more accurate measure of the dissociation rate. After subtraction of the sensorgram observed for injection of running buffer, data were analyzed according to a 1:1 model using BiaEval software v4.1 (GE Healthcare) to extract the kinetics and affinity constants.

Replacement of light chain residue Tyr-49 with Arg (hu20D12.v2.1) results in a ≥4-fold improvement in binding to fD. See FIG. 11. The increased affinity is the result of a slower off-rate for dissociation. Replacement of Tyr-49 with Ser (hu20D12.v2.6), Lys (hu20D12.v2.7) or Gln (hu20D12.v2.8) does not increase affinity for fD. Substitution of CDR-H2 Glu-50 with Trp (hu20D12.v2.9), or CDR-L2 Tyr-55 with Lys (hu20D12.v2.10) or Arg (hu20D12.v2.11), results in large decreases in affinity for fD. Individual replacement of CDR-L2 Gly-56 with Asp (hu20D12.v2.2) or Glu (hu20D12.v2.4), or Thr-53 with Tyr (hu20D12.v2.5), does not appear to result in increased affinity; however, combination of these changes with Y49R in variants (hu20D12.v2.12, v2.14, v2.15, v2.3) does appear to further increase affinity. Comparing sequences of hu20D12 with lampalizumab implicates that replacing Tyr-55 on CDR-L2 would result in a variant with increased affinity due to its expected interaction with fD Asp-173. However, crystal structure indicates that replacement of Tyr-49 with Arg (Y49R) is a better choice for increasing affinity. Although not tested individually, the CDR-L3 substitution N92E does appear to combine with Y49R in variant (hu20D12.v2.13) to produce a favorable increase in binding-affinity.

The Factor D-binding affinities to human Factor D (hFD) of hu20D12 variants v2.1, v2.3, v2.12-v2.15, and also lampalizumab, are at the limits of detection (KD~10 pM) for current SPR technology. Several of the hu20D12 variants v2.1, v2.3, v2.14 and v2.15 bind to cynomolgus monkey factor D (cyfD), with hu20D12.v2.1 having the highest affinity (KD=17 pM). In addition, binding affinity of hu20D12.v2.1 to cynomolgus monkey Factor D is improved almost 10-fold relative to hu20D12.v2.0 and improved 2-fold relative to lampalizumab. Cynomolgus monkeys are often used in pre-clinical safety and efficacy assessments of therapeutic candidates so high binding affinity to cFD is a desirable property. Fabs were tested for thermal stability by differential scanning calorimetry (DSC). Table 6 shows the results of the thermal stability analysis.

TABLE 6

| Melting temperatures by DSC | |
|---|---|
| Fab | Tm (° C.) |
| AFD.v8 | 70.5 |
| AFD.v14 | 70.3 |
| Hu20D12.v2.0 | 79.8 |
| Hu20D12.v2.3 | 80.3 |
| Hu20D12.v2.13 | 73.6 |
| Hu20D12.v2.14 | 81.0 |
| Hu20D12.v2.15 | 81.2 |

All of the hu20D12 variants tested showed high thermal stability with melting points higher than observed for AFD.v8 and AFD.v14, two variants of lampalizumab.

Example 6

Potency of hu20D12 Variants for Inhibition of Factor D

Potency of hu20D12 variants and conjugated hu20D12 Fab-C versions for inhibition of Factor D was determined in a time-resolved fluorescence energy transfer (TR-FRET) assay of Factor D-dependent factor B activation. Dilutions of hu20D12 Fab, conjugated hu20D12 Fab-C versions, or control were prepared in enzymatic reaction buffer (ERB; 75 mM NaCl, 1 mM MgCl2, 25 mM Tris, 0.005% polysorbate 20, pH 7.3) at a 4× concentration and combined in equal volumes with 0.5 nM or 0.2 nM factor D (fD, Complement Technology; Tyler, Tex.) or ERB (no enzyme control). Ranibizumab (anti-VEGF) was used as the negative control. The Factor D/AFD.Ab mixtures (7 µl/well) were added to 364-well Proxiplate F plus black plates (Perkin Elmer Health Sciences; Waltham, Mass.) followed by 7 µl/well of substrate. The substrate consisted of a mixture of C3b (Complement Technology) at 7 µg/mL (40 nM) and factor B (Complement Technology) at 1 µg/mL (15 nM). The Fab or conjugated Fab-C versions, enzyme, cofactor, and substrate were incubated for 45 min at room temperature with gentle agitation. The reaction was stopped with 7 µl/well of a detection reagent cocktail mixture consisting of biotinylated anti-factor Bb (2F12, GNE PRO282909) at 8 nM, Europium-conjugated anti-factor Ba (custom conjugation of 1C3, GNE PRO282908 by Life Technologies; Madison, Wis.) at 4 nM, and streptavidin-Alexa 647 at 25 nM. The plate was incubated at room temperature in the dark for 30 min. Time-resolved fluorescence energy transfer was detected with a PHERAstar FS microplate reader (BMG LabTech; Cary, N.C.) by exciting at 337 nm and detecting Europium emission at 620 nm and Alexa fluor emission at 665 nm. The AFD.Ab concentrations causing half-maximal inhibition (IC50) were determined by nonlinear regression analysis using a four-parameter fit model (KaleidaGraph Synergy Software; Reading, Pa.).

Figure 5A:
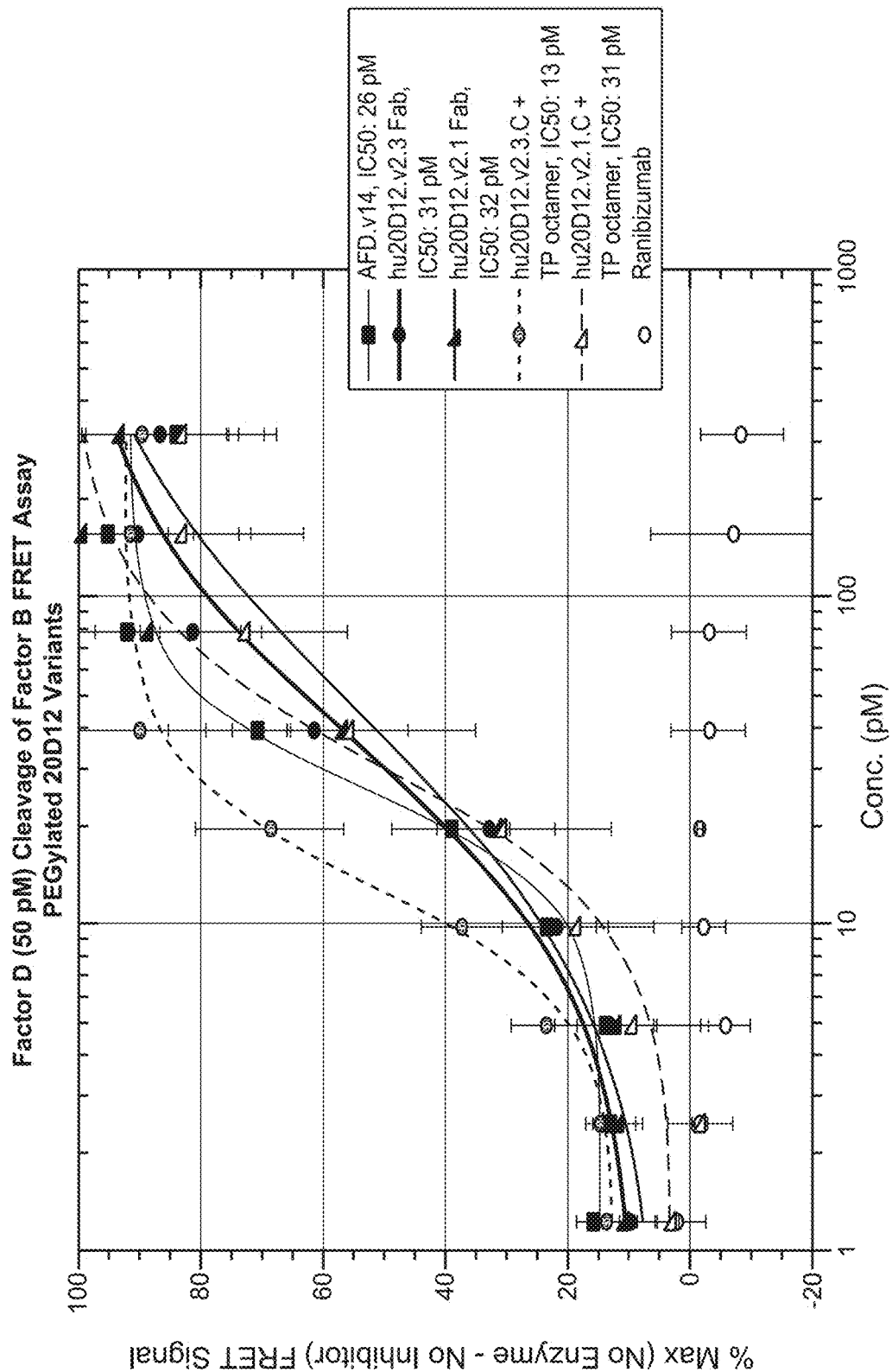

Inhibition curves for the TR-FRET assay are shown in FIG. 5A, FIG. 5B (and Table 7) and FIG. 11 (conditions for this assay were 50 pM Factor D, 15 nM Factor B (fB), and 40 nM Factor C3b). Lampalizumab has an IC50 for inhibition of Factor D-dependent fB activation of 24 pM, and the standard error in IC50 is ±25% (FIG. 5B (Table 7) and FIG. 11). The sensitivity of the assay precludes testing at Factor D concentrations lower than 50 pM. Thus, the lowest IC50 that can be measured, equivalent to the concentration where 50% of the Factor D is inhibited, and assuming a 1:1 interaction of inhibitor and factor D, is 25 pM. The IC50 for hu20D12.v2.0 is about 2-fold higher than measured for lampalizumab. See FIG. 5B (Table 7) and FIG. 11. All of the variants tested (v2.1, 2.14, 2.15, 2.3) have increased potency relative to hu20D12.v2.0 with IC50 values the same as, or approaching, the value measured for lampalizumab. See FIG. 5A, 5B (Table 7) and FIG. 11.

TABLE 7

IC50

| Molecule | AVG IC50 (pM) |
|---|---|
| hu20D12.v2.0 | 59.22 |
| AFD.v8 | 27.65 |
| AFD.v14 | 34.03 |
| hu20D12.v2.3 | 31.20 |
| AFD.v8.C + PEG tetramer | 11.03 |
| AFD.v14.C + PEG tetramer | 14.77 |
| hu20D12.v2.3.C + PEG tetramer | 35.22 |
| RANIBIZUMAB | N/A |
| LAMPALIZUMAB | 24.38 |

Example 7

Stability and Molecular Assessment of Affinity Matured hu20D12

Figure 6C:
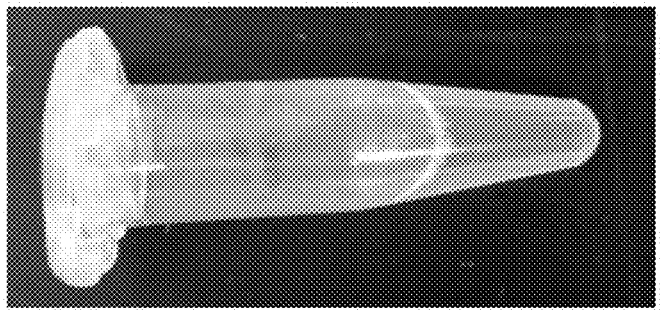
FIGS. 6A-C show that hu20D12.v2.0 (6A) and hu20D12.v2.1 (6C) are soluble at 292 mg/ml, and 260 mg/ml, respectively, while lampalizumab precipitates from solution at 227 mg/ml (6B).
Figure 6B:
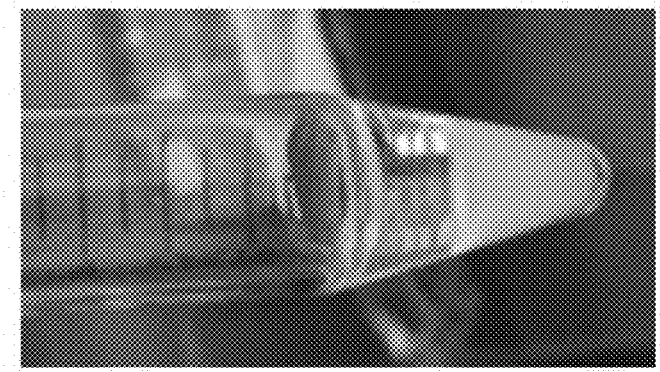
Figure 6A:
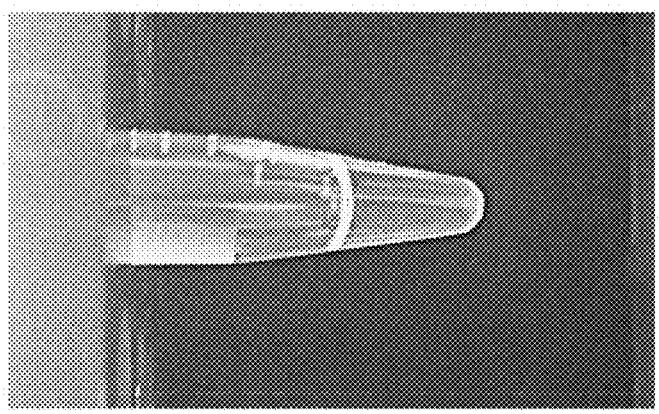

Molecular assessment was performed on hu20D12.v2.1 and hu20D12.v2.3. No issues requiring non-standard practices were identified for hu20D12.v2.1. In contrast, lampalizumab has several risks for formulation and long acting delivery (results of stress test for lampalizumab in Table 8). The concentration-dependence of the viscosity for hu20D12.v2.1 was determined, and indicated that this Fab has low viscosity in a buffer used for ocular formulations and is suitable for high concentration formulation. Hu20D12.v2.0 is soluble in PBS at concentrations at least as high as tested, 292 mg/ml, whereas lampalizumab shows precipitation at 227 mg/ml. See FIGS. 6A and 6B. In addition, the hu20D12.v2.0 solution remained clear with no evidence of precipitate after 27 weeks at 4° C. This indicates that a high concentration formulation of the Fab, which is useful for less frequent dosing with improved efficacy, is more readily obtainable for the humanized variants of 20D12 than for lampalizumab. Table 8 shows the results of the stress test of hu20D12.v2.1.

TABLE 8

Stress test of lampalizumab

| Category | Parameter | Lampalizumab |
|---|---|---|
| Stability | Thermal Stress: 40° C., 2 weeks | CDR-L1 $^{30}$DD unstable<br>CDR-H2 $^{61}$DD unstable |
|  | Trp/Met Oxidation Assay | CDR-H2 Trp-50 >35% |
| Ocular Specific TCP Tests | High Conc. Thermal Stress: 40° C., 2 weeks | IEC main peak loss >16% |
|  | Sustained delivery stress:<br>37° C., 4 weeks | High conc.<br>5.8% loss of monomer at 40 days<br>30% loss in antigen binding capacity at 70 days |

TABLE 9

Stress test of hu20D12.v2.1

| Category | Parameter | hu20D12.v2.1 |
|---|---|---|
| Stability | Thermal Stress: 40° C., 2 weeks | NP (CDR-H2) Stable<br>DT (CDR-L1) Stable<br>NNY (CDR-L3) Stable<br>SEC monomer loss: 0.3%<br>IEC main peak loss: 0.5% |
|  | Thermal Stress: 40° C., 2 weeks | NP (CDR-H2): no observed hydrolysis<br>DT (CDR-L1): 2.3% increase in isomerization<br>NNY (CDR-L3): 0.0% increase in deamidation<br>SEC monomer loss: 0.3%<br>IEC main peak loss: 5.3% |
|  | Trp/Met Oxidation Assay | M (CDR-H1) Stable |
| Ocular Specific TCP Tests | Viscosity in pH 5.5 buffer | 7 cP at 177 mg/mL |
|  | High Conc. Thermal Stress: 40° C., 2 weeks | SEC monomer loss: 1.7%<br>IEC main peak loss: 7.1% |
|  | Solubility in PBS, pH 7.4 | No insoluble particulates<br>Low turbidity at 150 mg/mL |
|  | Sustained delivery stress:<br>37° C., 4 weeks | No loss in antigen binding<br>1.6% loss of monomer by SEC |

To simulate conditions that may be experienced by hu20D12.v2.1 Fab in long-acting delivery systems, high concentration samples of hu20D12.v2.1 Fab were held at 37° C. for a month in two formulation conditions: (1) ~200 mg/mL, PBS, pH 7.4, and (2) ~170 mg/mL, 20 mM histidine hydrochloride, pH 5.5. PBS was chosen to mimic the pH and ionic strength of the human vitreous humor. Histidine hydrochloride was chosen as a representative formulation for liquid ophthalmology therapeutics. The formulation concentration (170 mg/mL-200 mg/mL) was chosen to reflect a clinically relevant dose formulation for long-acting delivery of anti-Factor D. Molecule stability was assessed via ion-exchange chromatography (IEC) for chemical stability and size exclusion chromatography (SEC) for aggregation propensity. Surface plasmon resonance (SPR) measurements of antigen binding were used to assess activity retention.

Hu20D12.v2.1, formulated at 200 mg/mL in PBS pH 7.4 or at 170 mg/mL in 20 mM HisHCl pH 5.5, was sterile filtered using 0.22 μm SteriFlip units (EMD Millipore), aliquoted (100 μL), and incubated at 37° C. for 0, 2 or 4 weeks. Upon incubation completion, samples were diluted in a sucrose-containing formulation buffer and frozen at −20° C. After thawing, samples were analyzed by IEC, SEC and SPR, as described below.

Chemical Stability Assessment by Ion Exchange Chromatography. Chemical stability of hu20D12.v2.1 was monitored using Ion Exchange Chromatography (IEC). IEC was performed on an Agilent 1200 HPLC with an in-line diode array detector (DAD). Thawed protein samples were prepared for IEC by being diluted to 1 mg/mL in PBS. Samples were held at 2-8° C. prior to injection on column to maintain stability. Separation of a 20 μg protein injection was performed using a ProPac SAX-10 2×250 mm column (Dionex) at 40° C. Solvent A was 20 mM Tris pH 8.2 and Solvent B was 250 mM sodium chloride in Solvent A. A PBS buffer blank was included for subtraction of buffer contribution to UV signal. The salt gradient used for separation of the chemical degradants is shown in Table 10.

TABLE 10

Ion Exchange Chromatography Gradient for hu20D12.v2.1

| Time (min) | % Solvent A | % Solvent B |
|---|---|---|
| 0 | 100 | 0 |
| 45 | 20 | 80 |
| 45.5 | 0 | 100 |
| 50 | 0 | 100 |
| 50.1 | 100 | 0 |
| 60 | 100 | 0 |

Data were processed using Chromeleon 6.8 software (Thermo Scientific) to integrate all chromatogram peaks attributed to protein. The percent peak area was calculated using Equation 1 and was reported for all peaks of interest, termed acid variants, main peak, and basic variants. If no peak for acid or basic variant was detected, the peak area percentage was reported as zero.

$$\% \text{ Peak Area} = \frac{\text{area of peak}}{\text{total area of protein peaks}} \times 100 \quad \text{(Equation 1)}$$

The IEC results for the 37° C. high concentration stability samples of hu20D12.v2.1 are reported in Table 11A-B.

TABLE 11A

Chemical Stability of 37° C. High Concentration Stability Samples (PBS) of hu20D12.v2.1 by Ion Exchange Chromatography

| Time (weeks) | % Acidic Variants | % Main Peak | % Basic Variants |
|---|---|---|---|
| 0 | 11.0 | 78.0 | 11.1 |
| 2 | 14.0 | 75.5 | 10.5 |
| 4 | 15.8 | 71.3 | 12.9 |

TABLE 11B

Chemical Stability of 37° C. High Concentration Stability Samples (His-HCl pH 5.5) of hu20D12.v2.1 by Ion Exchange Chromatography

| Time (weeks) | % Acidic Variants | % Main Peak | % Basic Variants |
|---|---|---|---|
| 0 | 11.1 | 76.3 | 12.7 |
| 2 | 13.6 | 75.9 | 10.6 |
| 4 | 15.5 | 71.7 | 12.8 |

Molecule Size Distribution Assessment by Size Exclusion Chromatography. Molecule size distribution of hu20D12.v2.1 was monitored using Size Exclusion Chromatography (SEC). SEC was performed on an Agilent 1200 HPLC with an in-line diode array detector (DAD). Thawed protein samples were prepared for SEC by being diluted to 1 mg/mL in PBS. Samples were held at 2-8° C. prior to injection on column to maintain stability. Separation of a 100 μg protein injection was performed using a TSKgel G3000SW×1 column (Tosoh Biosciences, part no. 08541) at ambient temperature. Mobile phase consisted of 0.20 M potassium phosphate, 0.25 M potassium chloride, pH 6.2±0.1. UV sample signal was monitored at 280 nm. A PBS buffer blank was included for subtraction of buffer contribution to UV signal.

Data were processed using Chromeleon 6.8 software (Thermo Scientific) to integrate all chromatogram peaks attributed to protein. The percent peak area was calculated using equation 1, above, and was reported for all peaks of interest, termed high molecular weight species (HMWS), main peak (monomer), and low molecular weight species (LMWS). If no peak for HMWS or LMWS was detected, the peak area percentage was reported as zero. The SEC results for the 37° C. high concentration stability samples of hu20D12.v2.1 are reported in Table 12A-B.

TABLE 12A

Molecule Size Distribution of 37° C. High Concentration Stability Samples (PBS) of hu20D12.v2.1 by Size Exclusion Chromatography

| Time (weeks) | % LMWS | % Monomer | % HMWS |
|---|---|---|---|
| 0 | 0 | 98.3 | 1.7 |
| 2 | 0 | 96.7 | 3.3 |
| 4 | 0 | 96.0 | 4.0 |

TABLE 12B

Molecule Size Distribution of 37° C. High Concentration Stability Samples (His-HCl pH 5.5) of hu20D12.v2.1 by Size Exclusion Chromatography

| Time (weeks) | % LMWS | % Monomer | % HMWS |
|---|---|---|---|
| 0 | 0 | 98.7 | 1.2 |
| 2 | 0 | 97.4 | 2.6 |
| 4 | 0 | 97.1 | 2.9 |

Factor D Binding Capacity by Surface Plasmon Resonance Measurements. Surface plasmon resonance (SPR) measurements were carried out using a BIAcore® T200 instrument (GE Healthcare) to determine the binding capacity of stressed hu20D12.v2.1 samples. A Series S carboxymethylated dextran (CM5) sensor chip was prepared by immobilizing human Factor D (target RU ~3,000) using an amine coupling kit (GE Healthcare) following a protocol described by the manufacturer. Standard solutions of unstressed hu20D12.v2.1 were prepared in HBS-P+ running buffer (GE Healthcare) from 106.5 nM to 3.31 nM in two-fold dilutions and were injected at 10 μL/min for 180 s to generate a standard curve. Stressed samples were diluted to ~40 nM in HBS-P+ buffer and injected at 10 μL/min for 180 s. After each injection, the sensor chip surface was regenerated with 10 mM Glycine-HCl, pH 2.1, at 30 μL/min for 30 s. Concentration analysis was carried out using the BIAcore® T200 analysis software (GE Healthcare). This type of analysis has a standard error of ±10% such that samples with binding capacities of 90-110% are considered to be fully active. The SPR Factor D binding capacity results for the 37° C. high concentration stability samples of hu20D12.v2.1 are shown in Table 13A-B.

TABLE 13A

Factor D Binding Capacity of 37° C. High Concentration Stability Samples (PBS) of hu20D12.v2.1 by Surface Plasmon Resonance Measurements

| Time (weeks) | % Factor D Binding |
| --- | --- |
| 0 | 90.0 |
| 2 | 100.0 |
| 4 | 90.1 |

TABLE 13B

Factor D Binding Capacity of 37° C. High Concentration Stability Samples (His-HCl pH 5.5) of hu20D12.v2.1 by Surface Plasmon Resonance Measurements

| Time (weeks) | % Factor D Binding |
| --- | --- |
| 0 | 91.0 |
| 2 | 92.2 |
| 4 | 88.3 |

Overall, these results indicate that hu20D12.v2.1 is well suited for high concentration formulation in both PBS and 20 mM His-HCl pH 5.5. There is only a slow rate of loss of main peak by both SEC and IEC, and very little decrease in factor D-binding, relative to the initial sample, for at least 4 weeks of thermal stress at 37° C.

Example 8

Polymer Conjugation of hu20D12 Variants

Vitreal half-life can be extended by increasing the hydrodynamic radius of the antibody Fab. Hydrodynamic radius of a Fab can be increased by covalent attachment of a polymer such as polyethylene glycol (PEG). It can be beneficial for this modification to be done in a site-specific manner, at a site removed from the antigen-binding region, so as to minimize the effect of conjugation on biological activity. Availability of a free cysteine residue for modification is desirable for this purpose. Single or multiple free cysteines can be employed to enable single or multiple sites of attachment. A single cysteine at the C-terminus of the heavy chain was included in the Fabs for modification. The Fab-C versions of the antibodies were made by extending the Fab heavy chain by one residue to include Cys-226 (EU numbering). In the IgG1 molecule, Cys-226 forms the first inter-heavy chain disulfide bond of the hinge. Oligonucleotide-directed mutagenesis was performed as described above to produce gene constructs for the Fab-C versions of hu20D12.v2.1.C (SEQ ID NO: 119) and hu20D12.v2.3.C (SEQ ID NO: 124). Similar mutagenesis procedures can be used to generate additional Fab-C constructs, for example, SEQ ID NOs: 71, 118 to 122, and 140 to 146 for hu20D12.v2.1.C, and SEQ ID NOs: 75, 123, 125 to 127, and 147 to 153 for hu20D12.v2.3.C.

Figure 8A:
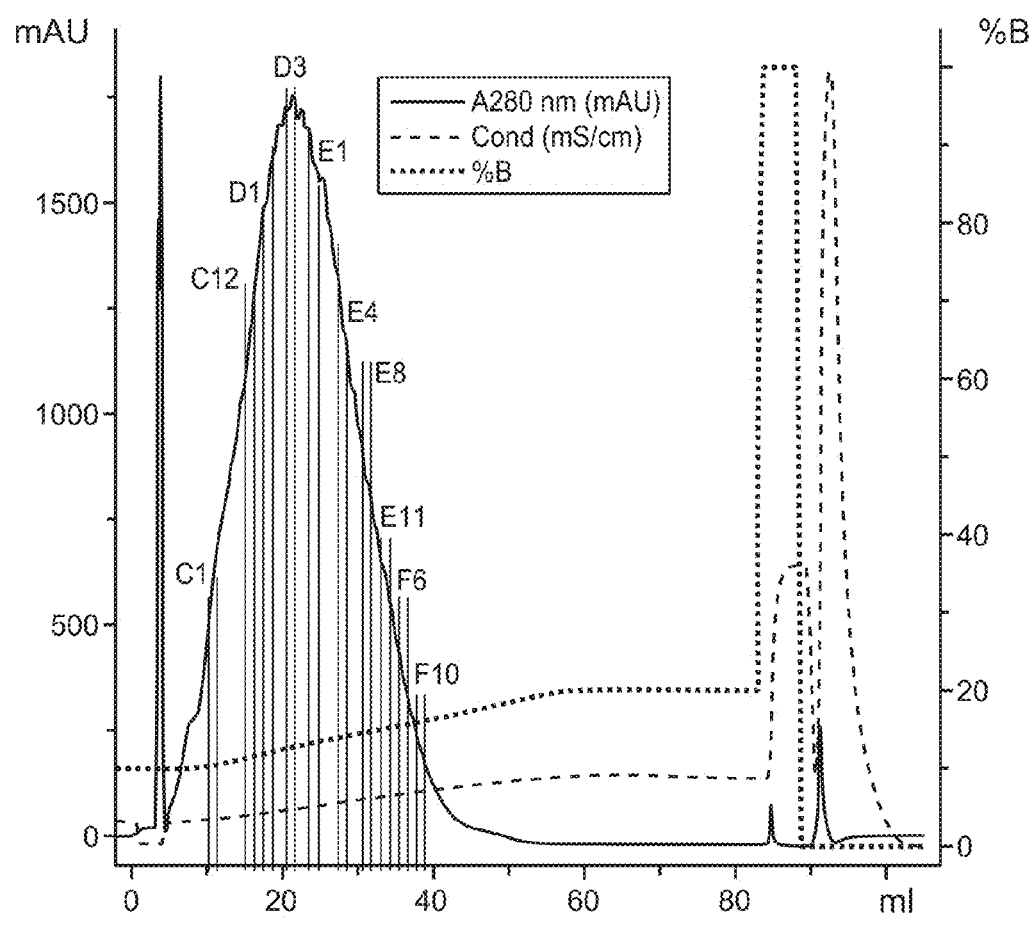
Figure 8B:
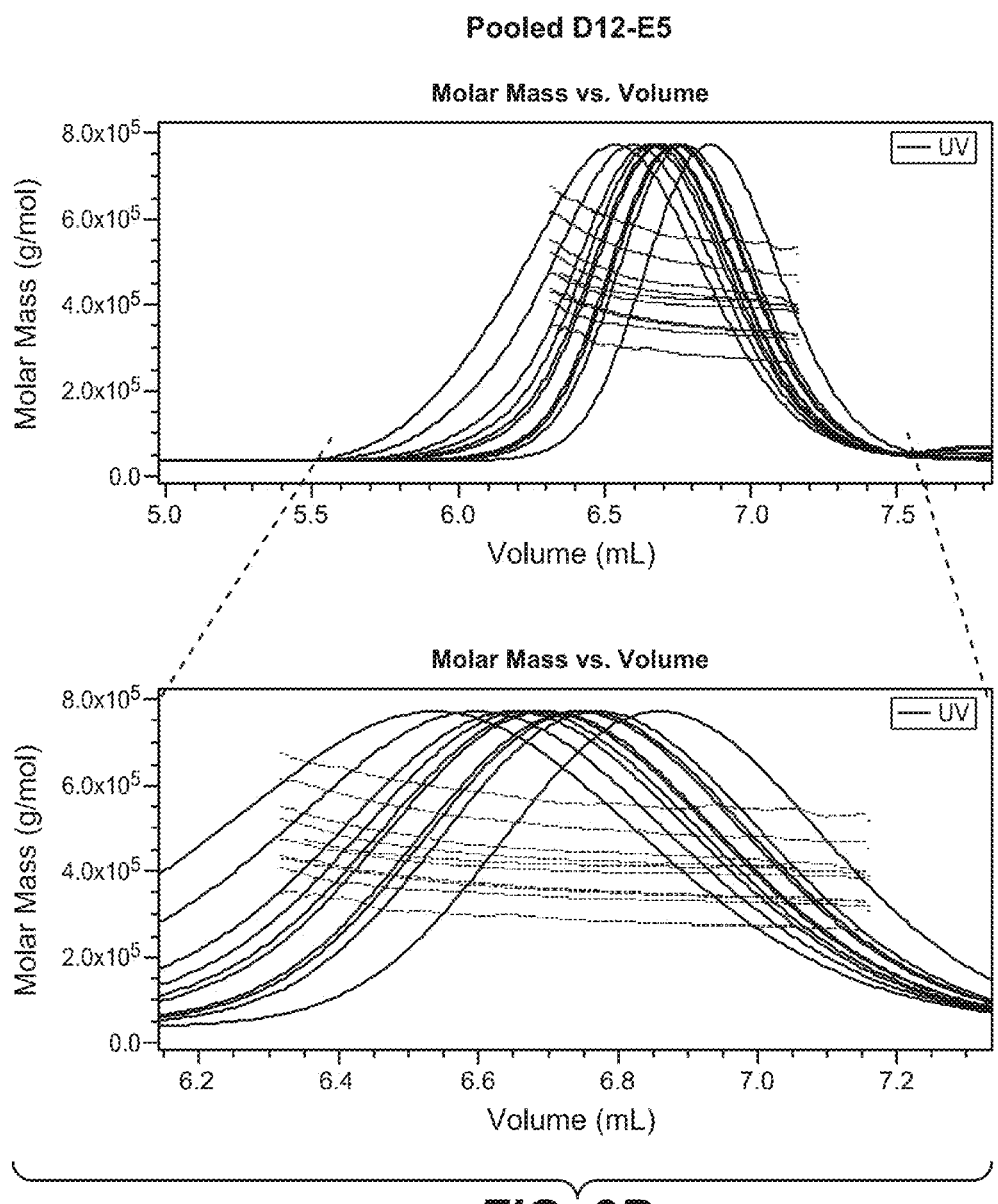

Fab-C versions of hu20D12.v2.1 ("hu20D12.v2.1.C") and hu20D12.v2.3 ("hu20D12.v2.3.C") were expressed in E. coli and purified substantially as follows. The Fab-C variants were captured using Gamma Plus resin, with a 6.5 mM GSH pH 8.5 wash for 5 column volumes to deblock c-terminal cysteine and disrupt Fab-C dimer formation, followed by elution into 0.1M acetic acid pH 2.9. The Fab-C monomers were further isolated using SP Sepharose High Performance strong cation exchange resin from GE in 25 mM Sodium Acetate pH 5.0, with a 0.05% Triton X-100+ 0.05% Triton X-114 was for 19 hours for endotoxin removal. Elution was performed with gradient between 0-20% 25 mM Sodium Acetate pH 5.0+1M NaCl over 20 column volumes. Hu20D12.v2.1.C or hu20D12.v2.3.Cwere conjugated to PEG octamer in 25 mM NaAcetate pH 6.5, 150 mM NaCl, 4 mM EDTA, at a concentration around 5 mg/mL. The Fab-C's were not further concentrated in order to minimize cysteine reactivity loss due to Fab-C dimerization. After equilibrating to room temperature, 40K TP PEG powder from JenKem was resuspended in 25 mM NaAcetate pH 5.0 to a concentration of 10 mg/mL. The pH was kept below pH 6 to avoid maleimide ring opening. Once PEG was solubilized, it was added to the Fab-C pool at a molar ratio of 0.1125:1 PEG to Fab-C. The mixture was then left at room temperature with gentle shaking overnight. The following day, the conjugation efficiency was checked by SEC-MALS. Following conjugation, hu20D12.v2.1.C+TP-Oct was purified using Size Exclusion Chromatography (SEC) on a Sephacryl S-300 HR (GE Healthcare) column in 20 mM His-acetate, pH 5.5, 50 mM NaCl (isocratic gradient) followed by Cation Exchange (CEX) using SP Sepharose High Performance strong cation exchange resin from GE to enrich for 8 Fabs/PEG. The CEX step was run in 25 mM Sodium Acetate pH 5.0 and eluted using a 10-20% 1M NaCl gradient over 50CV. An example of CEX chromatogram (FIG. 8A) and Fab distribution in the S300 pool (FIG. 8B) is presented. Data for different fractions are shown in FIG. 8C.

Figures 7A, 7C:
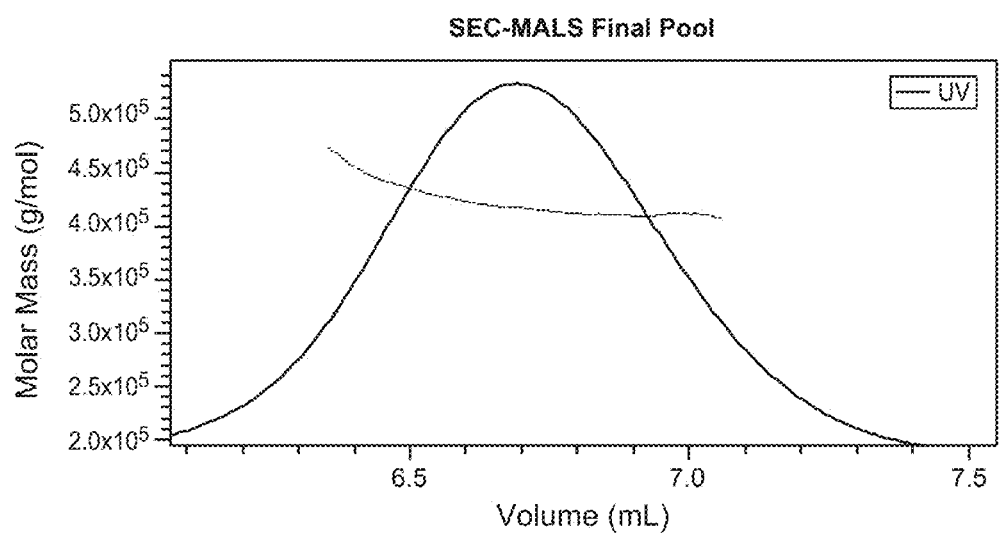
FIGS. 7A-C show a typical SEC-MALS profile of PEG-octamer conjugated hu20D12.v2.1.C (7A), and SEC-QELS analysis to determine hydrodynamic radii ($R_H$) (7B, 7C).
Figure 7B:
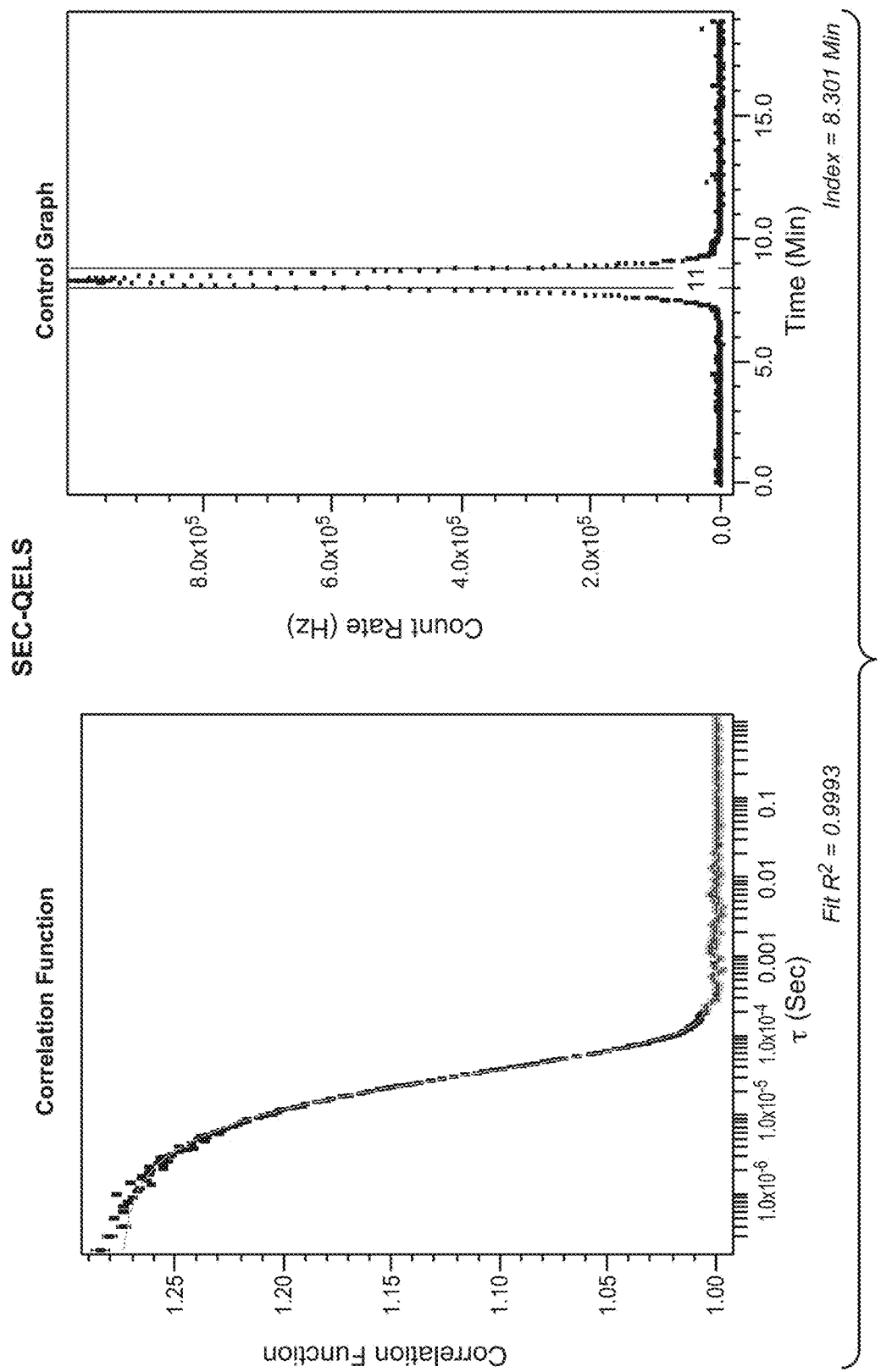

For all processes, the ratio of Fab/PEG was determined by Size Exclusion Chromatography (SEC) using a 300×8 mm Shodex OH pak SB-804 HQ run at 0.8 mL/min using phosphate buffered saline (PBS) pH 7.2, 150 mM NaCl under isocratic conditions. Molar mass was determined using in-line static Multi-Angle laser Light Scattering (MALS) by Wyatt Technology. A typical SEC-MALS profile for conjugated hu20D12.v2.1.C+TP-Oct is shown in FIG. 7A. Photon correlation spectroscopy was used to determine hydrodynamic radii (RH), using Quasi-Elastic Light Scattering (QELS), a single photon counting module with detection at a 99.0°, also by Wyatt Technology. See FIG. 7B. Raw data was analyzed using Wyatt's proprietary Astra software, where molar mass and RH constants were set using a rituximab standard. The RH value for hu20D12.v2.1.C+TP-Oct is 10.3 nm. See FIG. 7C.

Size Exclusion Chromatography (SEC) is also used to determine the size variant distribution of anti-factor D conjugates. Solutions of anti-factor D conjugates (300 μg) are diluted to 2 mg/ml with 20 mM Sodium Phosphate, 300 mM Sodium Chloride, pH 7.0 buffer. For the analysis, an HPLC system capable of gradient flow with UV detection at 280 nm is used. The chromatographic column is a Tosoh G4000 SWx1 (8 μm, 450 Å, 7.8 mmID×30 cm), operated at 0.5 ml/min. Fifty microliters of 2 mg/ml anti-factor D diluted in mobile phase are injected into the HPLC system.

Figure 20:
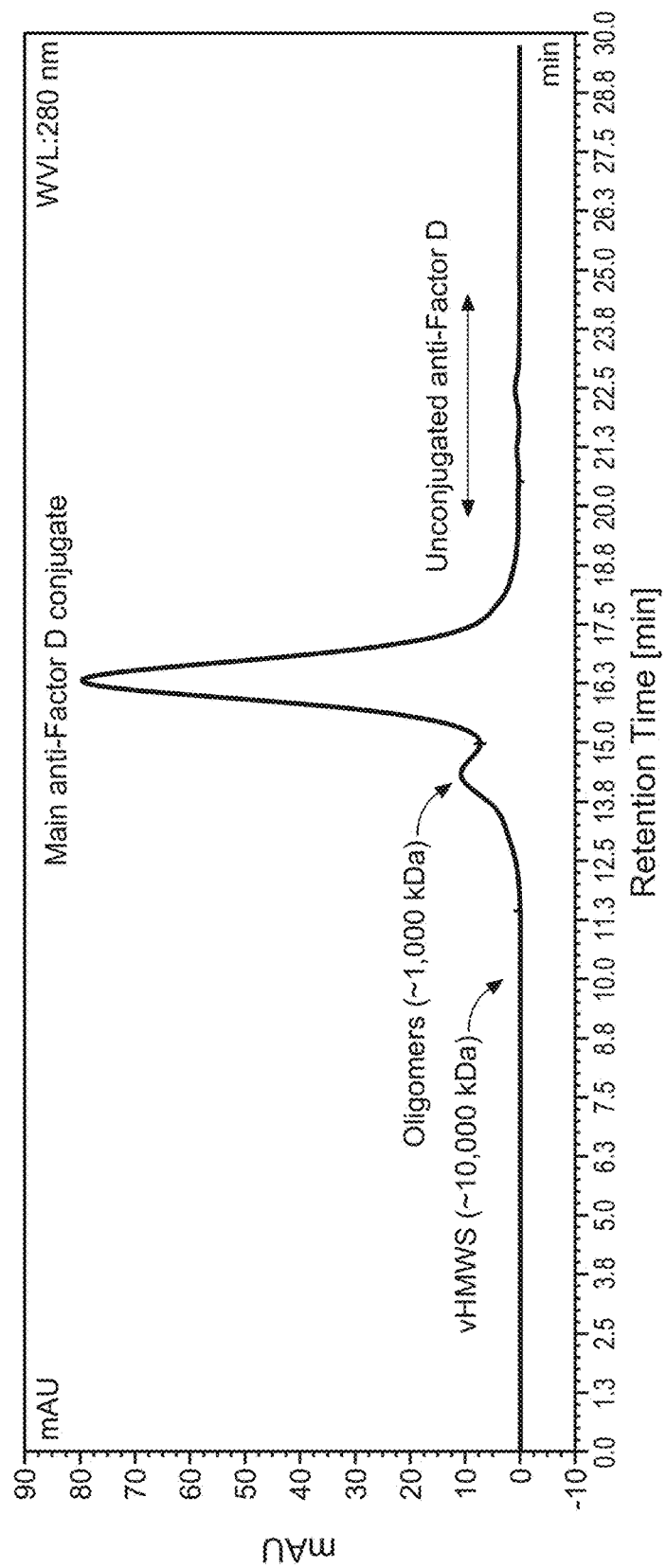
FIG. 20 shows SEC analysis of hu20D12.v2.1.C+TP-Oct.

The column temperature is ambient, the autosampler is at 2-8° C. the mobile phase is in isocratic mode. The column is equilibrated until a stable baseline is obtained and reference material is injected until a consistent chromatographic profile is observed for a minimum of two consecutive injections. This size variant based assay is capable of resolving the unconjugated Fab forms from the conjugate and the aggregate forms (FIG. 20).

Both hu20D12.v2.1.C+TP-Oct and hu20D12.v2.3.C+TP-Oct retained full activity in the TR-FRET inhibition assay after conjugation to octamer-PEG. See FIG. 5A. Site-specific conjugation appeared to preserve activity. Further, arranging the Fab on a multimeric scaffold does not significantly affect inhibitor potency.

Figure 9A:
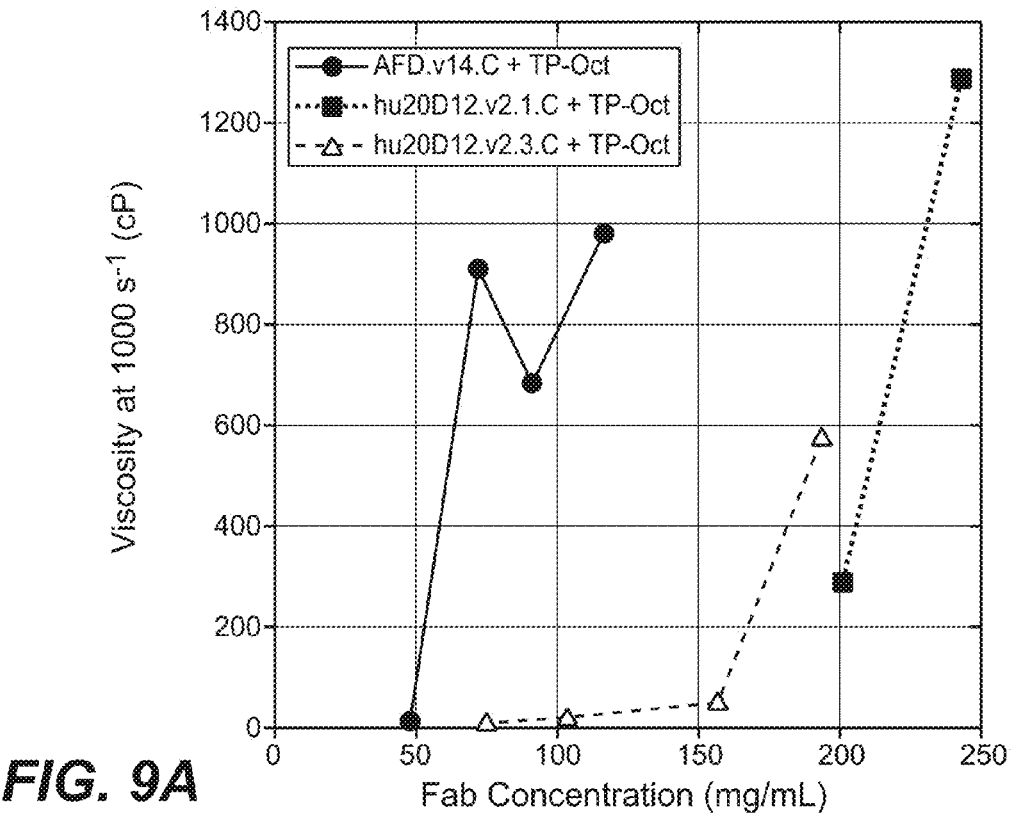
FIGS. 9A-B show the concentration-dependent viscosity of PEG-octamer conjugated antibodies. AFD.v14.C+TP-Oct; hu20D12.v2.1.C+TP-Oct; and hu20D12.v2.3.C+TP-Oct (9A), and AFD.v8.C+PEG tetramer; and hu20D12.v2.3+PEG tetramer (9B).
Figure 9B:
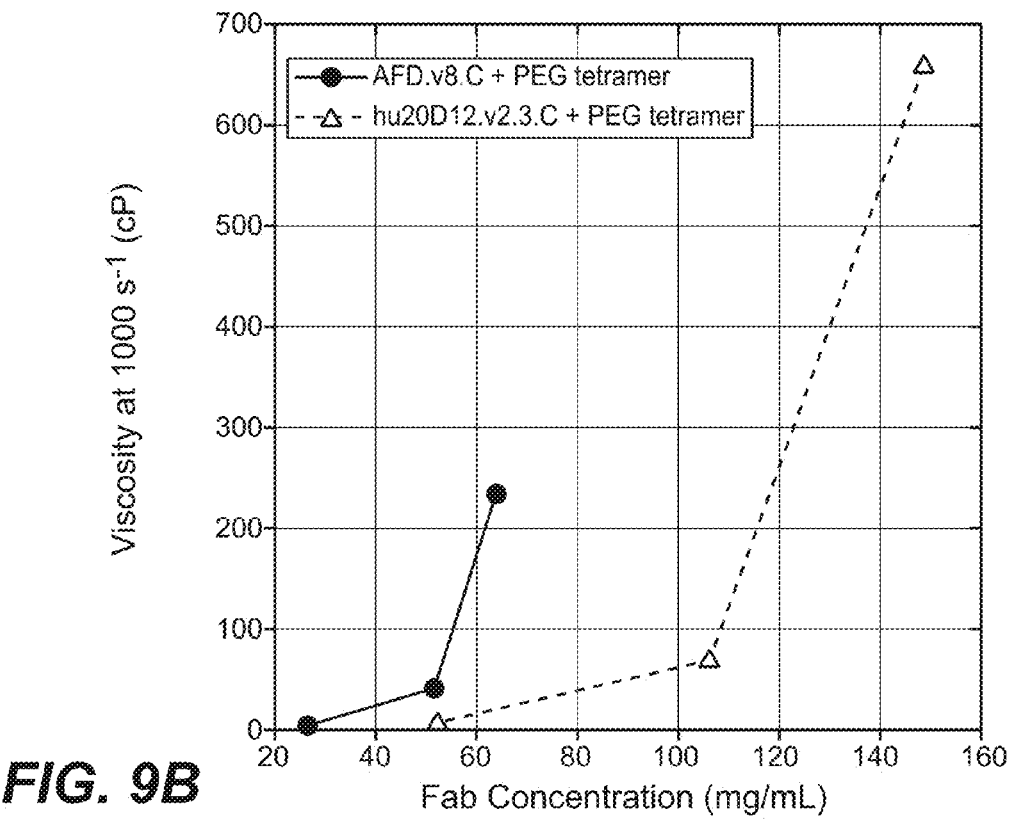

Viscosity of a formulation is an important parameter for determining suitability for injection. Therefore, viscosity measurements were carried out for the PEGylated Fab-C. Viscosity measurements were performed on a TA Instruments cone and plate rheometer thermostatted at 25° C. using a shear rate of 1000 s$^{-1}$. For measurements on Fabs, proteins were prepared in a pH 5.5, low salt buffer. Viscosity measurements on PEGylated Fab-C materials employed a buffer of 20 mM His-acetate, 50 mM NaCl, pH 6.5 and the temperature of measurement was 20° C. PEG-octamer conjugates of both hu20D12.v2.1.C ("hu20D12.v2.1.0 +TP-Oct") and hu20D12.v2.3.C("hu20D12.v2.3.C+TP-Oct") show low viscosity and a concentration dependence of viscosity that is suitable for injection of a high concentration formulation. See FIG. 9A. In contrast, the PEG-octamer conjugate of AFD.v14.C ("AFD.v14.C+TP-Oct"), which is a variant of lampalizumab, shows higher viscosity and a concentration dependence of viscosity that poses more challenge for injection of a high concentration formulation. See FIG. 9A. Viscosity measurements were also done on Fab-C proteins conjugated to 40K-tetramer-PEG (Sunbright® PTE-400 MA, see Table 15). The PEG tetramer conjugate of hu20D12.v2.3.C("hu20D12.v2.3.C+PEG tetramer") shows low viscosity and a concentration dependence of viscosity that is suitable for injection of a high concentration formulation. See FIG. 9B. In contrast, the PEG-tetramer conjugate of AFD.v8.0 ("AFD.v8.C+PEG tetramer"), which is a variant of lampalizumab, shows higher viscosity and a concentration dependence of viscosity that poses more challenge for injection of a high concentration formulation. See FIG. 9B.

Viscosity measurements were also performed on hu20D12.v2.1.C+TP-Oct using an AR-G2 Advanced Rheometer with anodized aluminum geometry 20 mm diameter, 1° angle (part #513204.905). Measurements were carried out on solutions of varied protein concentration in a buffer comprised of 20 mM His-HCl, pH 5.5, 0.02% polysorbate-20. The temperature was 25° C. and the shear rate was 1000 s$^{-1}$. As shown in Table 14 this formulation had a very good profile for dependence of viscosity on protein concentration and at the highest Fab concentration tested (235 mg/mL) the viscosity was only 203 centiPoise (cP).

TABLE 14

Viscosity of hu20D12.v2.1-C + TP-Oct formulated in 20 mM His-HCl, pH 5.5, 0.02% polysorbate-20, at varied protein concentration

| Protein Concentration (mg/mL) | Viscosity (cP) |
|---|---|
| 50 | 2.83 |
| 125 | 15.14 |
| 235 | 203.22 |

PEG Preparation: PEG powders were reconstituted to 10 mg/mL with water. A 10 mM Sodium trifluoroacetic acid solution was used as a cationizing agent. A 20 mg/ml α-Cyano-4-hydroxycinnaminic acid matrix solution dissolved in 50% acetonitrile: 0.1% triflououacetic acid was employed. PEG solution, sodium trifluoroacetic acid and 50% acetonitrile: 0.1% trifluoroacetic acid were mixed at a 3:3:4 ratio. One microliter of the PEG mixture was deposited onto a MALDI target plate. One microliter of matrix was added to the spot and allowed to dry at ambient temperature. Analysis was performed on a 4800 MALDI TOF/TOF instrument (Sciex, Framingham, Mass.) equipped with a 355 nm, 200 Hz Nd:Yag Laser in linear mode with m/z range from 5000-100000 and a laser power of 5000.

External calibrations were performed using PEG standards ranging in size from 2000 to 40000 daltons (Sigma, St. Louis, Mo.) under similar sample conditions. Mass readings were reported as the highest point on the unresolved spectrum, in cases where more than one peak existed, readings were reported as the apex of each peak. Peaks were visualized using Data Explorer software (Sciex, Framingham, Mass.).

Reconstituted PEG solutions were also analyzed by direct infusion via a Nanomate (Advion, Ithaca, N.Y.) onto Exactive Plus EMR (Extended Mass Range) orbitrap instrument (EMR, Thermo, San Jose, Calif.). A 1% (10 mg/1 ml) 1,8-Bis(tetramethylguanidino)naphthalene (Sigma, St. Louis, Mo.) solution dissolved in 70% H2O: 30% Dimethyl sulfoxide (DMSO) was used as charge reducing reagent. 10 ul of 10 mg/mL PEG solution was combined with 10 ul 1% 1,8-Bis(tetramethylguanidino)naphthalene, and direct infused onto the EMR at the following acquisition parameters: Spray Gas pressure,1.0 psi; Spray voltage to apply 1.50 kV; Capillary temp, 325° C.; S-lens RF leve1,100; Scan rage,1000 to 20000 m/z; Fragmentation, in-source CID 200 Ev, CE 200; Resolution, 17500; Polarity, positive; Microscans,10; AGC targe, 3e6; Maximum injection time, 50; AGC mode, fixed; Averaging, 100; Source DC offset, 25V; Injection Flatapole DC, 8V; Inter Flatapole lens, 7V; Bent Flatapole DC, 6V, Transfer multipole DC tune offset, 0V; C-Trap entrance lens tune offset, 0V; Trapping gas pressure setting, 8. Spectra were visualized using Thermo Xcalibur Qual Browser then annotated manually.

PEG-Fab conjugates, in which core PEG structure and number of conjugates varied by sample type, may be analyzed on a 4800 MALDI TOF/TOF, in linear mode. Four microliters of PEG-Fab conjugate are mixed with four microliters of sodium trifluoroacetic acid and two microliters of 50% acetonitrile: 0.1% trifluoroacetic acid. Equal volumes of PEG-Fab solution and 20 mg/mL sinapinic acid (in 50% acetonitrile: 0.1% trifluoroacetic acid, Agilent, Santa Clara, Calif.) matrix are deposited onto a MALDI target plate for analysis. The m/z range is set from 100000 to 500000, with target mass set to 400000. Spectra are visualized using Data Explorer then annotated manually.

Example 9

Thermal Stability of Polymer Conjugates

To simulate the exposure of the hu20D12 conjugates to conditions that may be found in long-acting delivery systems, samples of the hu20D12.v2.1.C and hu20D12.v2.3.C TP conjugates (prepared as above) were stressed under two different pH and salt conditions for several weeks at 37° C. Specifically, conjugates were evaluated in the following formulations:

~25 mg/mL, PBS,                                              Formulation 1

~25 mg/mL, 20 mM histidine HCl, 50 mM NaCl, at pH 6.5.                        Formulation 2

Figure 10A:
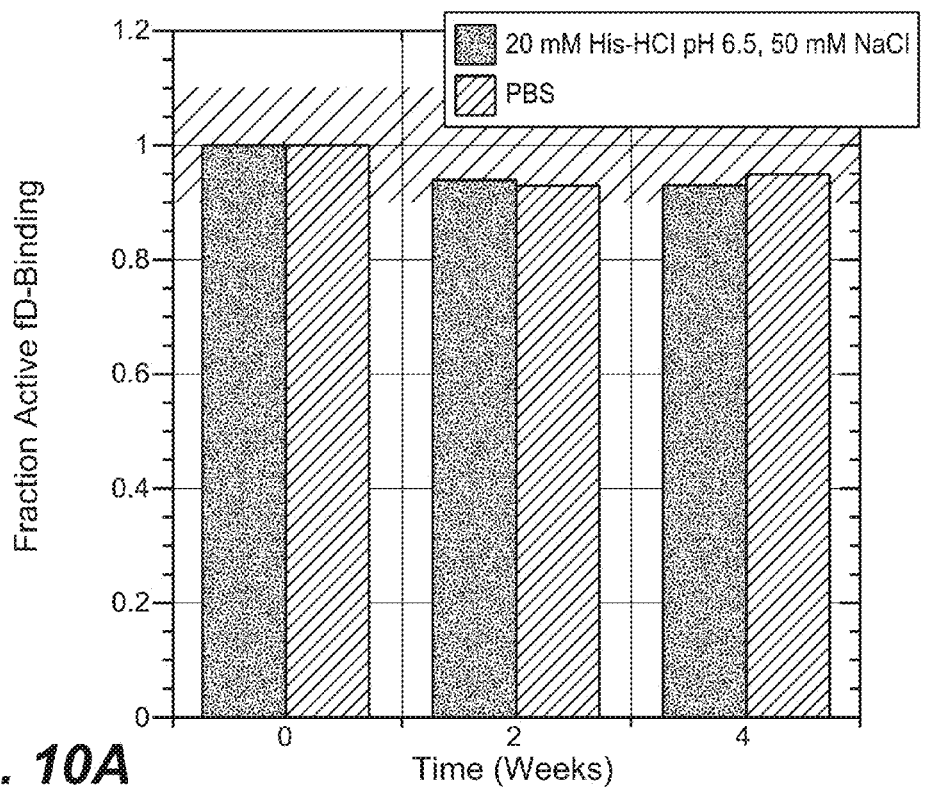
FIGS. 10A-B show thermal stability of PEG-octamer conjugated Fabs by binding capacity (10A) and CE-SDS (10B).
Figure 10B:
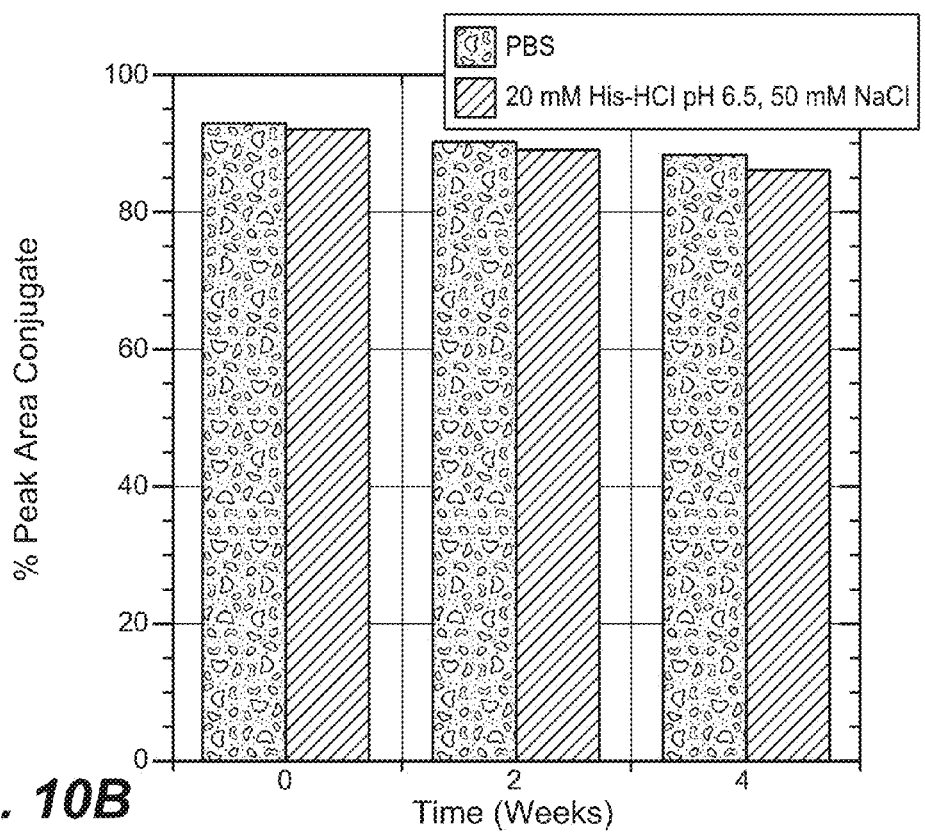

PBS was used as a mimic of the pH and ionic strength of human vitreous. Aliquots (100 μL) of solutions of hu20D12.v2.1 or hu20D12.v2.3 conjugate, formulated at 25 mg/mL in PBS or 20 mM His-Ac pH 6.5, 50 mM NaCl, were sterile filtered by centrifugal filtration using 0.22 μm Costar® Spin-X centrifuge tubes (Corning) and then incubated at 37° C. for 0, 2, 4, or 8 weeks. Incubations were terminated by freezing at −70° C. After thawing, samples were analyzed by SEC-MALS, CE-SDS, and by biacore to assess Factor D-binding capacity (methods described below). No change in binding capacity greater than the standard error in the measurements (±10%) was determined for incubation of the conjugate at 37° C. See FIG. 10A, showing thermal stability (37° C.) of hu20D12.v2.1.C+TP-Oct analyzed by binding capacity (SPR). Cross-hatched region shows standard error of ±10%. The binding capacity remained steady even after 4 weeks at 37° C. in PBS and after 4 weeks at pH 6.5. Analysis of hu20D12.v2.1.C+TP-Oct conjugate by CE-SDS showed good thermal stability (37° C.) in both formulations. See FIG. 10B. A loss in % peak area of the conjugate of only ~1%/week was observed.

a. FQ Labeling Procedure

Samples were labeled according to the following procedure. Solutions of hu20D12.2.1-C+TP-Oct (300 μg) were exchanged into 0.5 mL sodium phosphate reaction buffer using NAP-5 gel filtration columns (GE Healthcare, Piscataway, N.J., USA) to remove potentially competing formulation constituents. A 250 μL aliquot of the desalted conjugate was mixed with 30 μL of 150 mM N-ethylmaleimide dissolved in 4% SDS and incubated for 5 min at 70° C. to control disulfide reshuffling under denaturing conditions. Ten microliters of each 2.5 mM FQ and 30 mM KCN reagents were added to the SDS-hu20D12.2.1-C+TP-Oct solution, and the final solution was incubated for 10 min at 50° C. before diluted threefold with 1% SDS to quench the reaction. For reducing analysis, aliquots of the diluted samples were incubated with 50 mM DTT for 10 min at 70° C.

b. CE-SDS Analysis

Figure 21:
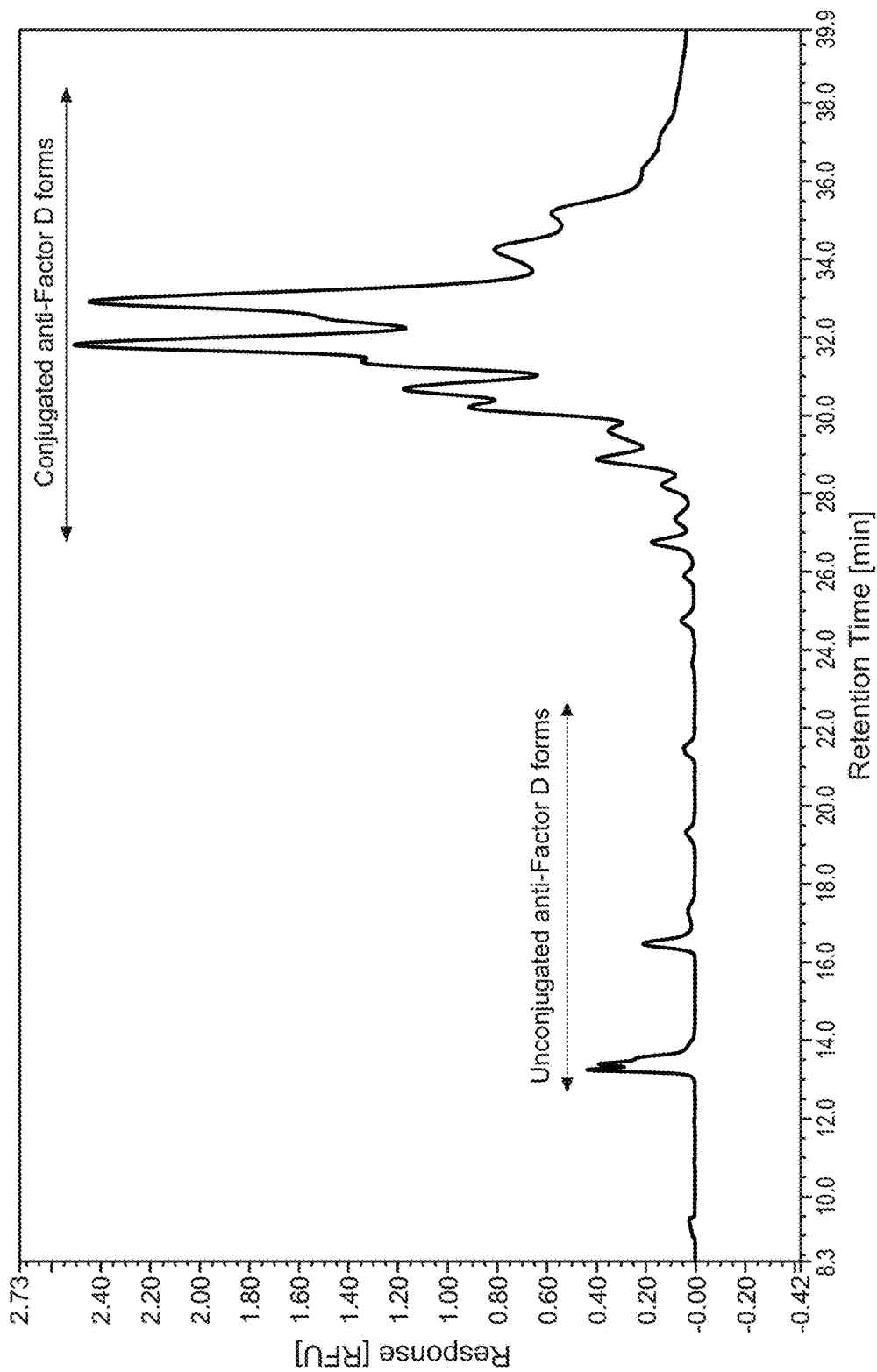
FIG. 21 shows CE-SDS non-reduced (NR) electropherogram of hu20D12.v2.1.C+TP-Oct.

Separation of PEGylated Fab samples was performed with 31.2 cm (21 cm effective length) fused-silica capillaries of 50 μm ID (Polymicro technologies, Phoenix, Ariz., USA) encased in 40° C. thermal controlled cartridges. Fully automated Beckman PA800+ systems (Beckman Coulter, Brea, Calif., USA) were equipped with LIF detection and used 32 Karat version 9.1 to control the instrument. The LIF detector used a 3.5 mW argon-ion laser having an excitation at 488 nm; emission was collected through a 600 ±20 nm bandpass filter (Edmund Optics, Barrington, N.J., USA). Voltage was applied in the negative mode (reverse polarity). Sample solutions were introduced electrokinetically at 5 kV for 25 s and separated at 17 kV. Between runs, the capillary was washed with 0.1 M NaOH, 0.1 M HCl and Beckman gel buffer for 5 min, 1 min, 1 min and 10 min, respectively. See, e.g., Michels et al., 2007, *Anal. Chem.*, 79: 5963-71; Michels et al., 2012, *Electrophoresis*, 33: 815-26. An example electropherogram of a non-reduced sample of hu20D12.2.1-C+TP-Oct is shown in FIG. 21.

c. Surface Plasmon Resonance Analysis

A Series S, CM5 sensor chip was docked into a Biacore® T200 instrument (GE Healthcare), primed with 1× running buffer and normalized with 70% glycerol following a protocol supplied by the manufacturer. The sensor chip surface was activated for amine-coupling of antigens using the amine coupling kit with the materials provided and the protocol suggested by the manufacturer. Human factor D (fD) was covalently immobilized by injecting a solution containing 100 μg/mL antigen prepared by dilution of fD (PUR #20491, 2.4 mg/mL) with 10 mM sodium acetate pH 5. The flow rate was 10 μL/min and an injection volume of 70 was used. This yielded a typical coupling density across multiple experiments of about 5000 Resonance Units (RU) for fD. Unreacted amine coupling sites were blocked by injection of 70 μL 1 M ethanolamine.

Antigen-binding active concentrations of antibody Fab were determined using the calibration-dependent concentration analysis routine of the Biacore® T200 evaluation software. A standard curve of hu20D12.v2.1.C+TP-Oct was prepared through gravimetric dilution of a stock solution to 5 μg/mL followed by serial 2-fold dilutions to produce samples of 2.5, 1.25, 0.625, 0.313, 0.156, and 0.078 μg/mL. Test samples were prepared by gravimetric dilution to obtain protein concentrations of about 0.5, 1.0, or 1.5 μg/mL. All samples (200 μL volume) were prepared using 1× running buffer. 60 μL aliquots were injected over the specific antigen surface using a flow rate of 10 μL/min with the sensor chip maintained at 25° C. and primed with 1× running buffer. Antibody bound to specific antigen was determined from the SPR signal near the end of the sample injection. Bound antibody was eluted at the end of each binding cycle through injection of 30 μL of 10 mM Gly-HCl pH 2.1 to cause dissociation of the antibody-antigen complex. The standard curve of hu20D12.2.1-C+TP-Oct was used to determine the relationship of SPR signal to antibody concentration using a four-parameter function to analyze the data. Parameters calculated from the standard curve were used to calculate the antigen-binding concentration of test samples based on the observed SPR signal. The ratio of this concentration to the protein concentration determined by absorbance measurements gives the fraction or percent binding.

Example 10

Additional Anti-Factor D Antibody Variants for Polymer Conjugation

As discussed above, including a free cysteine in the constant region of the anti-Factor D Fab can improve conjugation and minimize interference with binding to antigen. In addition to the heavy chain Fab C-terminus "CDKTHTC," the heavy chains of the Fab fragments may also be modified by adding the first four residues from the hinge region of the Fab-C counterpart, to give the C-terminus "CDKTHTCPPC." The C-terminus "CDKTHTCPPS," "CDKTHTSPPC," "CDKTH," "CDKT," "CDK," "CD," "APPC," "SGGC," or "CYGPPC" may also be used. In some embodiments, the "CDKTHTCPPC" terminus allows attachment of two PEG molecules. The resulting Fabs can be conjugated with a multi-arm PEG.

Example 11

Preparation of Anti-Factor D Antibody Conjugates

Humanized anti-Factor D Fab variants with the heavy chain Fab terminus "CDKTHTC," "CDKTHTCPPC," "CDKTHTSPPC," "CDKTHTCPPS," "CDKTH," "CDKT," "CDK," "CD," "APPC," "SGGC," or "CYGPPC"

are conjugated with commercially available maleimide-functionalized multi-armed PEGs having varying core structures.

a. Maleimide-Functionalized Multi-Armed PEGs

The maleimide-functionalized multi-armed PEGs detailed in Table 15, below, are used in the conjugation reactions:

TABLE 15
Maleimide-functionalized multi-armed PEGs
| PEG | Vendor | Core structure | Functional Group (X) | Poly-dispersity | Average MW |
|---|---|---|---|---|---|
| 8ARM (TP)-PEG-MAL | JenKem Technology, U.S.A. | Tripentaerythritol (TP) 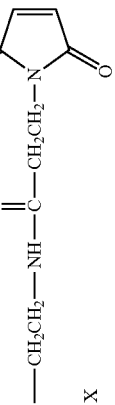 |  | ~1.04 | 40,000 |
| 8ARM-PEG-MAL | JenKem Technology, U.S.A. | Hexaglycerin (HG) 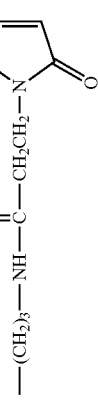 |  | ~1.08 | 40,000 |
| Sunbright® HGEO-400MA | NOF America Corp. | Hexaglycerol (HGEO)  |  | ~1.33 | 40,000 |
| Sunbright® DX-400MA | NOF America Corp. | Butanediol |  | ~1.01 | 40,000 |

TABLE 15-continued

Maleimide-functionalized multi-armed PEGs

| PEG | Vendor | Core structure | Functional Group (X) | Poly-dispersity | Average MW |
|---|---|---|---|---|---|
| Sunbright® PTE-400MA | NOF America Corp. | X—(OCH$_2$CH$_2$)m—O—CH$_2$—C(CH$_2$—O(CH$_2$CH$_2$O)m—X)(CH$_2$—O(CH$_2$CH$_2$O)m—X)—CH$_2$—O(CH$_2$CH$_2$O)m—X | —(CH$_2$)$_3$—NH—C(=O)—CH$_2$CH$_2$—N(maleimide) | Not provided | 40,000 |

Figure 12A:
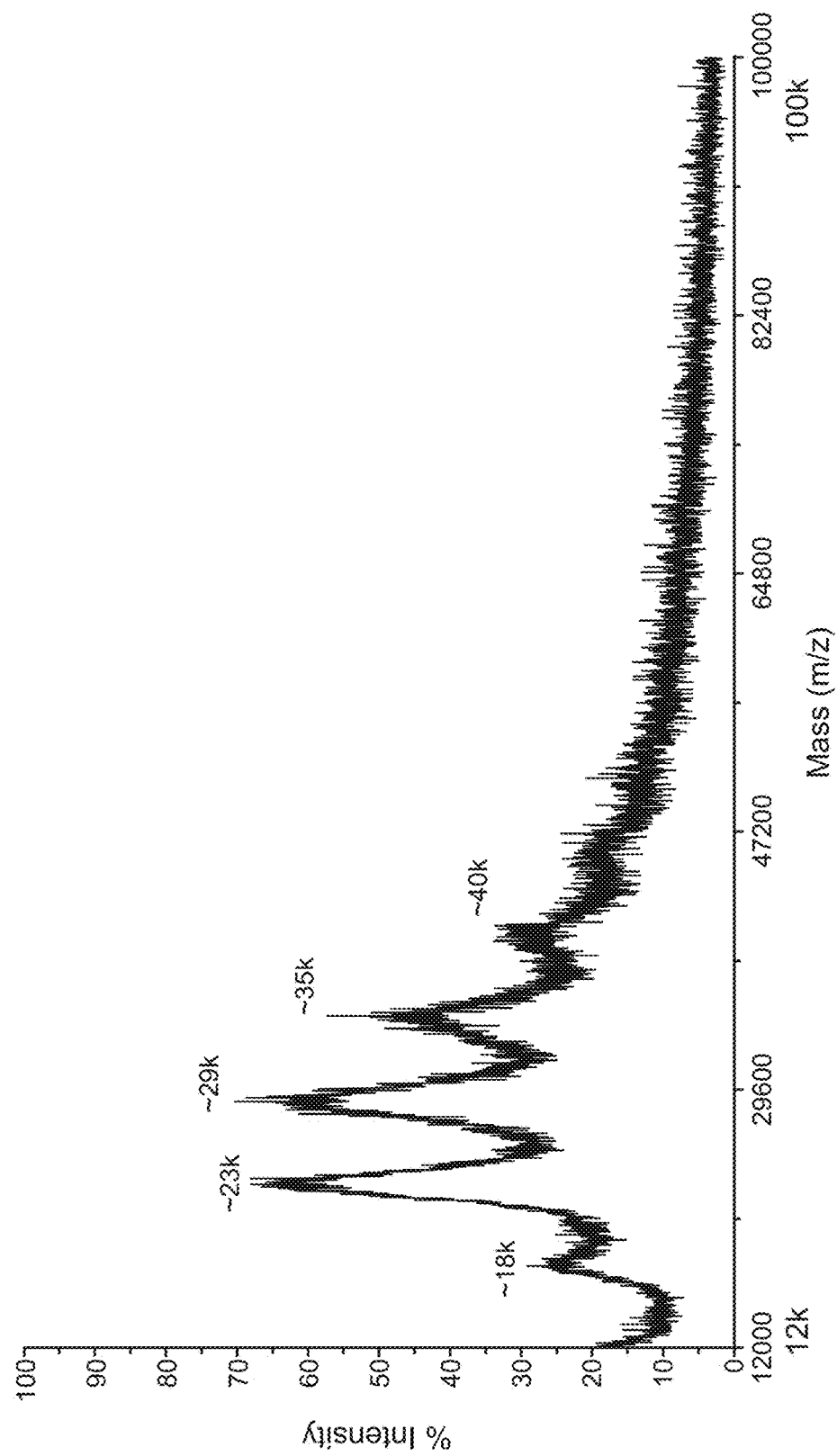
FIGS. 12A-B show MALDI analysis of a multi-armed PEG comprising a hexaglycerol (HGEO) core (Sunbright® HGEO-400MA, NOF America, Corp.) and a tripentaerythritol (TP) core (8ARM (TP)-PEG-MAL, JenKem Technology, USA) (12A: HGEO core; 12B: TP core).
Figure 12B:
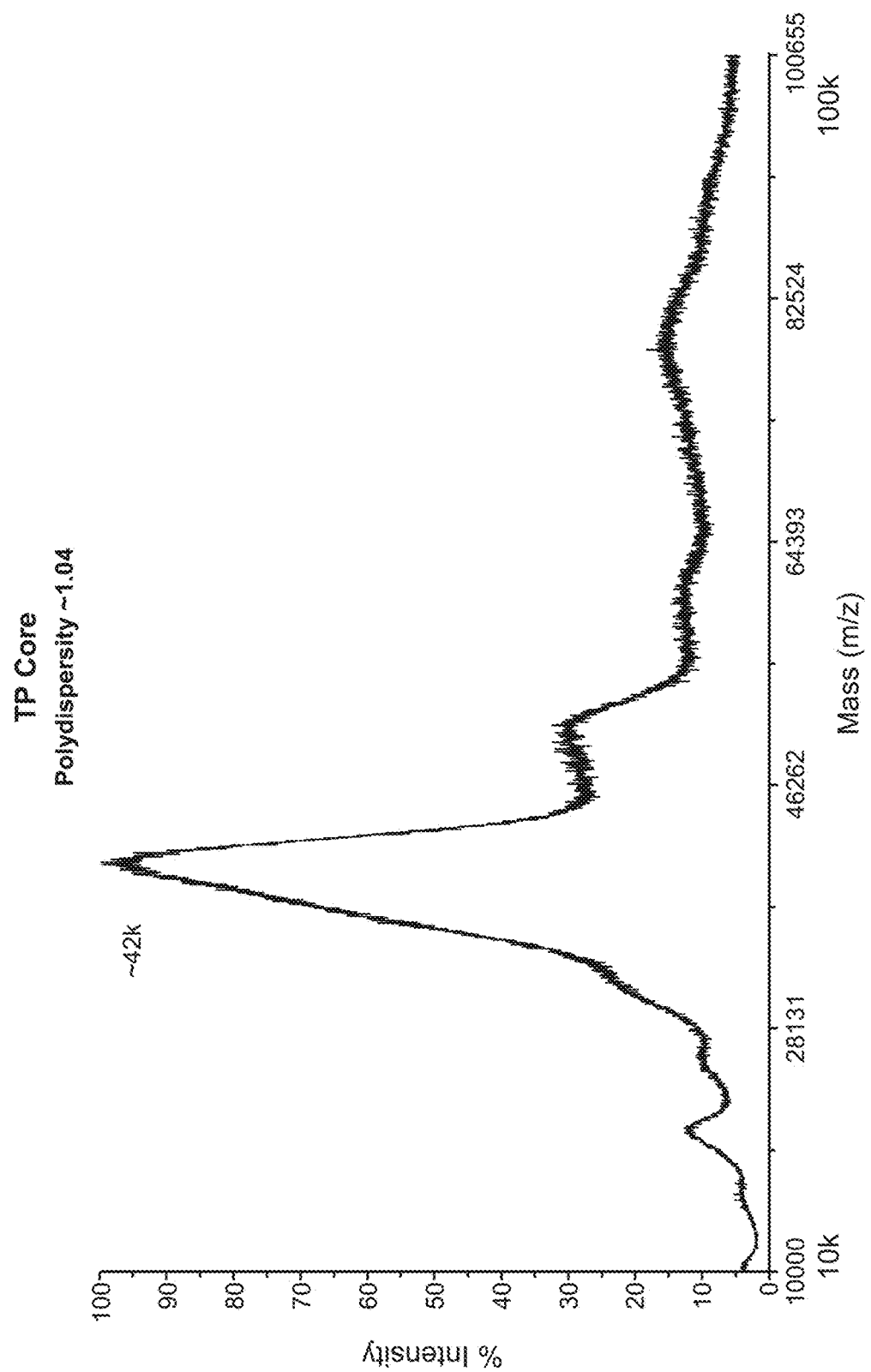

The 8ARM (TP)-PEG-MAL (JenKem Technology, USA) and Sunbright® HGEO-400MA (NOF America, Corp.) were analyzed using MALDI to compare the homogeneity of PEG octamers containing either the TP core or the HGEO core. The results are shown in FIGS. 12A and 12B. As can be seen from those figures, the 8ARM (TP)-PEG-MAL containing the TP core was more homogeneous than the Sunbright® HGEO-400MA containing the HGEO core.

b. Conjugation of Fabs with Maleimide-Functionalized Multi-Armed PEGs

The cysteine-modified Fab is captured using Gamma Plus resin, with 6.5 mM GSH pH 8.5 wash for 5 column volumes to deblock C-terminal cysteine and disrupt Fab-C dimer formation, followed by elution into 0.1M acetic acid pH 2.9. The cysteine-modified Fab monomer is further isolated using SP Sepharose High Performance strong cation exchange resin from GE in 25 mM Sodium Acetate pH 5.0, with 0.05% Triton X-100+0.05% Triton X-114 was for 19 hours for endotoxin removal. Elution is performed with gradient between 0-20% 25 mM Sodium Acetate pH 5.0+ 1M NaCl over 20 column volumes. The monomeric Fab-C with deblocked c-terminal cysteine is then prepared for PEGylation by being titrated to pH 6.5 using 1M HEPES pH 7.2. Fab-C is then conjugated to PEG octamer in 25 mM NaAcetate pH 6.5, 150 mM NaCl, 4 mM EDTA, at a concentration around 5 mg/mL. Fab-C is not further concentrated in order to minimize cysteine reactivity loss due to Fab-C dimerization. After equilibrating to room temperature, 40K TP PEG powder from JenKem is resuspended in 25 mM NaAcetate pH 5.0 to a concentration of 10 mg/mL. The pH is kept below pH 6 to avoid maleimide ring opening. Once PEG is solubilized, it is added to the Fab-C pool at a molar ratio of 0.1125:1 PEG to Fab-C. The mixture is then left at room temperature with gentle shaking overnight. The following day, the conjugation efficiency is checked by SEC-MALS.

Example 12

Exemplary Purification and Characterization of Conjugates

The conjugates prepared in Example 10 are purified and analyzed using SEC-MALS to confirm PEGylation and determine conjugation efficiency for different PEG core structures. Conjugation efficiency is determined by Size Exclusion Chromatography (SEC) using a 300×8 mm Shodex OH pak SB-804 HQ run at 0.8 mL/min using phosphate buffered saline (PBS) pH 7.2, 150 mM NaCl under isocratic conditions. Molar mass is determined using in-line static Multi-Angle laser Light Scattering (MALS) by Wyatt Technology. Photon correlation spectroscopy was used to determine hydrodynamic radii (RH), using Quasi-Elastic Light Scattering (QELS), a single photon counting module with detection at a 99.0 o, also by Wyatt Technology. Raw data is analyzed using Wyatt's proprietary Astra software, where molar mass and RH constants are set using a rituximab standard.

a. Cys-Modified Fab-8ARM (TP)-PEG-MAL Conjugate ("Fab TP Conjugate")

The conjugates are purified using Size Exclusion Chromatography (SEC) on a Sephacryl S-300 HR (GE Healthcare) column in 20 mM His-acetate, pH 5.5, 50 mM NaCl (isocratic gradient). Molar mass is determined using in-line static Multi-Angle laser Light Scattering (MALS) by Wyatt Technology and Shodex OHpak SB804 (13C). Raw data is analyzed using Wyatt's proprietary Astra software, where molar mass constants were set using a rituximab standard. Molar mass is used to estimate the average number of Fabs attached to each PEG. Fabylation is determined by subtracting 40 g/mol (average mass of PEG octamer) from the MALS measured mass, then dividing by the average mass of cysteine-modified Fab. The theoretical molar mass for 8 Fab's+40K PEG octamer is 416,056 g/mol. Exemplary data is shown in Table 16.

TABLE 16

| Fraction # | Molar Mass (g/mol) | Estimated Fabylation |
|---|---|---|
| B2 | 502,000 | agg |
| B3 | 470,200 | N/D |
| B4 | 453,200 | N/D |
| B5 | 444,300 | 8 Fabs/PEG |
| B6 | 430,400 | 8 Fabs/PEG |
| B7 | 410,900 | 8 Fabs/PEG |
| C1 | 388,100 | 7 Fabs/PEG |
| C2 | 349,100 | 6-7 Fabs/PEG | agg = aggregates

Conjugation of cysteine-modified Fab with a multi-armed PEG octamer having the TP core produces conjugates comprising 8 Fabs/PEG, demonstrating that good conjugation efficiency can be achieved with PEG octamers comprising a TP core.

b. Cys-Modified Fab-8ARM-PEG-MAL Conjugate ("Fab HG Conjugate")

The Cys-modified Fab-8ARM-PEG-MAL conjugate (containing the HG core structure (JenKem); hereinafter the "Fab HG conjugate") prepared in Example 10 is purified using SEC on a Sephacryl S-300 HR (GE Healthcare) column in 20 mM His-acetate, pH 5.5, 50 mM NaCl (isocratic gradient). The conjugate containing fractions are pooled, and further purified using SEC on a Sephacryl S-300 HR (GE Healthcare) column in 20 mM His-acetate, pH 5.5, 50 mM NaCl (isocratic gradient). Molar mass is determined using Tosoh G3000PW column and in-line static MALS by Wyatt Technology. Photon correlation spectroscopy is used to determine hydrodynamic radii (RH), using Quasi-Elastic Light Scattering (QELS), a single photon counting module with detection at a 99°, also by Wyatt Technology. Raw data is analyzed using Wyatt's proprietary Astra software, where molar mass and RH constants are set using a rituximab standard. Molar mass is used to estimate the number of Fabs attached to each PEG. Exemplary results are shown in Table 17.

TABLE 17

| Fraction # | Mw (kDa) | Estimated Fabylation | $R_H$ (nm) |
|---|---|---|---|
| A6 | 1146.6 (±0.1%) | Agg | 16.0 (±4.9%) |
| B3 | 861.6 (±0.1%) | Agg | 14.5 (±4.0%) |
| B6 | 758.3 (±0.1%) | Agg | 13.7 (±3.8%) |
| C1 | 649.3 (±3.8%) | n/d | 13.5 (±3.8%) |
| C6 | 562.6 (±0.1%) | n/d | 12.8 (±3.6%) |
| D2 | 546.7 (±0.1%) | n/d | 12.8 (±3.7%) |
| D4 | 536.6 (±0.1%) | n/d | 12.6 (±3.6%) |
| E2 | 525.4 (±0.1%) | n/d | 12.5 (±3.5%) |
| E5 | 489.2 (±0.2%) | 8 Fab/PEG | 12.3 (±3.7%) |
| F1 | 409.2 (±0.2%) | 7-8 Fab/PEG | 10.8 (±3.7%) |
| F4 | 342.2 (±0.1%) | 6-7 Fab/PEG | 9.7 (±2.9%) |
| F6 | 325.5 (±0.2%) | 6 Fab/PEG | 9.5 (±0.3%) |
| G2 | 302.4 (±0.2%) | 5-6 Fab/PEG | 9.3 (±3.1%) | agg = aggregates
n/d = not determined

As can be seen from Table 17, conjugation of the Cys-modified Fab with a PEG octamer comprising the HG core produces conjugates comprising 8 Fabs/PEG. Conjugation with the HG core also produced more conjugates comprising 5-7 Fabs/PEG, than was observed with the TP core.

In an effort to improve Fabylation estimate and RH measurement, the HG final pool prepared above may be alternately analyzed using SEC-MALS on a 10/300 Sephacryl S-400 HR (GE Healthcare) column in PBS, pH 7.4, run at 0.25mL/min. Molar mass and RH are determined as described above. In an exemplary experiment, the conjugates prepared using the 8ARM-PEG-MAL (HG core) and purified on Sephacryl S-400 HR have an average RH of 12.2 nm (±4.5%), an average molar mass of 340.3 kDa (±8.9%), and an average of 6.4 Fabs/PEG.

c. Cys-Modified Fab-HGEO-400MA Conjugate ("Fab-HGEO1 Conjugate")

The Cys-modified Fab-HGEO-400MA conjugate (containing the Sunbright® HGEO-400MA PEG; hereinafter the "Fab HGEO1 conjugate") prepared in Example 4 is purified using SEC on a Sephacryl S-400 HR (GE Healthcare) column in 20 mM His-acetate, pH 5.5, 50 mM NaCl (isocratic gradient). Molar mass and RH are determined using Sephacryl S-400 HR, run at 0.25 mL/min in PBS pH 7.4.

In an exemplary experiment, the conjugates prepared using the Sunbright® HGEO-400MA PEG (HGEO core) have an average RH of 15.2 nm (±4.5%), an average molar mass of 423.8 kDa (±10.6%), and an average of 8.2 Fabs/PEG.

d. Cys-Modified Fab-8ARM (HGEO)-PEG-MAL Conjugate ("Fab HGEO2 Conjugate")

The Cys-modified Fab-8ARM(HGEO)-PEG-MAL conjugate (containing the HGEO core structure (JenKem); hereinafter the "Fab HGEO2 conjugate") prepared as above is purified using SEC on a Sephacryl S-300 HR (GE Healthcare) column in 20 mM His-acetate, pH 5.5, 50 mM NaCl (isocratic gradient). Molar mass is determined as described above. Molar mass is used to estimate the number of Fabs attached to each PEG. Exemplary results are set forth in Table 18.

TABLE 18

| Fraction # | Molar Mass (g/mol) | Estimated Fabylation |
| --- | --- | --- |
| B1 | 2,145,000 (±0.8%) | aggregate |
| B2 | 665,800 (±0.7%) | aggregate |
| B3 | 426,400 (±0.8%) | 8 Fabs/PEG |
| B4 | 296,400 (±0.8%) | 6 Fabs/PEG |
| B5 | 246,200 (±0.8%) | 5 Fabs/PEG |
| B6 | 215,000 (±0.8%) | |

As can be seen from Table 18, conjugation of the Cys-modified Fab with a PEG octamer comprising the HGEO2 core produces conjugates comprising 8 Fabs/PEG. Conjugation with the HGEO2 core also produces more conjugates comprising 5-6 Fabs/PEG, than was observed with the TP core.

Example 13

Enrichment of Conjugates

One way to increase the Fab concentration in an intravitreal formulation without significantly increasing formulation viscosity, is to increase the percentage of highly fabylated conjugates in the formulation. In this example, cation exchange chromatography is used to enrich for highly fabylated conjugates.

Fractions containing estimated fabylation of 8 Fab/PEG from the SEC purification of the Fab TP conjugate described above are pooled and subjected to cation exchange chromatography using, e.g., SP Sepharose High Performance strong cation exchange resin from GE, with 0.05% Triton X-100+ 0.05% Triton X-114 wash for 19 hours to remove endotoxin, followed by gradient elution between 10-20% 1M NaCl over 50 column volumes (CV). Molar mass is determined as described above. Exemplary results are set forth in Table 19.

TABLE 19

| Fraction # | Molar mass (g/mol) | Estimated Fabylation | GEL Lane # |
| --- | --- | --- | --- |
| 3B11 | 335,000 | 6 Fabs/PEG | 1, 8 |
| 3E12 | 367,100 | 7 Fabs/PEG | 2, 9 |
| 4A7 | 414,200 | 8 Fabs/PEG | 3, 10 |
| 4C5 | 430,000 | 8 Fabs/PEG | 4, 11 |
| 4F3 | 483,900 | n/d | 5, 12 |
| 4H9 | 567,400 | n/d | 6, 13 |

The conjugate containing fractions are pooled, and further purified using a 300×8 mm Shodex OH pak SB-804 HQ, run at 0.8 mL/min using phosphate buffered saline (PBS), pH 7.4, 150 mM NaCl, under isocratic conditions. Molar mass and RH are determined as described above.

Following enrichment, conjugates prepared using the 8ARM (TP)-PEG-MAL (TP core) are obtained that have an average RH of 10.5 nm (±2.5%), an average molar mass of 407.1 kDa (±0.2%), and an average of 7.8 Fabs/PEG.

Example 14

Measurement of Systemic Alternative Complement Pathway Activity in Cynomolgus Monkeys Lampalizumab has previously been shown to transiently inhibit systemic complement function in cynomolgus monkeys (see Loyet, et al., *J. Pharmacol. Exp. Ther.*, 2014, Vol. 351, pp. 527-537). In the current example, the effect of intravitreal administration of an anti-Factor D antibody variant or an AFD.Ab conjugate on systemic alternative complement pathway (AP) activity was evaluated in cynomolgus monkeys.

a. Pharmacokinetic/Pharmacodynamic Studies in Cynomolgus Monkeys

The AFD.Ab variant and conjugate were administered by a single-dose IVT or intravenous injection to male cynomolgus monkeys (*M. fascicularis*) of Chinese origin to assess the pharmacokinetics (PK) and pharmacodynamics (PD) of the molecules. These studies were conducted at Covance Laboratories (Madison, Wis.). All procedures were conducted in compliance with the US Department of Agriculture Animal Welfare Act Regulations (9 CFR 3), Guide for the Care and Use of Laboratory Animals, and the Office of Laboratory Animal Welfare.

Four studies were performed. In the first (control) study (Study 1, n=10), lampalizumab was administered to both eyes, in two 50 μL IVT doses, separated by 15 minutes. These animals received 10 mg/eye for a total of 20 mg/animal. Blood was collected predose (day -2) and post dose at the following time points: 45 minutes, and 2, 6, 10, 24, 34, 48, 96, 120, 154, 192, 288, and 384 hours. After blood collections at 24, 48, 120, 192, and 384 hours, two animals per group were removed from the study and euthanized to collect ocular matrix. The lampalizumab control Study has previously been described in Loyet, et al., *J. Pharmacol. Exp. Ther.*, 2014, 351:527-537.

In Study 2 (n=3), AFD.v14 was administered to both eyes, in two 50 µL IVT doses, separated by 15 minutes. These animals received 25 mg/eye for a total of 50 mg/animal. Blood was collected predose (day-1 and -3) and post dose at the following time points: 30 minutes, and 2, 8, 24, 48, and 96 hours.

In Study 3 (n=10), the AFD.v14.C+TP octamer was administered to both eyes, in two 50 µL IVT doses, separated by 15 minutes, to provide 3.9 mg/eye of AFD.v14, for a total of 7.8 mg/animal of AFD.v14. Blood was collected predose (week-1 and week-2) and post dose at the following time points: 1, 6, 24, 48, 72, 96, 144, 192, 288, and 480 hours. Two animals per group at each time point (at 24, 96, 192, 288, and 480 hours) were removed from the study and euthanized to collect ocular matrix.

In Study 4, the AFD.v14.C+HG octamer was administered to both eyes in two 50 µL IVT doses, separated by 15 minutes, to provide either 7.1 mg/eye of AFD.v14 (n=2) or 11.8 mg/eye of AFD.v14 (n=1), for a total of 14.2 mg/animal or 23.6 mg/animal of AFD.v14. Blood was collected predose (day-7 and -1) and post dose at the following time points: 1, 6, 24, 96, and 168 hours.

For all studies, predose and postdose serum samples were collected from each animal via the femoral vein for PK and PD analyses. At each time point, whole blood was collected into serum separator tubes, allowed to clot at ambient temperature for at least 20 minutes, then centrifuged in a refrigerated centrifuge set at a temperature range of 2° C.-8° C. The serum was harvested within 20 minutes of centrifugation and stored between −60° C. and −80° C. until analysis.

b. Total AFD. v14/Conjugate Analysis

A Gyrolab XP assay was used to quantify AFD.v14, AFD.v14.C+TP octamer, and AFD.v14.C+HG octamer in cynomolgus monkey serum. Samples were diluted 1:4-1:3000 in sample buffer (phosphate buffered saline (PBS), 0.5% bovine serum albumin (BSA), 15 ppm Proclin (Sigma-Aldrich), 0.05% Tween 20, 0.25% CHAPS, 50 µg/mL muIgG (Equitech Bio, Cat. #SLM66), 5 mM EDTA (pH 7.4)). The AFD.v14 and AFD.v14 TP and HG conjugate standard curves were prepared by serially diluting AFD.v14, AFD.v14.C+TP octamer, or AFD.v14.C+HG octamer from 2.06-1500ng/mL in sample buffer. Capture and detection reagents were applied at 100 µg/mL of biotin-conjugated goat anti-human IgG (HC+LC, Bethyl, Cat #A80-319B) in PBS/0.01% Tween 20/0.02% NaN3 and Alexa-anti-CDR (clone 234, Genentech) at 25 nM in Rexxip F (Gyrolab). The assay was run on a Gyrolab Bioaffy 200 CD, and wash steps used PBS/0.01% Tween 20/0.02% NaN$_3$ followed by Gyros pH 11 wash buffer. The instrument was run and data analyzed as described by the manufacturer with a 1% PMT setting. The concentrations of AFD.v14, AFD.v14.C+TP octamer, and AFD.v14.C+HG octamer were determined from a five-parameter fit of its standard curve. The minimum quantifiable concentration was 8.24 ng/mL (0.16 nM) for AFD.v14, AFD.v14.C+TP octamer, and AFD.v14.C+HG octamer in cynomolgus monkey serum.

c. Pharmacodynamics Assay for Factor D in Cynomolgus Monkey Serum

A sandwich ELISA was used to quantify factor D (fD) in cynomolgus monkey serum. Mouse anti-human factor D clone 4676 (Genentech) was diluted to 1 µg/mL in coating buffer (0.05M Sodium Carbonate, pH 9.6) and incubated overnight at 4° C. on 384-well Maxisorp plates (Thermo Scientific, Cat. #464718). Plates were washed with PBS plus 0.05% Tween 20 and blocked during a 2 hour incubation with PBS plus 0.5% bovine serum albumin (BSA). This and all subsequent incubations were performed at room temperature with gentle agitation. The cynomolgus monkey fD standard curve was prepared by serially diluting fD from 0.04-5 ng/mL in sample buffer (assay buffer supplemented with 500 ng/mL of the AFD.v14 therapeutic and 50 µg/mL mouse IgG). The serum samples and controls were diluted to a minimum of 1:100 in sample buffer. The diluted standards, controls, and samples were then incubated on the plates for 2 hours, and plate-bound fD/AFD.Ab complex was detected using biotin-conjugated mouse-anti-CDR mAb to AFD.Ab (clone 242, 1 µg/mL) for one hour followed by High Sensitivity SA-HRP (3 ng/mL, Pierce Cat. #21130) also for one hour. After a final wash, tetramethyl benzidine (Moss, Cat. #TMBE-1000) was added and color was developed for 10-15 minutes, and the reaction was stopped with 1 M phosphoric acid. The plates were read at 450 nm with a 620 nm reference using a microplate reader. The concentrations of fD were determined from a four parameter fit of the standard curve. The minimum quantifiable concentration in cynomolgus monkey serum was 3.9 ng/mL (0.16 nM).

d. AP Hemolysis Assay

The ability of AFD.v14 and AFD.v14.C+TP octamer to inhibit AP activity was evaluated in a hemolytic assay in which serum (either human or monkey) was combined with rabbit erythrocytes, as designed and described by Pangburn (*Methods Enzymol*, 1988, 162:639-653) and Katschke et al. (*J. Biol. Chem.*, 2009, 284:10473-10479). To ensure complement activation did not occur through the classic complement pathway (CP), C1q-depleted human serum (Complement Technologies, Tyler, Tex.) was used, and the buffer included EGTA to chelate calcium, a cation essential for CP activity.

C1q-depleted human serum was used to activate the AP. The concentration of fD present in 10% C1q-depleted human serum was 9.6 nM in-well, a value in agreement with previously reported fD levels in serum (Barnum, et al., *J. Immunol. Methods*, 1984, 67:303-309; Loyet et al., *Invest. Ophthalmol. Vis. Sci.*, 2012, 53:6628-6637).

e. Determination of Inhibition of Systemic AP Activity in AFD.v14.C+HG Octamer-Treated Cynomolgus Monkey Serum To evaluate the time course and dose dependency of any potential inhibition of systemic AP activity subsequent to dosing with AFD.v14.C+HG octamer or AFD.v14.C+TP octamer, either a plate-based WIESLAB Complement System AP ELISA or an ex vivo assay was performed.

Figure 13A:
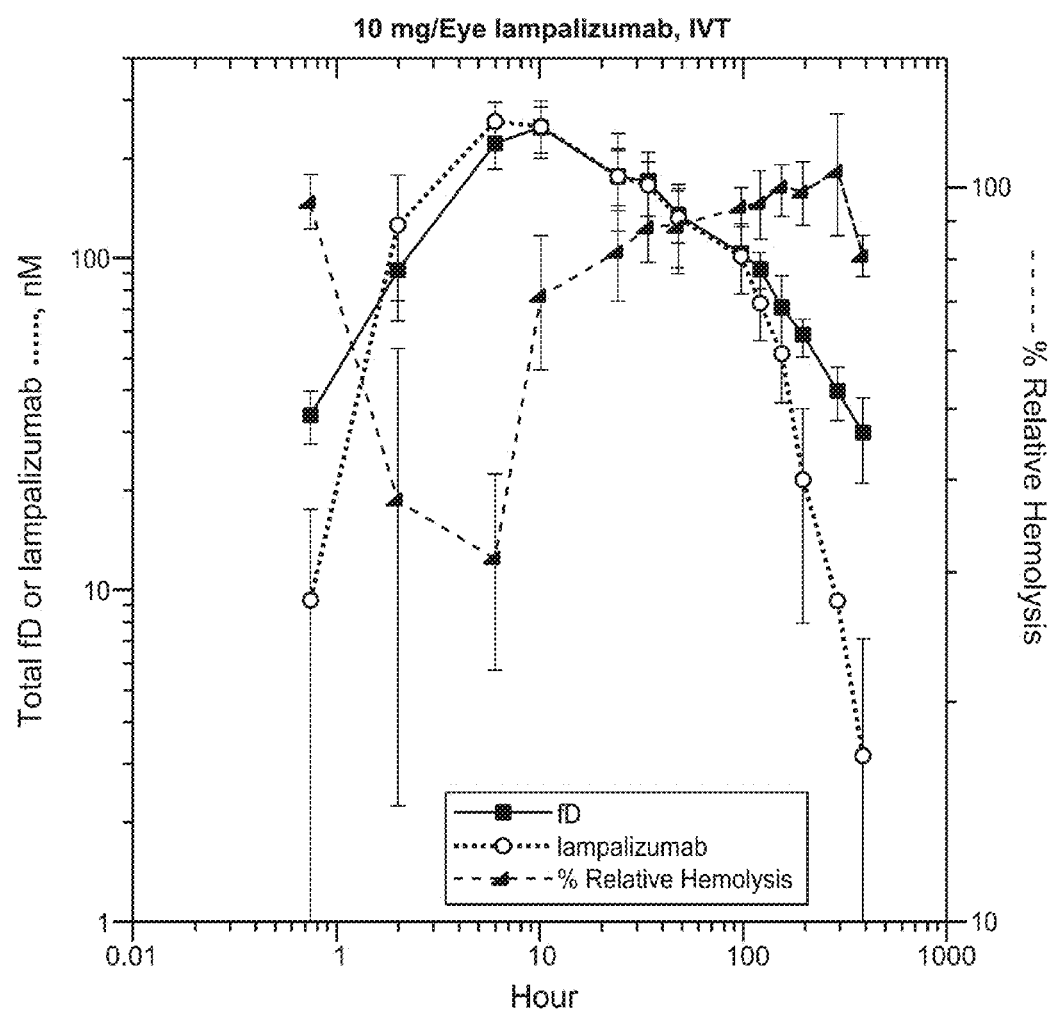
FIGS. 13A-B show percent systemic AP complement activity as measured by relative hemolysis of rRBCs over time in cynomolgus monkeys following intravitreal (IVT) injection of lampalizumab (13A) or unconjugated AFD.v14 (13B).
Figure 13B:
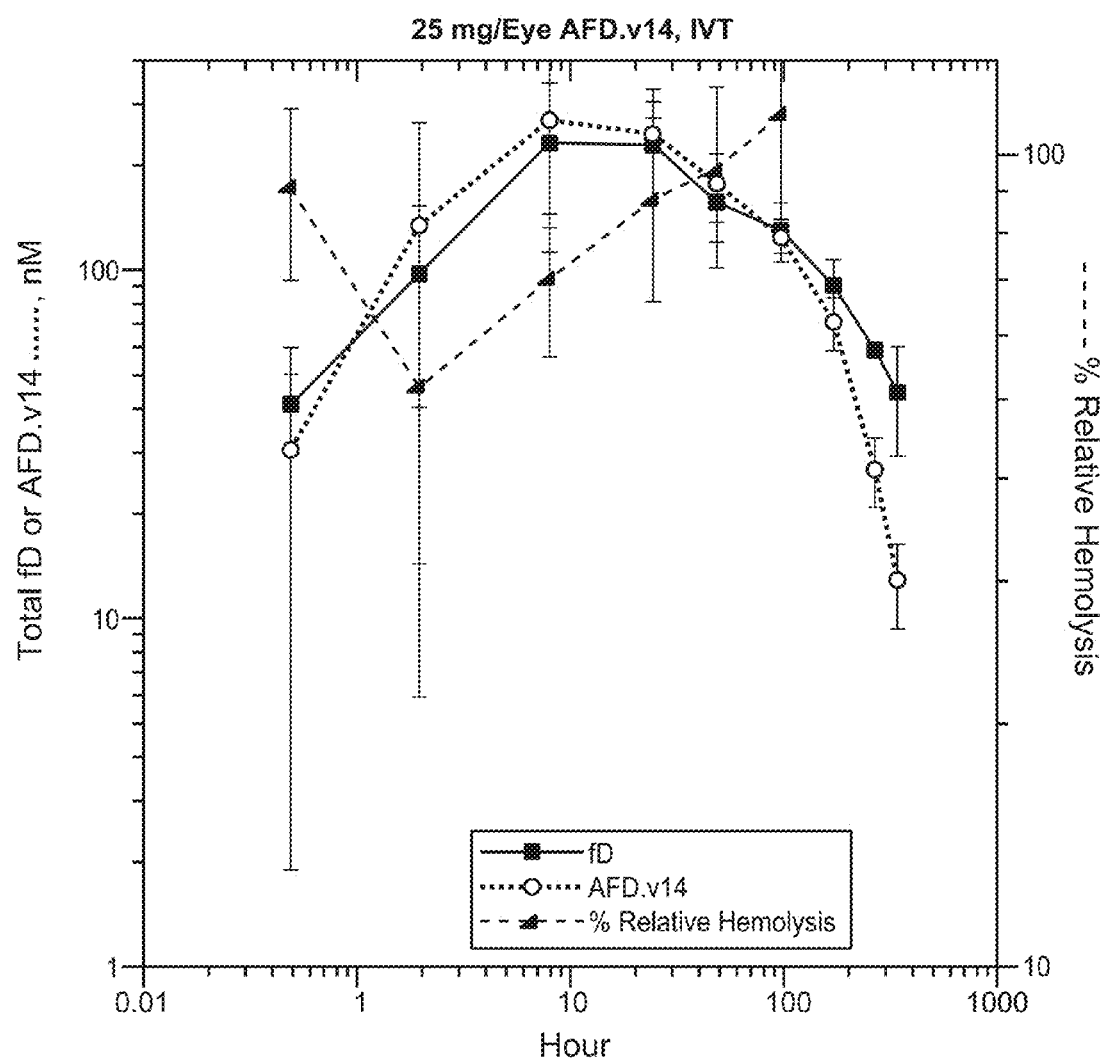
Figure 14A:
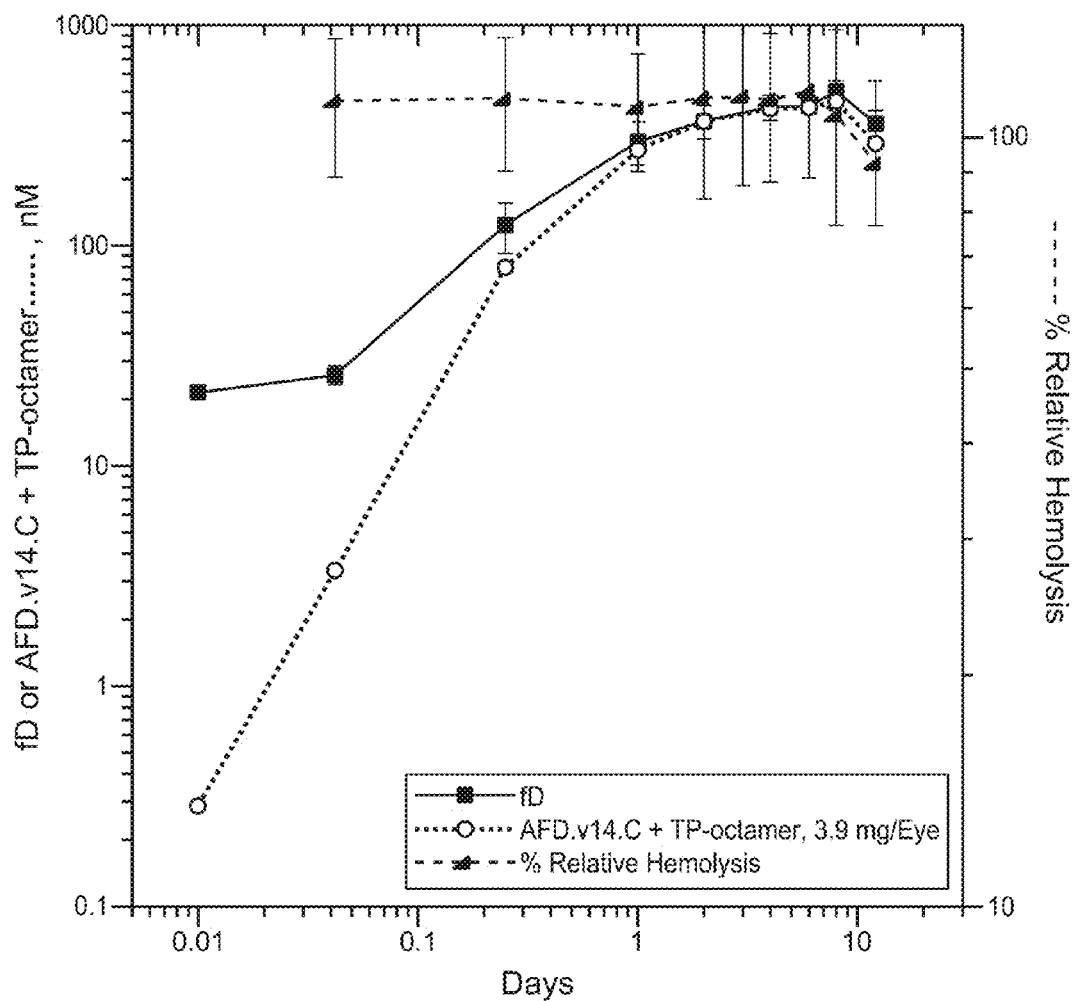
FIGS. 14A-C show percent systemic AP complement activity as measured by relative hemolysis of rRBCs or ELISA following IVT injection of AFD.v14.C+TP-Oct (14A) or AFD.v14.C+HG-Oct (14B, 14C) in the eye of cynomolgus monkeys.
Figure 14B:
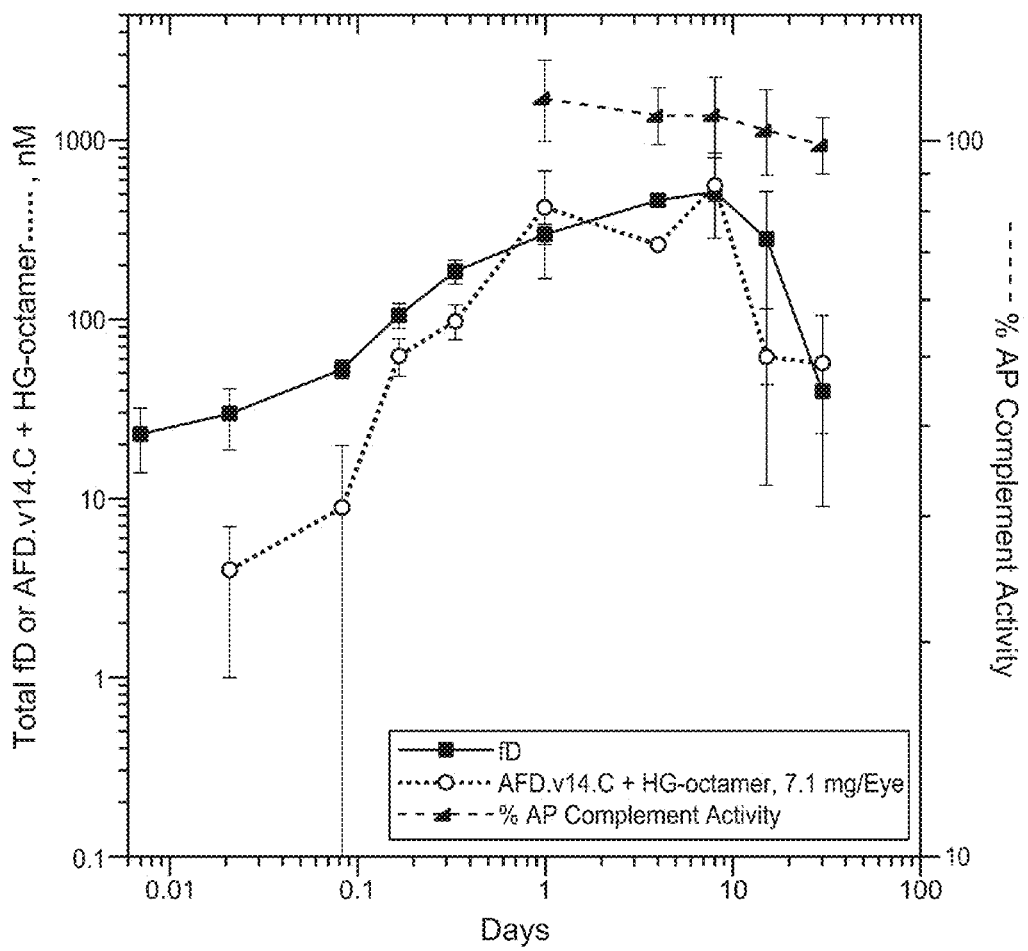
Figure 14C:
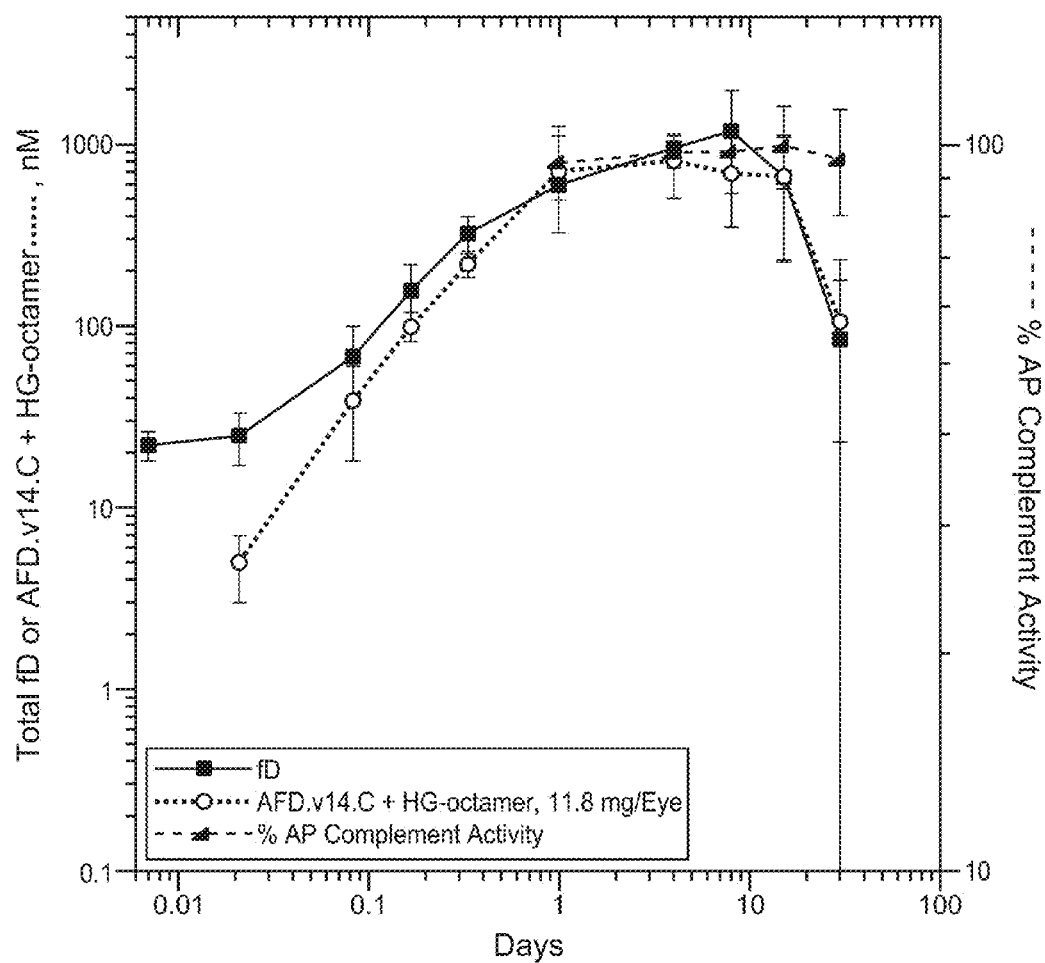

To evaluate the time course and dose dependency of any potential inhibition of systemic AP activity subsequent to dosing with AFD.v14.C+HG octamer or AFD.v14.C+TP octamer, either a plate-based WIESLAB Complement System AP ELISA (the data from this assay are referred to in FIGS. 13 and 14 as "% AP complement activity") or an ex vivo assay similar to the in vitro AP hemolysis assay described above was performed (the data from this assay are referred to in FIG. 14 as "% relative hemolysis." In this assay, however, instead of adding a dilution curve of exogenous AFD.v14.C+HG octamer or AFD.v14.C+TP octamer to the serum samples, the samples themselves were serially diluted, with any inhibition of hemolytic activity attributed to the injected dose of AFD.v14.C+HG octamer or AFD.v14.0+TP octamer.

Erythrocytes were prepared, and the assay was performed, as described herein, for the AP hemolysis assay with the following modifications. To determine the absorbance corresponding to maximum lysis, total lysis controls were prepared with sterile water (80 µl/well), whereas GVB was added to all other wells (50 µl). Cynomolgus monkey serum samples were serially diluted 1:1.5 over six points and added along with a negative control (buffer only) to 96-well U-bottom polypropylene plates (30 µl/well). The total lysis controls represented maximum (100%) hemolysis. Data points were collected in triplicate, and the mean percent maximum hemolysis was plotted against the reciprocal of the final serum dilution in the assay. The 50% maximal hemolysis (AH50) values, defined as 50% maximal hemolysis, were determined by nonlinear regression analysis using a four-parameter fit model. For those curves that did not reach saturation, the AH50 was estimated using a curve fit in which the upper asymptote was fixed at 100%. The percent relative hemolysis was calculated for each individual time point as [(postdose AH50 for the individual time point)/(predose AH50)]×100. The AH50 value for serum from each individual normal cynomolgus monkey can vary as much as 2-fold from the overall average of AH50 values. Therefore, the predose and postdose samples from each study animal were run on the same assay plate to ensure that postdose changes in AP activity were directly compared with the individual animal's baseline complement activity.

The percent relative hemolysis in comparison to total fD and the therapeutic active is shown in FIGS. 13A (lampalizumab, 10 mg/eye), 13B (AFD.v14, 25 mg/eye), and 14A (AFD.v14.C+TP octamer, 3.9 mg/eye). The lampalizumab data (FIG. 33A) is comparative data obtained following IVT administration of 10 mg/eye of lampalizumab, as described in Loyet, et al., *J. Pharmacol. Exp. Ther.*, 2014, 351:527-537). As can be seen from FIG. 13B, administration of 25 mg/eye of AFD.v14 transiently inhibited systemic AP activity, with activity returning to baseline by 24 hours post administration, similar to results previously observed for lampalizumab (FIG. 13A). In comparison, no systemic AP inhibition was observed following administration of 3.9 mg/eye of the AFD.v14.C+TP octamer (FIG. 14A). Without wishing to be bound to any particular theory, it is believed that the slower clearance from the eye obtained with the conjugate compared to Fab (e.g., lampalizumab and AFD.v14) allows fD to saturate the AFD.Ab at earlier time points, preventing systemic complement inhibition.

The percent relative AP complement activity in comparison to total fD and total conjugate is shown in FIGS. 14B (AFD.v14.C+HG octamer, 7.1 mg/eye) and 14C (AFD.v14.C+HG octamer, 11.8 mg/eye). As can be seen from these figures, negligible systemic complement inhibition was observed for the AFD.v14.C+HG octamer for IVT dosage up to 11.8 mg/eye. Due to the slower clearance from the eye, the conjugate concentration remains below the molar concentration of fD, in particular at time points earlier than 10 hours. This is in contrast to similar eye-dosed concentrations of the AFD.Ab Fab in which at these early time points the molar concentration exceeds the molar fD concentration and leads to systemic AP inhibition.

PEG octamers of 20D12.v2.1, 20D12.v2.1.C, 20D12.v2.3, and 20D12.v2.3.C would be expected to behave similarly as AFD.v14.C+TP-Oct and AFD.v14.C+HG-Oct conjugates by showing decreased levels of systemic complement inhibition compared to unconjugated versions of 20D12.v2.1, 20D12.v2.1.C, 20D12.v2.3 and 20D12.v2.3.C.

Example 15

Cynomolgus Monkey PK for AFD.Ab Variants and Conjugates

One way to assess in vivo PK profiles of AFD.Ab variants or conjugates is single dose experiments performed in cynomolgus monkeys. In vivo PK studies for the AFD.v14+TP-Oct conjugate were performed in Cynomolgus monkey. PK parameters were determined from single dose experiments. Unconjugated, unmodified AFD.v14 (SIESD.N103S) was used as a control. The animals' care was in accordance with Genentech Institutional Animal Care and Use Committee guidelines.

a. Study Parameters

Cynomolgus monkeys (28 male animals; 2 kg to 4 kg and approximately 2-7 years in age at the time of dosing) were assigned to one of four dosing groups. Group 1 (control) animals (4 animals) received bilateral intravitreal doses of 5 mg/eye (10 mg/animal) of AFD.v14 through a 30 gauge needle (100 µl dose volume). Group 2 and 3 animals (10 animals in each group) received a bilateral intravitreal dose of 1 or 4 mg/eye (2 or 8 mg/animal), respectively based on Fab weight, of the AFD.v14.C+TP-Oct conjugate through a 30-gauge needle (100 µl dose volume). Animals were sedated (10 mg/kg ketamine HCl, 0.5 mg/kg diazepam) and treated with topical proparacaine prior to injection. The AFD.v14 or AFD.v14.C+TP-Oct conjugate was then administered through the sclera and pars plana, 4 mm posterior to the limbus, with the needle directed posterior to the lens into the midvitreous. The Group 4 animals (4 animals) received a single IV bolus (1 mL) of the AFD.v14.C+TP-Oct conjugate at 0.4 mg/animal. For IV administration, the AFD.v14.C+TP-Oct conjugate was formulated as 10 mM sodium succinate, 10% trehalose, and 0.05% Tween-20 (pH 5.0).

Ocular tissues were collected from all Groups. One animal (2 eyes) per group was euthanized for Group 1 and two animals (4 eyes) were euthanized for Groups 2 and 3 at the following times after dosing: Group 1—days 1 (24 hours), 2, 4, and 8; Groups 2 and 3—days 1 (24 hours), 4, 8, 12, and 20. After euthanasia, both eyes were enucleated, and the AFD.v14 and AFD.v14.C+TP-Oct conjugate concentrations were determined in the vitreous and aqueous humor and retinal tissues. After flash freezing of the eyes, filter paper was later used to collect the entire retinal layer.

All blood samples (approximately 1 mL) were collected via a femoral or cephalic vein. Samples were drawn at the following times after IVT or IV dosing: Group 1—1 hour, 6 hours, and days 1 (24 hours), 2, 3, 4, 5, and 7; Groups 2 and 3—1 hour, 6 hours, and days 1 (24 hours), 2, 4, 6, 8, 12, and 20; Group 4—1 hour, 6 hours, and days 1 (24 hours), 2, 4, 7, 11, 14, 17, 21, 24, and 28. Within one hour of blood collection, samples were clotted at room temperature, and serum was separated by centrifugation and stored at −60° C. to −80° C. Details of the study protocol are set forth in Table 20.

TABLE 20

Cynomolgus Monkey PK Study Parameters

| Group | Dose | Route | Number of Animals | Ocular time points (days) | Serum time points |
|---|---|---|---|---|---|
| 1 | 5 mg/eye | IVT (bilateral) | 4 | 1, 2, 4, 8 | 1 and 6 hr; 1, 2, 3, 4, 5, 7 days |
| 2 | 1 mg/eye | IVT (bilateral) | 10 | 1, 4, 8, 12, 20 | 6 hr; 1, 2, 4, 5, 8, 12, 20 days |
| 3 | 4.0 mg/eye | IVT (bilateral) | 10 | 1, 4, 8, 12, 20 | 6 hr; 1, 2, 4, 6, 8, 12, 20 days |
| 4 | 0.3 mg/animal | IV | 4 | n/a | 6 hr; 1, 2, 4, 7, 11, 14, 17, 21, 24, 28 days | b. Pharmacokinetics Assay for AFD.v14 and AFD.v14.C+TP-Oct Conjugate

A Gyrolab XP assay was used to quantify AFD.v14 and AFD.v14.C+TP-Oct conjugate in cynomolgus monkey serum, vitreous humor, aqueous humor, and retinal homogenate. Samples were diluted 1:4-1:3000 in sample buffer (phosphate buffered saline (PBS), 0.5% bovine serum albumin (BSA), 15 ppm Proclin (Sigma-Aldrich), 0.05% Tween 20, 0.25% CHAPS, 50 µg/mL muIgG (Equitech Bio, Cat. #SLM66), 5 mM EDTA (pH 7.4)). The AFD.v14 and AFD.v14.C+TP-Oct conjugate standard curves were prepared by serially diluting AFD.v14 or AFD.v14.C+TP-Oct conjugate from 2.06-1500 ng/mL in sample buffer. Capture and detection reagents were applied at 100 µg/mL of biotin-conjugated goat anti-human IgG (HC+LC, Bethyl, Cat #A80-319B) in PBS/0.01% Tween 20/0.02% NaN$_3$ and Alexa-anti-CDR (clone 234, Genentech) at 25 nM in Rexxip F (Gyrolab). The assay was run on a Gyrolab Bioaffy 200 CD, and wash steps used PBS/0.01% Tween 20/0.02% NaN$_3$ followed by Gyros pH 11 wash buffer. The instrument was run and data analyzed as described by the manufacturer with a 1% PMT setting. The concentrations of AFD.v14 and AFD.v14.C+TP-Oct conjugate were determined from a five-parameter fit of its standard curve. The minimum quantifiable concentration was 8.24 ng/mL (0.16 nM) for AFD.v14 and AFD.v14.C+TP-Oct conjugate in cynomolgus monkey serum, vitreous humor, aqueous humor and retinal homogenate.

The vitreous humor, aqueous humor, and retinal PK results are set forth in Tables 21-23 below, and FIGS. 17A (vitreous), 17B (vitreous normalized), 18A (acqueous), 18B (acqueous normalized), 19A (retina), and 19B (retina, normalized).

TABLE 21

Vitreous PK for AFD.v14 control (Group 1) and AFD.v14.C + TP-Octconjugate (Group 2 & 3)

| Group | Dose (µg/eye) | T½ (days) | AUC (Day * µg/mL) | AUC/dose (Day * µg/mL/mg dose) | T½ ext (increase compared to control) | Vss (mL) | Cl (mL/day) |
|---|---|---|---|---|---|---|---|
| 1 | 5000 | 2.7 | — | — | — | 3 | 0.79 |
| 2 | 1000 | 3.5 | 2530 | 2100 | 1.3 | 2.3 | 0.47 |
| 3 | 4000 | 5 | 7730 | 1980 | 1.9 | 3.4 | 0.46 |

TABLE 22

Aqueous PK for AFD.v14.C + TP-Oct conjugate

| Group | Dose (µg/eye) | T½ (days) | AUClast (Day*µg/mL) | Vz (mL) | Cl/F (mL/Day) |
|---|---|---|---|---|---|
| 2 | 1000 | 3 | 434 | 12 | 2.73 |
| 3 | 4000 | 5.2 | 1430 | 20 | 2.58 |

TABLE 23

Retinal PK AFD.v14.C + TP-Oct conjugate

| Group | Dose (µg/eye) | T½ (days) | AUClast (Day*µg/mL) | Vz (mL) | Cl/F (mL/Day) |
|---|---|---|---|---|---|
| 2 | 1000 | 3.6 | 31 | 196 | 38 |
| 3 | 4000 | 5.9 | 98 | 309 | 36 |

Figure 17A:
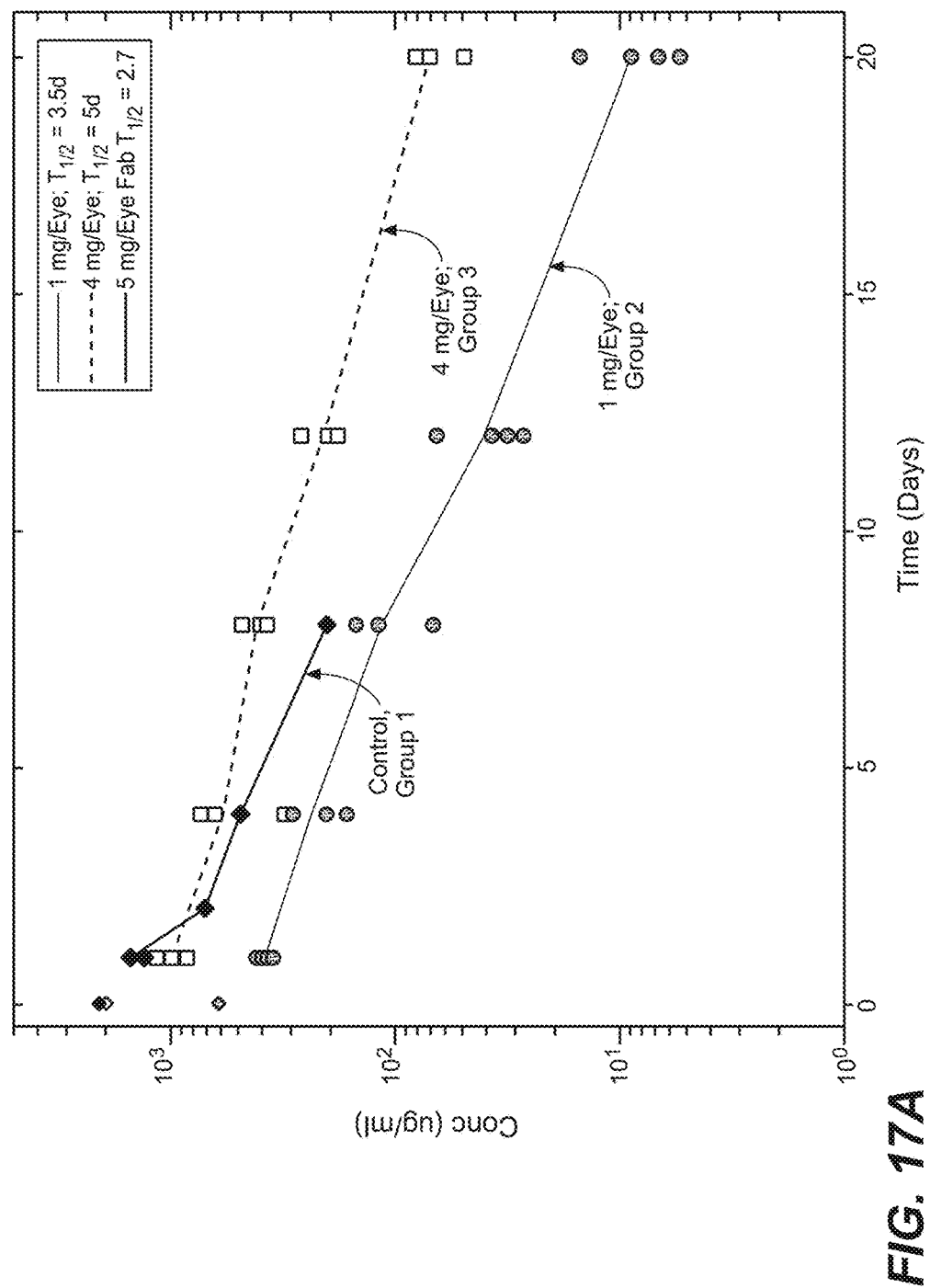
FIGS. 17A-B show PK results from a Gyrolab XP assay with AFD.v14 and AFD.v14.C+TP-Oct in cynomolgus monkey vitreous humor.
Figure 17B:
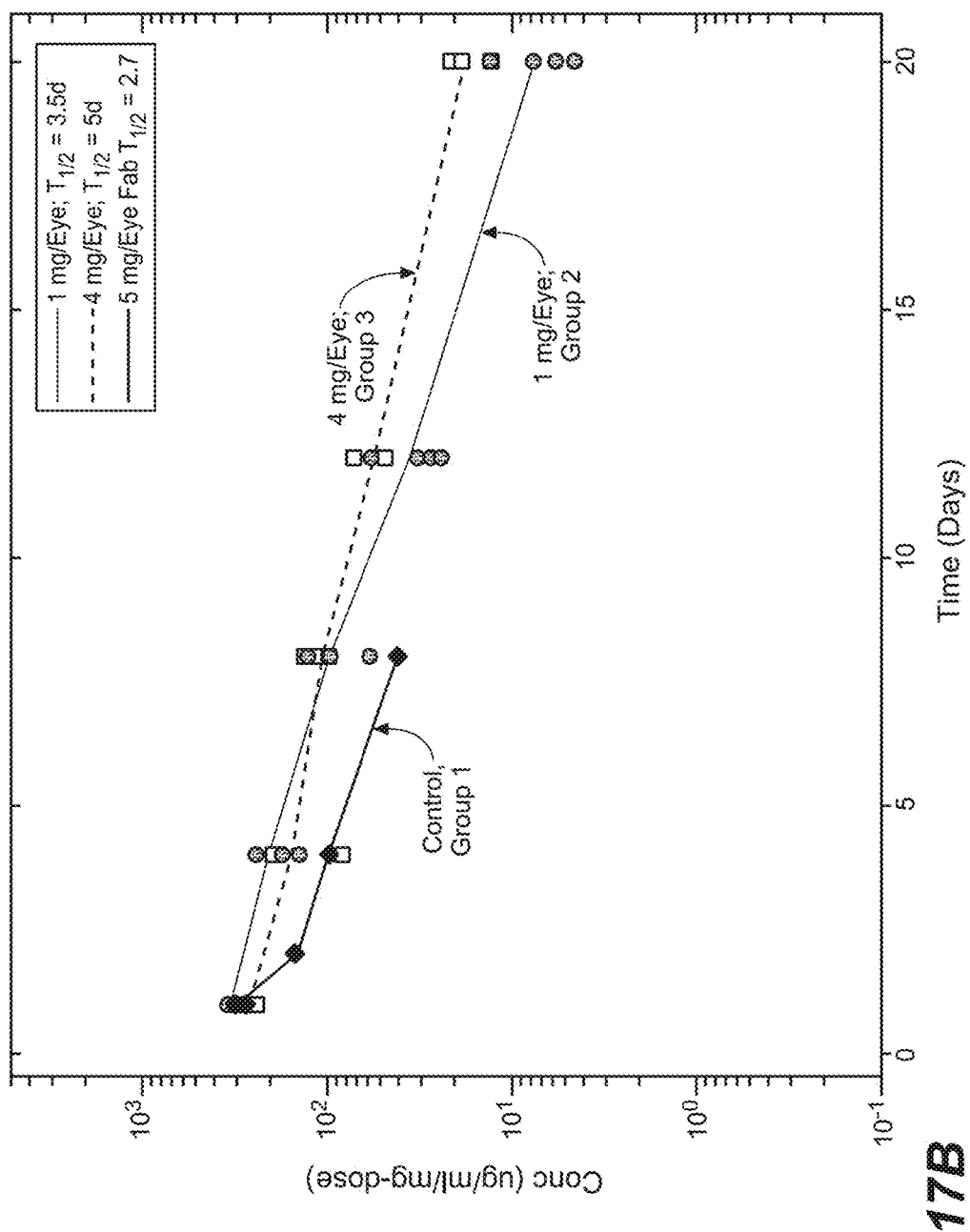
Figure 18A:
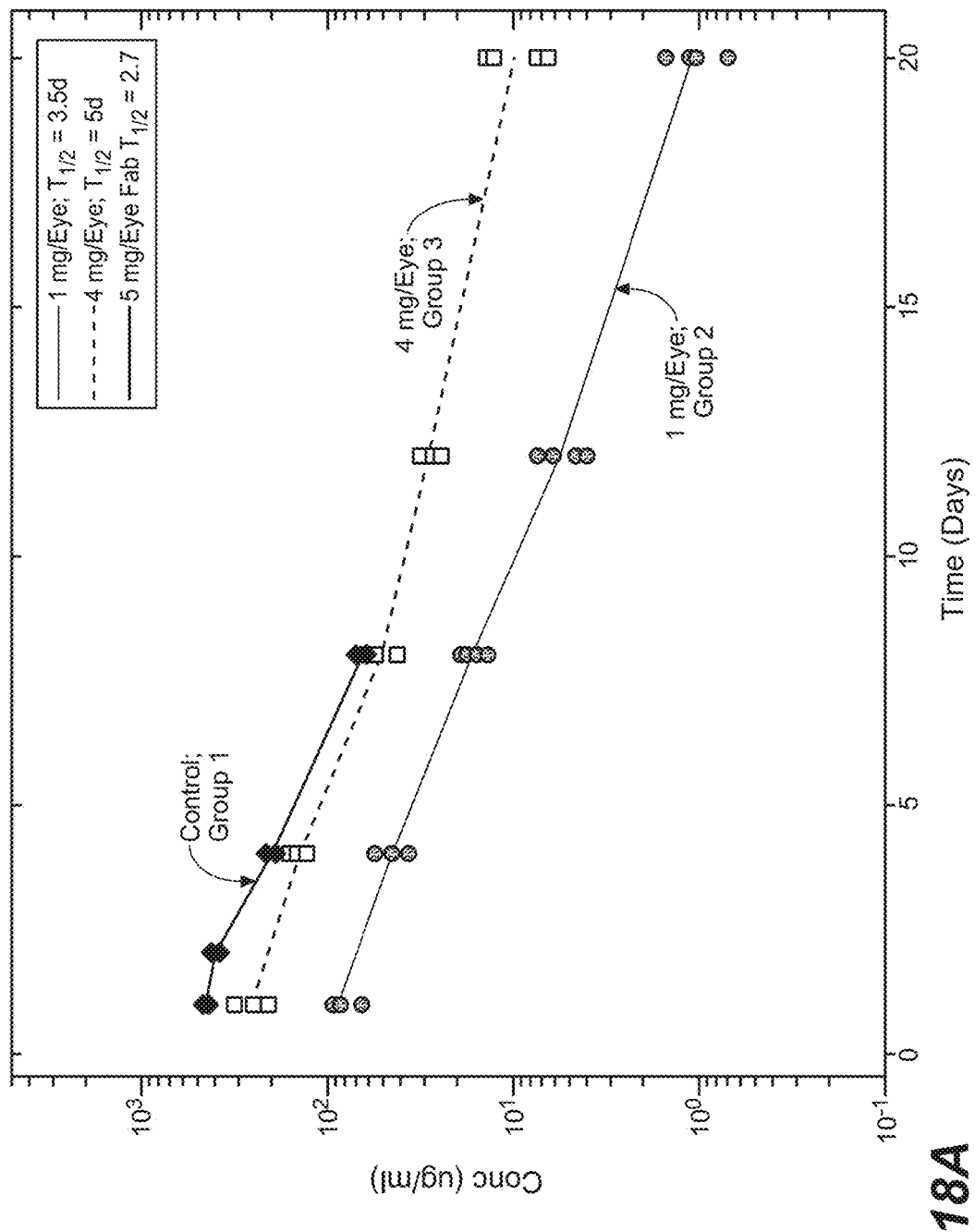
FIGS. 18A-B show PK results from a Gyrolab XP assay with AFD.v14 and AFD.v14.C+TP-Oct in cynomolgus monkey acqueous humor.
Figure 18B:
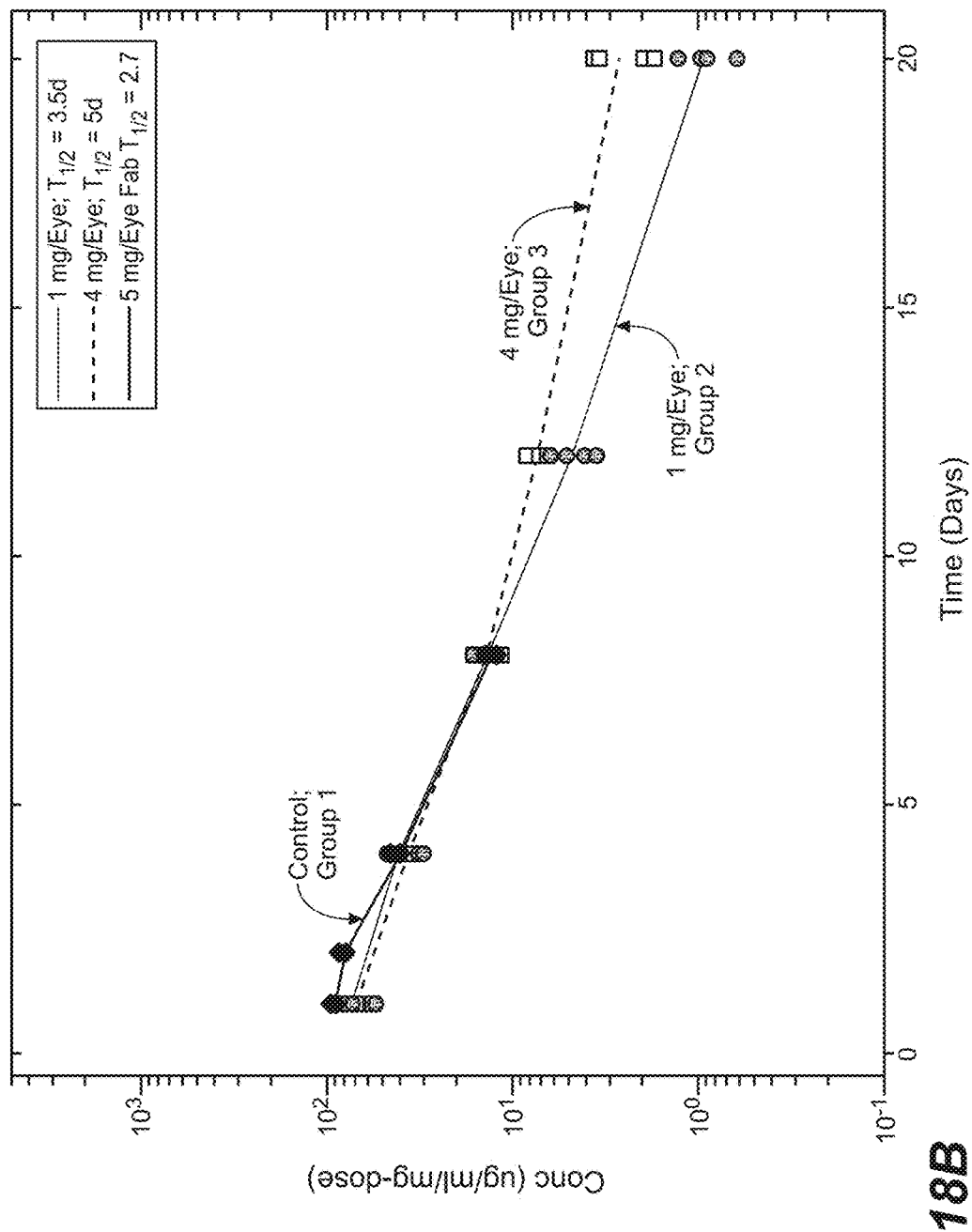
Figure 19A:
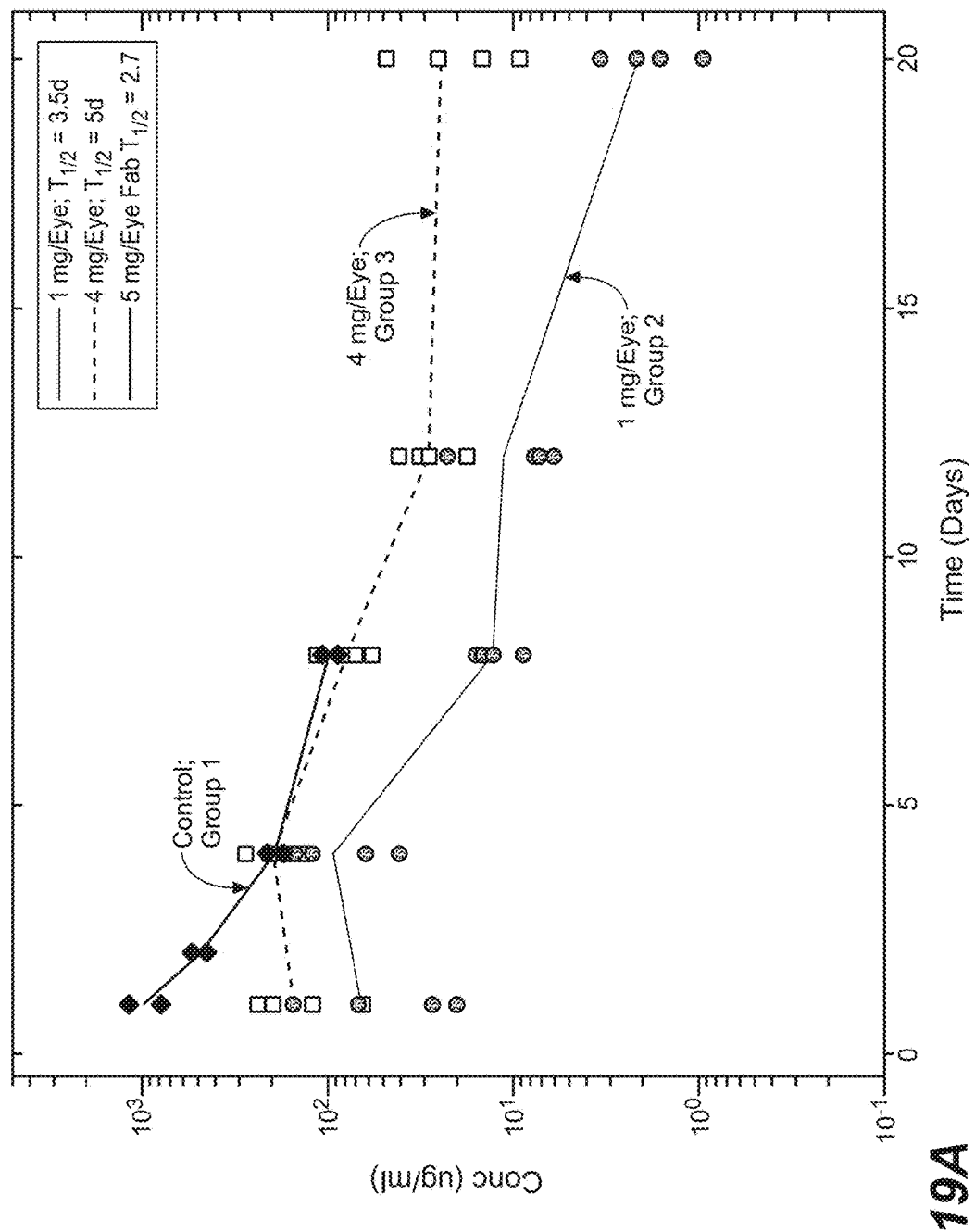
FIGS. 19A-B show PK results from a Gyrolab XP assay with AFD.v14 and AFD.v14.C+TP-Oct in cynomolgus monkey retinal humor.
Figure 19B:
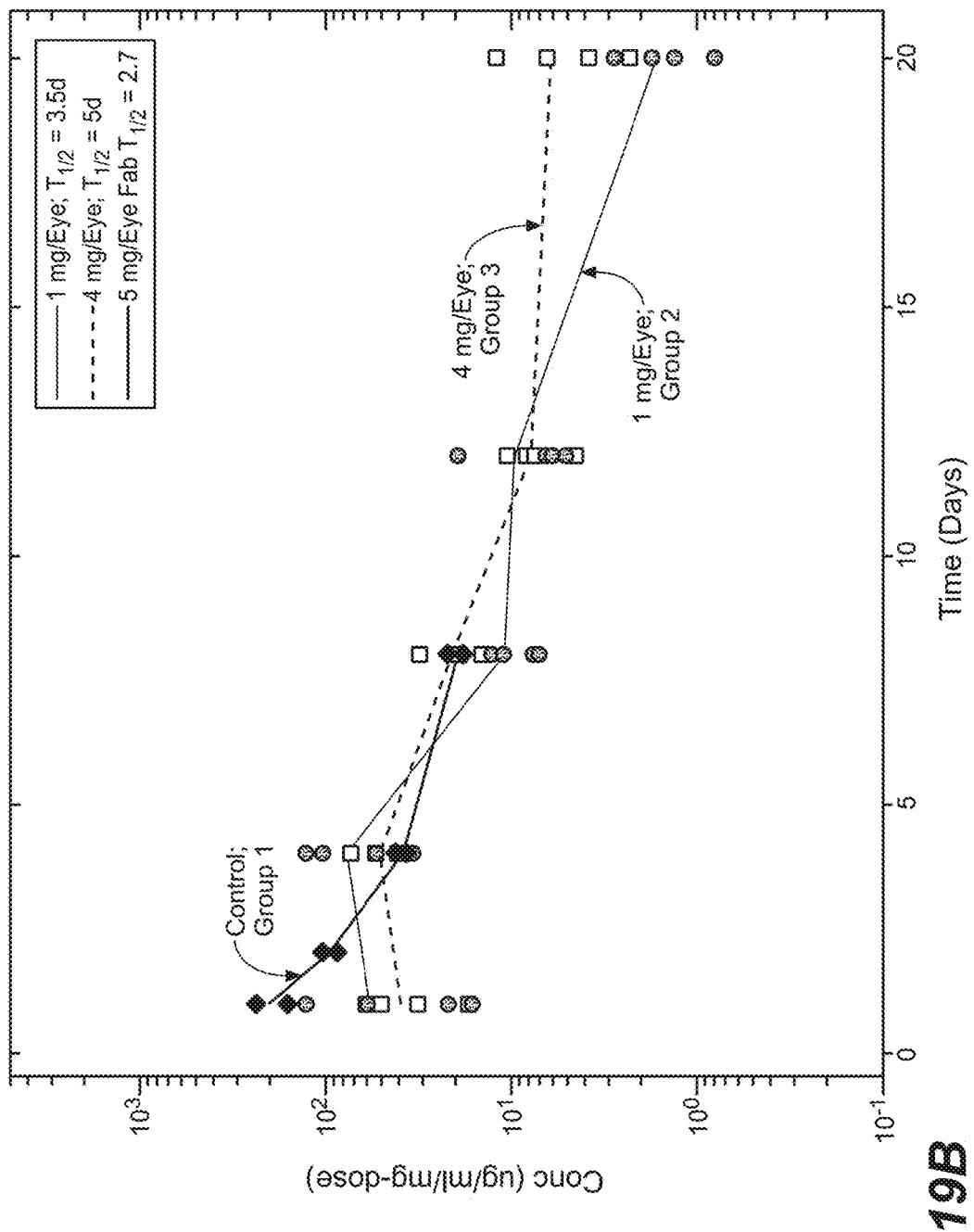

As can be seen from Table 21 and FIGS. 17A-B, the vitreal terminal half-life for both the conjugated AFD.v14 groups (Groups 2 and 3) was longer than that of the unconjugated AFD.v14 control (Group 1), and longer than the average half-life of unconjugated lampalizumab and ranibizumab Fabs (about 2.34 days). The average AUC/mg-dose for conjugated AFD.v14 Groups 2 and 3 (about 2040) was higher than the average AUC/mg-dose for the unconjugated lampalizumab Fab (about 1733). Based on vitreal terminal half-life, the 4.0 mg/eye dose cleared more slowly than the 1.0 mg/eye dose. As can be seen from Tables 22 and 23, and FIGS. 18 and 19, a longer terminal half-life was also observed in aqueous humor and retina for Groups 2 and 3 (conjugated AFD.v14), as compared to unconjugated Fab.

Figure 15A:
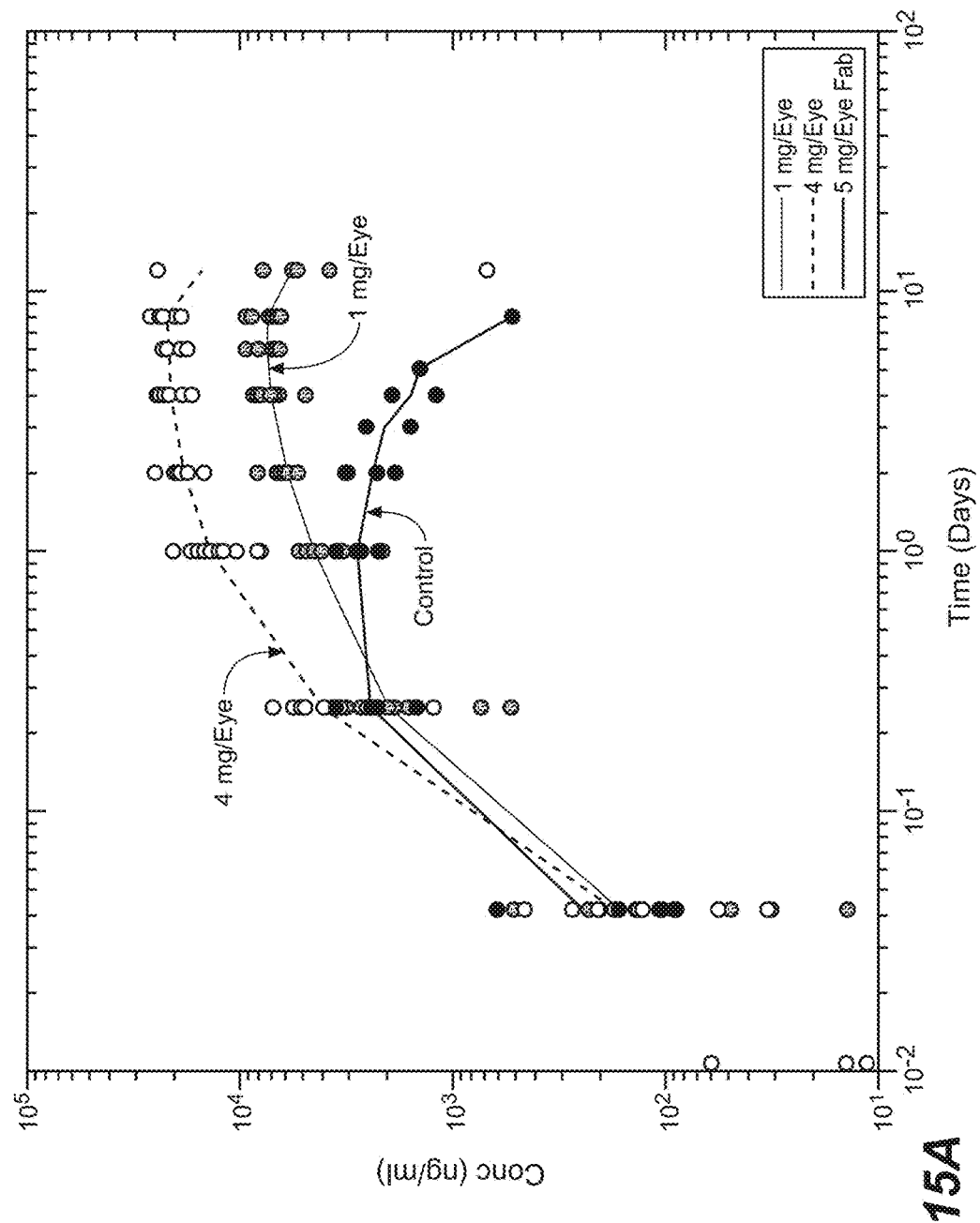
FIGS. 15A-C show serum PK for AFD.v14.C+TP-Oct compared to unconjugated AFD.v14 in a cynomolgus monkey Gyrolab XP assay.
Figure 15B:
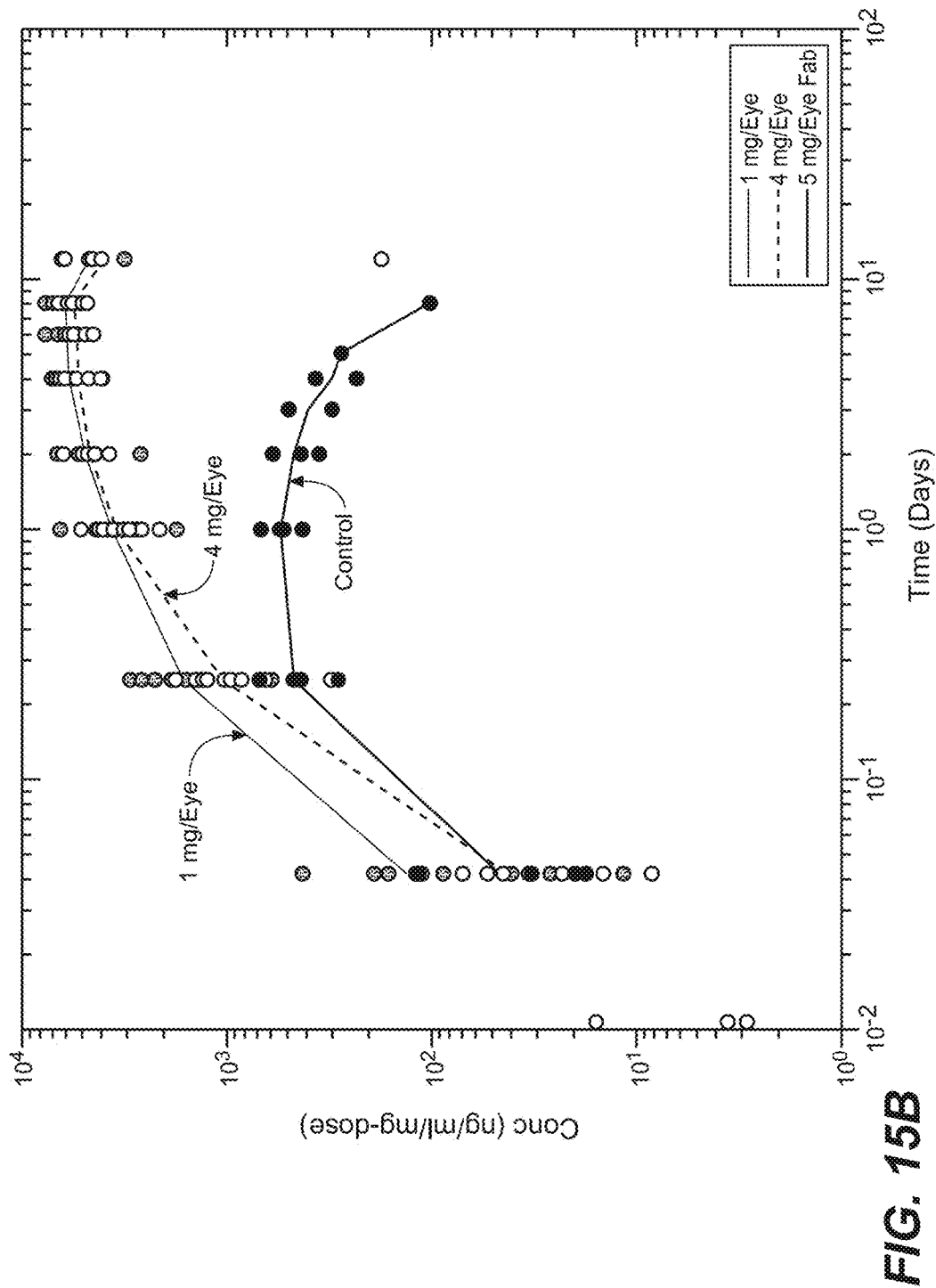
Figure 15C:
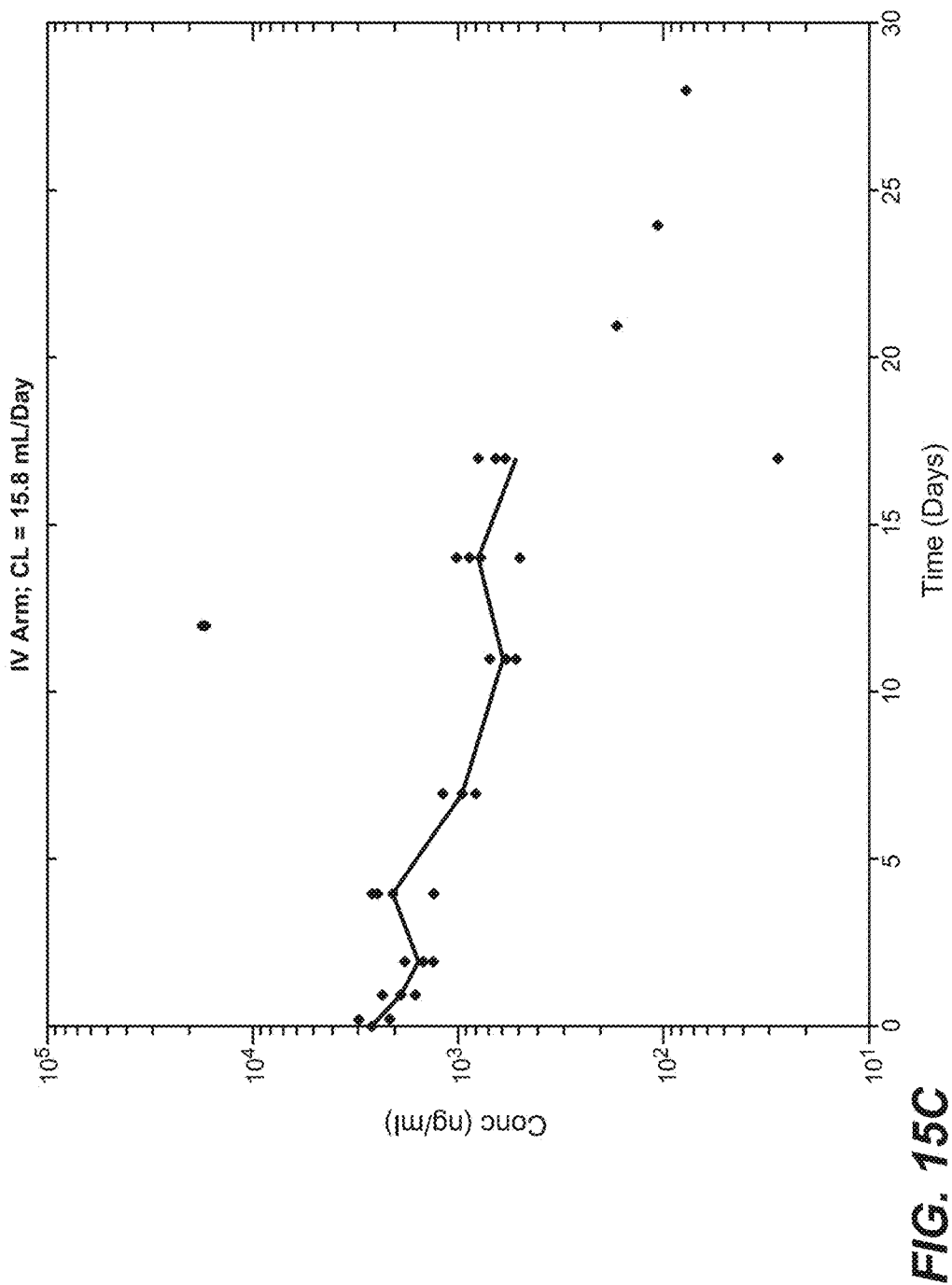

The serum PK results for Groups 2 and 3 are set forth in FIGS. 15A and 15B (normalized), and the serum PK results for Group 4 are set forth in FIG. 15C. The serum PK curves for Groups 2 and 3 (AFD.v14.C+TP-Oct conjugate) are parallel to each other, and overlap after dose normalization. See FIGS. 15A and 15B. The serum AUC for Groups 2 and 3 is dose proportional, up until the last measured time point.

The terminal half-life for Group 4 (AFD.v14.C+TP-Oct conjugate; IV dose) was 7.5 days, and the clearance was 15.8 mL/day (5.64 mL/kg/day (average weight of Group 4 monkeys was 2.8 kg)). On measurement days 21, 24, and 28, the serum concentration dropped below the limit of detection for 3 out of the 4 Group 4 monkeys.

c. Pharmacodynamics Assay for Factor D in Cynomolgus Monkey Serum

A sandwich ELISA was used to quantify factor D (fD) in cynomolgus monkey serum, vitreous humor, aqueous humor and retinal homogenate. Mouse anti-human factor D clone 4676 (Genentech) was diluted to 1 µg/mL in coating buffer (0.05M Sodium Carbonate, pH 9.6) and incubated overnight at 4° C. on 384-well Maxisorp plates (Thermo Scientific, Cat. #464718). Plates were washed with PBS plus 0.05% Tween 20 and blocked during a 2 hour incubation with PBS plus 0.5% bovine serum albumin (BSA). This and all subsequent incubations were performed at room temperature with gentle agitation. The cynomolgus monkey fD standard curve was prepared by serially diluting fD from 0.04-5 ng/mL in sample buffer (assay buffer supplemented with 500 ng/mL of the AFD.v14 therapeutic and 50 µg/mL mouse IgG). The serum samples and controls were diluted to a minimum of 1:100 in sample buffer. The vitreous humor, aqueous humor, and retinal homogenate samples and controls were diluted to a minimum of 1:10 in sample buffer. The diluted standards, controls, and samples were then incubated on the plates for 2 hours, and plate-bound fD/AFD.Ab complex was detected using biotin-conjugated mouse-anti-CDR mAb to AFD.Ab (clone 242, 1 µg/mL) for one hour followed by High Sensitivity SA-HRP (3 ng/mL, Pierce Cat. #21130) also for one hour. After a final wash, tetramethyl benzidine (Moss, Cat. #TMBE-1000) was added and color was developed for 10-15 minutes, and the reaction was stopped with 1 M phosphoric acid. The plates were read at 450 nm with a 620 nm reference using a microplate reader. The concentrations of fD were determined from a four parameter fit of the standard curve. The minimum quantifiable concentration in cynomolgus monkey serum was 3.9 ng/mL (0.16 nM). The minimum quantifiable concentration in cynomolgus monkey vitreous humor, aqueous humor and retinal homogenate was 0.39 ng/ml (0.016 nM).

Figure 16A:
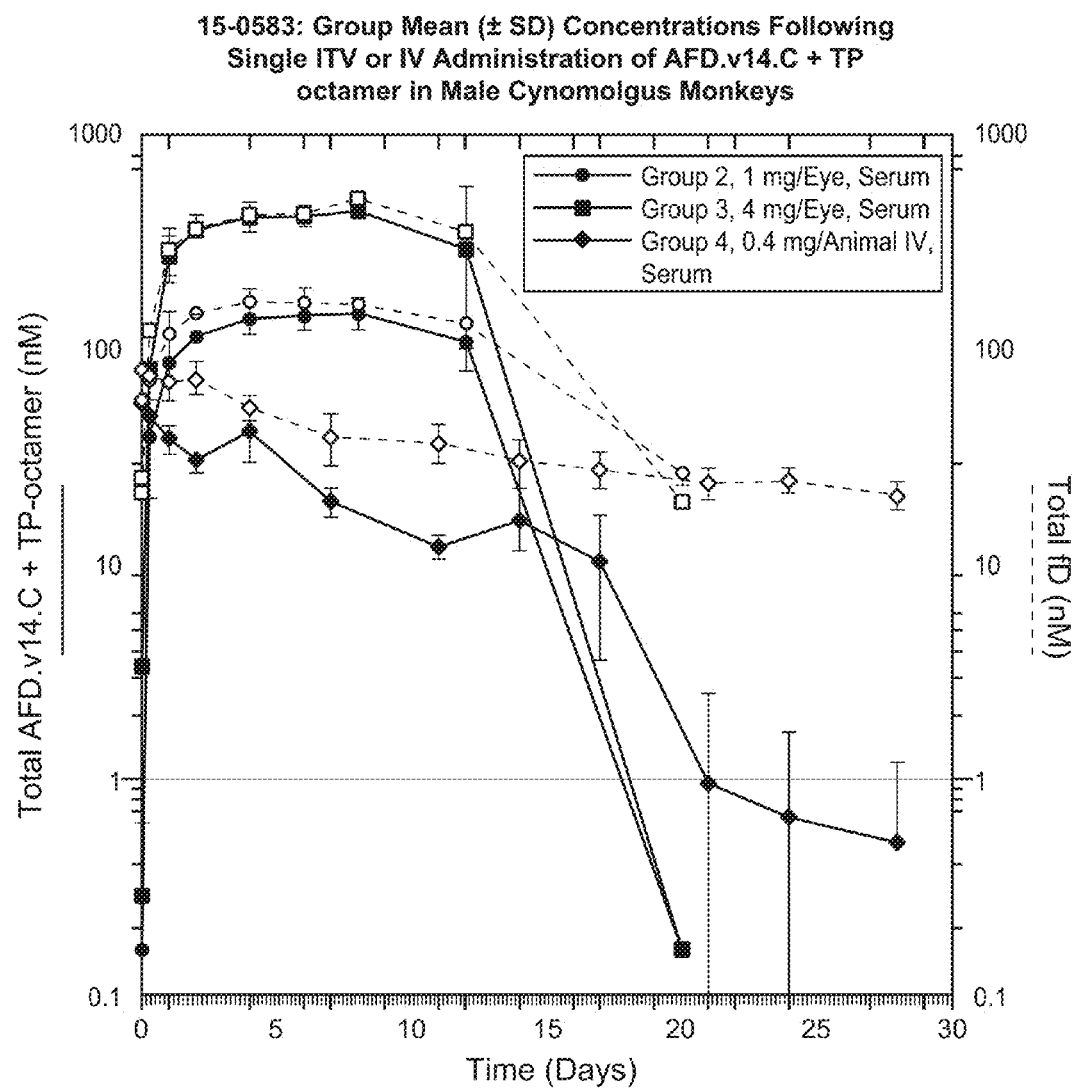
FIGS. 16A-B show group mean (+/−SD) concentrations in serum (16A), and in vitreous humor, aqueous humor, or retinal homogenate (16B) following single ITV or IV administration of AFD.v14.C+TP-Oct in male cynomolgus monkeys.

The average serum fD and AFD.v14.C+TP-Oct conjugate concentrations for Groups 2, 3, and 4 are set forth in FIG. 16. FIG. 16A shows that the serum fD concentration was higher than the AFD.Ab concentration at all time points tested. These results indicate that systemic AP complement activity is maintained in all groups.

Figure 16B:
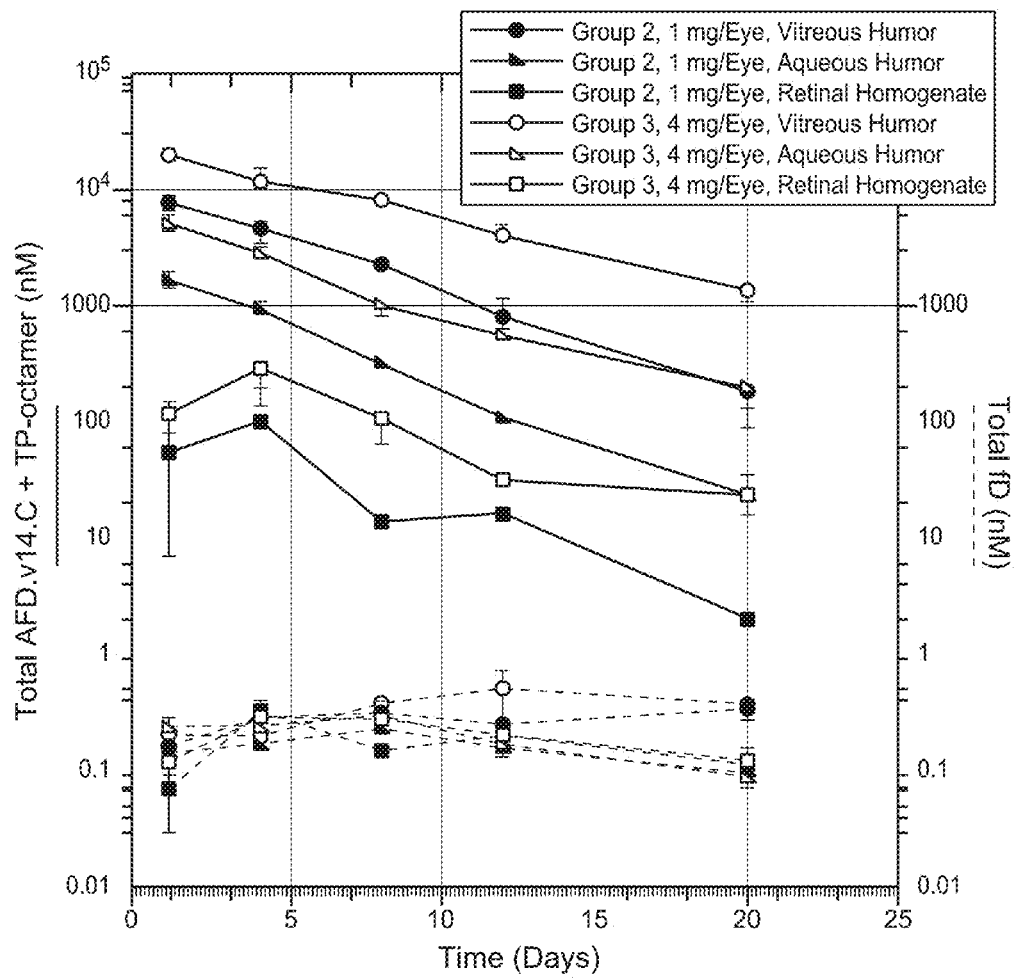

The average ocular fD and AFD.v14.C+TP-Oct conjugate concentrations for Groups 2 and 3 are set forth in FIG. 16B, which shows that the AFD.Ab concentration in the vitreous humor, aqueous humor, and retinal homogenate exceeded the fD concentration at all time points tested.

Based on the data set forth in this example for the PK parameters following IVT administration of AFD.v14.C+TP-Oct conjugates, conjugation of AFD.v14 resulted in sustained levels of conjugates in the vitreous humor and aqueous humor of the eye. However, while AFD.Ab concentrations in the vitreous humor, aqueous humor, and retinal homogenate exceeded the fD concentration at all timepoints tested, this was not seen for any timepoint in serum samples with IVT dosing. Similar methods as those described in this example can be used to evaluate PEG octamers of 20D12.v2.1, 20D12.v2.1.C, 20D12.v2.3, and 20D12.v2.3.C. It is expected that when dosed IVT conjugated 20D12.v2.1, 20D12.v2.1.C, 20D12.v2.3 and 20D12.v2.3.C would behave similarly to conjugated AFD.v14.C+TP-Oct.

Example 16

Cynomolgus Monkey PK for hu20D12.v2.1.C+TP-Oct and hu20D12.v2.1.C

To assess in vivo pharmacokinetic (PK) profiles of hu20D12.v2.1.C+TP-Oct and hu20D12.v2.1.C, an in vivo PK study was performed in cynomolgus monkeys using radioiodinated hu20D12.v2.1.C+TP-Oct ($^{125}$I-hu20D12.v2.1.C+TP-Oct) and hu20D12.v2.1.C ($^{125}$I-20D12.v2.1.C). PK parameters were determined from single dose experiments following conversion of the radioactive signal to µg-equivalents/mL or gram concentrations in each tissue collected. The animals' care was in accordance with Genentech Institutional Animal Care and Use Committee guidelines.

a. Study Parameters

Cynomolgus monkeys (43 female animals; 2 kg to 4 kg and approximately 3-4 years in age at the time of dosing) were assigned to one of five dosing groups. Group 1, 2, and 3 animals (n=10/group) received bilateral intravitreal doses of 1 mg/eye (2 mg/animal), 7.5 mg/eye (15 mg/animal), or 15 mg/eye (30 mg/animal), respectively, of $^{125}$I-hu20D12.v2.1.C+TP-Oct through a 27 gauge needle (100 µl dose volume). Group 4 animals (n=10) received a bilateral intravitreal dose of 15 mg/eye (30 mg/animal of unconjugated $^{125}$I-hu20D12.v2.1.C through a 27-gauge needle (100 µl dose volume). Animals were sedated (5-15 mg/kg ketamine HCl and isoflurane to inhalation effect) and treated with topical 0.5% propoaracaine HCl, 2.5% phenylephrine HCl, and 1% Tropicamide prior to injection. $^{125}$I-hu20D12.v2.1.C+TP-Oct or unconjugated $^{125}$I-hu20D12.v2.1.C was then administered through the sclera, with the needle directed towards the posterior axis of the globe and into the midvitreous.

Ocular tissues were collected from all groups. Two animals (4 eyes) per group were euthanized at the following times after dosing: Days 1 (4 hours post-dose), 3, 8, 13, and 29. After euthanasia, both eyes were enucleated, and the $^{125}$I-hu20D12.v2.1.C+TP-Oct and unconjugated $^{125}$I-hu20D12.v2.1.C radioactivity levels were determined in the vitreous humor, aqueous humor, and retina. Details of the study protocol are set forth in Table 24.

TABLE 24

Cynomolgus Monkey Radioactive PK Study Parameters

| Group | Dose | Route | Animal | Ocular time points (days) | Serum time points |
|---|---|---|---|---|---|
| 1 | 1 mg/eye | IVT (bilateral) | 10 | Day 1 (4 hours post-dose), Day 3 (48 hours post-dose) and Days 8, 13, and 29 | Predose, Day 1 (1, 4, 6, 8, 12 hours post-dose), Day 2 (24 hours post-dose), Day 3 (48 hours post-dose) and Days 5, 8, 11, 13, 15, 22 and 29 |
| 2 | 7.5 mg/eye | IVT (bilateral) | 10 | | |
| 3 | 15 mg/eye | IVT (bilateral) | 10 | | |
| 4 | 15 mg/eye | IVT (bilateral) | 10 | | | b. Pharmacokinetics RadioAssay for $^{125}$I-hu20D12.v2.1.C+TP-Oct and Unconjugated $^{125}$I-hu20D12.v2.1.C A radiodection assay was used to detect the amount of radioactivity in cynomolgus monkey vitreous humor, aqueous humor, and retinal homogenate. The vitreous was homogenized using cermanic beads and then triplicate weighed aliquots of 0.025-0.05 g were removed from the homogenate for gamma counting. The aqueous humor was counted for radioactivity as is. The retina was homogenized and then counted for radioactivity in its entirety. Radioactivity in all matrices were detected using a Wallac Wizard 1470 Gamma Counter. Following radioactivity detection, the concentrations of $^{125}$I-hu20D12.v2.1.C+TP-Oct and unconjugated $^{125}$I-hu20D12.v2.1.C were calculated by converting the radioactivity per mL of tissue into µg-equivalents per mL of tissue using the specific activity of the dose solution for each arm (in units of µCi/mL). An assumption of 1 g equaling 1 mL was applied during the conversion.

The vitreous humor, aqueous humor, and retina PK results are set forth in Tables 25-27 below, and FIGS. 22 (vitreous), 23 (aqueous), and 24 (retina).

TABLE 25

Vitreous humor PK for hu20D12.v2.1.C + TP-Oct and unconjugated hu20D12.v2.1.C

| Group | Dose (µg/eye) | $T_{1/2}$ (days) | AUC (Day * µg/mL) | AUC/dose (Day * µg/mL/mg dose) | Vss (mL) | CL (mL/day) |
|---|---|---|---|---|---|---|
| 1 | 1000 | 4.62 | 3770 | 3770 | 1.64 | 0.265 |
| 2 | 7500 | 4.64 | 15700 | 2093 | 2.89 | 0.478 |
| 3 | 15000 | 5.01 | 36300 | 2420 | 2.89 | 0.413 |
| 4 | 15000 | 2.70 | 31000 | 2067 | 1.82 | 0.484 |

TABLE 26

Aqueous humor PK for hu20D12.v2.1.C + TP-Oct and unconjugated hu20D12.v2.1.C

| Group | Dose (µg/eye) | $T_{1/2}$ (days) | AUC (Day*µg/mL) | Vz/F (mL) | CL/F (mL/Day) |
|---|---|---|---|---|---|
| 1 | 1000 | 4.31 | 768 | 8.10 | 1.30 |
| 2 | 7500 | 4.30 | 3950 | 11.8 | 1.90 |
| 3 | 15000 | 4.89 | 7420 | 14.3 | 2.02 |
| 4 | 15000 | 2.47 | 12400 | 4.31 | 1.21 |

TABLE 27

Retina PK for hu20D12.v2.1.C + TP-Oct and unconjugated hu20D12.v2.1.C following IVT administration

| Group | Dose (µg/eye) | $T_{1/2}$ (days) | AUC (Day*µg/mL) | Vz/F (mL) | CL/F (mL/Day) |
|---|---|---|---|---|---|
| 1 | 1000 | 5.26 | 520 | 14.6 | 1.92 |
| 2 | 7500 | 5.44 | 2130 | 27.7 | 3.53 |
| 3 | 15000 | 5.51 | 6970 | 17.1 | 2.15 |
| 4 | 15000 | 3.31 | 6620 | 10.8 | 2.27 |

Figure 22:
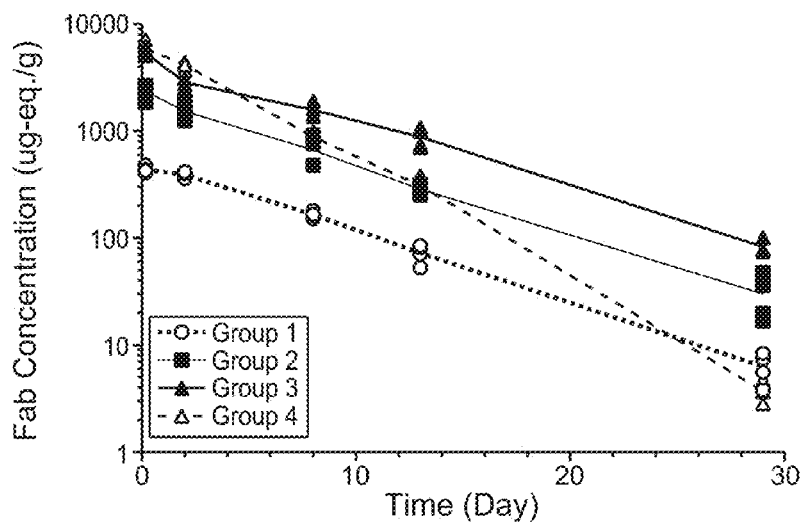
FIG. 22 shows Fab concentration over time in vitreous humor of cynomolgus monkeys administered $^{125}$I-hu20D12.v2.1.C+TP-Oct (Groups 1, 2, and 3) or $^{125}$I-hu20D12.v2.1.C (Group 4) intravitreally.
Figure 23:
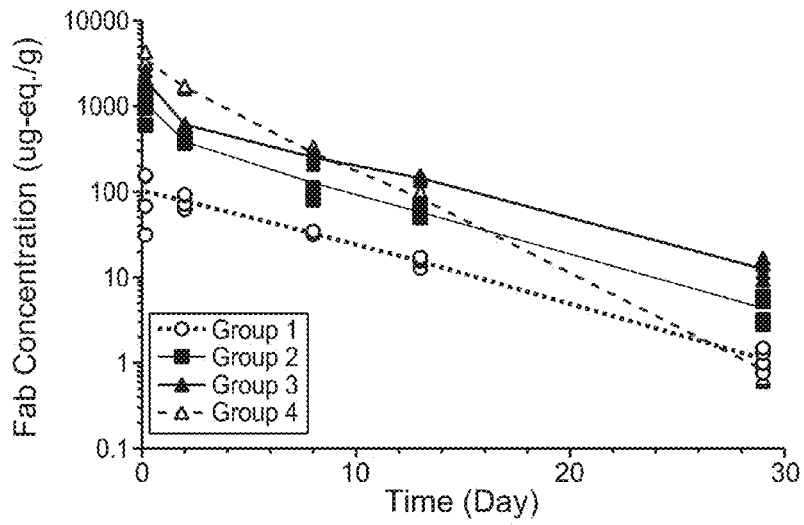
FIG. 23 shows Fab concentration over time in aqueous humor of cynomolgus monkeys administered $^{125}$I-hu20D12.v2.1.C+TP-Oct (Groups 1, 2, and 3) or $^{125}$I-hu20D12.v2.1.C (Group 4) intravitreally.
Figure 24:
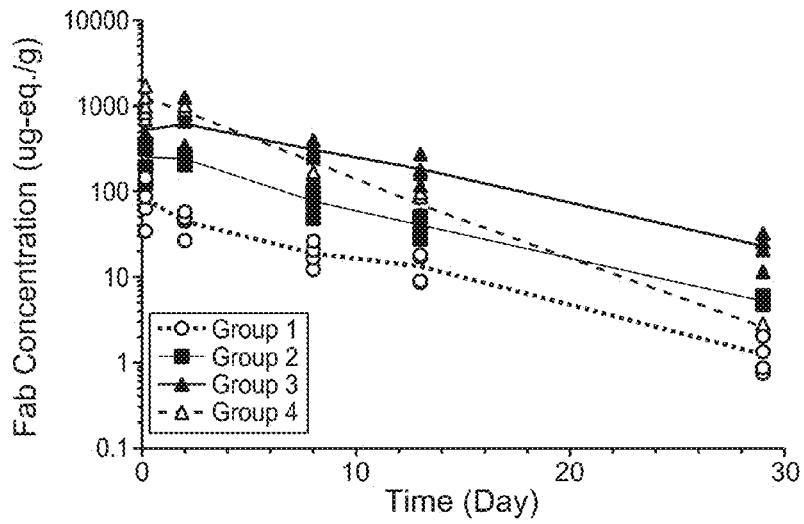
FIG. 24 shows Fab concentration over time in retina of cynomolgus monkeys administered $^{125}$I-hu20D12.v2.1.C+TP-Oct (Groups 1, 2, and 3) or $^{125}$I-hu20D12.v2.1.C (Group 4) intravitreally.

As can be seen from Table 25 and FIG. 22, the vitreal terminal half-life for the hu20D12.v2.1.C+TP-Oct groups (Groups 1, 2 and 3) was statistically significantly longer than that of the unconjugated hu20D12.v2.1.C control (Group 4), and longer than the average half-life of unconjugated lampalizumab and ranibizumab Fabs (about 2.34 days). The average AUC/mg-dose for hu20D12.v2.1.C+TP-Oct groups was higher than the average AUC/mg-dose for the unconjugated hu20D12.v2.1.C control (about 2067 Day*µg/mL/mg dose) and the unconjugated lampalizumab Fab (about 1733). As can be seen from Tables 26 and 27, and FIGS. 23 and 24, a longer terminal half-life was also observed in aqueous humor and retina for hu20D12.v2.1.C+TP-Oct groups, as compared to unconjugated hu20D12.v2.1.C.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Description | Sequence |
|---|---|---|
| 1 | mu20D12 HVR-L1 | KASQNVDTDVA |
| 2 | mu20D12 HVR-L2 | SASSRYS |
| 3 | mu20D12 HVR-L3 | QQYNNYPLT |
| 4 | mu20D12 HVR-H1 | SYYMY |
| 5 | mu20D12 HVR-H2 | EINPTNGGTNFNEKFKS |
| 6 | mu20D12 HVR-H3 | EGGFAY |
| 7 | mu20D12 light chain variable region (VL) | DIVMTQSQKF MSTSVGDRVS VTCKASQNVD TDVAWFQQKP GQSPRGLIYS ASSRYSGVPD RFTGSGSGTD FTLTISNVQS EDLAEYFCQQ YNNYPLTFGS GTKVEIK |
| 8 | murine 20D12 (mu20D12) heavy chain variable region (VH) | QVQLQQSGAE LVKPGASVKL SCKASGYTFT SYYMYWVKER PGQGLEWIGE INPTNGGTNF NEKFKSKATL TVDTSSNTAY MQLSSLTSED SAVYYCAREG GFAYWGQGTL VTVSA |
| 9 | HVR-L1 of antibodies: hu20D12.v1 hu20D12.v1.1 hu20D12.v2.0 hu20D12.v2.1 hu20D12.v2.2 hu20D12.v2.3 hu20D12.v2.4 hu20D12.v2.5 hu20D12.v2.6 hu20D12.v2.7 hu20D12.v2.8 hu20D12.v2.9 hu20D12.v2.10 | KASQNVDTDVA |

Table of Sequences

| SEQ ID NO | Description | Sequence |
|---|---|---|
| | hu20D12.v2.11<br>hu20D12.v2.12<br>hu20D12.v2.13<br>hu20D12.v2.14<br>hu20D12.v2.15 | |
| 10 | HVR-L2 of antibodies:<br>hu20D12.v1<br>hu20D12.v1.1<br>hu20D12.v2.0<br>hu20D12.v2.1<br>hu20D12.v2.2<br>hu20D12.v2.3<br>hu20D12.v2.4<br>hu20D12.v2.5<br>hu20D12.v2.6<br>hu20D12.v2.7<br>hu20D12.v2.8<br>hu20D12.v2.9<br>hu20D12.v2.12<br>hu20D12.v2.13<br>hu20D12.v2.14<br>hu20D12.v2.15 | SASSRYS |
| 11 | hu20D12.v2.10 HVR-L2 | SASSRKS |
| 12 | hu20D12.v2.11 HVR-L2 | SASSRRS |
| 13 | HVR-L3 of antibodies:<br>hu20D12.v1<br>hu20D12.v1.1<br>hu20D12.v2.0<br>hu20D12.v2.1<br>hu20D12.v2.2<br>hu20D12.v2.3<br>hu20D12.v2.4<br>hu20D12.v2.5<br>hu20D12.v2.6<br>hu20D12.v2.7<br>hu20D12.v2.8<br>hu20D12.v2.9<br>hu20D12.v2.10<br>hu20D12.v2.11<br>hu20D12.v2.12<br>hu20D12.v2.14<br>hu20D12.v2.15 | QQYNNYPLT |
| 14 | hu20D12.v2.13 HVR-L3 | QQYENYPLT |
| 15 | HVR-H1 of antibodies:<br>hu20D12.v1<br>hu20D12.v1.1<br>hu20D12.v2.0<br>hu20D12.v2.1<br>hu20D12.v2.2<br>hu20D12.v2.3<br>hu20D12.v2.4<br>hu20D12.v2.5<br>hu20D12.v2.6<br>hu20D12.v2.7<br>hu20D12.v2.8<br>hu20D12.v2.9<br>hu20D12.v2.10<br>hu20D12.v2.11<br>hu20D12.v2.12<br>hu20D12.v2.13<br>hu20D12.v2.14<br>hu20D12.v2.15 | SYYMY |
| 16 | HVR-H2 of antibodies:<br>hu20D12.v2.0<br>hu20D12.v2.1<br>hu20D12.v2.6 | EINPTSGGTNFNEKFKS |

Table of Sequences

| SEQ ID NO | Description | Sequence |
|---|---|---|
|  | hu20D12.v2.7<br>hu20D12.v2.8<br>hu20D12.v2.10<br>hu20D12.v2.11<br>hu20D12.v2.13 |  |
| 17 | hu20D12.v1 HVR-H2 | EINPTNGGTNFNEKFKS |
| 18 | hu20D12.v1.1 HVR-H2 | EINPTQGGTNFNEKFKS |
| 19 | hu20D12.v2.2 HVR-H2 | EINPTSGDTNFNEKFKS |
| 20 | hu20D12.v2.3 HVR-H2 | EINPYSGDTNFNEKFKS |
| 21 | hu20D12.v2.4 HVR-H2<br>hu20D12.v2.14 HVR-H2 | EINPTSGETNFNEKFKS |
| 22 | hu20D12.v2.5 HVR-H2<br>hu20D12.v2.12 HVR-H2 | EINPYSGGTNFNEKFKS |
| 23 | hu20D12.v2.9 HVR-H2 | WINPTSGGTNFNEKFKS |
| 24 | hu20D12.v2.15 HVR-H2 | EINPYSGETNFNEKFKS |
| 25 | HVR-H3 of antibodies:<br>hu20D12.v1<br>hu20D12.v1.1<br>hu20D12.v2.0<br>hu20D12.v2.1<br>hu20D12.v2.2<br>hu20D12.v2.3<br>hu20D12.v2.4<br>hu20D12.v2.5<br>hu20D12.v2.6<br>hu20D12.v2.7<br>hu20D12.v2.8<br>hu20D12.v2.9<br>hu20D12.v2.10<br>hu20D12.v2.11<br>hu20D12.v2.12<br>hu20D12.v2.13<br>hu20D12.v2.14<br>hu20D12.v2.15 | EGGFAY |
| 26 | human VL kappa I (VL$_{KI}$) | DIQMTQSPSS LSASVGDRVT ITCRASQGIS SYLAWYQQKP<br>GKAPKLLIYA ASSLQSGVPS RFSGSGSGTD FTLTISSLQP<br>EDFATYYCQQ YYSYPFTFGQ GTKVEIK |
| 27 | human VH subgroup I | EVQLVQSGAE VKKPGASVKV SCKASGYTFT SYYIHWVRQA<br>PGQGLEWIGW INPGSGNTNY AQKFQGRVTI TRDTSTSTAY<br>LELSSLRSED TAVYYCARFD YWGQGTLVTV SS |
| 28 | hu20D12.v1 VL | DIQMTQSPSS LSASVGDRVT ITCKASQNVD TDVAWFQQKP<br>GKAPKGLIYS ASSRYSGVPS RFSGSGSGTD FTLTISSLQP<br>EDFATYYCQQ YNNYPLTFGQ GTKVEIK |
| 29 | hu20D12.v1 VH | EVQLVQSGAE VKKPGASVKV SCKASGYTFT SYYMWVRQA<br>PGQGLEWIGE INPTNGGTNF NEKFKSRATL TVDTSTSTAY<br>LELSSLRSED TAVYYCAREG GFAYWGQGTL VTVSS |
| 30 | hu20D12.v1.1 VL | DIQMTQSPSS LSASVGDRVT ITCKASQNVD TDVAWFQQKP<br>GKAPKGLIYS ASSRYSGVPS RFSGSGSGTD FTLTISSLQP<br>EDFATYYCQQ YNNYPLTFGQ GTKVEIK |
| 31 | hu20D12.v1.1 VH | EVQLVQSGAE VKKPGASVKV SCKASGYTFT SYYMWVRQA<br>PGQGLEWIGE INPTQGGTNF NEKFKSRATL TVDTSTSTAY<br>LELSSLRSED TAVYYCAREG GFAYWGQGTL VTVSS |
| 32 | hu20D12.v2.0 VL | DIQMTQSPSS LSASVGDRVT ITCKASQNVD TDVAWFQQKP<br>GKAPKGLIYS ASSRYSGVPS RFSGSGSGTD FTLTISSLQP<br>EDFATYYCQQ YNNYPLTFGQ GTKVEIK |

| SEQ ID NO | Description | Sequence |
|---|---|---|
| 33 | hu20D12.v2.0 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 34 | hu20D12.v2.1 VL | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIK |
| 35 | hu20D12.v2.1 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 36 | hu20D12.v2.2 VL | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIK |
| 37 | hu20D12.v2.2 VH | EVQLVQSGAE VKKPGASVKV SCKASGYTFT SYYMYWVRQA PGQGLEWIGE INPTSGDTNF NEKFKSRATL TVDTSTSTAY LELSSLRSED TAVYYCAREG GFAYWGQGTL VTVSS |
| 38 | hu20D12.v2.3 VL | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIK |
| 39 | hu20D12.v2.3 VH | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSS |
| 40 | hu20D12.v2.4 VL | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIK |
| 41 | hu20D12.v2.4 VH | EVQLVQSGAE VKKPGASVKV SCKASGYTFT SYYMYWVRQA PGQGLEWIGE INPTSGETNF NEKFKSRATL TVDTSTSTAY LELSSLRSED TAVYYCAREG GFAYWGQGTL VTVSS |
| 42 | hu20D12.v2.5 VL | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIK |
| 43 | hu20D12.v2.5 VH | EVQLVQSGAE VKKPGASVKV SCKASGYTFT SYYMYWVRQA PGQGLEWIGE INPYSGGTNF NEKFKSRATL TVDTSTSTAY LELSSLRSED TAVYYCAREG GFAYWGQGTL VTVSS |
| 44 | hu20D12.v2.6 VL | DIQMTQSPSS LSASVGDRVT ITCKASQNVD TDVAWFQQKP GKAPKGLISS ASSRYSGVPS RFSGSGSGTD FTLTISSLQP EDFATYYCQQ YNNYPLTFGQ GTKVEIK |
| 45 | hu20D12.v2.6 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 46 | hu20D12.v2.7 VL | DIQMTQSPSS LSASVGDRVT ITCKASQNVD TDVAWFQQKP GKAPKGLIKS ASSRYSGVPS RFSGSGSGTD FTLTISSLQP EDFATYYCQQ YNNYPLTFGQ GTKVEIK |
| 47 | hu20D12.v2.7 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 48 | hu20D12.v2.8 VL | DIQMTQSPSS LSASVGDRVT ITCKASQNVD TDVAWFQQKP GKAPKGLIQS ASSRYSGVPS RFSGSGSGTD FTLTISSLQP EDFATYYCQQ YNNYPLTFGQ GTKVEIK |
| 49 | hu20D12.v2.8 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 50 | hu20D12.v2.9 VL | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIK |

Table of Sequences

| SEQ ID NO | Description | Sequence |
|---|---|---|
| 51 | hu20D12.v2.9 VH | EVQLVQSGAE VKKPGASVKV SCKASGYTFT SYYMYWVRQA PGQGLEWIGW INPTSGGTNF NEKFKSRATL TVDTSTSTAY LELSSLRSED TAVYYCAREG GFAYWGQGTL VTVSS |
| 52 | hu20D12.v2.10 VL | DIQMTQSPSS LSASVGDRVT ITCKASQNVD TDVAWFQQKP GKAPKGLIYS ASSRKSGVPS RFSGSGSGTD FTLTISSLQP EDFATYYCQQ YNNYPLTFGQ GTKVEIK |
| 53 | hu20D12.v2.10 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 54 | hu20D12.v2.11 VL | DIQMTQSPSS LSASVGDRVT ITCKASQNVD TDVAWFQQKP GKAPKGLIYS ASSRRSGVPS RFSGSGSGTD FTLTISSLQP EDFATYYCQQ YNNYPLTFGQ GTKVEIK |
| 55 | hu20D12.v2.11 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 56 | hu20D12.v2.12 VL | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIK |
| 57 | hu20D12.v2.12 VH | EVQLVQSGAE VKKPGASVKV SCKASGYTFT SYYMYWVRQA PGQGLEWIGE INPYSGGTNF NEKFKSRATL TVDTSTSTAY LELSSLRSED TAVYYCAREG GFAYWGQGTL VTVSS |
| 58 | hu20D12.v2.13 VL | DIQMTQSPSS LSASVGDRVT ITCKASQNVD TDVAWFQQKP GKAPKGLIRS ASSRYSGVPS RFSGSGSGTD FTLTISSLQP EDFATYYCQQ YENYPLTFGQ GTKVEIK |
| 59 | hu20D12.v2.13 VH | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSS |
| 60 | hu20D12.v2.14 VL | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIK |
| 61 | hu20D12.v2.14 VH | EVQLVQSGAE VKKPGASVKV SCKASGYTFT SYYMYWVRQA PGQGLEWIGE INPTSGETNF NEKFKSRATL TVDTSTSTAY LELSSLRSED TAVYYCAREG GFAYWGQGTL VTVSS |
| 62 | hu20D12.v2.15 VL | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIK |
| 63 | hu20D12.v2.15 VH | EVQLVQSGAE VKKPGASVKV SCKASGYTFT SYYMYWVRQA PGQGLEWIGE INPYSGETNF NEKFKSRATL TVDTSTSTAY LELSSLRSED TAVYYCAREG GFAYWGQGTL VTVSS |
| 64 | hu20D12.v1 light chain (LC) | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 65 | hu20D12.v1 heavy chain Fab (HC Fab) | EVQLVQSGAE VKKPGASVKV SCKASGYTFT SYYMYWVRQA PGQGLEWIGE INPTNGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 66 | hu20D12.v1.1 LC | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

-continued

Table of Sequences

| SEQ ID NO | Description | Sequence |
|---|---|---|
| 67 | hu20D12.v1.1 HC Fab | EVQLVQSGAE VKKPGASVKV SCKASGYTFT SYYMYWVRQA PGQGLEWIGE INPTQGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 68 | hu20D12.v2.0 LC | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 69 | hu20D12.v2.0 HC Fab | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 70 | hu20D12.v2.1 LC | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 71 | hu20D12.v1.1 HC Fab ("CDKTHT") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 72 | hu20D12.v2.2 LC | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 73 | hu20D12.v2.2 HC Fab | EVQLVQSGAE VKKPGASVKV SCKASGYTFT SYYMYWVRQA PGQGLEWIGE INPTSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 74 | hu20D12.v2.3 LC | DIQMTQSPSS LSASVGDRVT ITCKASQNVD TDVAWFQQKP GKAPKGLIRS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 75 | hu20D12.v2.3 HC Fab ("CDKTHT") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 76 | hu20D12.v2.4 LC | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 77 | hu20D12.v2.4 HC Fab | EVQLVQSGAE VKKPGASVKV SCKASGYTFT SYYMYWVRQA PGQGLEWIGE INPTSGETNF NEKFKSRATL TVDTSTSTAY LELSSLRSED TAVYYCAREG GFAYWGQGTL VTVSSASTKG |

| SEQ ID NO | Description | Sequence |
|---|---|---|
| | | PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 78 | hu20D12.v2.5 LC | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 79 | hu20D12.v.5 HC Fab | EVQLVQSGAE VKKPGASVKV SCKASGYTFT SYYMYWVRQA PGQGLEWIGE INPYSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 80 | hu20D12.v2.6 LC | DIQMTQSPSS LSASVGDRVT ITCKASQNVD TDVAWFQQKP GKAPKGLISS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 81 | hu20D12.v2.6 HC Fab | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 82 | hu20D12.v2.7 LC | DIQMTQSPSS LSASVGDRVT ITCKASQNVD TDVAWFQQKP GKAPKGLIKS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 83 | hu20D12.v2.7 HC Fab | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 84 | hu20D12.v2.8 LC | DIQMTQSPSS LSASVGDRVT ITCKASQNVD TDVAWFQQKP GKAPKGLIQS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 85 | hu20D12.v2.8 HC Fab | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 86 | hu20D12.v2.9 LC | DIQMTQSPSS LSASVGDRVT ITCKASQNVD TDVAWFQQKP GKAPKGLIYS ASSRYSGVPS RFSGSGSGTD FTLTISSLQP EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 87 | hu20D12.v2.9 HC Fab | EVQLVQSGAE VKKPGASVKV SCKASGYTFT SYYMYWVRQA PGQGLEWIGW INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |

Table of Sequences

| SEQ ID NO | Description | Sequence |
|---|---|---|
| 88 | hu20D12.v2.10 LC | DIQMTQSPSS LSASVGDRVT ITCKASQNVD TDVAWFQQKP<br>GKAPKGLIYS ASSRKSGVPS RFSGSGSGTD FTLTISSLQP<br>EDFATYYCQQ YNNYPLTFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 89 | hu20D12.v2.10 HC Fab | EVQLVQSGAE VKKPGASVKV SCKASGYTFT SYYMYWVRQA<br>PGQGLEWIGE INPTSGGTNF NEKFKSRATL TVDTSTSTAY<br>LELSSLRSED TAVYYCAREG GFAYWGQGTL VTVSSASTKG<br>PSVFPLAPSS KSTSGGTAAL GCLVKDYFPE PVTVSWNSGA<br>LTSGVHTFPA VLQSSGLYSL SSVVTVPSSS LGTQTYICNV<br>NHKPSNTKVD KKVEPKSCDK THT |
| 90 | hu20D12.v2.11 LC | DIQMTQSPSS LSASVGDRVT ITCKASQNVD TDVAWFQQKP<br>GKAPKGLIYS ASSRRSGVPS RFSGSGSGTD FTLTISSLQP<br>EDFATYYCQQ YNNYPLTFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 91 | hu20D12.v2.11 HC Fab | EVQLVQSGAE VKKPGASVKV SCKASGYTFT SYYMYWVRQA<br>PGQGLEWIGE INPTSGGTNF NEKFKSRATL TVDTSTSTAY<br>LELSSLRSED TAVYYCAREG GFAYWGQGTL VTVSSASTKG<br>PSVFPLAPSS KSTSGGTAAL GCLVKDYFPE PVTVSWNSGA<br>LTSGVHTFPA VLQSSGLYSL SSVVTVPSSS LGTQTYICNV<br>NHKPSNTKVD KKVEPKSCDK THT |
| 92 | hu20D12.v2.12 LC | DIQMTQSPSS LSASVGDRVT ITCKASQNVD TDVAWFQQKP<br>GKAPKGLIRS ASSRYSGVPS RFSGSGSGTD FTLTISSLQP<br>EDFATYYCQQ YNNYPLTFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 93 | hu20D12.v2.12 HC Fab | EVQLVQSGAE VKKPGASVKV SCKASGYTFT SYYMYWVRQA<br>PGQGLEWIGE INPYSGGTNF NEKFKSRATL TVDTSTSTAY<br>LELSSLRSED TAVYYCAREG GFAYWGQGTL VTVSSASTKG<br>PSVFPLAPSS KSTSGGTAAL GCLVKDYFPE PVTVSWNSGA<br>LTSGVHTFPA VLQSSGLYSL SSVVTVPSSS LGTQTYICNV<br>NHKPSNTKVD KKVEPKSCDK THT |
| 94 | hu20D12.v2.13 LC | DIQMTQSPSS LSASVGDRVT ITCKASQNVD TDVAWFQQKP<br>GKAPKGLIRS ASSRYSGVPS RFSGSGSGTD FTLTISSLQP<br>EDFATYYCQQ YENYPLTFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 95 | hu20D12.v2.13 HC Fab | EVQLVQSGAE VKKPGASVKV SCKASGYTFT SYYMYWVRQA<br>PGQGLEWIGE INPTSGGTNF NEKFKSRATL TVDTSTSTAY<br>LELSSLRSED TAVYYCAREG GFAYWGQGTL VTVSSASTKG<br>PSVFPLAPSS KSTSGGTAAL GCLVKDYFPE PVTVSWNSGA<br>LTSGVHTFPA VLQSSGLYSL SSVVTVPSSS LGTQTYICNV<br>NHKPSNTKVD KKVEPKSCDK THT |
| 96 | hu20D12.v2.14 LC | DIQMTQSPSS LSASVGDRVT ITCKASQNVD TDVAWFQQKP<br>GKAPKGLIRS ASSRYSGVPS RFSGSGSGTD FTLTISSLQP<br>EDFATYYCQQ YNNYPLTFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 97 | hu20D12.v2.14 HC Fab | EVQLVQSGAE VKKPGASVKV SCKASGYTFT SYYMYWVRQA<br>PGQGLEWIGE INPTSGETNF NEKFKSRATL TVDTSTSTAY<br>LELSSLRSED TAVYYCAREG GFAYWGQGTL VTVSSASTKG<br>PSVFPLAPSS KSTSGGTAAL GCLVKDYFPE PVTVSWNSGA<br>LTSGVHTFPA VLQSSGLYSL SSVVTVPSSS LGTQTYICNV<br>NHKPSNTKVD KKVEPKSCDK THT |
| 98 | hu20D12.v2.15 LC | DIQMTQSPSS LSASVGDRVT ITCKASQNVD TDVAWFQQKP<br>GKAPKGLIRS ASSRYSGVPS RFSGSGSGTD FTLTISSLQP |

| Table of Sequences | | |
|---|---|---|
| SEQ ID NO | Description | Sequence |
| | | EDFATYYCQQ YNNYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 99 | hu20D12.v2.15 HC Fab | EVQLVQSGAE VKKPGASVKV SCKASGYTFT SYYMYWVRQA PGQGLEWIGE INPYSGETNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 100 | Lampalizumab VL | DIQVTQSPSS LSASVGDRVT ITCITSTDID DDMNWYQQKP GKVPKLLISG GNTLRPGVPS RFSGSGSGTD FTLTISSLQP EDVATYYCLQ SDSLPYTFGQ GTKVEIK |
| 101 | Lampalizumab VH | EVQLVQSGPE LKKPGASVKV SCKASGYTFT NYGMNWVRQA PGQGLEWMGW INTYTGETTY ADDFKGRFVF SLDTSVSTAY LQISSLKAED TAVYYCEREG GVNNWGQGTL VTVSS |
| 102 | Lampalizumab LC | DIQVTQSPSS LSASVGDRVT ITCITSTDID DDMNWYQQKP GKVPKLLISG GNTLRPGVPS RFSGSGSGTD FTLTISSLQP EDVATYYCLQ SDSLPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQGLSSPVTKSFNRGEC |
| 103 | Lampalizumab HC Fab | EVQLVQSGPE LKKPGASVKV SCKASGYTFT NYGMNWVRQA PGQGLEWMGW INTYTGETTY ADDFKGRFVF SLDTSVSTAY LQISSLKAED TAVYYCEREG GVNNWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 104 | Human complement Factor D, prepropeptide (UniProtKB/Swiss-Prot: P00746.5, 14-OCT-2015) | MHSWERLAVL VLLGAAACAA PPRGRILGGR EAEAHARPYM ASVQLNGAHL CGGVLVAEQW VLSAAHCLED AADGKVQVLL GAHSLSQPEP SKRLYDVLRA VPHPDSQPDT IDHDLLLLQL SEKATLGPAV RPLPWQRVDR DVAPGTLCDV AGWGIVNHAG RRPDSLQHVL LPVLDRATCN RRTHHDGAIT ERLMCAESNR RDSCKGDSGG PLVCGGVLEG VVTSGSRVCG NRKKPGIYTR VASYAAWIDS VLA |
| 105 | Human complement Factor D, propeptide | APPRGRILGGR EAEAHARPYM ASVQLNGAHL CGGVLVAEQW VLSAAHCLED AADGKVQVLL GAHSLSQPEP SKRLYDVLRA VPHPDSQPDT IDHDLLLLQL SEKATLGPAV RPLPWQRVDR DVAPGTLCDV AGWGIVNHAG RRPDSLQHVL LPVLDRATCN RRTHHDGAIT ERLMCAESNR RDSCKGDSGG PLVCGGVLEG VVTSGSRVCG NRKKPGIYTR VASYAAWIDS VLA |
| 106 | Human complement Factor D, mature, aa26-253 | LGGREAEAHA RPYMASVQLN GAHLCGGVLV AEQWVLSAAH CLEDAADGKV QVLLGAHSLS QPEPSKRLYD VLRAVPHPDS QPDTIDHDLL LLQLSEKATL GPAVRPLPWQ RVDRDVAPGT LCDVAGWGIV NHAGRRPDSL QHVLLPVLDR ATCNRRTHHD GAITERLMCA ESNRRDSCKG DSGGPLVCGG VLEGVVTSGS RVCGNRKKPG IYTRVASYAA WIDSVLA |
| 107 | Cynomolgus monkey complement Factor D, precursor, predicted (NCBI Reference Sequence: XP_005587397.1, 18-SEP-2013) | MHSWEHLAVL VLLGVAACAA QPRGRILGGR EAEAHARPYM ASVQVNGEHL CGGVLVAEQW VLSAAHCLED AADGKVQVLL GAHSLSQPEP SKRLYDVLRA VPHPDSRPDT IDHDLLLLQL SEKATLGPAV RPLPWQRVDR DVEPGTLCDV AGWGIVSHAG RRPDRLQHVL LPVLDRATCN RRTHHDGAIT QRMMCAESNR RDSCKGDSGG PLVCGGVLEG VVTSGSRVCG NRKKPGIYTR VASYAAWIDS VLA |
| 108 | hu20D12 consensus HVR-L2 | SASSRX$_1$S, wherein X$_1$ is selected from Y, K, and R |
| 109 | hu20D12 consensus extended HVR-L2 | X$_2$SASSRX$_1$S, wherein X$_1$ is selected from Y, K, and R; X$_2$ is selected from Y, R, S, K, and Q |

Table of Sequences

| SEQ ID NO | Description | Sequence |
|---|---|---|
| 110 | hu20D12consensusHVR-L3 | QQYX$_3$NYPLT, wherein X$_3$ is selected from N and E |
| 111 | hu20D12 consensus HVR-H2 | X$_4$INPX$_5$X$_6$GX$_7$TNFNEKFKS, wherein X$_4$ is selected from E and W; X$_5$ is selected from T and Y; X$_6$ is selected from N, S, and Q; and X$_7$ is selected from G, D, and E |
| 112 | Fab light chain constant region | RTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 113 | Fab heavy chain constant region ("CDKTHT") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 128 | Fab heavy chain constant region ("CDKTHL") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THL |
| 129 | Fab heavy chain constant region ("CDKTHTC"); "Fab-C" in Examples refers to this sequence | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTC |
| 130 | Fab heavy chain constant region ("CDKTHTCPPC") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPC |
| 131 | Fab heavy chain constant region ("CDKTHTCPPS") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPS |
| 132 | Fab heavy chain constant region ("CDKTHTSPPC") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTSPPC |
| 154 | Fab heavy chain constant region ("CDKTHTAPPC") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTAPPC |
| 155 | Fab heavy chain constant region ("CDKTHTSGGC") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTSGGC |
| 156 | Fab heavy chain constant region ("CYGPPC") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCYGPPC |
| 134 | Fab heavy chain constant region ("CDKTH") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK TH |
| 135 | Fab heavy chain constant region ("CDKT") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK T |
| 136 | Fab heavy chain constant region ("CDK") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK |
| 137 | Fab heavy chain constant region ("CD") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCD |
| 138 | Fab heavy chain constant region (IgG2) | ASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERK |
| 139 | Fab heavy chain constant region (IgG4) ("KYGPP (SEQ ID NO:181)) | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGPP |

| SEQ ID NO | Description | Sequence |
|---|---|---|
| 157 | Fab heavy chain constant region (IgG2 Fab-C) ("VERKC") | ASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKC |
| 158 | Fab heavy chain constant region (IgG4 Fab-C) KYGPPC") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGPPC |
| 159 | Fab heavy chain constant region (IgG4) ("KYG") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYG |
| 160 | Fab heavy chain constant region (IgG4) ("KY") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKY |
| 161 | Fab heavy chain constant region (IgG4) ("K") | STKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESK |
| 114 | AFD.v8 LC | DIQVTQSPSS LSASVGDRVT ITCITSTSIE SDMNWYQQKP GKVPKLLISG GNTLRPGVPS RFSGSGSGTD FTLTISSLQP EDVATYYCLQ SDSLPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 115 | AFD.v8 HC Fab | EVQLVQSGPE LKKPGASVKV SCKASGYTFT NYGMNWVRQA PGQGLEWMGW INTYTGETTY AEDFKGRFVF SLDTSVSTAY LQISSLKAED TAVYYCEREG GVNNWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 116 | AFD.v14 LC | DIQVTQSPSS LSASVGDRVT ITCITSTSIE SDMNWYQQKP GKVPKLLISG GNTLRPGVPS RFSGSGSGTD FTLTISSLQP EDVATYYCLQ SDSLPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 117 | AFD.v14 HC Fab | EVQLVQSGPE LKKPGASVKV SCKASGYTFT NYGMNWVRQA PGQGLEWMGW INTYTGETTY AEDFKGRFVF SLDTSVSTAY LQISSLKAED TAVYYCEREG GVSNWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT |
| 133 | AFD.v14 HC Fab ("CDKTHTC"; also referred to as AFD.v14.C) | EVQLVQSGPE LKKPGASVKV SCKASGYTFT NYGMNWVRQA PGQGLEWMGW INTYTGETTY AEDFKGRFVF SLDTSVSTAY LQISSLKAED TAVYYCEREG GVSNWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTC |
| 118 | hu20D12.v2.1 HC Fab ("CDKTHL") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THL |
| 119 | hu20D12.v2.1 HC Fab ("CDKTHTC"; also referred to as hu20D12.v2.1.C) | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTC |
| 120 | hu20D12.v2.1 HC Fab ("CDKTHTCPPC") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG |

Table of Sequences

| SEQ ID NO | Description | Sequence |
|---|---|---|
| | | PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPC |
| 121 | hu20D12.v2.1 HC Fab ("CDKTHTSPPC") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTSPPC |
| 122 | hu20D12.v2.1 HC Fab ("CDKTHTCPPS") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPS |
| 140 | hu20D12.v2.1 HC Fab ("CDKTH") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK TH |
| 141 | hu20D12.v2.1 HC Fab ("CDKT") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK T |
| 142 | hu20D12.v2.1 HC Fab ("CDK") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK |
| 143 | hu20D12.v2.1 HC Fab ("CD") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCD |
| 144 | hu20D12.v2.1 HC Fab ("APPC") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSAPP C |
| 145 | hu20D12.v2.1 HC Fab ("SGGC") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSSGG C |
| 146 | hu20D12.v2.1 HC Fab ("CYGPPC") | EVQLVQSGAE VKKPGASVKV SCKASGYTFT SYYMYWVRQA PGQGLEWIGE INPTSGGTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCYG PPC |
| 123 | hu20D12.v2.3 HC Fab ("CDKTHL") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THL |

| SEQ ID NO | Description | Sequence |
|---|---|---|
| 124 | hu20D12.v2.3 HC Fab ("CDKTHTC") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTC |
| 125 | hu20D12.v2.3 HC Fab ("CDKTHTCPPC") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPC |
| 126 | hu20D12.v2.3 HC Fab ("CDKTHTSPPC") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTSPPC |
| 127 | hu20D12.v2.3 HC Fab ("CDKTHTCPPS") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPS |
| 147 | hu20D12.v2.3 HC Fab ("CDKTH") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK TH |
| 148 | hu20D12.v2.3 HC Fab ("CDKT") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK T |
| 149 | hu20D12.v2.3 HC Fab ("CDK") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK |
| 150 | hu20D12.v2.3 HC Fab ("CD") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCD |
| 151 | hu20D12.v2.3 HC Fab ("APPC") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSAPP C |
| 152 | hu20D12.v2.3 HC Fab ("SGGC") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSSGG C |

| SEQ ID NO | Description | Sequence |
|---|---|---|
| 153 | hu20D12.v2.3 HC Fab ("CYGPPC") | EVQLVQSGAE VKKPGASVKV SCKASGYTFT SYYMYWVRQA PGQGLEWIGE INPYSGDTNF NEKFKSRATL TVDTSTSTAY LELSSLRSED TAVYYCAREG GFAYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCYG PPC |
| 162 | CPPC | CPPC |
| 163 | Fab heavy chain constant region (IgG4) ("KYGP") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGP |
| 164 | Fab heavy chain constant region ("CDKTHX") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THX8, wherein $X_8$ is selected from any amino acid except T |
| 165 | C-terminus of heavy chain of a Fab fragment | CDKTHT |
| 166 | C-terminus of heavy chain of a Fab fragment | CDKTHL |
| 167 | C-terminus of heavy chain of a Fab fragment | CDKTH |
| 168 | C-terminus of heavy chain of a Fab fragment | CDKT |
| 169 | C-terminus of heavy chain of a Fab fragment | CDKTHX; wherein X is selected from any amino acid except T |
| 170 | C-terminus of heavy chain of a Fab fragment | CDKTHTC |
| 171 | C-terminus of heavy chain of a Fab fragment | CDKTHTCPPC |
| 172 | C-terminus of heavy chain of a Fab fragment | CDKTHTCPPS |
| 173 | C-terminus of heavy chain of a Fab fragment | CDKTHTSPPC |
| 174 | C-terminus of heavy chain of a Fab fragment | CDKTHTAPPC |
| 175 | C-terminus of heavy chain of a Fab fragment | CDKTHTSGGC |
| 176 | C-terminus of heavy chain of a Fab fragment | CYGPPC |
| 177 | C-terminus of heavy chain of a Fab fragment | APPC |
| 178 | C-terminus of heavy chain of a Fab fragment | SGGC |
| 179 | C-terminus of heavy chain of a Fab fragment | VERK |
| 180 | C-terminus of heavy chain of a Fab fragment | VERKC |
| 181 | C-terminus of heavy chain of a Fab fragment | KYGPP |

Table of Sequences

| SEQ ID NO | Description | Sequence |
|---|---|---|
| 182 | C-terminus of heavy chain of a Fab fragment | KYGP |
| 183 | C-terminus of heavy chain of a Fab fragment | KYGPPC |

What is claimed is:

1. An isolated antibody that binds to Factor D, wherein the antibody comprises (a) HVR-H1 comprising the amino acid sequence SYYMY (SEQ ID NO: 15); (b) HVR-H2 comprising the amino acid sequence $X_4INPX_5X_6GX_7TNFNEKFKS$ (SEQ ID NO: 111), wherein $X_4$ is selected from E and W; $X_5$ is selected from T and Y; $X_6$ is selected from S and Q; and $X_7$ is selected from G, D, and E; (c) HVR-H3 comprising the amino acid sequence EGGFAY (SEQ ID NO: 25); (d) HVR-L1 comprising the amino acid sequence KASQNVDTDVA (SEQ ID NO:9); (e) HVR-L2 comprising the amino acid sequence $SASSRX_1S$ (SEQ ID NO: 108), wherein $X_1$ is selected from Y, K, and R; and (f) HVR-L3 comprising the amino acid sequence $QQYX_3NYPLT$ (SEQ ID NO: 110), wherein $X_3$ is selected from N and E.

2. The antibody of claim 1, wherein the antibody comprises the sequence $X_2SASSRX_1S$ (SEQ ID NO: 109), wherein $X_1$ is selected from Y, K, and R; $X_2$ is selected from Y, R, S, K, and Q.

3. The antibody of claim 2, wherein $X_2$ is R.

4. The antibody of claim 2, wherein $X_1$ is Y.

5. The antibody of claim 1, wherein the antibody comprises HVR-H1 comprising the amino acid sequence of SEQ ID NO: 15, HVR-H2 comprising an amino acid sequence selected from SEQ ID NOs: 16 and 18 to 24, HVR-H3 comprising the amino acid sequence of SEQ ID NO: 25, HVR-L1 comprising the amino acid sequence of SEQ ID NO: 9, HVR-L2 comprising an amino acid sequence selected from SEQ ID NOs: 10 to 12, and HVR-L3 comprising the amino acid sequence of SEQ ID NO: 13 or 14.

6. The antibody of claim 1, wherein the antibody comprises:

a) HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

b) HVR-H1 comprising the amino acid sequence of SEQ ID NO: 15, HVR-H2 comprising the amino acid sequence of SEQ ID NO: 20, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

c) HVR-H1 comprising the amino acid sequence of SEQ ID NO: 15, HVR-H2 comprising the amino acid sequence of SEQ ID NO: 18, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

d) HVR-H1 comprising the amino acid sequence of SEQ ID NO: 15, HVR-H2 comprising the amino acid sequence of SEQ ID NO: 19, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

e) HVR-H1 comprising the amino acid sequence of SEQ ID NO: 15, HVR-H2 comprising the amino acid sequence of SEQ ID NO: 21, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

f) HVR-H1 comprising the amino acid sequence of SEQ ID NO: 15, HVR-H2 comprising the amino acid sequence of SEQ ID NO: 22, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

g) HVR-H1 comprising the amino acid sequence of SEQ ID NO: 15, HVR-H2 comprising the amino acid sequence of SEQ ID NO: 23, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13;

h) HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 11, HVR-L3 comprising the amino acid sequence of SEQ ID NO: 13;

i) HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 12, HVR-L3 comprising the amino acid sequence of SEQ ID NO: 13;

j) HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 14; or k) HVR-H1 comprising the amino acid sequence of SEQ ID NO: 15, HVR-H2 comprising the amino acid sequence of SEQ ID NO: 24, HVR-H3 comprising the amino acid sequence of SEQ ID NO: 25, HVR-L1 comprising the amino acid sequence of SEQ ID NO: 9, HVR-L2 comprising the amino acid sequence of SEQ ID NO: 10, HVR-L3 comprising the amino acid sequence of SEQ ID NO: 13.

7. The antibody of claim 1, wherein the amino acid at position 49 of the light chain according to Kabat numbering is arginine (R).

8. The antibody of claim 1, wherein the antibody comprises a heavy chain variable region comprising an amino acid sequence selected from SEQ ID NOs: 27, 29, 31, 33, 35, 37, 39, 41, 43, 45, 47, 49, 51, 53, 55, 57, 59, 61, and 63.

9. The antibody of claim 1, wherein the antibody comprises a light chain variable region comprising an amino acid sequence selected from SEQ ID NOs: 26, 28, 30, 32, 34, 36, 38, 40, 42, 44, 46, 48, 50, 52, 54, 56, 58, 60, and 62.

10. The antibody of claim 1, wherein the antibody comprises:

a) a heavy chain variable region comprising the amino acid sequence of SEQ ID NO: 35 and a light chain variable region comprising the amino acid sequence of SEQ ID NO: 34;

b) a heavy chain variable region comprising the amino acid sequence of SEQ ID NO: 39 and a light chain variable region comprising the amino acid sequence of SEQ ID NO: 38;

c) a heavy chain variable region comprising the amino acid sequence of SEQ ID NO: 33 and a light chain variable region comprising the amino acid sequence of SEQ ID NO: 32;

d) a heavy chain variable region comprising the amino acid sequence of SEQ ID NO: 45 and a light chain variable region comprising the amino acid sequence of SEQ ID NO: 44;

e) a heavy chain variable region comprising the amino acid sequence of SEQ ID NO: 47 and a light chain variable region comprising the amino acid sequence of SEQ ID NO: 46;

f) a heavy chain variable region comprising the amino acid sequence of SEQ ID NO: 49 and a light chain variable region comprising the amino acid sequence of SEQ ID NO: 48;

g) a heavy chain variable region comprising the amino acid sequence of SEQ ID NO: 29 and a light chain variable region comprising the amino acid sequence of SEQ ID NO: 28;

h) a heavy chain variable region comprising the amino acid sequence of SEQ ID NO: 31 and a light chain variable region comprising the amino acid sequence of SEQ ID NO: 30;

i) a heavy chain variable region comprising the amino acid sequence of SEQ ID NO: 37 and a light chain variable region comprising the amino acid sequence of SEQ ID NO: 36;

j) a heavy chain variable region comprising the amino acid sequence of SEQ ID NO: 41 and a light chain variable region comprising the amino acid sequence of SEQ ID NO: 40;

k) a heavy chain variable region comprising the amino acid sequence of SEQ ID NO: 61 and a light chain variable region comprising the amino acid sequence of SEQ ID NO: 60;

l) a heavy chain variable region comprising the amino acid sequence of SEQ ID NO: 43 and a light chain variable region comprising the amino acid sequence of SEQ ID NO: 42;

m) a heavy chain variable region comprising the amino acid sequence of SEQ ID NO: 57 and a light chain variable region comprising the amino acid sequence of SEQ ID NO: 56;

n) a heavy chain variable region comprising the amino acid sequence of SEQ ID NO: 51 and a light chain variable region comprising the amino acid sequence of SEQ ID NO: 50;

o) a heavy chain variable region comprising the amino acid sequence of SEQ ID NO: 53 and a light chain variable region comprising the amino acid sequence of SEQ ID NO: 52;

p) a heavy chain variable region comprising the amino acid sequence of SEQ ID NO: 55 and a light chain variable region comprising the amino acid sequence of SEQ ID NO: 54;

q) a heavy chain variable region comprising the amino acid sequence of SEQ ID NO: 59 and a light chain variable region comprising the amino acid sequence of SEQ ID NO: 58; or r) a heavy chain variable region comprising the amino acid sequence of SEQ ID NO: 63 and a light chain variable region comprising the amino acid sequence of SEQ ID NO: 62.

11. The antibody of claim 1, wherein the antibody comprises a heavy chain variable region comprising the amino acid sequence of SEQ ID NO: 35 and a light chain variable region comprising the amino acid sequence of SEQ ID NO: 34, or wherein the antibody comprises a heavy chain variable region comprising the amino acid sequence of SEQ ID NO: 39and a light chain variable region comprising the amino acid sequence of SEQ ID NO: 38.

12. The antibody of claim 1, which is a monoclonal antibody.

13. The antibody of claim 1, which is a humanized or chimeric antibody.

14. The antibody of claim 1, which is an antibody fragment that binds Factor D.

15. The antibody of claim 14, which is a Fab fragment.

16. The antibody of claim 15, wherein the light chain comprises a light chain constant region comprising the sequence of SEQ ID NO: 112.

17. The antibody of claim 15, wherein the heavy chain comprises a heavy chain constant region comprising a sequence selected from SEQ ID NOs: 113, 128 to 132, 134 to 137, and 154-156.

18. The antibody of claim 14, wherein the antibody comprises:
   a) a heavy chain comprising an amino acid sequence selected from SEQ ID NOs: 71, 118 to 122, and 140 to 146, and a light chain comprising the amino acid sequence of SEQ ID NO: 70;
   b) a heavy chain comprising an amino acid sequence selected from SEQ ID NO: 75, 123 to 127, and 147 to 153 and a light chain comprising the amino acid sequence of SEQ ID NO: 74;
   c) a heavy chain comprising the amino acid sequence of SEQ ID NO: 65 and a light chain comprising the amino acid sequence of SEQ ID NO: 64;
   d) a heavy chain comprising the amino acid sequence of SEQ ID NO: 65 and a light chain comprising the amino acid sequence of SEQ ID NO: 65;
   e) a heavy chain comprising the amino acid sequence of SEQ ID NO: 67 and a light chain comprising the amino acid sequence of SEQ ID NO: 66;
   f) a heavy chain comprising the amino acid sequence of SEQ ID NO: 69 and a light chain comprising the amino acid sequence of SEQ ID NO: 68;
   g) a heavy chain comprising the amino acid sequence of SEQ ID NO: 73 and a light chain comprising the amino acid sequence of SEQ ID NO: 72;
   h) a heavy chain comprising the amino acid sequence of SEQ ID NO: 77 and a light chain comprising the amino acid sequence of SEQ ID NO: 76;
   i) a heavy chain comprising the amino acid sequence of SEQ ID NO: 79 and a light chain comprising the amino acid sequence of SEQ ID NO: 78;
   j) a heavy chain comprising the amino acid sequence of SEQ ID NO: 81 and a light chain comprising the amino acid sequence of SEQ ID NO: 80;
   k) a heavy chain comprising the amino acid sequence of SEQ ID NO: 83 and a light chain comprising the amino acid sequence of SEQ ID NO: 82;
   l) a heavy chain comprising the amino acid sequence of SEQ ID NO: 85 and a light chain comprising the amino acid sequence of SEQ ID NO: 84;
   m) a heavy chain comprising the amino acid sequence of SEQ ID NO: 87 and a light chain comprising the amino acid sequence of SEQ ID NO: 86;
   n) a heavy chain comprising the amino acid sequence of SEQ ID NO: 89 and a light chain comprising the amino acid sequence of SEQ ID NO: 88;
   o) a heavy chain comprising the amino acid sequence of SEQ ID NO: 91 and a light chain comprising the amino acid sequence of SEQ ID NO: 90;
   p) a heavy chain comprising the amino acid sequence of SEQ ID NO: 93 and a light chain comprising the amino acid sequence of SEQ ID NO: 92;
   q) a heavy chain comprising the amino acid sequence of SEQ ID NO: 95 and a light chain comprising the amino acid sequence of SEQ ID NO: 94;
   r) a heavy chain comprising the amino acid sequence of SEQ ID NO: 97 and a light chain comprising the amino acid sequence of SEQ ID NO: 96; or
   s) a heavy chain comprising the amino acid sequence of SEQ ID NO: 99 and a light chain comprising the amino acid sequence of SEQ ID NO: 98.

19. The antibody of claim 14, wherein the antibody comprises:
   a) a heavy chain comprising an amino acid sequence selected from SEQ ID NOs: 71, 118 to 122, and 140 to 146, and a light chain comprising the amino acid sequence of SEQ ID NO: 70; or
   b) a heavy chain comprising an amino acid sequence selected from SEQ ID NO: 75, 123 to 127, and 147 to 153 and a light chain comprising the amino acid sequence of SEQ ID NO: 74.

20. The antibody of claim 1, wherein the antibody comprises an engineered cysteine.

21. The antibody of claim 20, wherein the engineered cysteine is selected from a T110C, A136C, L170C, L175C, T183C, or T205C mutation in the heavy chain, and I106C, R108C, R142C, K149C, and V205C mutation in the light chain, wherein the residue number is according to Kabat numbering.

22. The antibody of claim 19, wherein the antibody comprises a heavy chain comprising the amino acid sequence of SEQ ID NO: 119 and a light chain comprising the amino acid sequence of SEQ ID NO: 70.

23. An isolated antibody that binds to Factor D, wherein the antibody comprises a heavy chain comprising the amino acid sequence of SEQ ID NO: 119 and a light chain comprising the amino acid sequence of SEQ ID NO: 70.

24. An isolated antibody that binds to Factor D, wherein the antibody comprises a heavy chain consisting of the amino acid sequence of SEQ ID NO: 119 and a light chain consisting of the amino acid sequence of SEQ ID NO: 70.

25. The antibody of claim 1, wherein Factor D is human Factor D comprising the amino acid sequence of SEQ ID NO: 106.

26. The antibody of claim 1, wherein the antibody binds to cynomolgus monkey Factor D.

27. The antibody of claim 26, wherein the cynomolgus monkey Factor D comprises the amino acid sequence of SEQ ID NO: 107.

28. The antibody of claim 27, wherein the antibody binds to cynomolgus monkey Factor D with a KD that is less than 10-fold, or less than 7-fold, or less than 5-fold, or less than 3-fold higher than the KD for human Factor D.

29. An isolated nucleic acid encoding the antibody of claim 1.

30. An isolated host cell comprising the nucleic acid of claim 29.

31. A pharmaceutical formulation comprising the antibody of claim 1 and a pharmaceutically acceptable carrier.

32. The pharmaceutical formulation of claim 31, wherein the pharmaceutically acceptable carrier comprises about a buffer having a pH between about 5.5 and about 8.0.

33. The pharmaceutical formulation of claim 31, wherein the antibody is present at a concentration of at least 150 mg/ml.

34. The pharmaceutical formulation of claim 33, wherein the antibody is present at a concentration of between 150 mg/ml and 350 mg/ml.

35. The pharmaceutical formulation of claim 34, wherein the composition comprises no visible precipitate after storage at 4° C. for at least one week.

36. The pharmaceutical formulation of claim 34, wherein the viscosity of the composition at 25° C. is less than 30cP.

37. The pharmaceutical formulation of claim 35, wherein the pharmaceutical formulation is suitable for intravitreal administration through a narrow bore needle.

38. The pharmaceutical formulation of claim 37, wherein the narrow bore needle is about 30, 29, 28, 27, 26, 25, 24, 23, or 22 gauge.

39. An isolated antibody that binds to Factor D, wherein the antibody comprises HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L 2 comprising the amino acid sequence of SEQ ID NO: 10, HVR-L3 comprising the amino acid sequence of SEQ ID NO: 13.

40. An isolated antibody that binds to Factor D, wherein the antibody comprises a heavy chain variable region comprising the amino acid sequence of SEQ ID NO: 35 and a light chain variable region comprising the amino acid sequence of SEQ ID NO: 34.

41. An isolated antibody that binds to Factor D, wherein the antibody comprises a heavy chain comprising the amino acid sequence of SEQ ID NO: 71 and a light chain comprising the amino acid sequence of SEQ ID NO: 70.

42. An isolated antibody that binds to Factor D, wherein the antibody comprises a heavy chain consisting of the amino acid sequence of SEQ ID NO: 71 and a light chain consisting of the amino acid sequence of SEQ ID NO: 70.

43. A method of producing an antibody that binds to Factor D comprising culturing the host cell of claim 30 so that the antibody is produced.

44. A conjugate comprising at least one antibody of claim 1 covalently linked to one or more polyols.

45. The conjugate of claim 44, wherein the polyol is a multi-armed polyol.

46. The conjugate of claim 44, wherein the conjugate comprises at least two antibodies covalently linked to a multi-armed polyol.

47. The conjugate of claim 44, wherein the polyol is covalently linked to at least one antibody through a free sulfhydryl group of a cysteine amino acid.

48. The conjugate of claim 47, wherein the cysteine amino acid is an engineered cysteine.

49. The conjugate of claim 48, wherein the cysteine amino acid is in a constant region of the antibody.

50. The conjugate of claim 49, wherein the cysteine amino acid is at the C-terminus of the heavy chain or light chain of the antibody.

51. The conjugate of claim 44, wherein the polyol is covalently linked to at least one antibody through a free amino group of a lysine amino acid.

52. The conjugate of claim 51, wherein the lysine amino acid is in a constant region of the antibody.

53. The conjugate of claim 51, wherein the lysine amino acid is at the C-terminus of the heavy chain or light chain of the antibody.

54. The conjugate of claim 46, wherein the polyol is a multi-armed polyol selected from a dimer, a tetramer, a hexamer, and an octamer.

55. The conjugate of claim 54, wherein the multi-armed polyol is an octamer.

56. The conjugate of claim 44, wherein the polyol is polyethylene glycol.

57. The conjugate of claim 56, wherein the polyethylene glycol has a weight average molecular weight of from about 500 D to about 300,000 D.

58. The conjugate of claim 56, wherein the polyethylene glycol has a weight average molecular weight of from about 20,000 D to about 60,000 D.

59. The conjugate of claim 56, wherein the polyethylene glycol has a weight average molecular weight of about 40,000 D.

60. The conjugate of claim 56, wherein the polyethylene glycol has the structure of general formula (Ia):

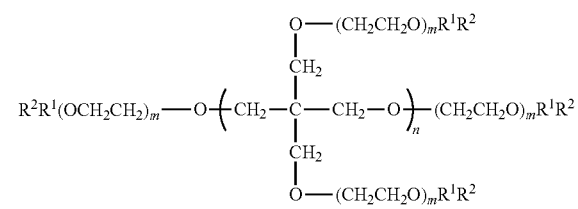

(Ia)

wherein each m is independently an integer from 3-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the antibody.

61. The conjugate of claim 56, wherein the polyethylene glycol has the structure of general formula (Ib):

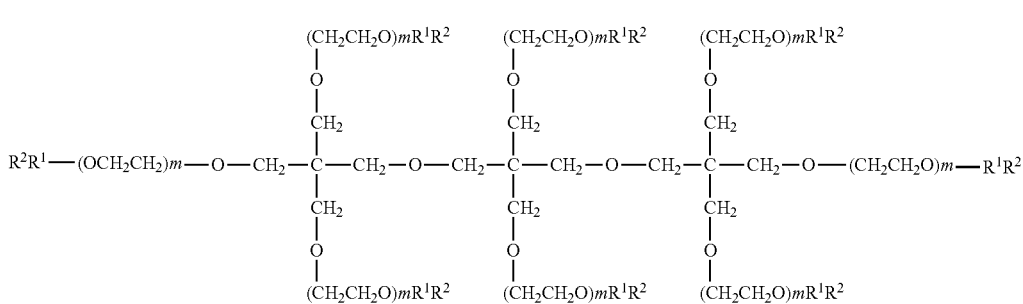

wherein each m is independently an integer from 3-250; each $R^1$ is independently either absent, or is a linking group; and each $R^2$ is independently either hydrogen or a terminal reactive group; wherein at least one $R^2$ is a terminal reactive group and is covalently linked to the antibody.

62. The conjugate of claim 56, wherein the polyethylene glycol has the structure of general formula (IIa):

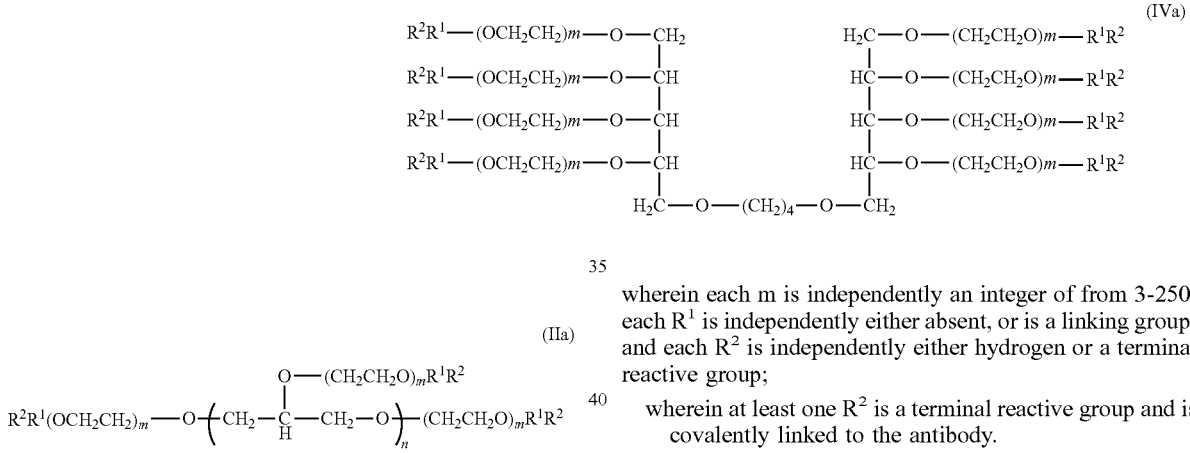

wherein each m is independently an integer of from 3-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the antibody.

63. The conjugate of claim 62, wherein n is 4.

64. The conjugate of claim 56, wherein the polyethylene glycol has the structure of general formula (IIIa):

wherein each m is independently an integer of from 3-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the antibody.

65. The conjugate of claim 64, wherein n is 4.

66. The conjugate of claim 56, wherein the polyethylene glycol has the structure of general formula (IVa):

wherein each m is independently an integer of from 3-250; each $R^1$ is independently either absent, or is a linking group; and each $R^2$ is independently either hydrogen or a terminal reactive group; wherein at least one $R^2$ is a terminal reactive group and is covalently linked to the antibody.

67. The conjugate of claim 61, wherein m is an integer of 50-200.

68. The conjugate of claim 67, wherein m is an integer of 100-150.

69. The conjugate of claim 61, wherein at least one $R^1$ is a linking group, wherein $R^1$ and $R^2$ when taken together are selected from;

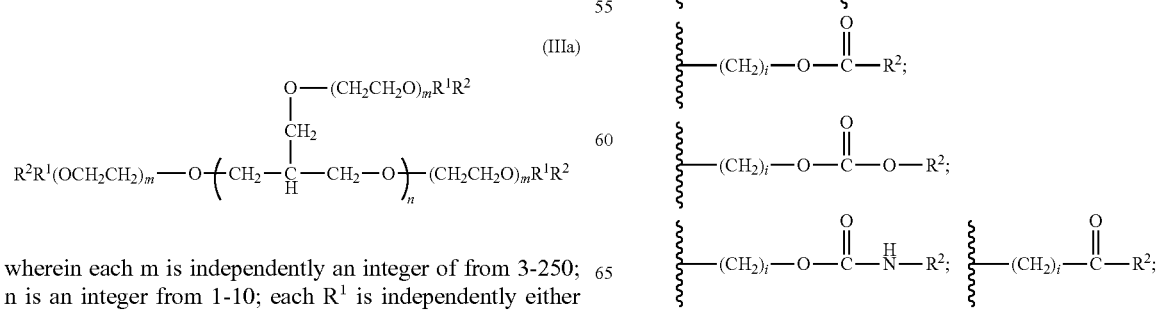

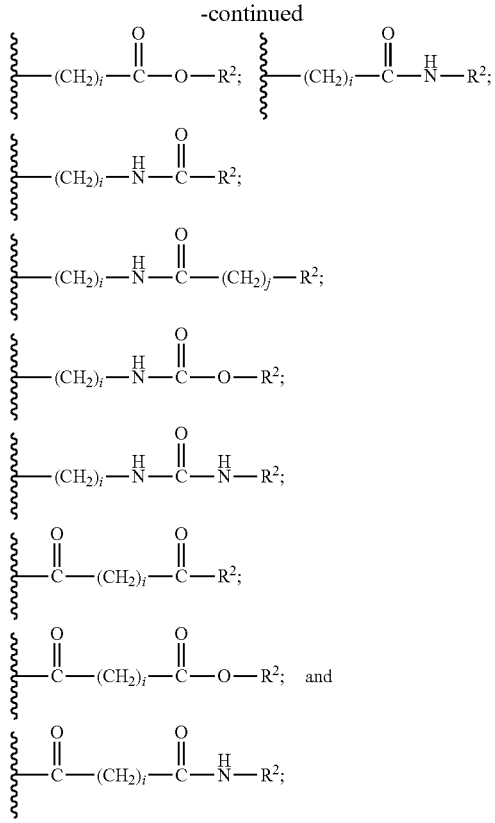

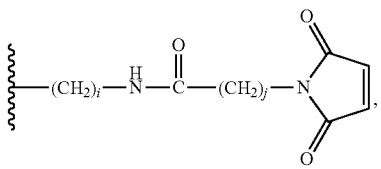

i is an integer of 0-10; and j is an integer of 0-10.

74. The conjugate of claim 61, wherein at least seven of the $R^2$ groups are covalently linked to one of the antibodies.

75. The conjugate of claim 74, wherein eight of the $R^2$ groups are covalently linked to one of the antibodies.

76. The conjugate of claim 44, comprising at least one antibody covalently linked to one or more polyols, wherein at least one antibody comprises a heavy chain comprising the amino acid sequence of SEQ ID NO: 119 and a light chain comprising the amino acid sequence of SEQ ID NO: 70.

77. A conjugate comprising at least one antibody covalently linked to a polyethylene glycol having the structure of general formula (Ib):

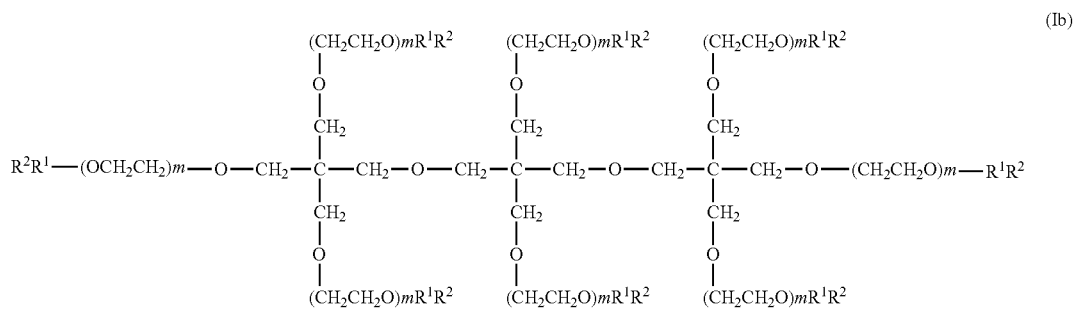

and combinations thereof; wherein each i is independently an integer of 0-10; and j is an integer of 0-10.

70. The conjugate of claim 61, wherein each $R^2$ is independently selected from a thiol reactive group, an amino reactive group, and combinations thereof.

71. The conjugate of claim 70, wherein each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate.

72. The conjugate of claim 71, wherein $R^2$ is a maleimide.

73. The conjugate of claim 61, wherein $R^1$ and $R^2$, when taken together, are wherein each m is independently an integer from 3-250; each $R^1$ is independently either absent, or is a linking group; and each $R^2$ is independently either hydrogen or a terminal reactive group; wherein at least one $R^2$ is a terminal reactive group and is covalently linked to the antibody; wherein each antibody comprises a heavy chain comprising the amino acid sequence of SEQ ID NO: 119 and a light chain comprising the amino acid sequence of SEQ ID NO: 70.

78. The conjugate of claim 77, wherein m is an integer of 50-200.

79. The conjugate of claim 77, wherein m is an integer of 100-150.

80. A conjugate of claim 45, wherein the conjugate is prepared by covalently linking the at least one antibody to a multi-armed polyol.

81. A pharmaceutical formulation comprising the conjugate according to claim 77 and a pharmaceutically acceptable carrier.

82. The pharmaceutical formulation of claim 81, wherein the concentration of the antibody is at least 100 mg/ml.

83. The pharmaceutical formulation of claim 81, wherein the concentration of the antibody is from about 50 mg/ml to about 300 mg/ml.

84. The pharmaceutical formulation of claim 83, wherein the viscosity of the composition at 25° C. is less than 500 cP.

85. The pharmaceutical formulation of claim 84, wherein the concentration of the anti-Factor D antibody in the composition is at least 150 mg/ml.

86. A delivery device for ocular delivery comprising the pharmaceutical formulation of claim 81 and a means for delivering the formulation intravitreally to a patient.

87. The delivery device of claim 86, wherein the formulation remains effective on site for a prolonged period of time.

88. A method of treating a complement-mediated disorder in a subject comprising administering to the subject an effective amount of the antibody of claim 1.

89. The method of claim 88, wherein the complement-mediated disorder is systemic.

90. The method of claim 88, wherein the complement-mediated disorder is a complement-associated eye condition.

91. The method of claim 90, wherein the complement-associated eye condition is selected from age-related macular degeneration (AMD), choroidal neovascularization (CNV), uveitis, diabetic retinopathy, ischemia-related retinopathy, diabetic macular edema, pathological myopia, von Hippel-Lindau disease, histoplasmosis of the eye, Central Retinal Vein Occlusion (CRVO), corneal neovascularization, and retinal neovascularization.

92. The method of claim 90, wherein the complement-associated eye condition is selected from intermediate dry form AMD or geographic atrophy (GA).

93. The method of claim 90, wherein the method comprises administering the antibody using an implantable port delivery system.

94. The method of claim 90, wherein the method comprises administering the antibody by intravitreal administration.

95. The method of claim 94, wherein the intravitreal administration is through a narrow bore needle.

96. The method of claim 95, wherein the narrow bore needle is about 30, 29, 28, 27, 26, 25, 24, 23, or 22 gauge.

97. The method of claim 90, further comprising administering an additional therapeutic agent to the individual.

98. The method of claim 97, wherein the additional therapeutic agent is selected from an ANG2 antagonist, a TIE2 antagonist, a VEGF antagonist, and a second complement component antagonist.

99. The method of claim 97, wherein the additional therapeutic agent is an anti-ANG 2 antibody.

100. The method of claim 97, wherein the additional therapeutic agent is an anti-TIE 2 antibody.

101. The method of claim 97, wherein the additional therapeutic agent is selected from a VEGF trap and an anti-VEGF antibody.

102. The method of claim 97, wherein the additional therapeutic agent is a second complement component antagonist, wherein the second complement component antagonist inhibits a complement component selected from C1, C2, C3, C4, C5, C6, C7, C8 and C9.

103. A method of treating a complement-mediated disorder in a subject comprising administering to the subject an effective amount of the conjugate of claim 77.

104. The method of claim 103, wherein the complement-mediated disorder is systemic.

105. The method of claim 103, wherein the complement-mediated disorder is a complement-associated eye condition.

106. The method of claim 105, wherein the complement-associated eye condition is selected from age-related macular degeneration (AMD), choroidal neovascularization (CNV), uveitis, diabetic retinopathy, ischemia-related retinopathy, diabetic macular edema, pathological myopia, von Hippel-Lindau disease, histoplasmosis of the eye, Central Retinal Vein Occlusion (CRVO), corneal neovascularization, and retinal neovascularization.

107. The method of claim 105, wherein the complement-associated eye condition is selected from intermediate dry form AMD or geographic atrophy (GA).

108. The method of claim 105, wherein the method comprises administering the antibody using an implantable port delivery system.

109. The method of claim 105, wherein the method comprises administering the antibody, conjugate, or pharmaceutical formulation by intravitreal administration.

110. The method of claim 109, wherein the intravitreal administration is through a narrow bore needle.

111. The method of claim 110, wherein the narrow bore needle is about 30, 29, 28, 27, 26, 25, 24, 23, or 22 gauge.

112. The method of claim 105, further comprising administering an additional therapeutic agent to the individual.

113. The method of claim 112, wherein the additional therapeutic agent is selected from an HTRA1 antagonist, an ANG2 antagonist, a TIE2 antagonist, a VEGF antagonist, and a second complement component antagonist.

114. The method of claim 112, wherein the additional therapeutic agent is an anti-HTRA 1 antibody.

115. The method of claim 112, wherein the additional therapeutic agent is an anti-ANG 2 antibody.

116. The method of claim 112, wherein the additional therapeutic agent is an anti-TIE 2 antibody.

117. The method of claim 112, wherein the additional therapeutic agent is selected from a VEGF trap and an anti-VEGF antibody.

118. The method of claim 112, wherein the additional therapeutic agent is a second complement component antagonist, wherein the second complement component antagonist inhibits a complement component selected from C1, C2, C3, C4, C5, C6, C7, C8 and C9.

119. The method of claim 97, wherein the additional therapeutic agent is an anti-HTRA 1 antibody.

120. A delivery device for ocular delivery comprising the pharmaceutical formulation of claim 31 and a means for delivering the formulation intravitreally to a patient.

121. The delivery device of claim 120, wherein the formulation remains effective on site for a prolonged period of time.

122. A method of producing a conjugate comprising at least one antibody that binds to Factor D covalently linked to a polyethylene glycol, comprising:

reacting a polyethylene glycol having the structure of general formula (Ib):

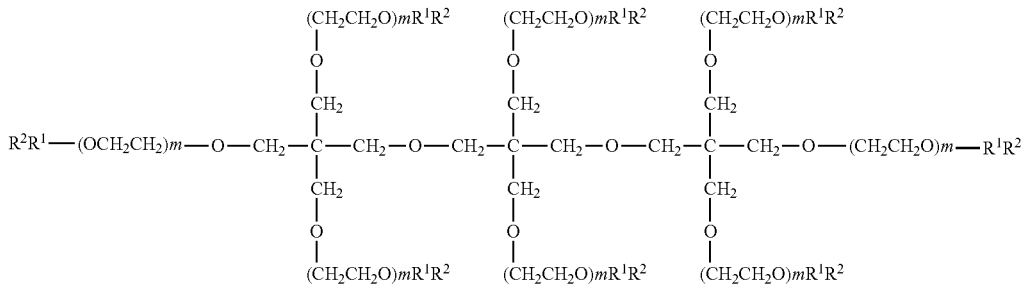

wherein each m is independently an integer from 3-250; each $R^1$ is independently either absent, or is a linking group; and each $R^2$ is independently either hydrogen or a terminal reactive group; with an antibody comprising a heavy chain comprising the amino acid sequence of SEQ ID NO: 119 and a light chain comprising the amino acid sequence of SEQ ID NO: 70;

such that the conjugate is produced.

123. A conjugate comprising at least one antibody covalently linked to a polyethylene glycol having the structure of general formula (Ib):

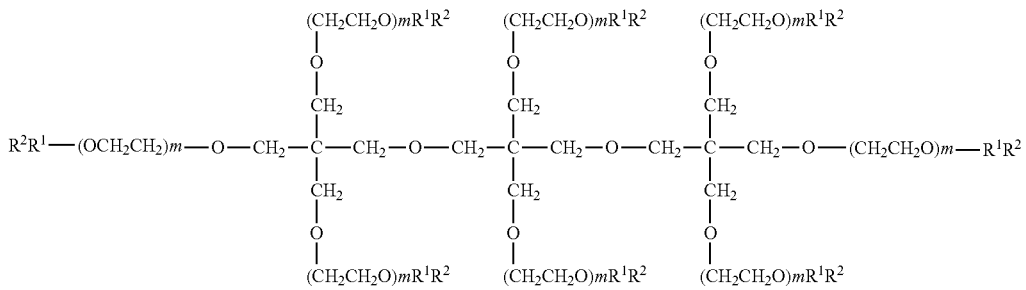

wherein each m is independently an integer from 3-250; each $R^1$ is independently either absent, or is a linking group; and each $R^2$ is independently either hydrogen or a terminal reactive group; wherein at least one $R^2$ is a terminal reactive group and is covalently linked to the antibody; wherein each antibody comprises HVR-H1 comprising the amino acid sequence of SEQ ID NO: 15, HVR-H2 comprising the amino acid sequence of SEQ ID NO: 16, HVR-H3 comprising the amino acid sequence of SEQ ID NO: 25, HVR-L1 comprising the amino acid sequence of SEQ ID NO: 9, HVR-L 2 comprising the amino acid sequence of SEQ ID NO: 10, HVR-L3 comprising the amino acid sequence of SEQ ID NO: 13.

124. A conjugate comprising at least one antibody covalently linked to a polyethylene glycol having the structure of general formula (Ib):

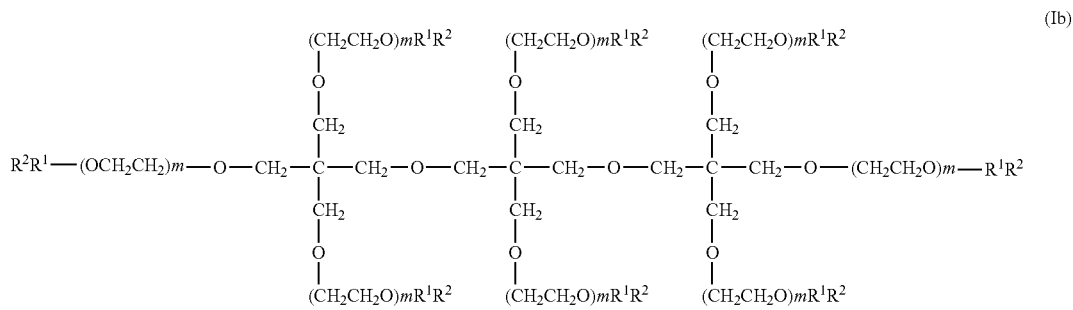

wherein each m is independently an integer from 3-250; each $R^1$ is independently either absent, or is a linking group; and each $R^2$ is independently either hydrogen or a terminal reactive group; wherein at least one $R^2$ is a terminal reactive group and is covalently linked to the antibody; wherein each antibody comprises a heavy chain variable region comprising the amino acid sequence of SEQ ID NO: 35 and a light chain variable region comprising the amino acid sequence of SEQ ID NO: 34.

125. The method of claim 91, wherein the AMD is dry (non-exudative) AMD or wet (exudative) AMD.

126. The method of claim 106, wherein the AMD is dry (non-exudative) AMD or wet (exudative) AMD.

* * * * *

UNITED STATES PATENT AND TRADEMARK OFFICE
CERTIFICATE OF CORRECTION

| | |
|---|---|
| PATENT NO. | : 10,407,510 B2 |
| APPLICATION NO. | : 15/335847 |
| DATED | : September 10, 2019 |
| INVENTOR(S) | : Robert F. Kelley et al. |

It is certified that error appears in the above-identified patent and that said Letters Patent is hereby corrected as shown below:

In the Claims

In Claim 5, Column 305, Line 61, "13or" should be --13 or--.
In Claim 6, Column 307, Line 2, "HVR-H2comprising" should be --HVR-H2 comprising--.
In Claim 6, Column 307, Line 3, "HVR-H3comprising" should be --HVR-H3 comprising--.
In Claim 6, Column 307, Line 26, "HVR-H1comprising" should be --HVR-H1 comprising--.
In Claim 6, Column 307, Line 34, "HVR-H1comprising" should be --HVR-H1 comprising--.
In Claim 6, Column 307, Line 43, "HVR-H1comprising" should be --HVR-H1 comprising--.
In Claim 11, Column 309, Line 11, "39and" should be --39 and--.
In Claim 18, Column 309, Lines 41-43, "d) a heavy chain comprising the amino acid sequence of SEQ ID NO: 65 and a light chain comprising the amino acid sequence of SEQ ID NO: 65;" should be deleted.
In Claim 28, Column 310, Line 61, "KD" should be --$K_D$--.
In Claim 28, Column 310, Line 63, "KD" should be --$K_D$--.
In Claim 38, Column 311, Line 27, "HVR-H1comprising" should be --HVR-H1 comprising--.
In Claim 39, Column 311, Line 33, "HVR-L 2 comprising" should be --HVR-L2 comprising--.
In Claim 99, Column 317, Line 54, "anti-ANG 2 antibody" should be --anti-ANG2 antibody--.
In Claim 100, Column 317, Line 56, "anti-TIE 2 antibody" should be --anti-TIE2 antibody--.
In Claim 114, Column 318, Line 39, "anti-HTRA 1 antibody" should be --anti-HTRA1 antibody--.
In Claim 115, Column 318, Line 41, "anti-ANG 2 antibody" should be --anti-ANG2 antibody--.
In Claim 116, Column 318, Line 44, "anti-TIE 2 antibody" should be --anti-TIE2 antibody--.
In Claim 119, Column 318, Line 55, "anti-HTRA 1 antibody" should be --anti-HTRA1 antibody--.
In Claim 123, Column 319, Line 64, "HVR-L 2" should be --HVR-L2--.

Signed and Sealed this
Seventh Day of January, 2020

Andrei Iancu
*Director of the United States Patent and Trademark Office*